United States Patent
Lee et al.

(10) Patent No.: US 12,049,472 B2
(45) Date of Patent: Jul. 30, 2024

(54) HETEROCYCLIC COMPOUND AND ORGANIC LIGHT EMITTING DEVICE COMPRISING SAME

(71) Applicant: LT MATERIALS CO., LTD., Yongin-Si (KR)

(72) Inventors: Nam-Jin Lee, Osan-si (KR); Young-Jin Lee, Osan-si (KR); Won-Jang Jeong, Hwaseong-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 569 days.

(21) Appl. No.: 17/293,527

(22) PCT Filed: Nov. 18, 2019

(86) PCT No.: PCT/KR2019/015751
§ 371 (c)(1),
(2) Date: May 13, 2021

(87) PCT Pub. No.: WO2020/111617
PCT Pub. Date: Jun. 4, 2020

(65) Prior Publication Data
US 2022/0024948 A1    Jan. 27, 2022

(30) Foreign Application Priority Data

Nov. 26, 2018 (KR) .......................... 10-2018-0147458

(51) Int. Cl.
*C07D 519/00* (2006.01)
*C07F 9/54* (2006.01)
*H01L 51/00* (2006.01)
*H10K 85/60* (2023.01)
*H10K 50/18* (2023.01)

(52) U.S. Cl.
CPC .......... *C07D 519/00* (2013.01); *C07F 9/5442* (2013.01); *H10K 85/654* (2023.02); *H10K 85/6572* (2023.02); *H10K 50/18* (2023.02)

(58) Field of Classification Search
None
See application file for complete search history.

(56) References Cited

U.S. PATENT DOCUMENTS

2004/0027059 A1 * 2/2004 Tsutsui ................... H10K 50/17
                                                                  313/504
2016/0141515 A1   5/2016  Hayama et al.
2017/0033295 A1   2/2017  Xia et al.
(Continued)

FOREIGN PATENT DOCUMENTS

| CN | 105198883 A | 12/2015 |
| KR | 10-2016-0001702 A | 1/2016 |
| KR | 10-2017-0015216 A | 2/2017 |

(Continued)

OTHER PUBLICATIONS

International Search Report (PCT/ISA/210) issued in PCT/KR2019/015751 mailed on Mar. 4, 2020.

*Primary Examiner* — Jay Yang
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device including the same.

11 Claims, 2 Drawing Sheets

(56) References Cited

U.S. PATENT DOCUMENTS

2017/0141325 A1    5/2017  Lee et al.
2017/0155049 A1    6/2017  Kim et al.

FOREIGN PATENT DOCUMENTS

| KR | 10-2017-0061770 A | 6/2017 |
| KR | 10-2019-0033885 A | 4/2019 |
| KR | 10-2019-0033911 A | 4/2019 |
| WO | WO 2014/199637 A1 | 12/2014 |
| WO | WO-2015/199489 A2 * | 12/2015 |

* cited by examiner

【FIG. 1】
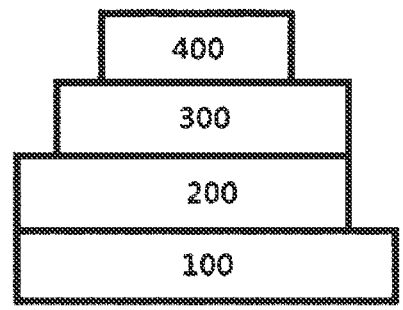
【FIG. 2】
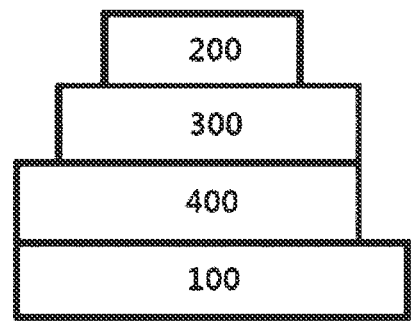
【FIG. 3】
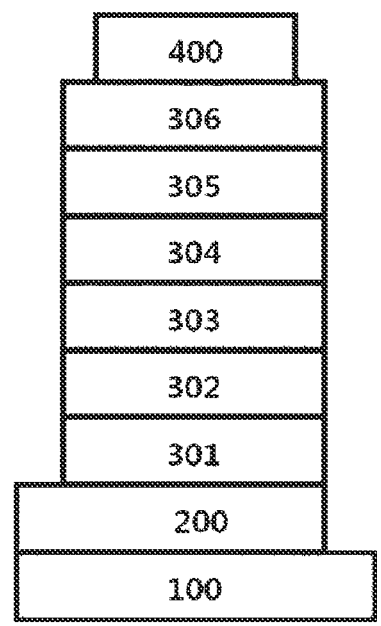

[FIG. 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DEVICE COMPRISING SAME

TECHNICAL FIELD

This application claims priority to and the benefits of Korean Patent Application No. 10-2018-0147458, filed with the Korean Intellectual Property Office on Nov. 26, 2018, the entire contents of which are incorporated herein by reference.

The present specification relates to a heterocyclic compound, and an organic light emitting device including the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a heterocyclic compound, and an organic light emitting device including the same.

Technical Solution

One embodiment of the present application provides a heterocyclic compound represented by the following Chemical Formula 1.

[Chemical Formula 1]

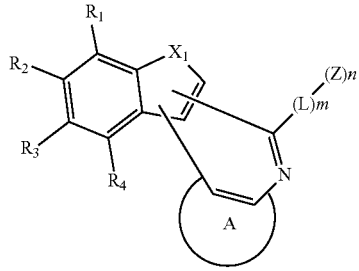

In Chemical Formula 1,

A is a substituted or unsubstituted aryl ring; or a substituted or unsubstituted heteroring, $X_1$ is O; or S, $R_1$ to $R_4$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring, L is a direct bond; a substituted or unsubstituted arylene group; or a substituted or unsubstituted heteroarylene group, Z is selected from the group consisting of deuterium; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, R, R' and R" are the same as or different from each other, and each independently hydrogen; a substituted or unsubstituted alkyl group; a substituted or unsubstituted aryl group; or a substituted or unsubstituted heteroaryl group, m is an integer of 0 to 5, and n is an integer of 1 to 6.

Another embodiment of the present application provides an organic light emitting device including a first electrode; a second electrode provided opposite to the first electrode; and one or more organic material layers provided between the first electrode and the second electrode, wherein one or more layers of the organic material layers include the heterocyclic compound represented by Chemical Formula 1.

Advantageous Effects

A compound described in the present specification can be used as a material of an organic material layer of an organic light emitting device. The compound is capable of performing a role of a hole blocking material, a hole injection material, a hole transfer material, a light emitting material, an electron transfer material, an electron injection material, a charge generation material and the like in an organic light emitting device. Particularly, the compound can be used as a hole blocking layer material, a charge generation layer material or an electron transfer layer material of an organic light emitting device.

When using the compound represented by Chemical Formula 1 in an organic material layer, a device driving voltage can be lowered, light efficiency can be enhanced, and device lifetime properties can be enhanced by thermal stability of the compound.

Particularly, the heterocyclic compound represented by Chemical Formula 1 has an excellent electron transfer ability as a hopping ability is enhanced due to an expansion of conjugation, and as a result, properties of improving driving and efficiency are obtained when used in a device.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20.

Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P (=O) $R_{101}R_{102}$, and $R_{101}$ and $R_{102}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide group may include a diphenylphosphine oxide group, a dinaphthylphosphine oxide group and the like, but are not limited thereto.

In the present specification, the silyl group is a substituent including Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

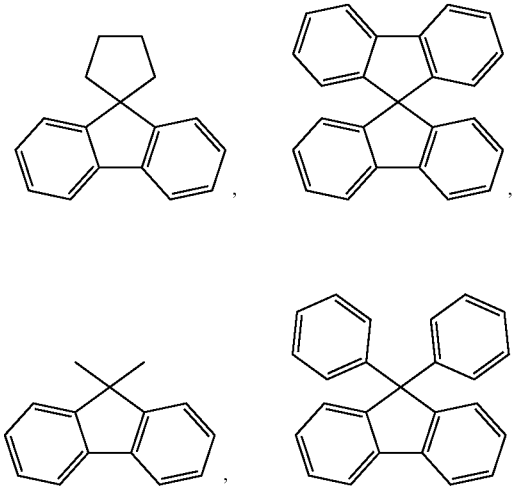

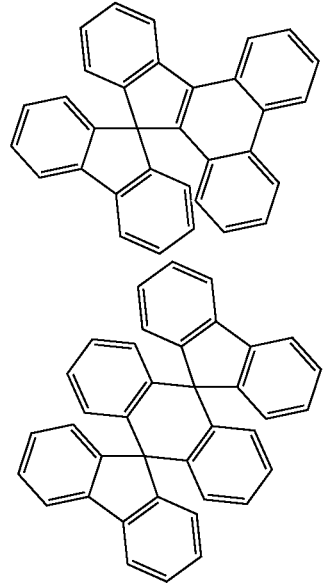

and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1, 2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group.

Descriptions on the heteroaryl group provided above may be applied thereto except for those that are each a divalent.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by the following Chemical Formula 2 or Chemical Formula 3.

[Chemical Formula 2]

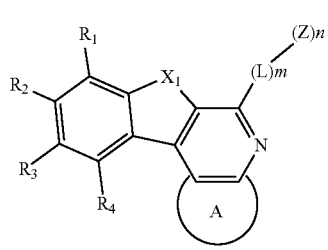

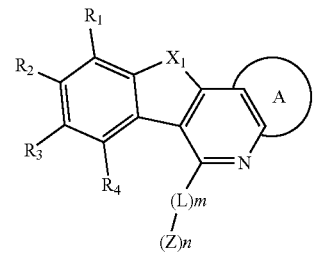

[Chemical Formula 3]

In Chemical Formulae 2 and 3, $R_1$ to $R_4$, $X_1$, L, Z, A, m and n have the same definitions as in Chemical Formula 1.

In one embodiment of the present application, Chemical Formula 1 may be represented by any one of the following Chemical Formula 4 to Chemical Formula 6.

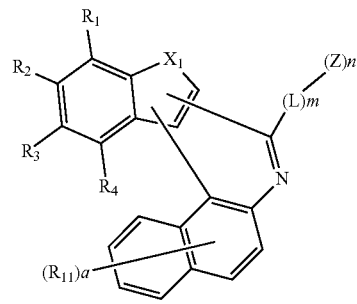

[Chemical Formula 4]

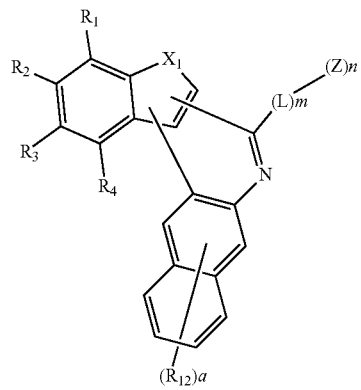

[Chemical Formula 5]

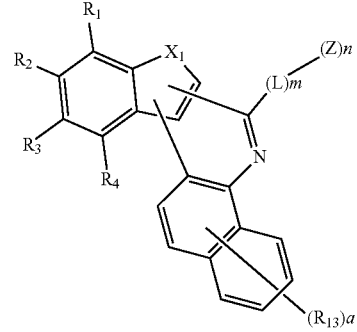

[Chemical Formula 6]

In Chemical Formulae 4 to 6, $R_1$ to $R_4$, $X_1$, L, Z, A, m and n have the same definitions as in Chemical Formula 1, $R_{11}$ to $R_{13}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring, R, R' and R'' are the same as or different from each other, and each independently hydrogen; a substituted or unsubstituted alkyl group; a substituted or unsubstituted aryl group; or a substituted or unsubstituted heteroaryl group, and a is an integer of 0 to 6.

In one embodiment of the present application, A may be a substituted or unsubstituted aryl ring; or a substituted or unsubstituted heteroring.

In another embodiment, A may be a substituted or unsubstituted C6 to C60 aryl ring; or a substituted or unsubstituted C2 to C60 heteroring.

In another embodiment, A may be a substituted or unsubstituted C6 to C40 aryl ring; or a substituted or unsubstituted C2 to C40 heteroring.

In another embodiment, A may be a C6 to C40 aryl ring; or a C2 to C40 heteroring.

In another embodiment, A may be a C6 to C40 aryl ring.

In another embodiment, A may be a C6 to C40 polycyclic aryl ring.

In another embodiment, A may be a C6 to C20 polycyclic aryl ring.

In another embodiment, A may be a naphthyl ring.

Particularly, when A has a substituted or unsubstituted aryl group in Chemical Formula 1, stability of the core itself may be enhanced, and thermal stability may be enhanced as well, and as a result, properties of particularly superior lifetime properties are obtained when used in an organic light emitting device later.

In one embodiment of the present application, $X_1$ may be O; or S.

In one embodiment of the present application, $X_1$ may be O.

In one embodiment of the present application, $X_1$ may be S.

In one embodiment of the present application, L may be a direct bond; a substituted or unsubstituted arylene group; or a substituted or unsubstituted heteroarylene group.

In another embodiment, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a C6 to C40 arylene group; or a C2 to C40 heteroarylene group unsubstituted or substituted with a C6 to C40 aryl group.

In another embodiment, L may be a direct bond; a C6 to C20 arylene group; or a C2 to C20 heteroarylene group unsubstituted or substituted with a C6 to C20 aryl group.

In another embodiment, L may be a direct bond; a phenylene group; a biphenylene group; or a divalent triazine group unsubstituted or substituted with a phenyl group.

In one embodiment of the present application, Z may be selected from the group consisting of deuterium; —CN; a substituted or unsubstituted alkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group.

In another embodiment, Z may be selected from the group consisting of deuterium; —CN; a substituted or unsubstituted C1 to C60 alkyl group; a substituted or unsubstituted C6 to C60 aryl group; a substituted or unsubstituted C2 to C60 heteroaryl group; —SiRR'R''; —P(=O)RR'; and an amine group unsubstituted or substituted with a substituted or unsubstituted C1 to C60 alkyl group, a substituted or unsubstituted C6 to C60 aryl group, or a substituted or unsubstituted C2 to C60 heteroaryl group.

In another embodiment, Z may be selected from the group consisting of a substituted or unsubstituted C6 to C60 aryl group; a substituted or unsubstituted C2 to C60 heteroaryl group; and —P(=O)RR'.

In another embodiment, Z may be selected from the group consisting of a C6 to C60 aryl group unsubstituted or substituted with one or more substituents selected from the group consisting of —P(=O)RR' and a C2 to C60 heteroaryl group; a C2 to C60 heteroaryl group unsubstituted or substituted with a C6 to C60 aryl group; and —P(=O)RR'.

In another embodiment, Z may be selected from the group consisting of a C6 to C40 aryl group unsubstituted or substituted with one or more substituents selected from the group consisting of —P(=O)RR' and a C2 to C40 heteroaryl group; a C2 to C40 heteroaryl group unsubstituted or substituted with a C6 to C40 aryl group; and —P(=O)RR'.

In another embodiment, Z may be selected from the group consisting of —P(=O)RR'; a phenyl group unsubstituted or substituted with one or more substituents selected from the group consisting of —P(=O)RR' and a phenyl group; a triazine group unsubstituted or substituted with one or more substituents selected from the group consisting of a phenyl group and a biphenyl group; a pyrimidine group unsubstituted or substituted with one or more substituents selected from the group consisting of a phenyl group and a biphenyl group; a benzo[4,5]thieno[3,2-d]pyrimidine group unsubstituted or substituted with a phenyl group; a phenanthroline group unsubstituted or substituted with a phenyl group; a quinazoline group unsubstituted or substituted with a phenyl group; and a carbazole group.

In one embodiment of the present application, Z may be represented by the following Chemical Formula 1-1.

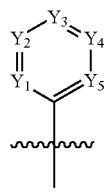

[Chemical Formula 1-1]

In Chemical Formula 1-1, $Y_1$ is $CR_{21}$; or N, $Y_2$ is $CR_{22}$; or N, $Y_3$ is $CR_{23}$; or N, $Y_4$ is $CR_{24}$; or N, and $Y_5$ is $CR_{25}$; or N, $R_{21}$ to $R_{25}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R''; —P(=O)RR';

and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring, and R, R' and R" are the same as or different from each other, and each independently hydrogen; a substituted or unsubstituted alkyl group; a substituted or unsubstituted aryl group; or a substituted or unsubstituted heteroaryl group.

In one embodiment of the present application, Chemical Formula 1-1 may be represented by any one of the following Chemical Formulae 1-1-1 to 1-1-7.

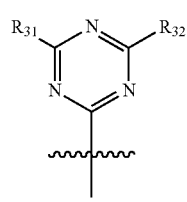

[Chemical Formula 1-1-1]

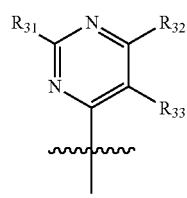

[Chemical Formula 1-1-2]

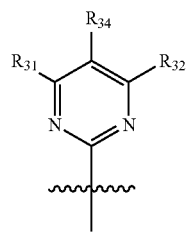

[Chemical Formula 1-1-3]

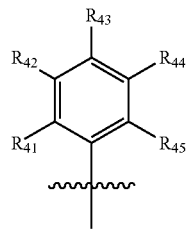

[Chemical Formula 1-1-4]

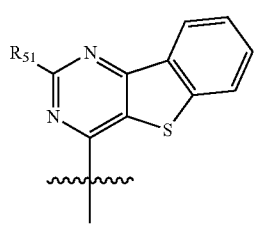

[Chemical Formula 1-1-5]

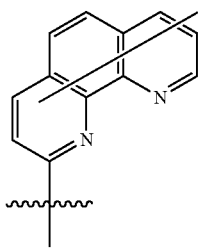

[Chemical Formula 1-1-6]

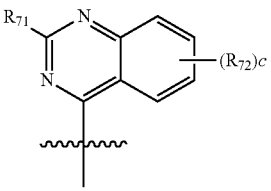

[Chemical Formula 1-1-7]

In Chemical Formulae 1-1-1 to 1-1-7, $R_{31}$ to $R_{34}$, $R_{41}$ to $R_{45}$, $R_{51}$, $R_{61}$, $R_{71}$ and $R_{72}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring, R, R' and R" are the same as or different from each other, and each independently hydrogen; a substituted or unsubstituted alkyl group; a substituted or unsubstituted aryl group; or a substituted or unsubstituted heteroaryl group, b is an integer of 1 to 7, and c is an integer of 1 to 4.

of Chemical Formulae 1-1-1 to 1-1-7 means a site linked to L of Chemical Formula 1.

In one embodiment of the present application, $R_1$ to $R_4$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_1$ to $R_4$ are the same as or different from each other, and may be each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; and an amine group unsubstituted or substituted with a substituted or unsubstituted C1 to C60 alkyl group, a substituted or unsubstituted C6 to C60 aryl group, or a substituted or unsubstituted C2 to C60 heteroaryl group.

In another embodiment, $R_1$ to $R_4$ may be hydrogen.

In one embodiment of the present application, $R_{11}$ to $R_{13}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_{11}$ to $R_{13}$ are the same as or different from each other, and may be each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; and an amine group unsubstituted or substituted with a substituted or unsubstituted C1 to C60 alkyl group, a substituted or unsubstituted C6 to C60 aryl group, or a substituted or unsubstituted C2 to C60 heteroaryl group.

In another embodiment, $R_{11}$ to $R_{13}$ may be hydrogen.

In one embodiment of the present application, $R_{21}$ to $R_{25}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_{21}$ to $R_{25}$ are the same as or different from each other, and each independently selected from the group consisting of hydrogen; a substituted or unsubstituted C6 to C60 aryl group; a substituted or unsubstituted C2 to C60 heteroaryl group; and —P(=O)RR', or two or more groups adjacent to each other may bond to each other to form a substituted or unsubstituted C6 to C60 aromatic hydrocarbon ring, or a substituted or unsubstituted C2 to C60 heteroring.

In another embodiment, $R_{21}$ to $R_{25}$ are the same as or different from each other, and each independently selected from the group consisting of hydrogen; a substituted or unsubstituted C6 to C40 aryl group; a substituted or unsubstituted C2 to C40 heteroaryl group; and —P(=O)RR', or two or more groups adjacent to each other may bond to each other to form a substituted or unsubstituted C6 to C40 aromatic hydrocarbon ring, or a substituted or unsubstituted C2 to C40 heteroring.

In another embodiment, $R_{21}$ to $R_{25}$ are the same as or different from each other, and each independently selected from the group consisting of hydrogen; a C6 to C40 aryl group unsubstituted or substituted with a C2 to C40 heteroaryl group; a C2 to C40 heteroaryl group; and —P(=O)RR', or two or more groups adjacent to each other may bond to each other to form a a C6 to C40 aromatic hydrocarbon ring, or C2 to C40 heteroring unsubstituted or substituted with a C6 to C40 aryl group.

In another embodiment, $R_{21}$ to $R_{25}$ are the same as or different from each other, and each independently selected from the group consisting of hydrogen; a phenyl group unsubstituted or substituted with a carbazole group; a biphenyl group; a carbazole group; and —P(=O)RR', or two or more groups adjacent to each other may bond to each other to form a benzene ring; a benzothiophene ring; or a quinoline ring unsubstituted or substituted with a phenyl group.

In one embodiment of the present application, $R_{31}$ to $R_{34}$ are the same as or different from each other, and may be each independently hydrogen; or a substituted or unsubstituted aryl group.

In another embodiment, $R_{31}$ to $R_{34}$ are the same as or different from each other, and may be each independently hydrogen; or a substituted or unsubstituted C6 to C60 aryl group.

In another embodiment, $R_{31}$ to $R_{34}$ are the same as or different from each other, and may be each independently hydrogen; or a substituted or unsubstituted C6 to C40 aryl group.

In another embodiment, $R_{31}$ to $R_{34}$ are the same as or different from each other, and may be each independently hydrogen; or a C6 to C40 aryl group unsubstituted or substituted with a C2 to C40 heteroaryl group.

In another embodiment, $R_{31}$ to $R_{34}$ are the same as or different from each other, and may be each independently hydrogen; a phenyl group unsubstituted or substituted with a carbazole group; or a biphenyl group.

In one embodiment of the present application, $R_{41}$ to $R_{45}$ are the same as or different from each other, and may be each independently hydrogen; a carbazole group; or —P(=O)RR'.

In one embodiment of the present application, $R_{31}$, $R_{61}$, $R_{71}$ and $R_{72}$ are the same as or different from each other, and may be each independently hydrogen; or a substituted or unsubstituted C6 to C60 aryl group.

In another embodiment, $R_{31}$, $R_{61}$, $R_{71}$ and $R_{72}$ are the same as or different from each other, and may be each independently hydrogen; or a substituted or unsubstituted C6 to C40 aryl group.

In another embodiment, $R_{31}$, $R_{61}$, $R_{71}$ and $R_{72}$ are the same as or different from each other, and may be each independently hydrogen; or a C6 to C40 aryl group.

In another embodiment, $R_{51}$, $R_{61}$, $R_{71}$ and $R_{72}$ are the same as or different from each other, and may be each independently hydrogen; or a phenyl group.

In one embodiment of the present application, Chemical Formula 1 may be represented by any one of the following Chemical Formulae 7 to 12.

[Chemical Formula 7]

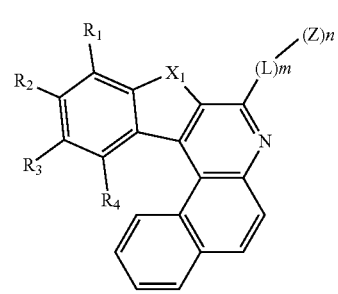

[Chemical Formula 8]

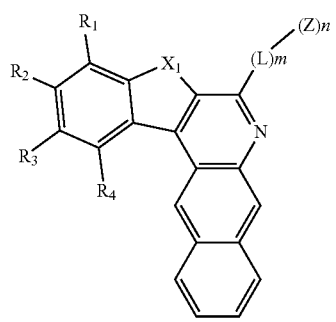

[Chemical Formula 9]

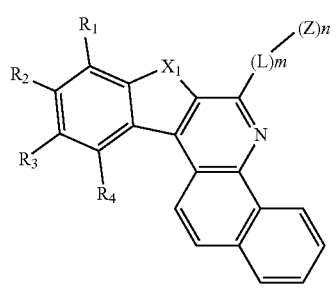

[Chemical Formula 10]

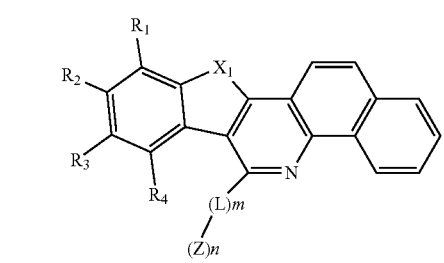

[Chemical Formula 11]

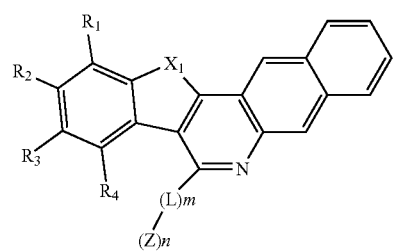

[Chemical Formula 12]

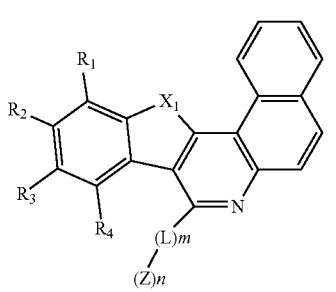

In Chemical Formulae 7 to 12, $R_1$ to $R_4$, $X_1$, L, Z, m and n have the same definitions as in Chemical Formula 1.

In one embodiment of the present application, Chemical Formula 1 may be represented by the following Chemical Formula 13 or Chemical Formula 14.

[Chemical Formula 13]

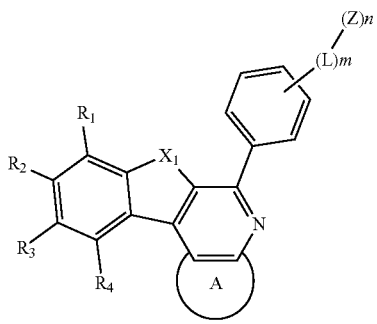

[Chemical Formula 14]

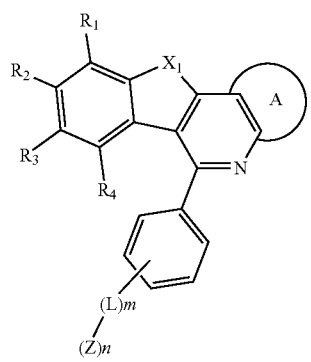

In Chemical Formulae 13 and 14, $R_1$ to $R_4$, $X_1$, L, Z, A, m and n have the same definitions as in Chemical Formula 1.

Particularly, when -(L)m-(Z)n is linked to the phenylene group as in Chemical Formulae 13 and 14, electrons may be delocalized, and electron mobility may be enhanced by widening electron density, and when -(L)m-(Z)n bonds to a para position of the phenylene group particularly, an excellent Tg (glass transition temperature) value is obtained, and properties of excellent thermal stability are obtained.

In one embodiment of the present application, R, R' and R" are the same as or different from each other, and may be each independently hydrogen; a substituted or unsubstituted alkyl group; a substituted or unsubstituted aryl group; or a substituted or unsubstituted heteroaryl group.

In another embodiment, R, R' and R" are the same as or different from each other, and may be each independently a substituted or unsubstituted C1 to C60 alkyl group; or a substituted or unsubstituted C6 to C60 aryl group.

In another embodiment, R, R' and R" are the same as or different from each other, and may be each independently a substituted or unsubstituted C1 to C40 alkyl group; or a substituted or unsubstituted C6 to C40 aryl group.

In another embodiment, R, R' and R" are the same as or different from each other, and may be each independently a C1 to C40 alkyl group; or a C6 to C40 aryl group.

In another embodiment, R, R' and R" are the same as or different from each other, and may be each independently a methyl group; or a phenyl group.

In another embodiment, R, R' and R" are the same as or different from each other, and may be each independently a C6 to C40 aryl group.

In another embodiment, R, R' and R" are the same as or different from each other, and may be each independently a phenyl group.

In the heterocyclic compound provided in one embodiment of the present application, Chemical Formula 1 is represented by any one of the following compounds.

17
1
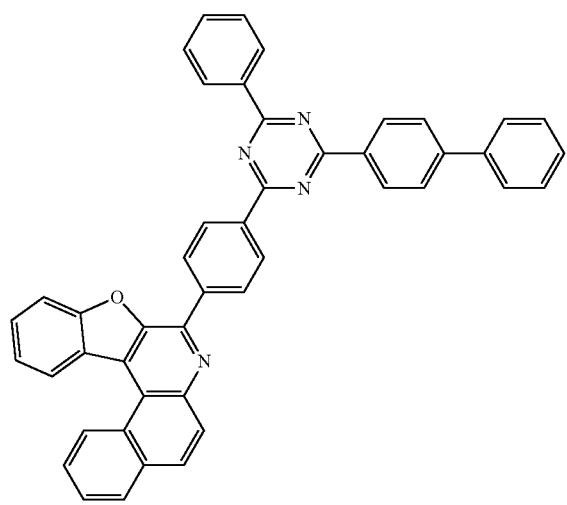
18
2
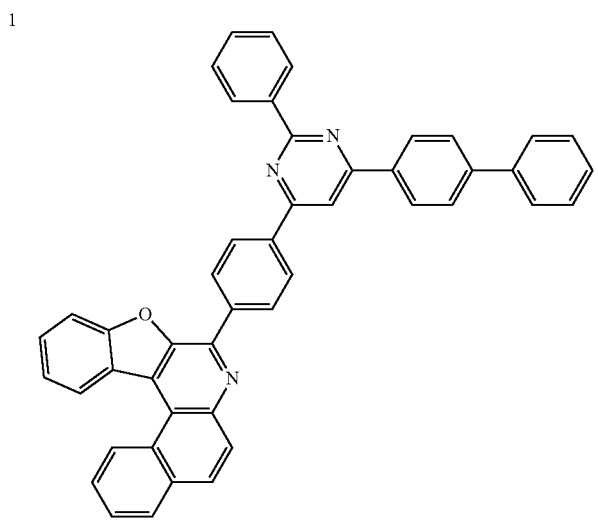
3
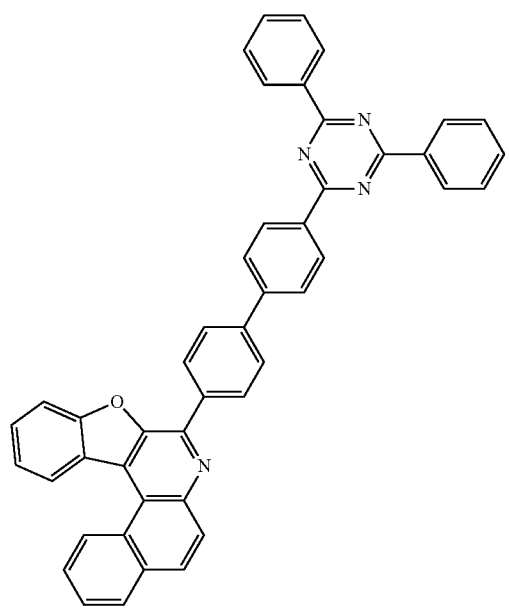
4
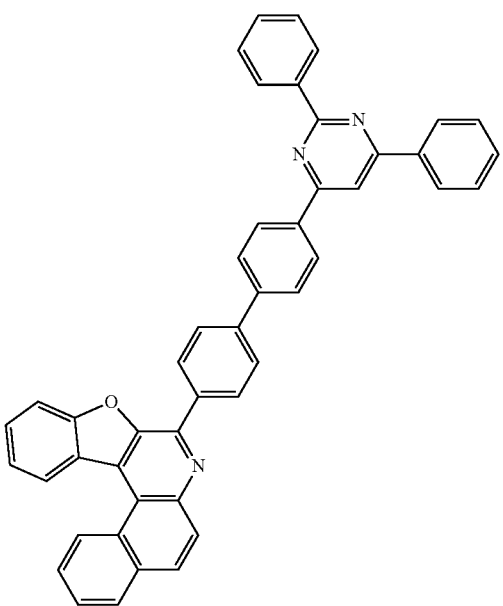 [SMILES: c1ccc(-c2nc(-c3ccccc3)nc(-c3ccc(-c4ccc(-c5nc6ccc7ccccc7c6c6c5oc5ccccc56)cc4)cc3)n2)cc1]
5
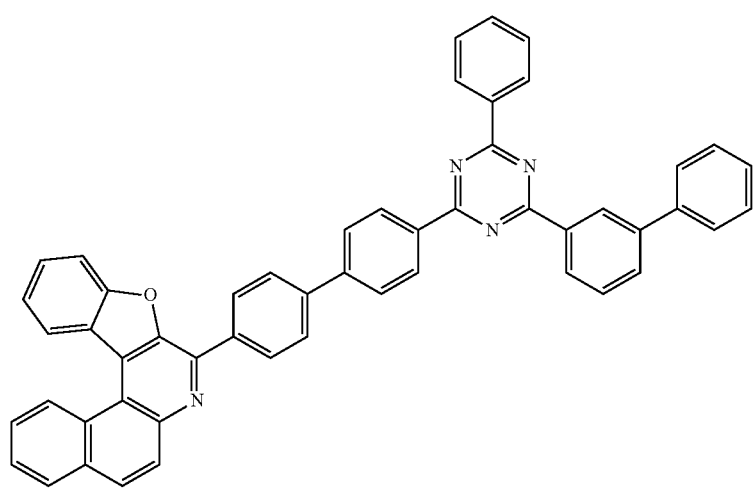

-continued
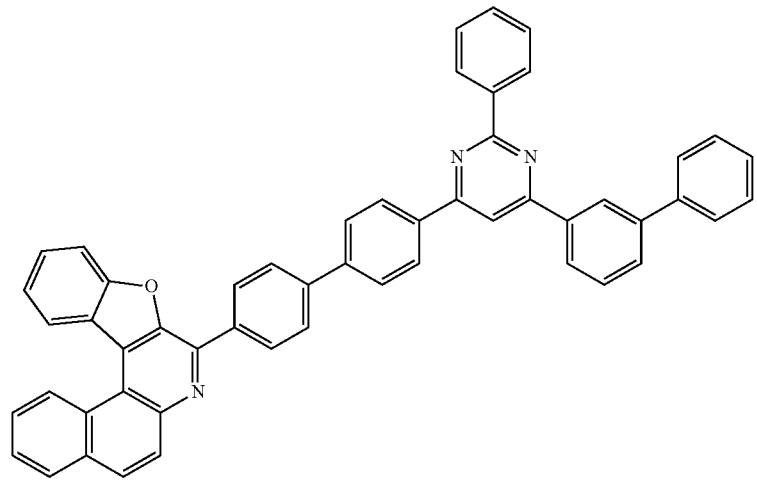
6
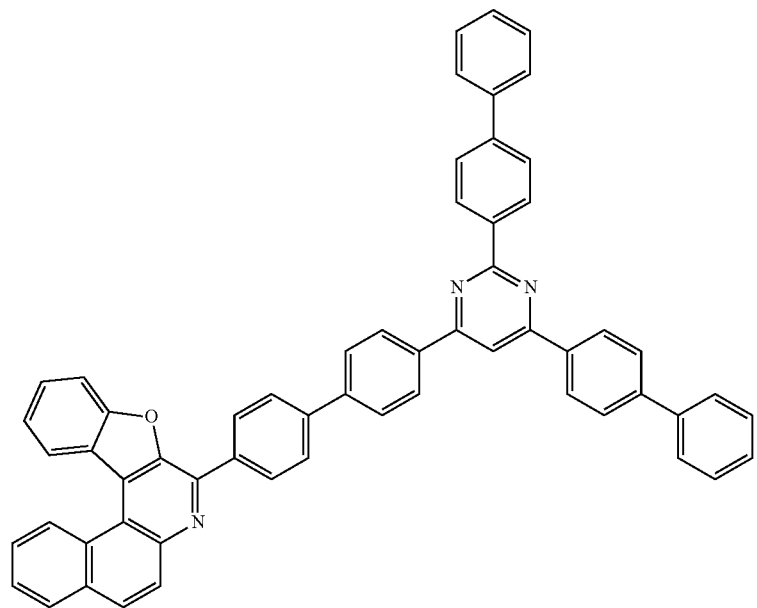
7

-continued
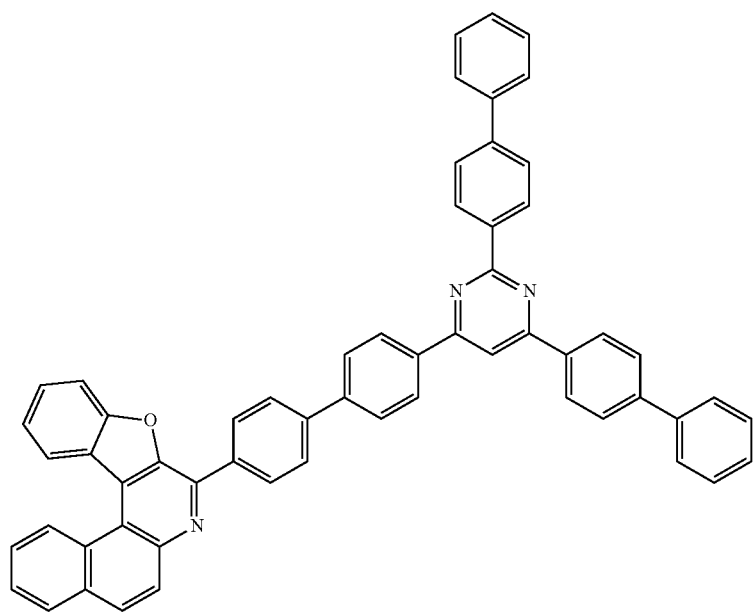
8
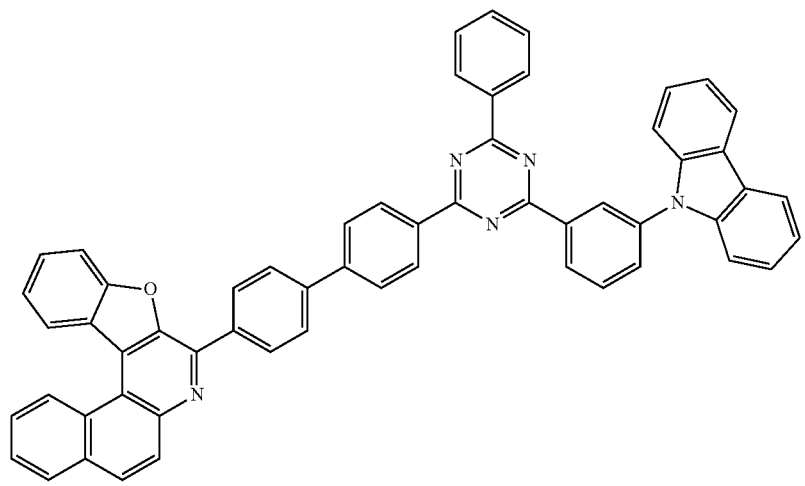
9
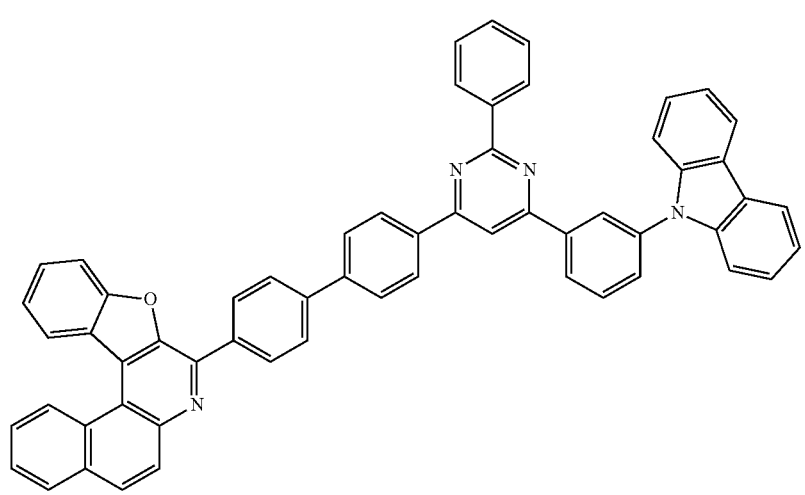
10

11
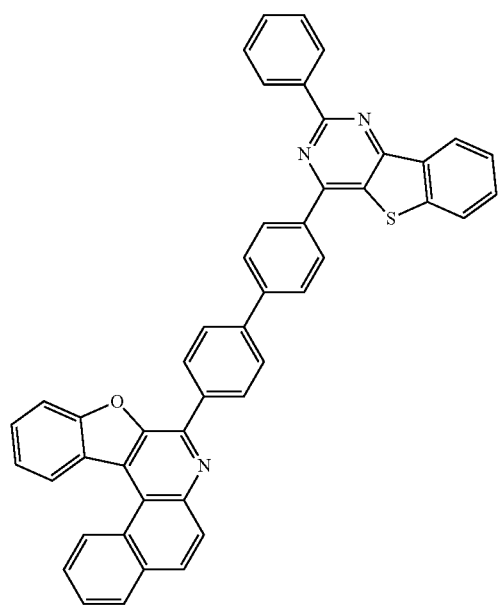
12
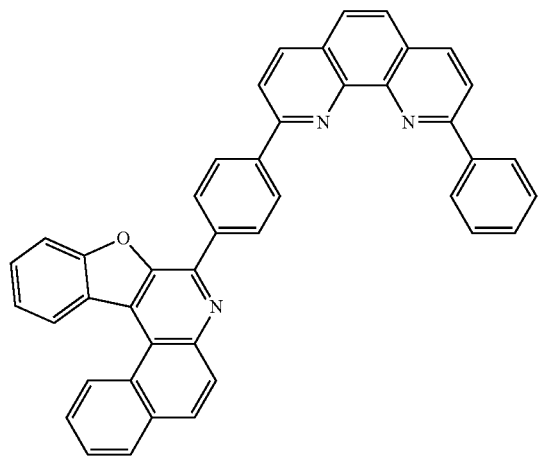
13
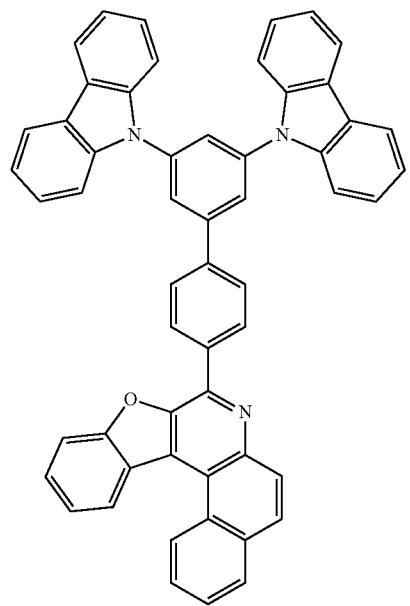
14
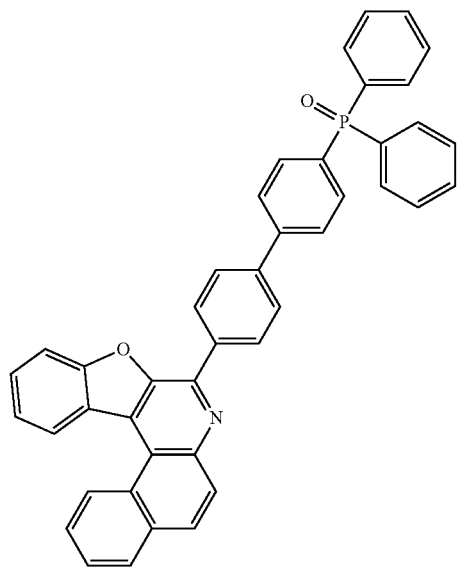

-continued
15
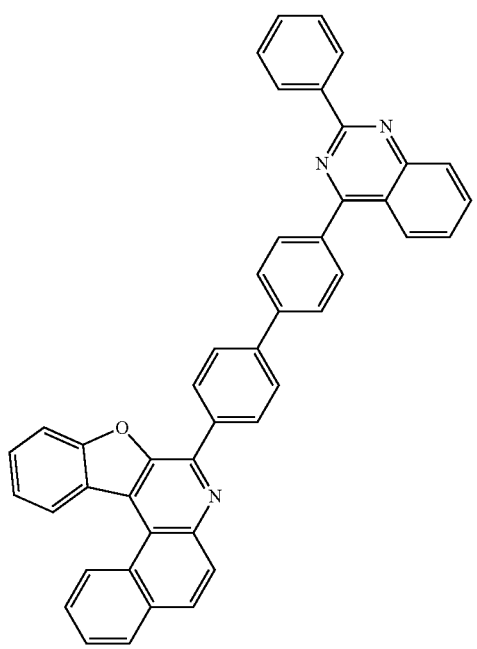
16
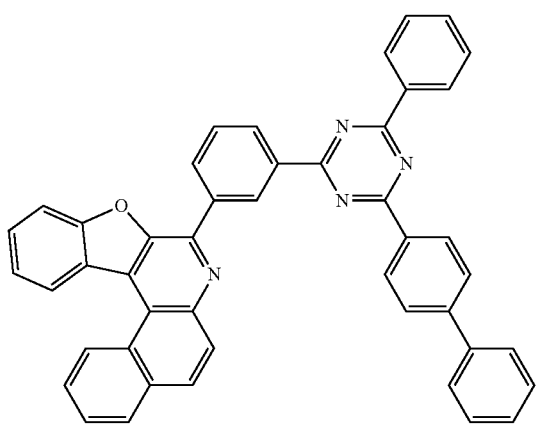
17
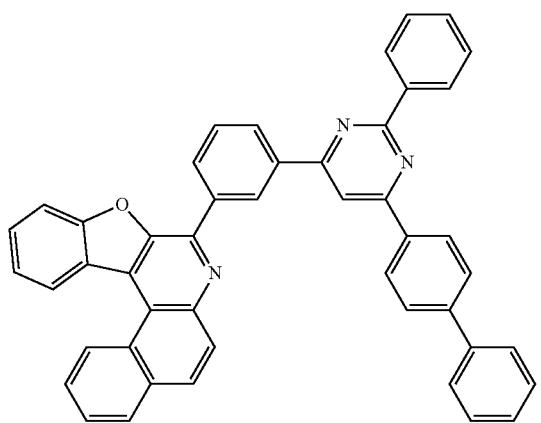
18
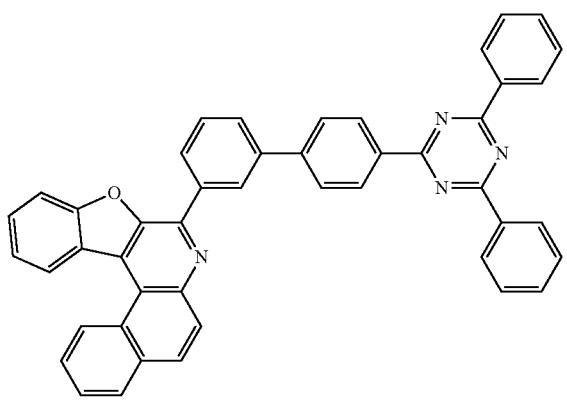
19
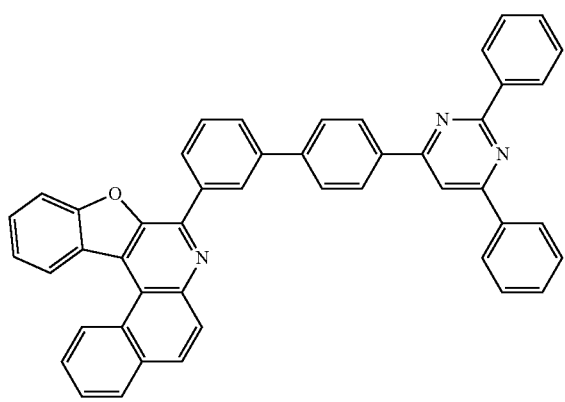
20
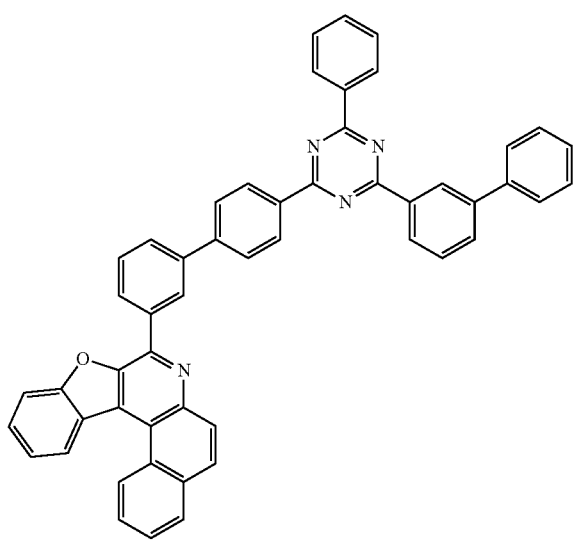

-continued
21
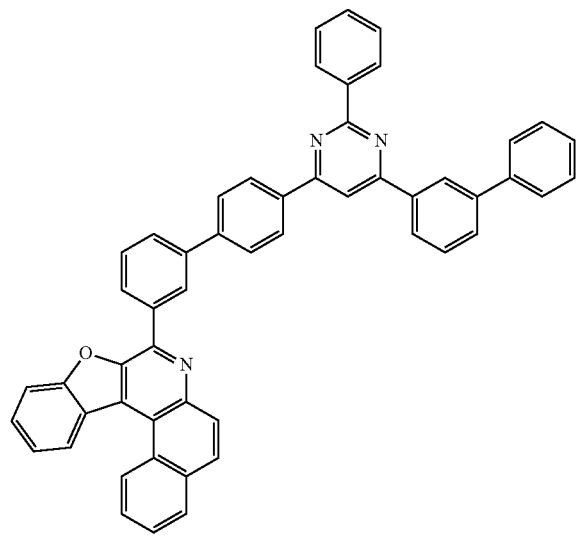
22
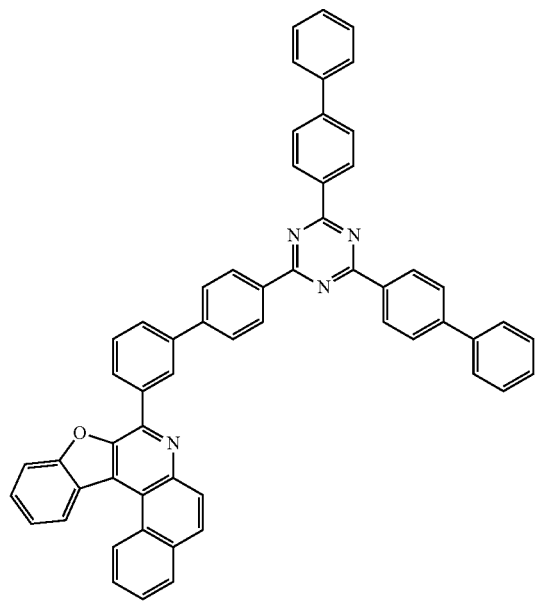
23
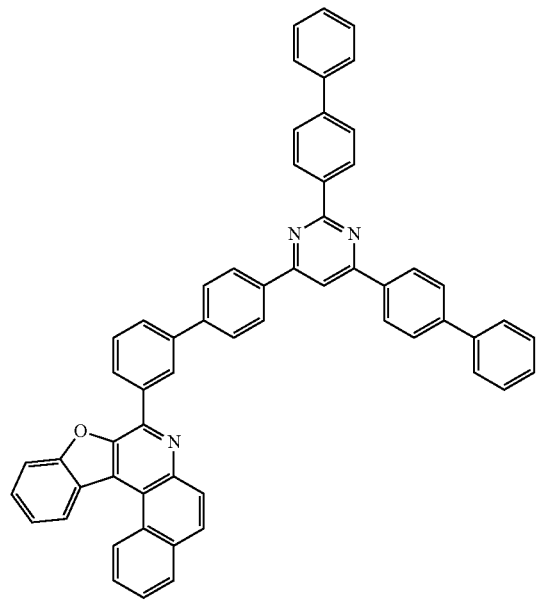
24
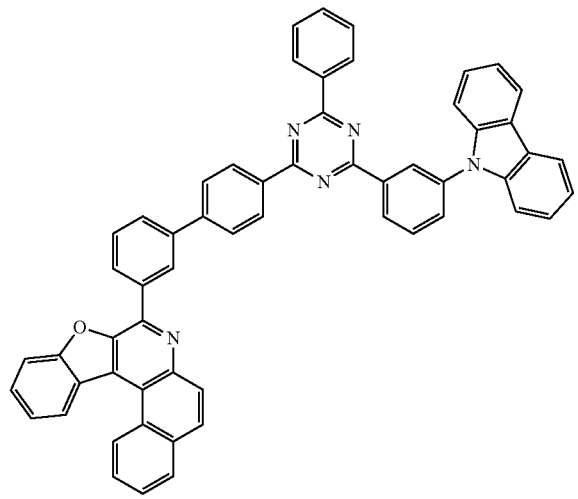

-continued
25
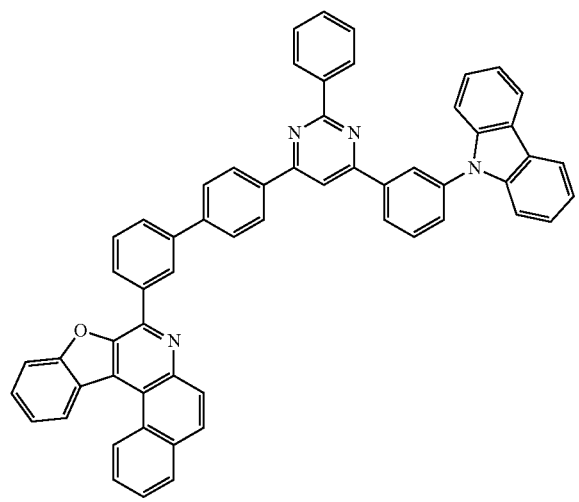
26
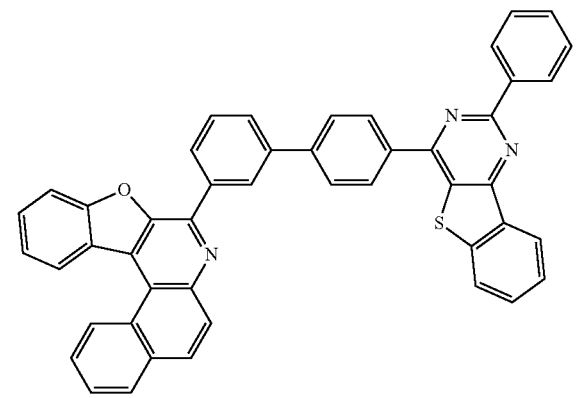
27
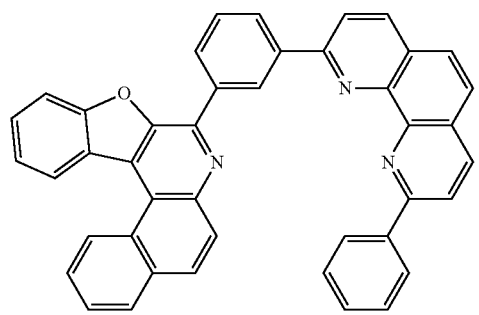
28
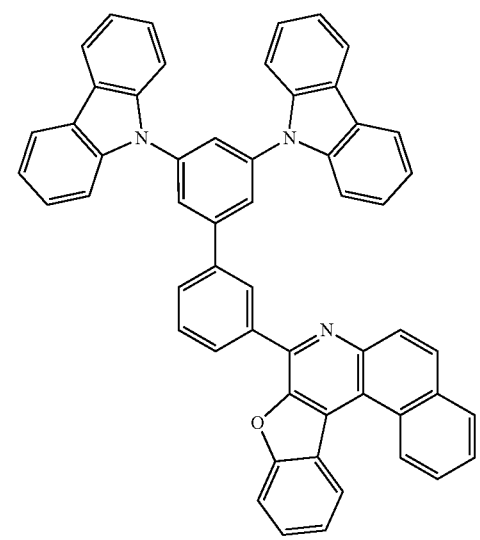
29
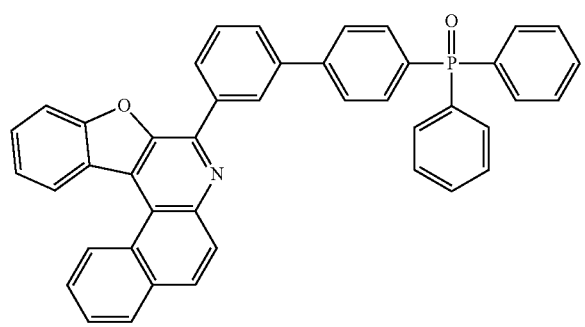
30
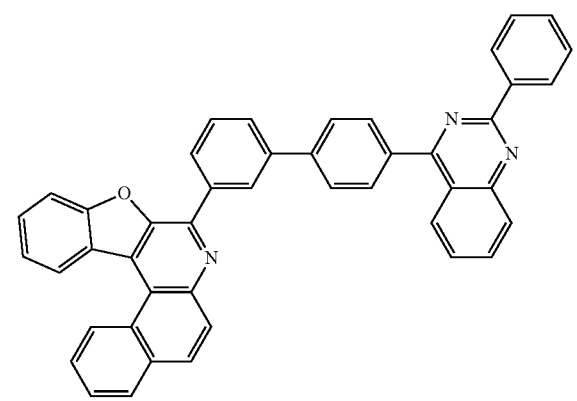

31
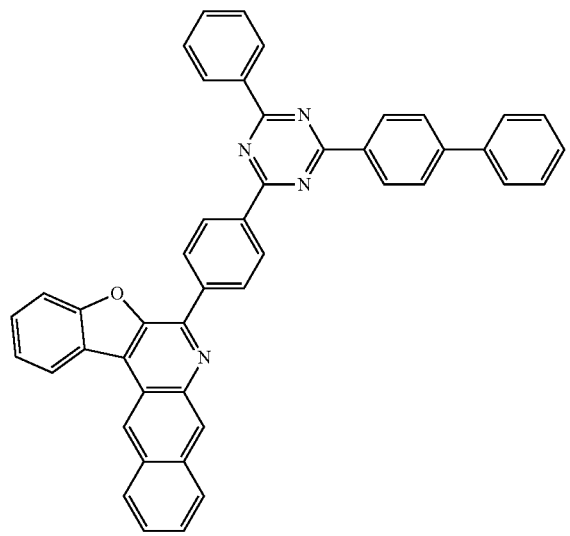
32
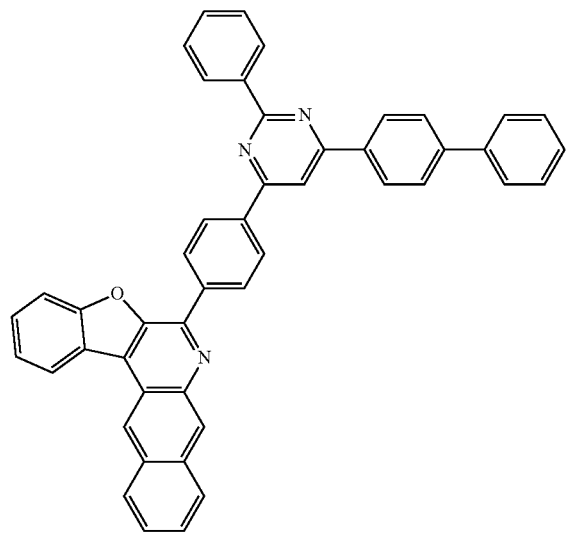
33
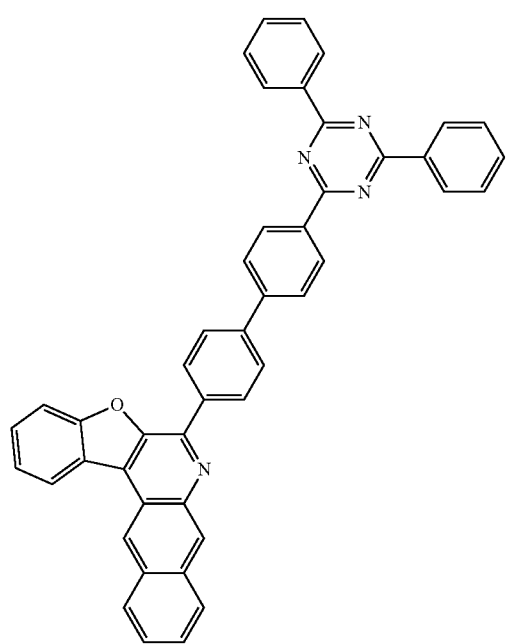
34
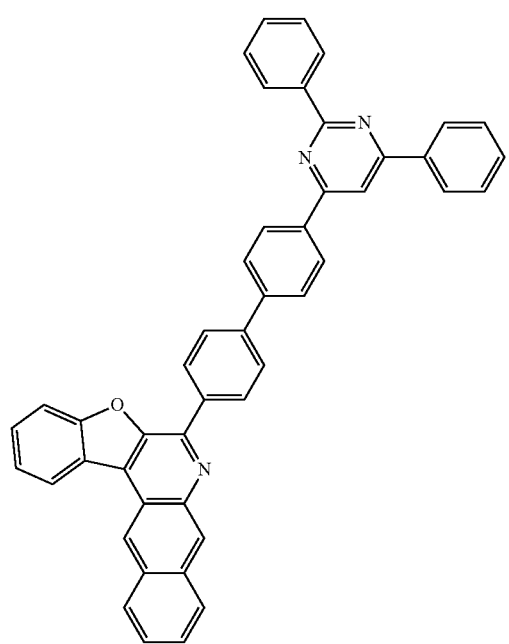

-continued
35
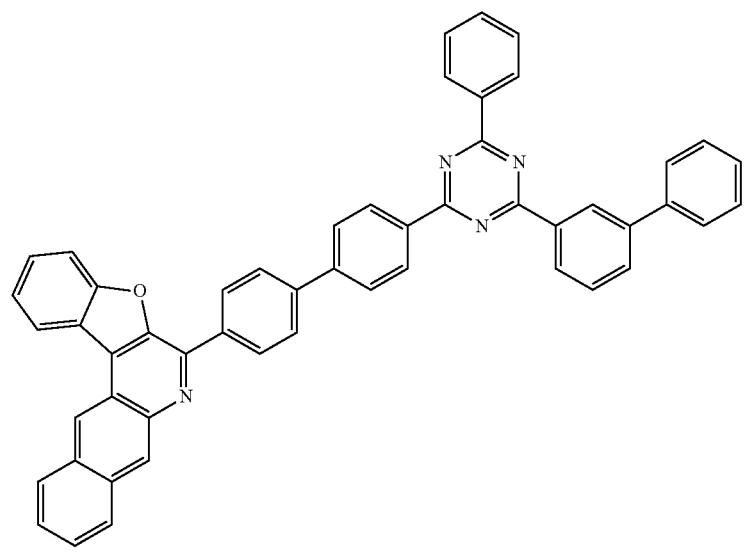
36
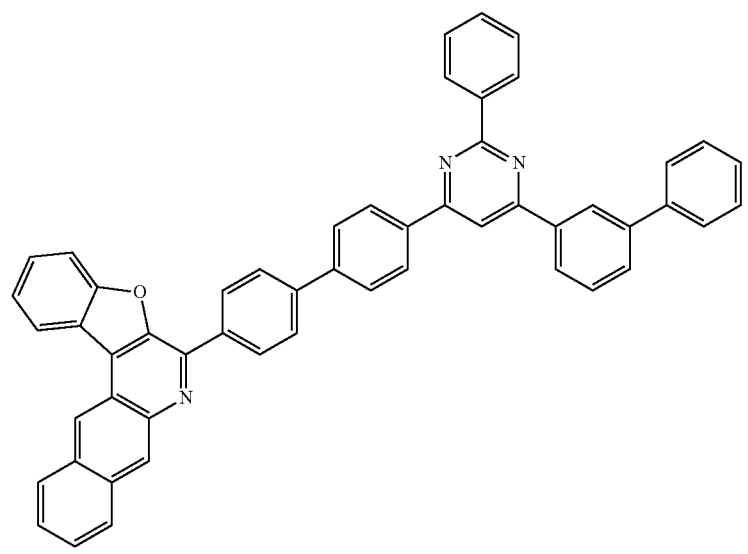

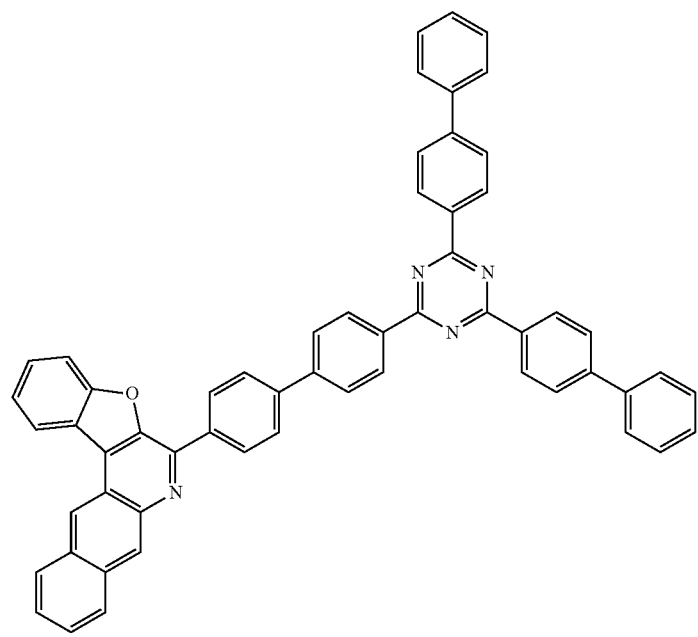
37
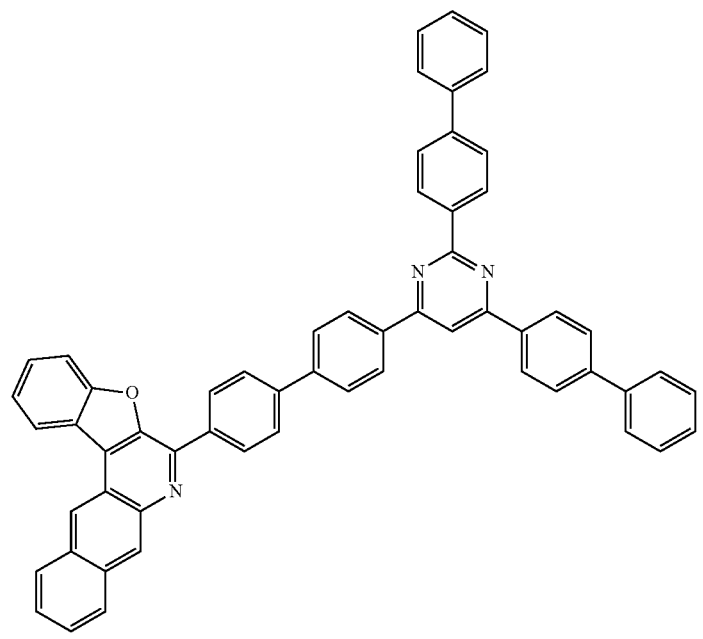
38

-continued
39
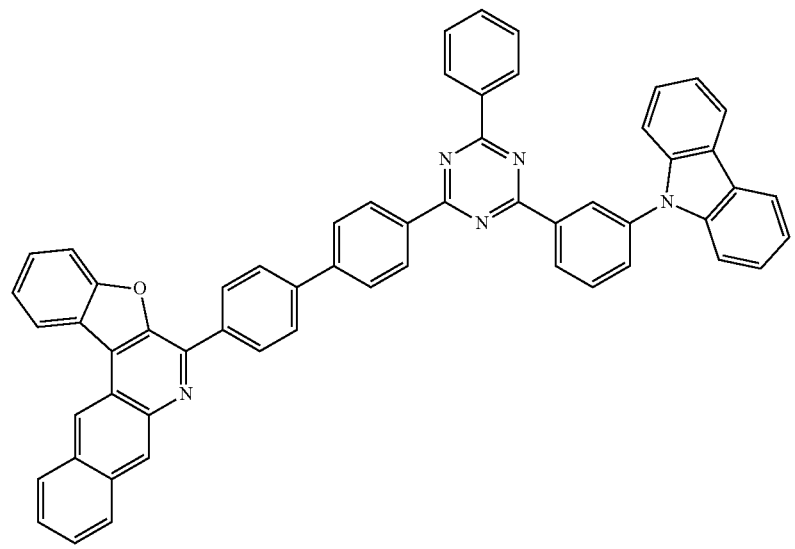
40
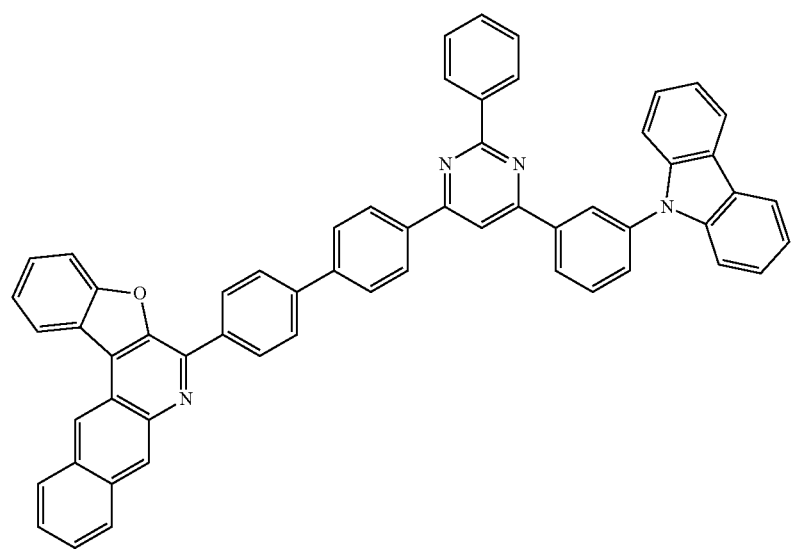

-continued
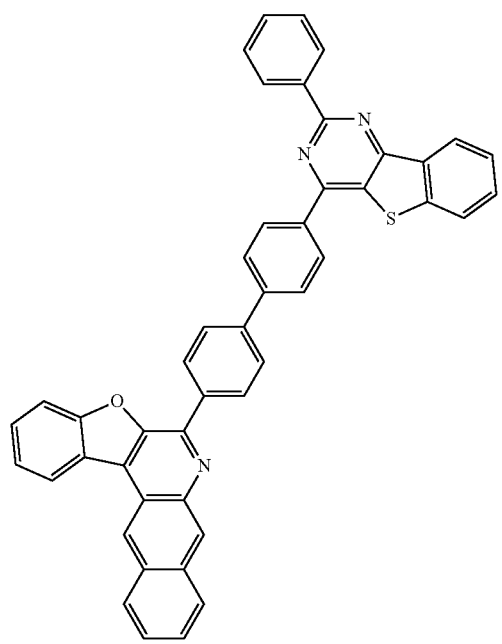
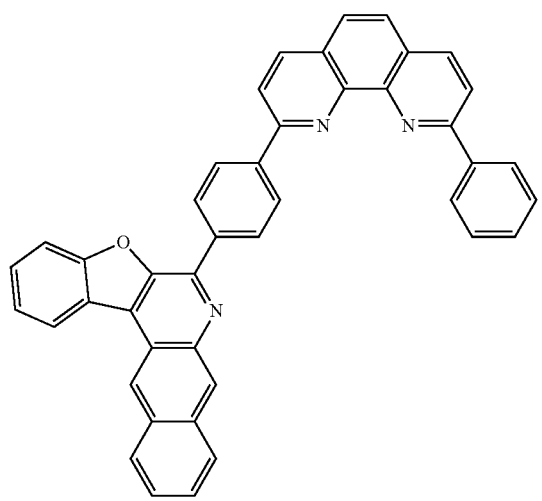
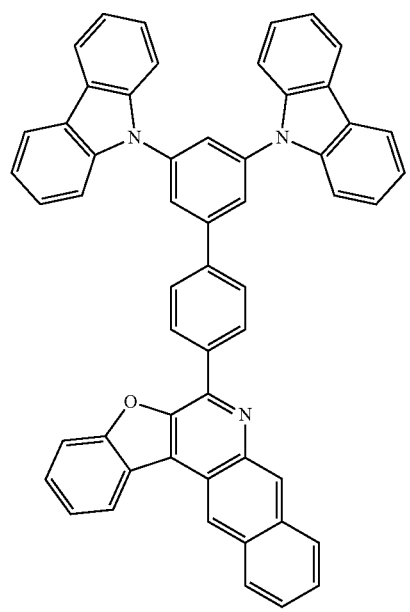
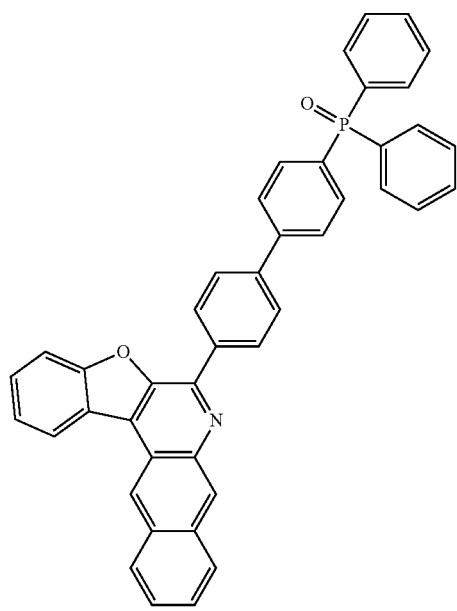

-continued
45
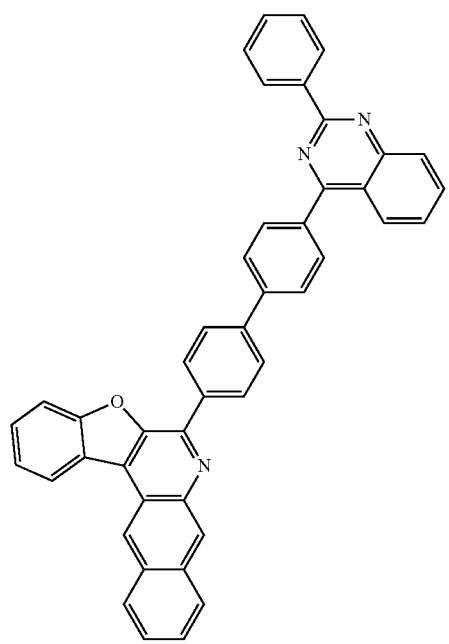
46
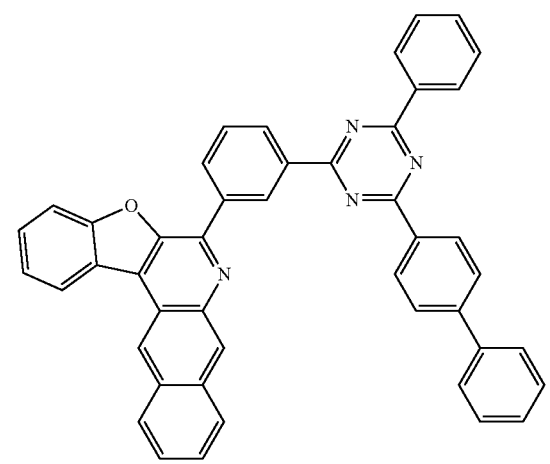
47
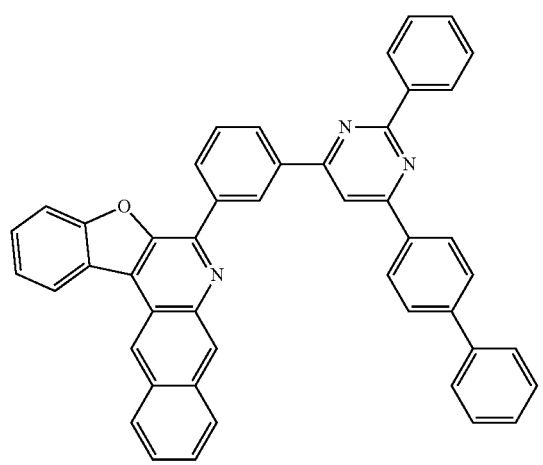
48
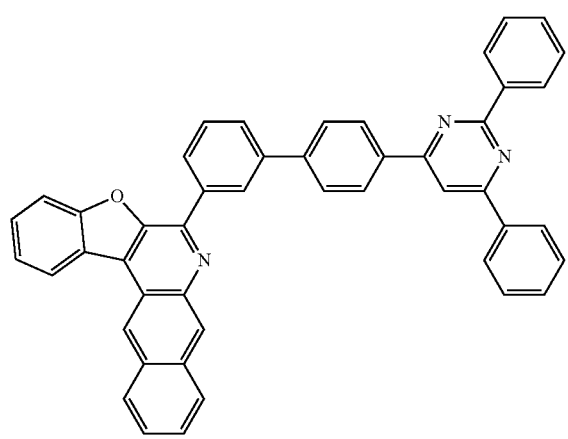
49
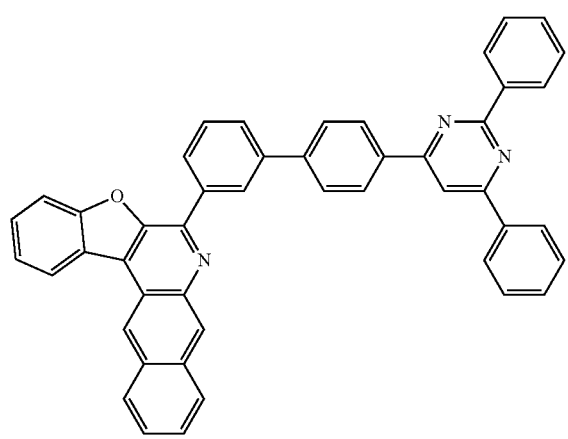
50
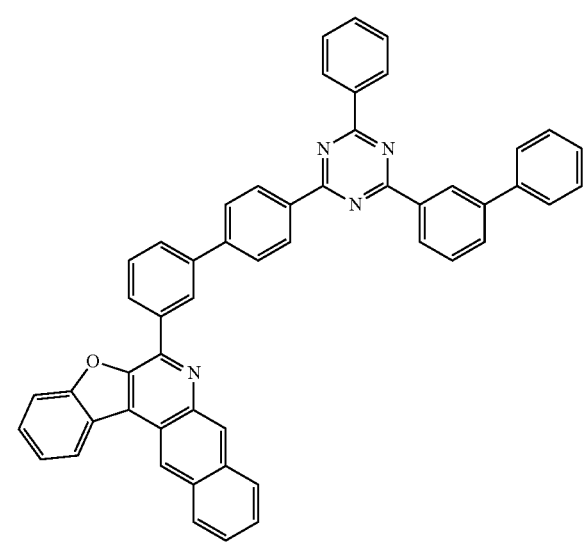

-continued
51
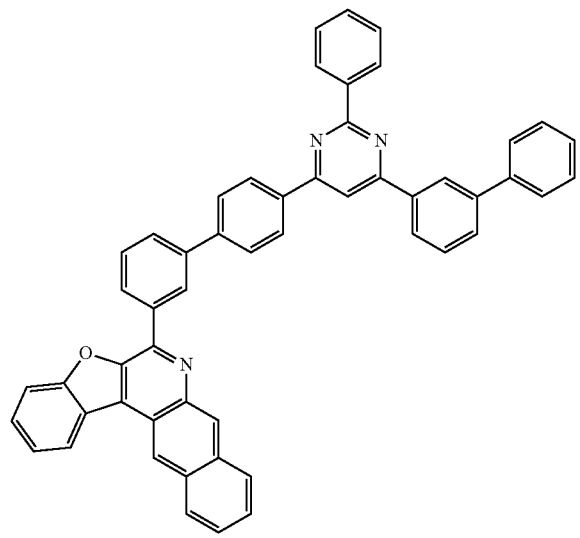
52
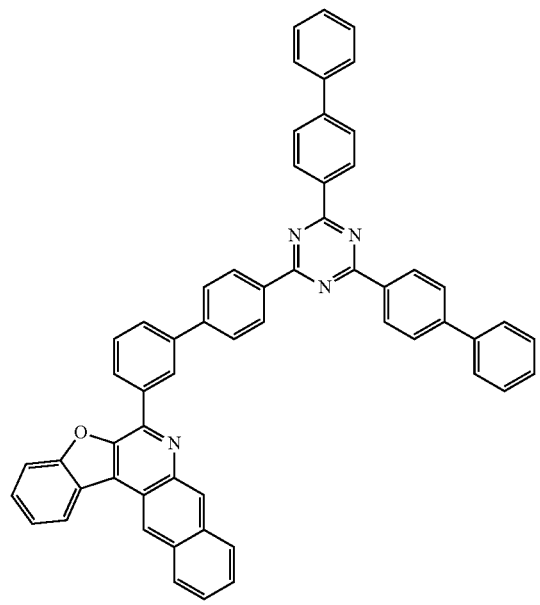
53
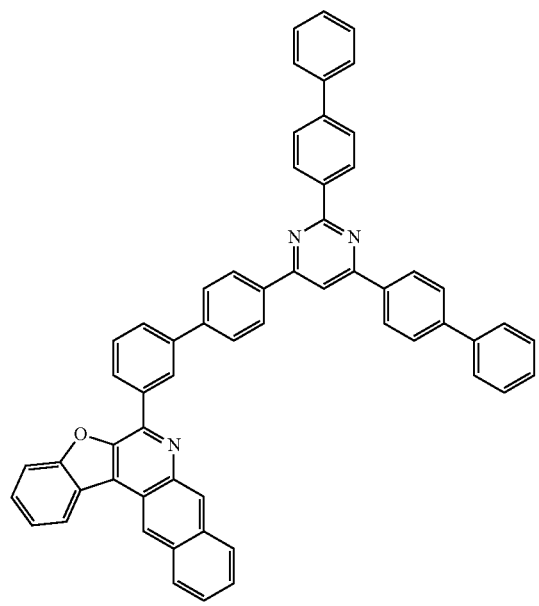
54
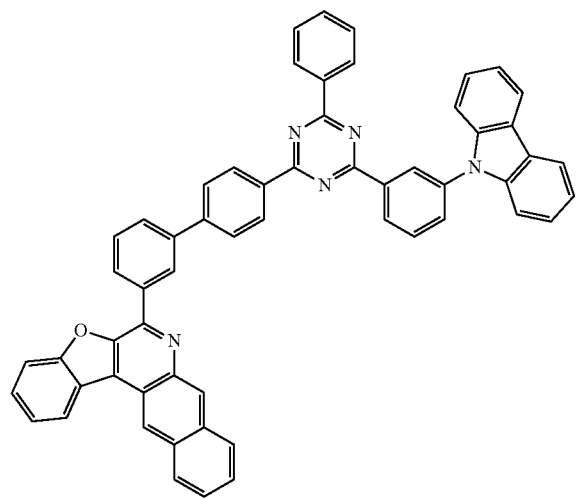

-continued
55
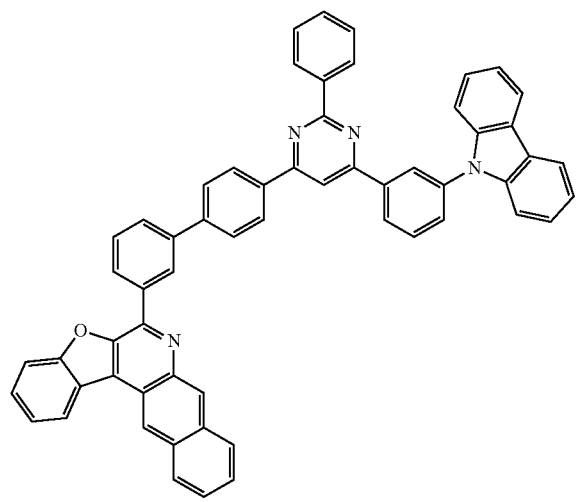
56
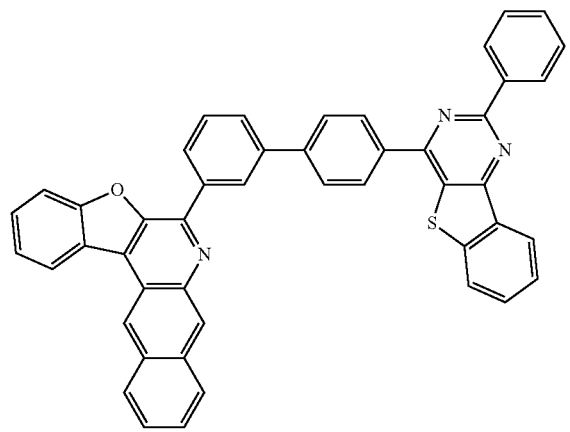
57
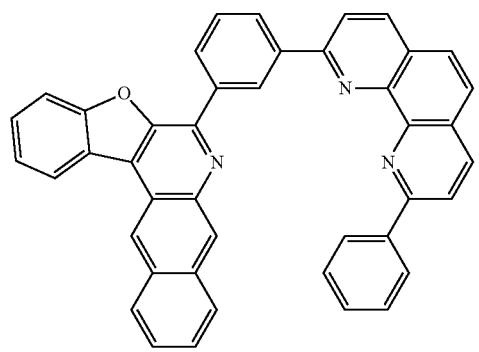
58
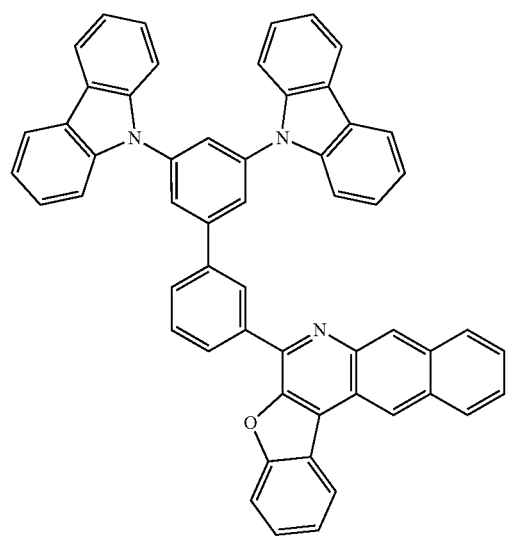
59
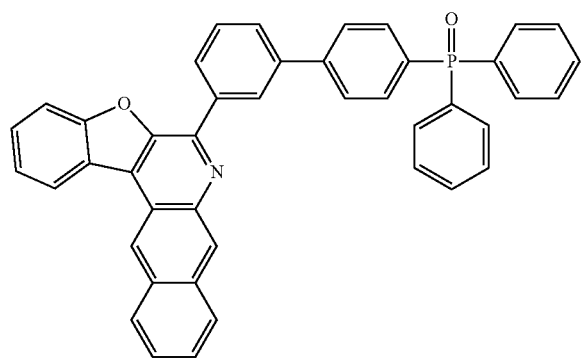
60
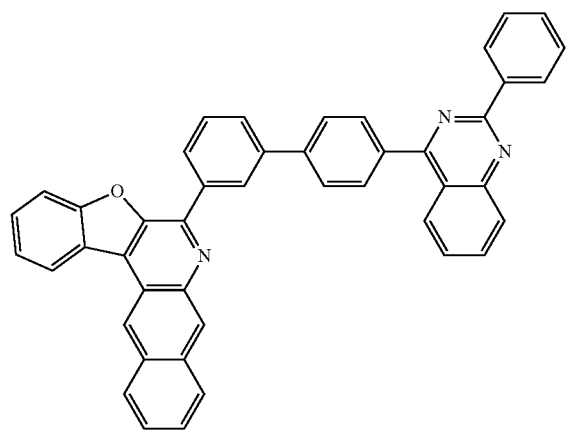

-continued
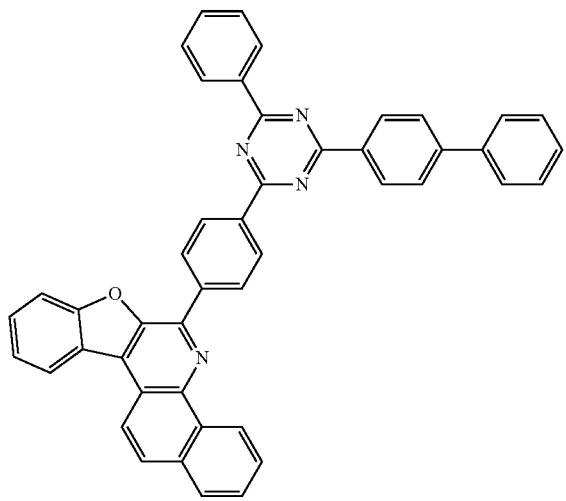
61
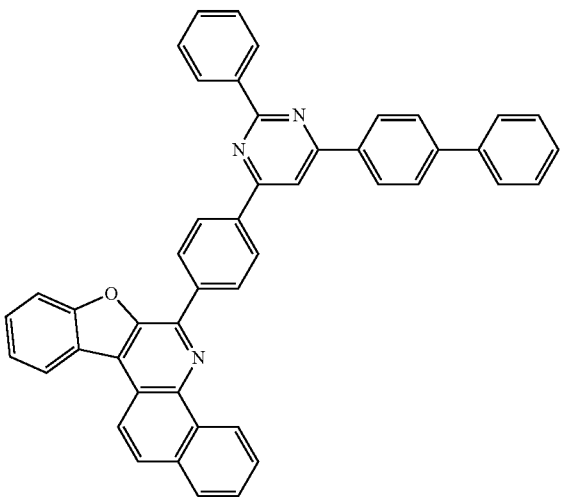
62
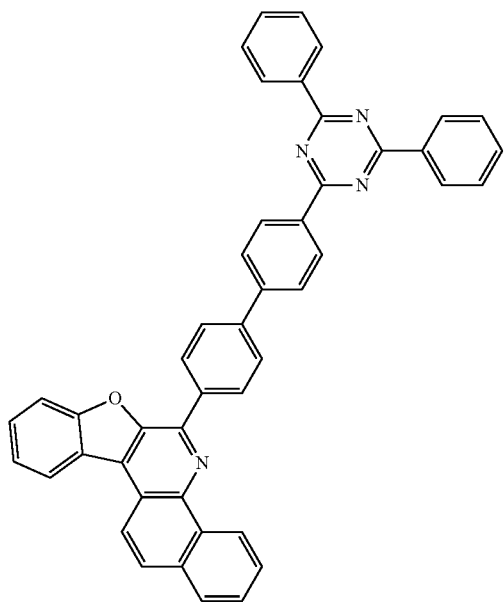
63
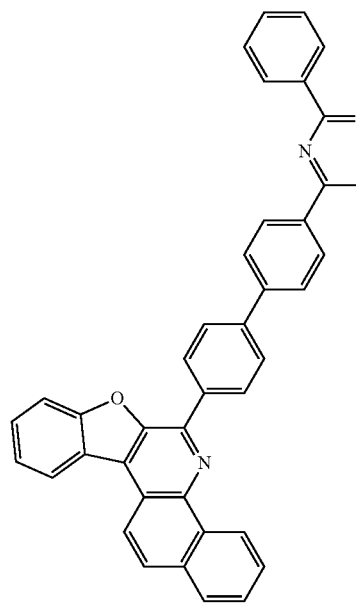
64
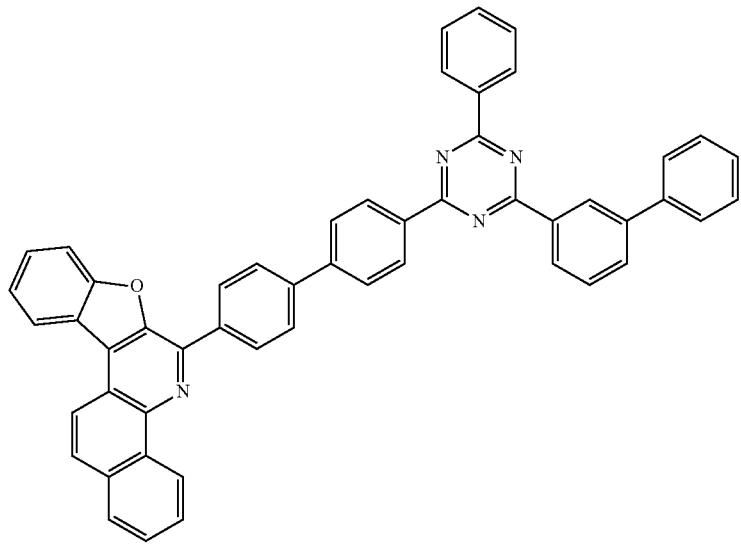
65

-continued
66
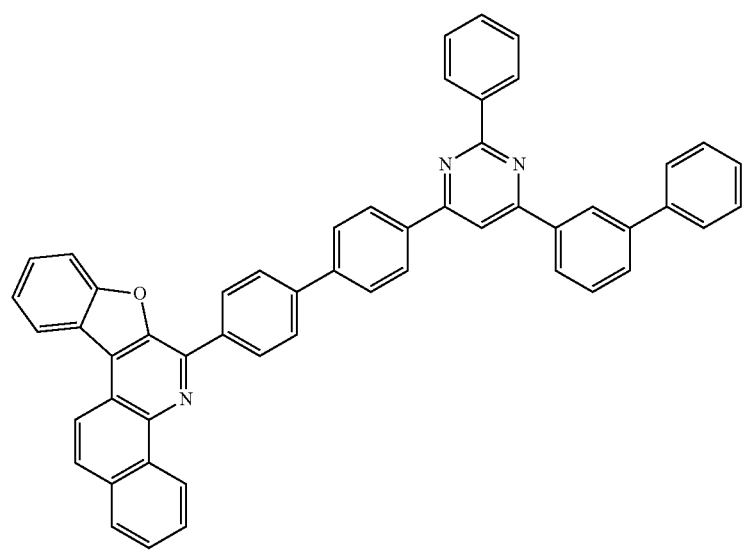
67
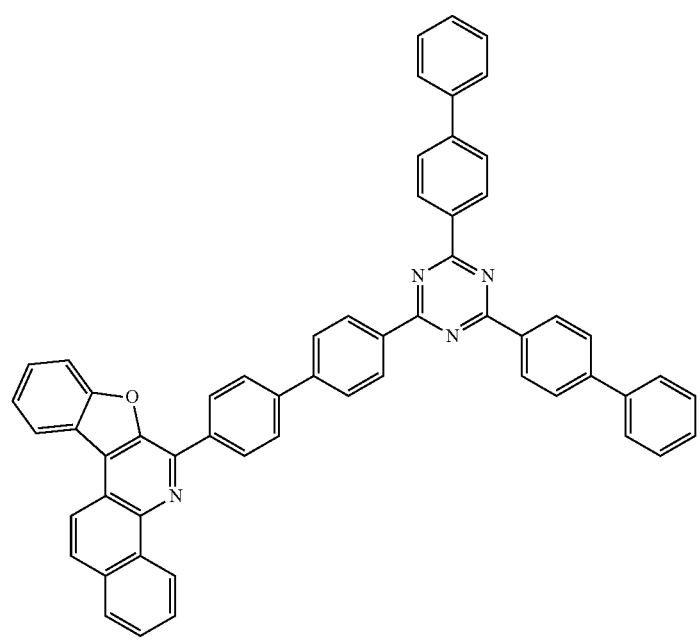

-continued
68
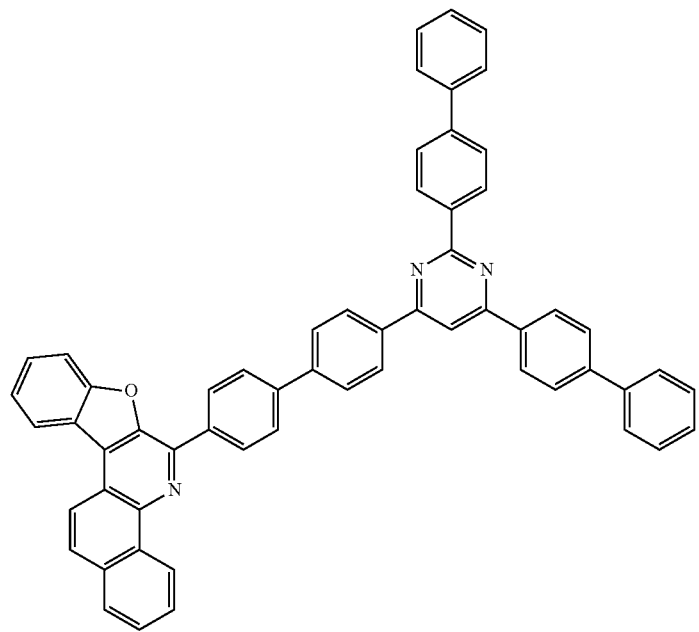
69
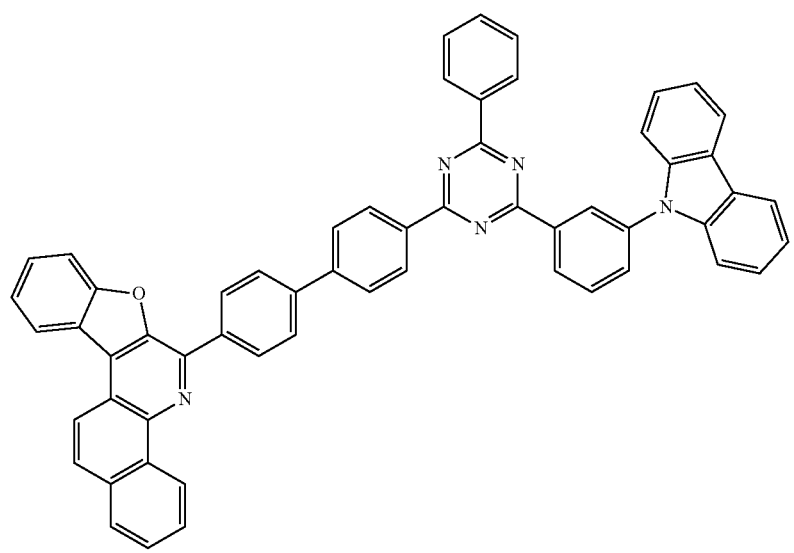

70
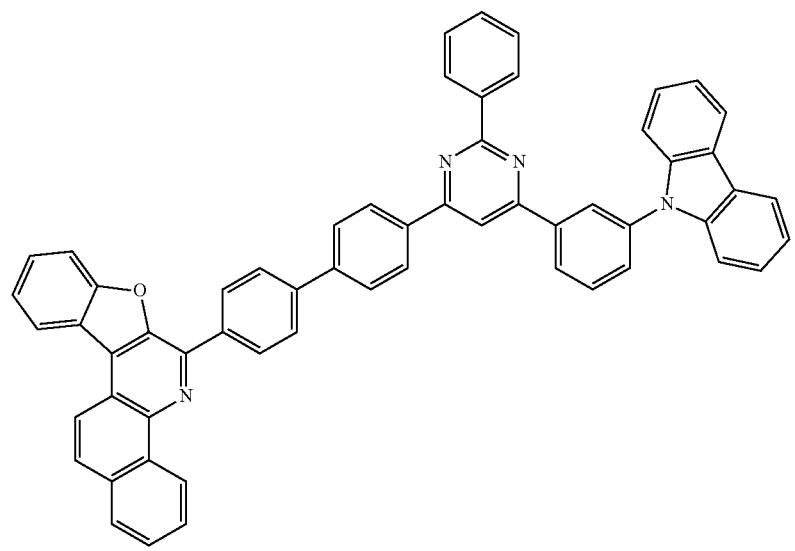
71
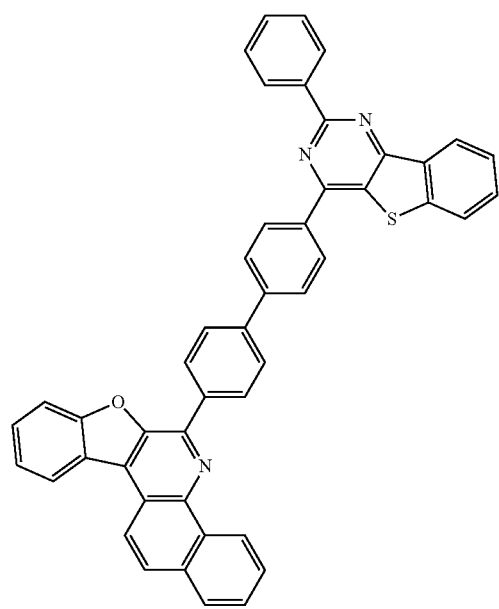
72
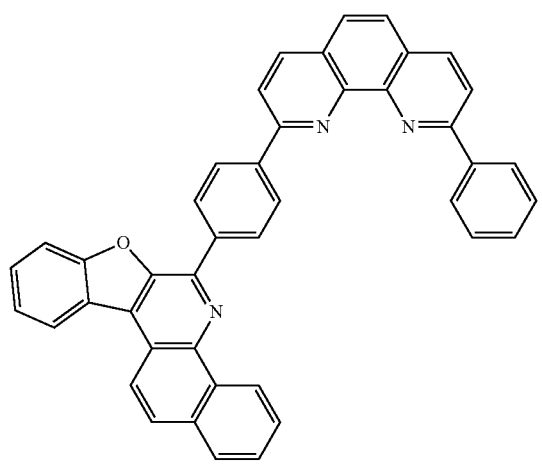

-continued
73
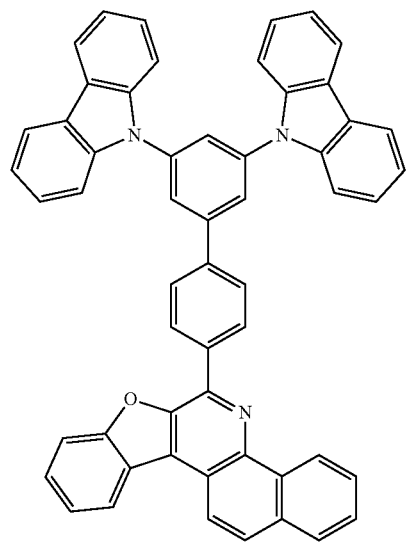
74
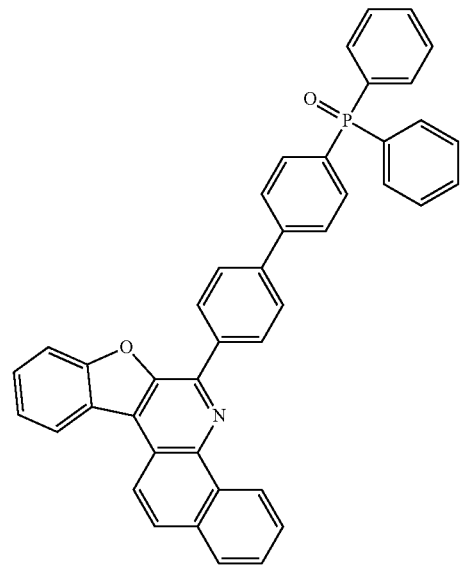
75
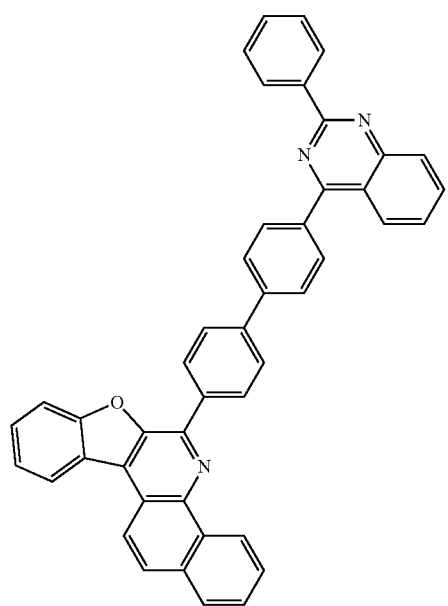
76
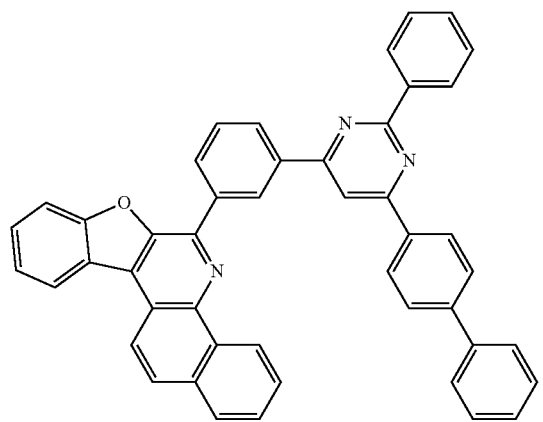
77
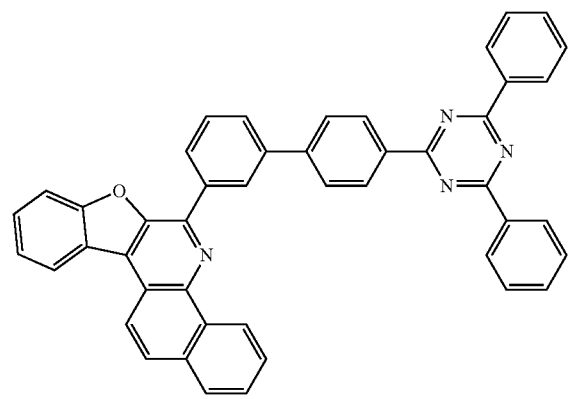
78

-continued
79
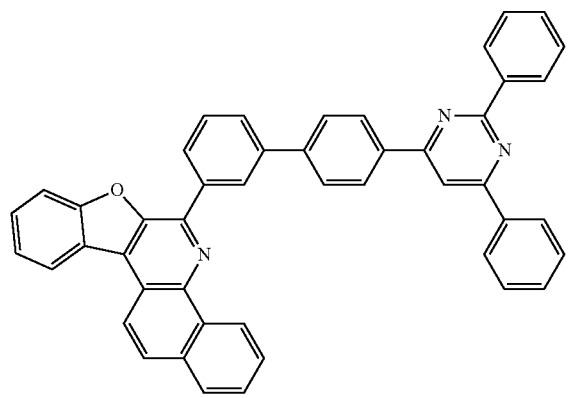
80
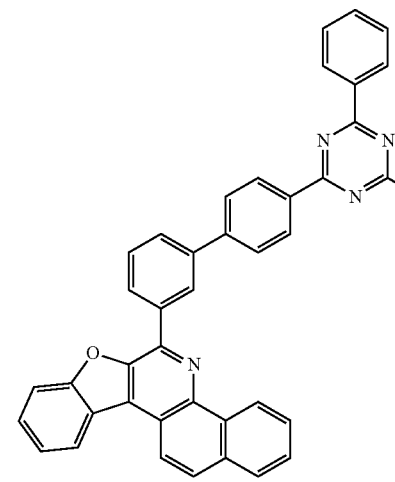
81
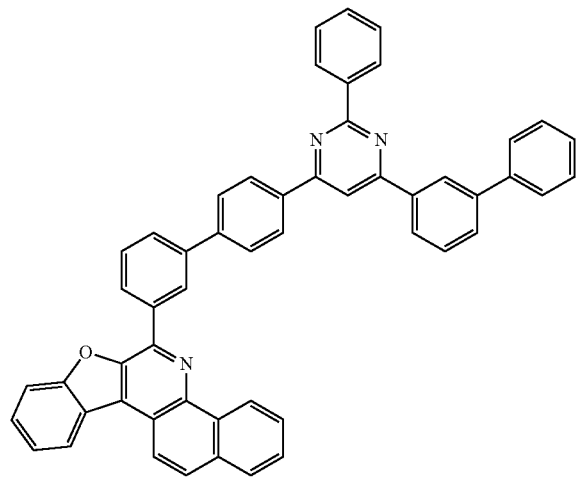
82
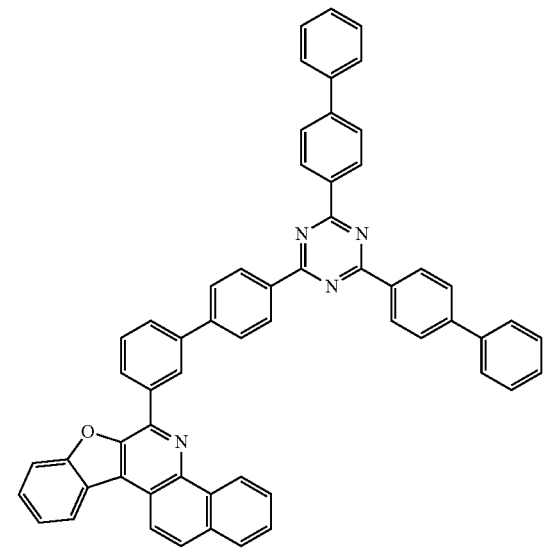
83
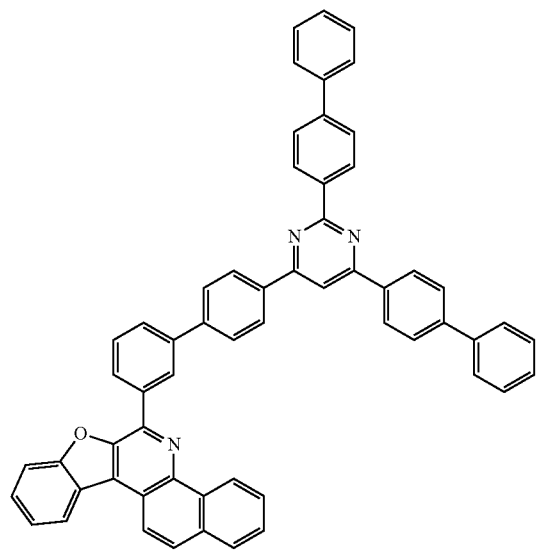
84
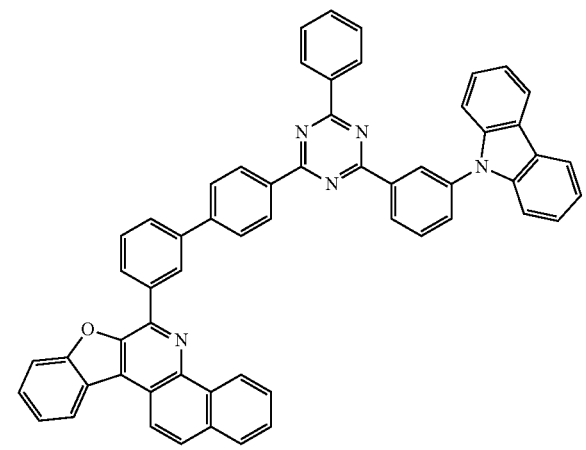

-continued
85
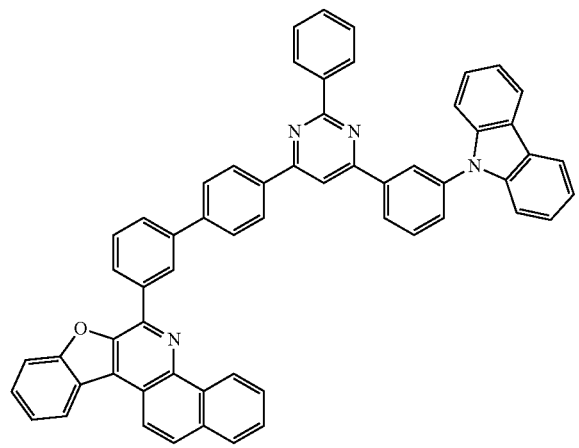
86
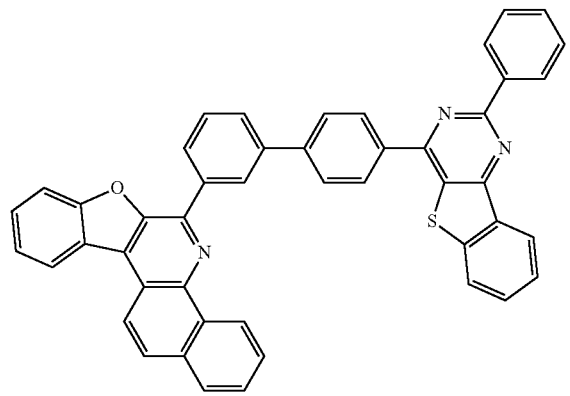
87
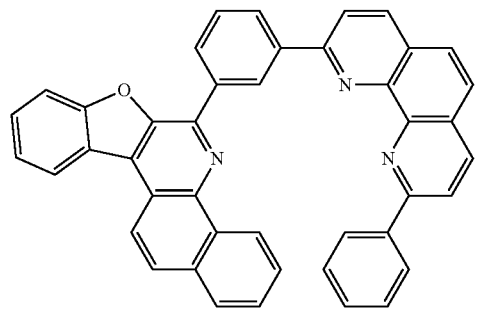
88
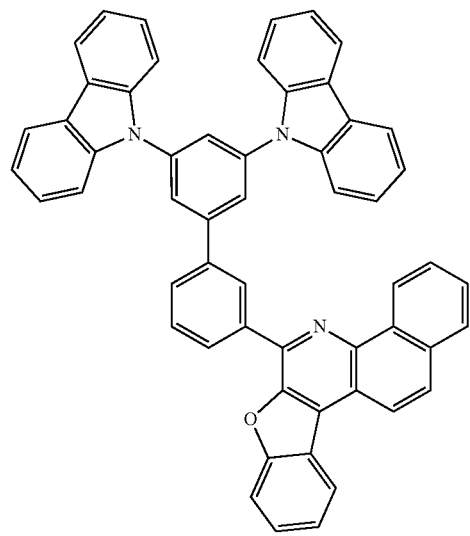
89
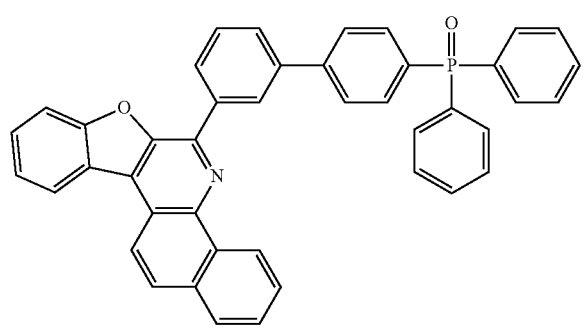
90
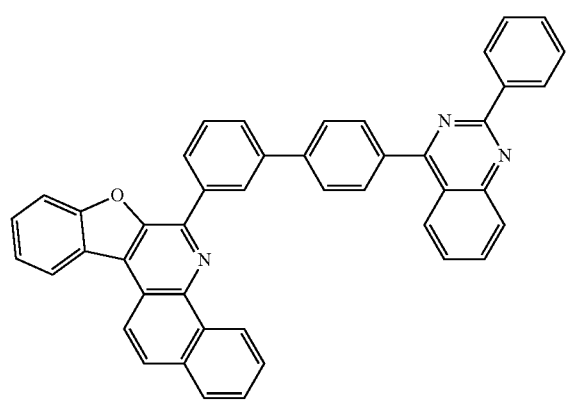

-continued
91
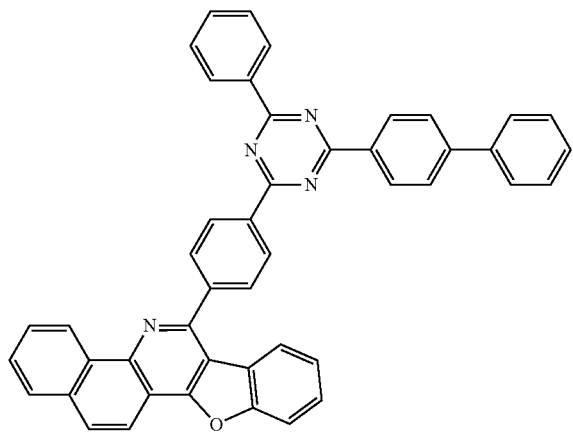
92
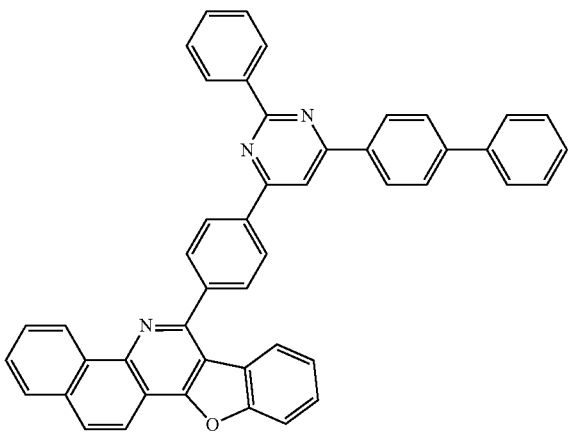
93
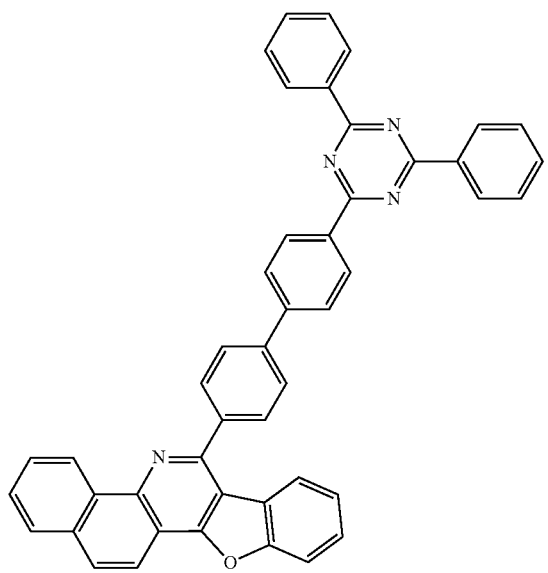
94
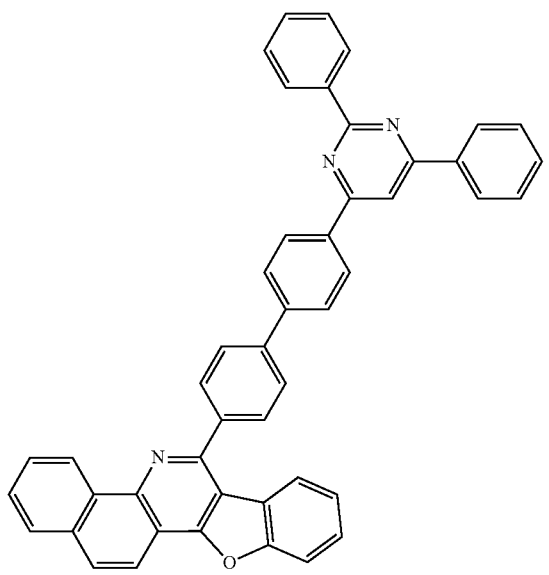
95
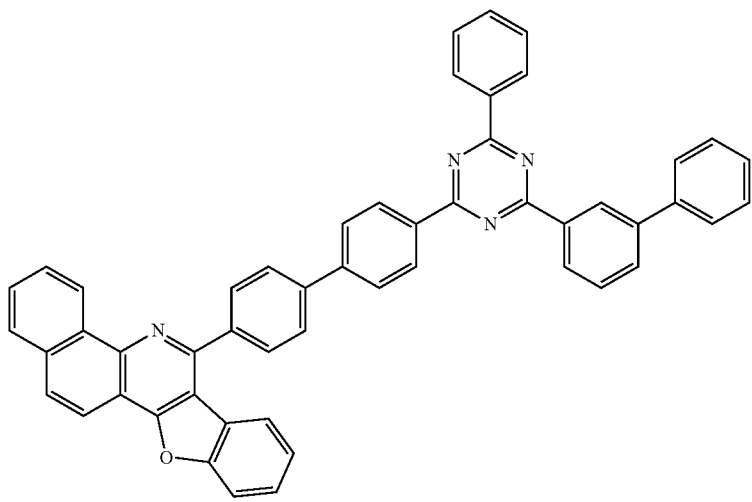

96
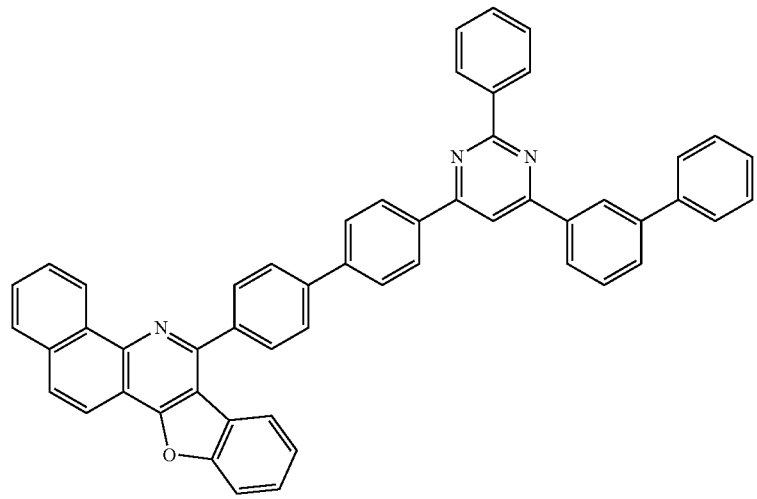
97
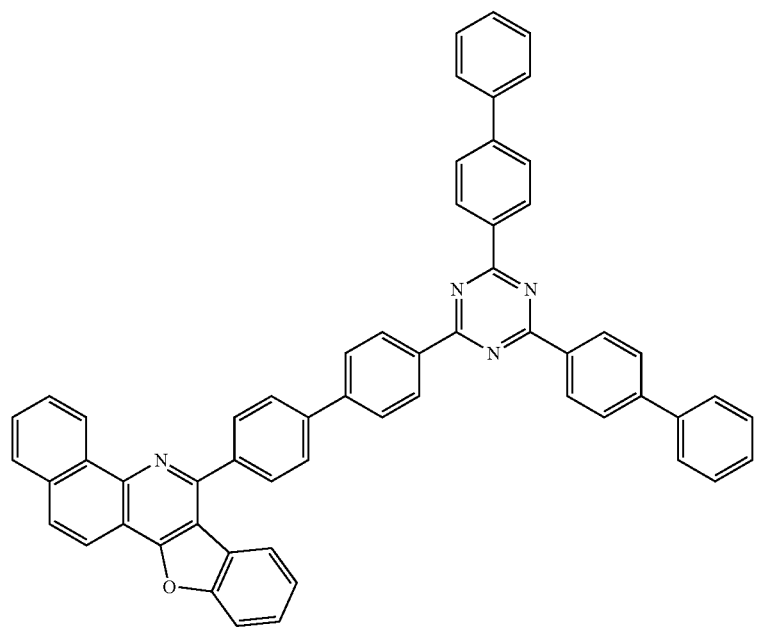

98
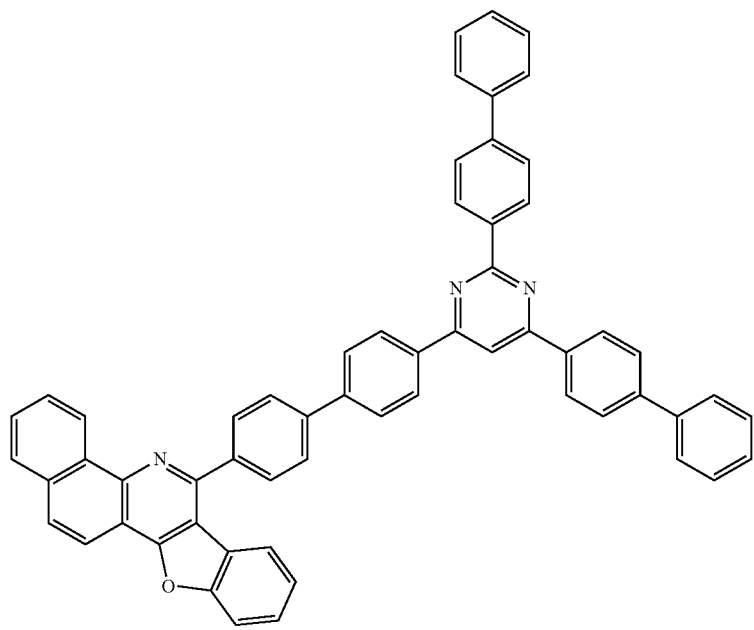
99
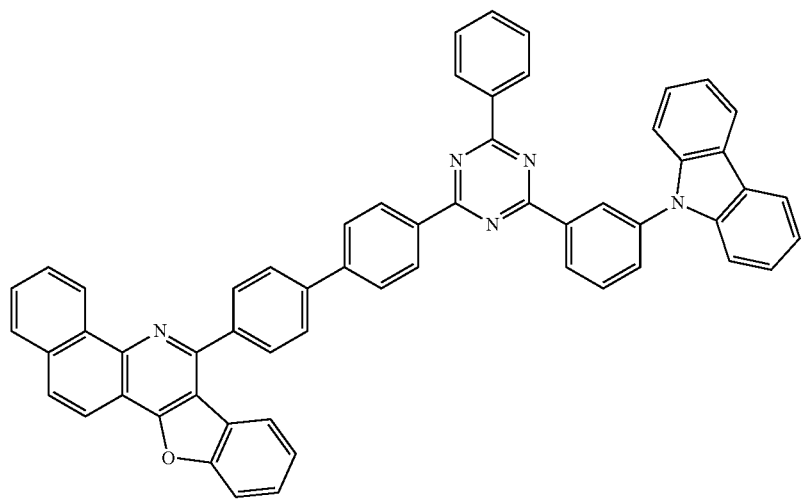
100
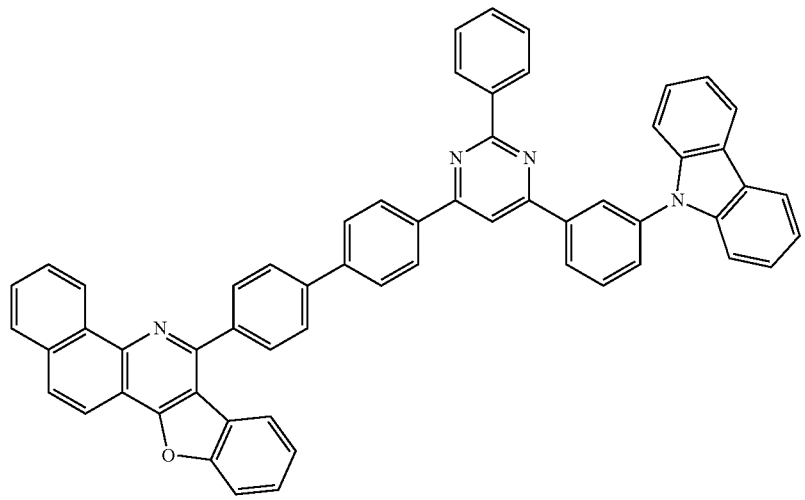

-continued
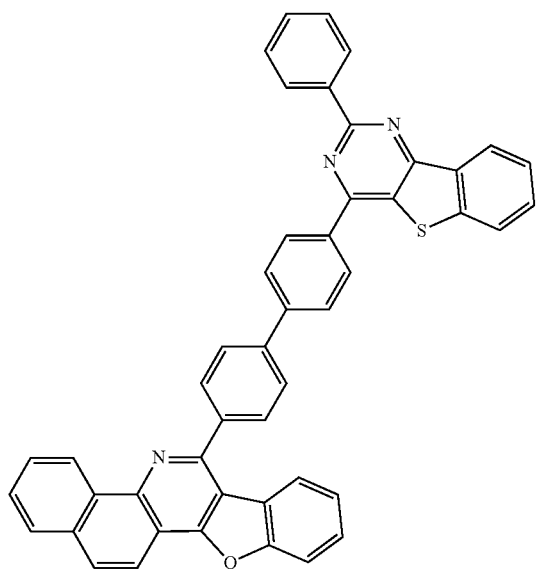
101
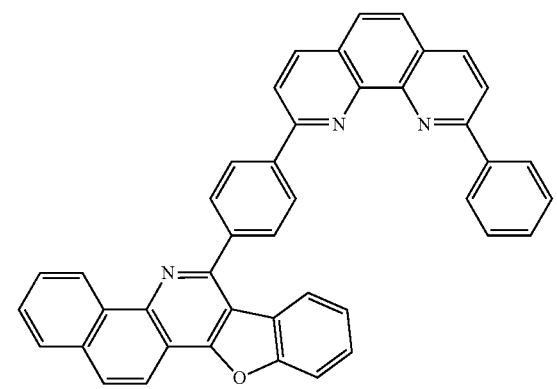
102
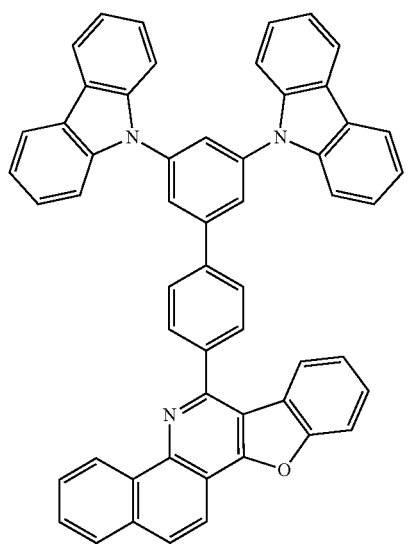
103
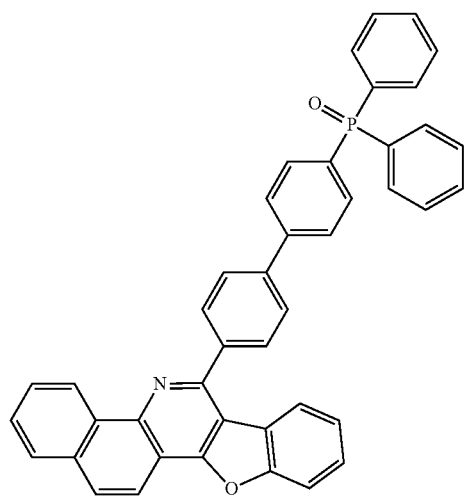
104

-continued
105
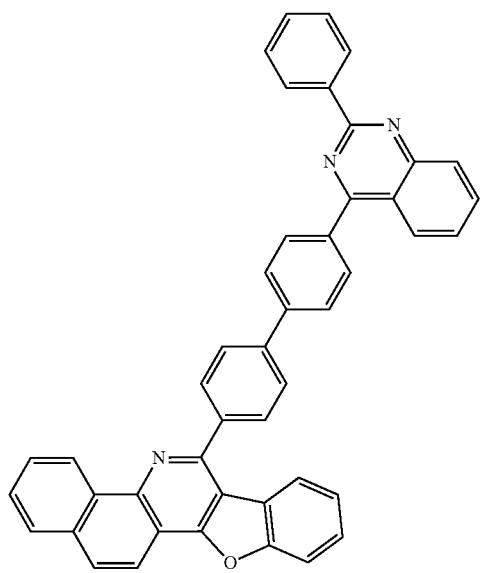
106
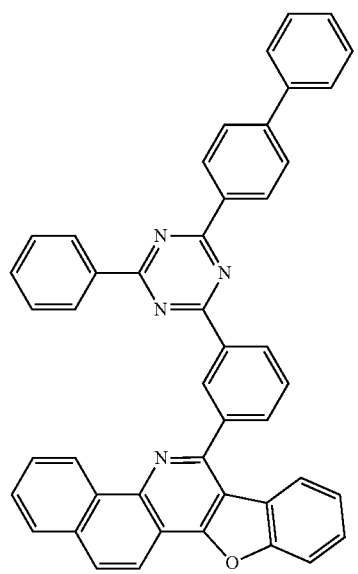
107
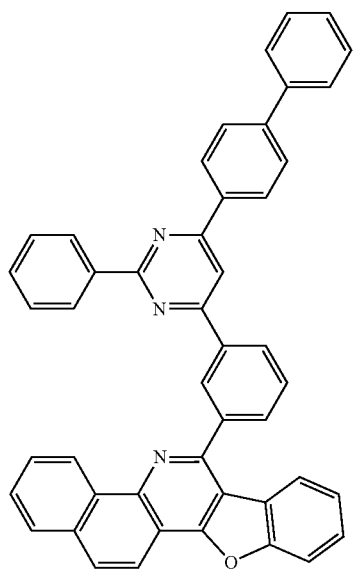
108
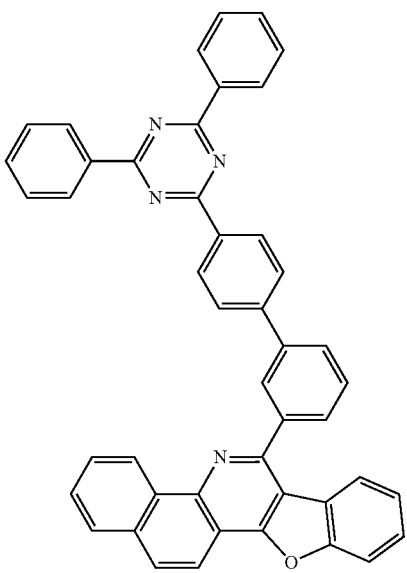

-continued
109
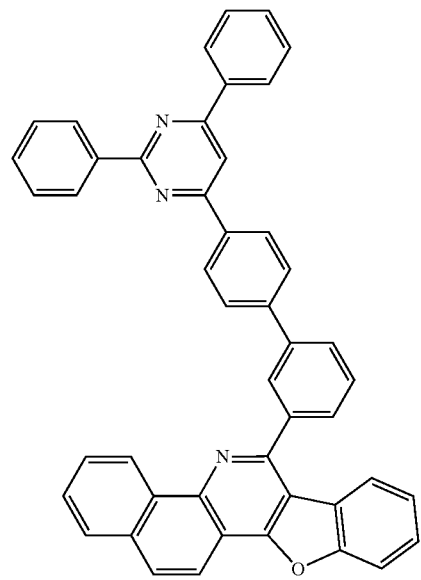
110
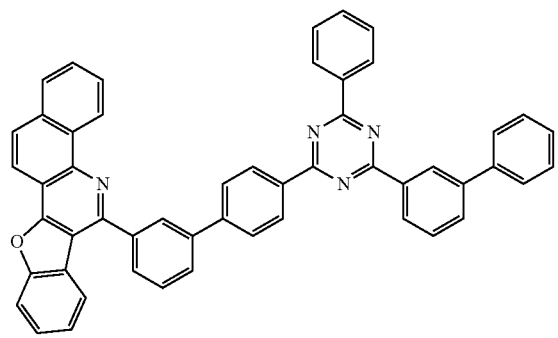
111
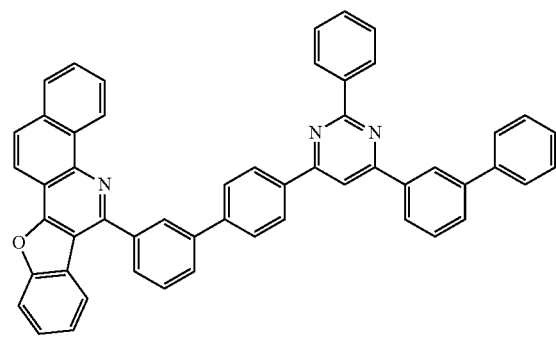
112
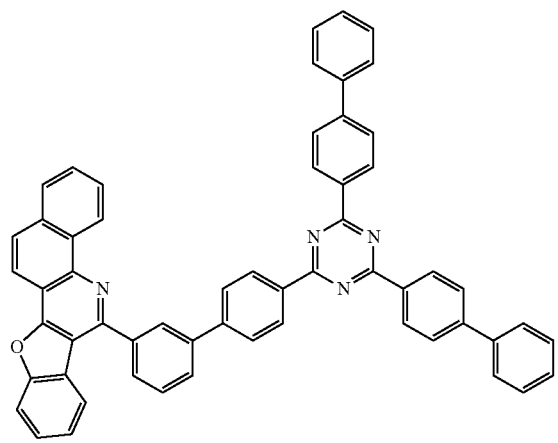
113
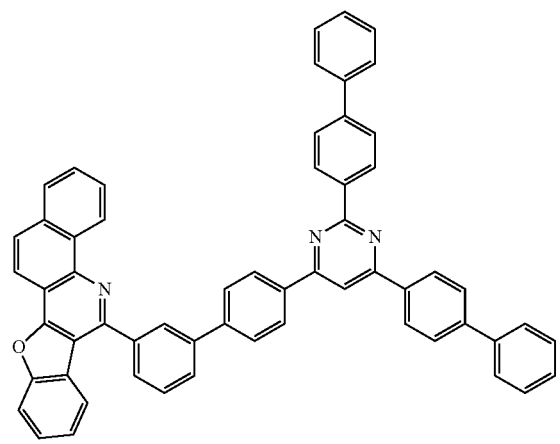
114
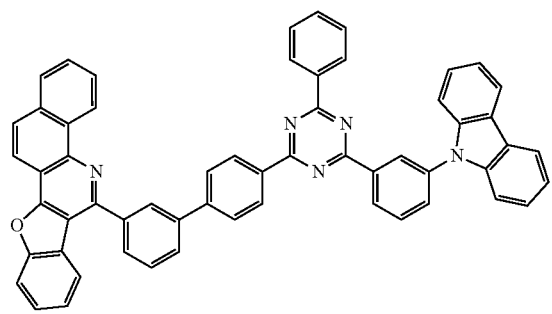

-continued
115
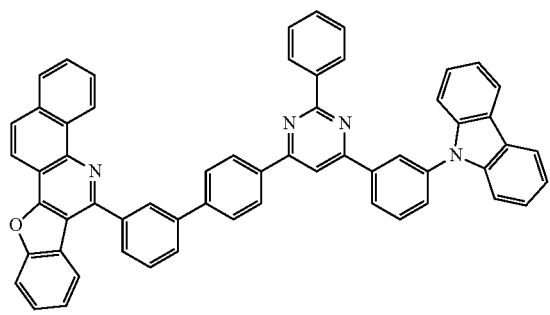
116
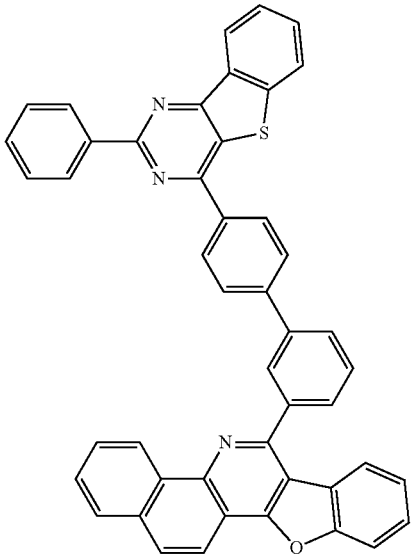
117
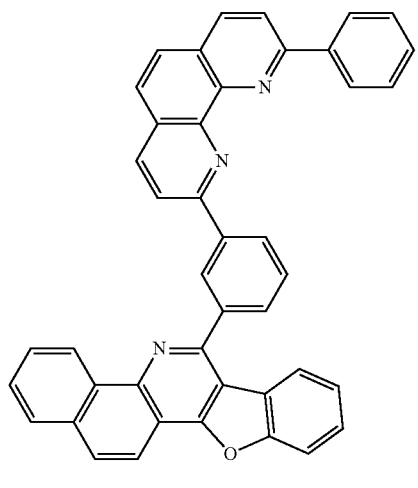
118
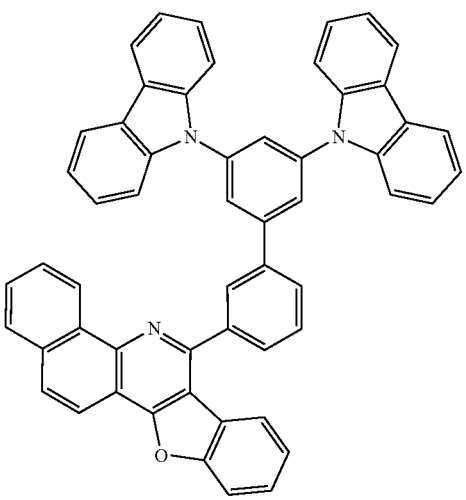
119
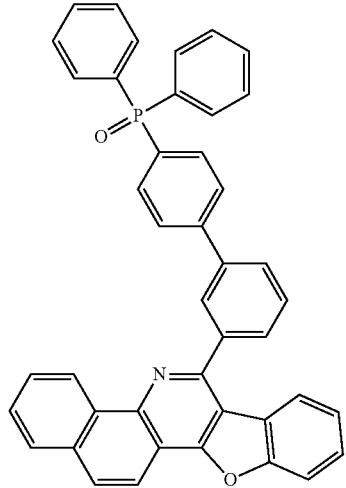
120
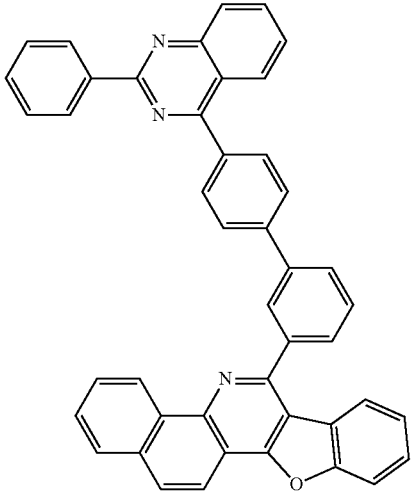

-continued
121
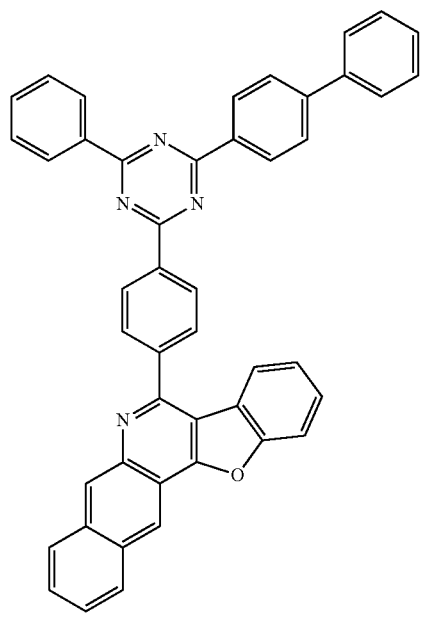
122
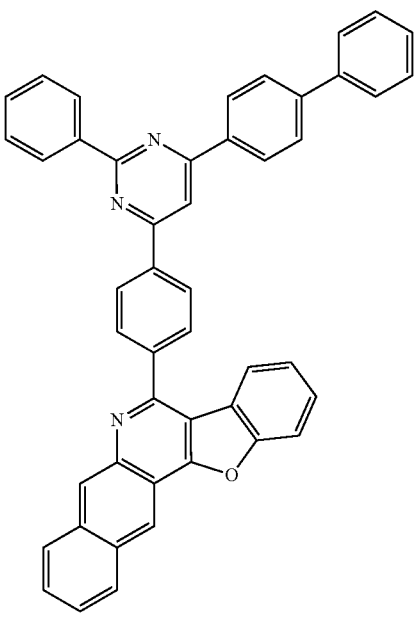
123
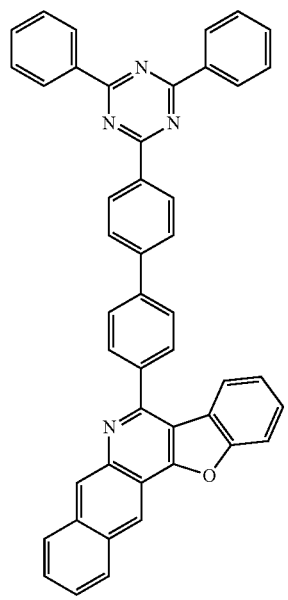
124
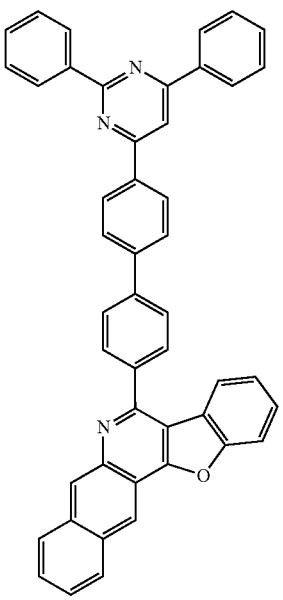

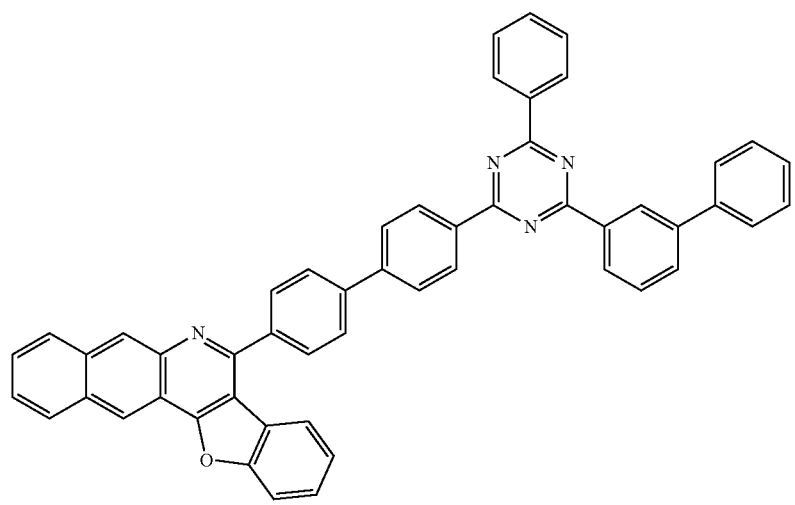
125
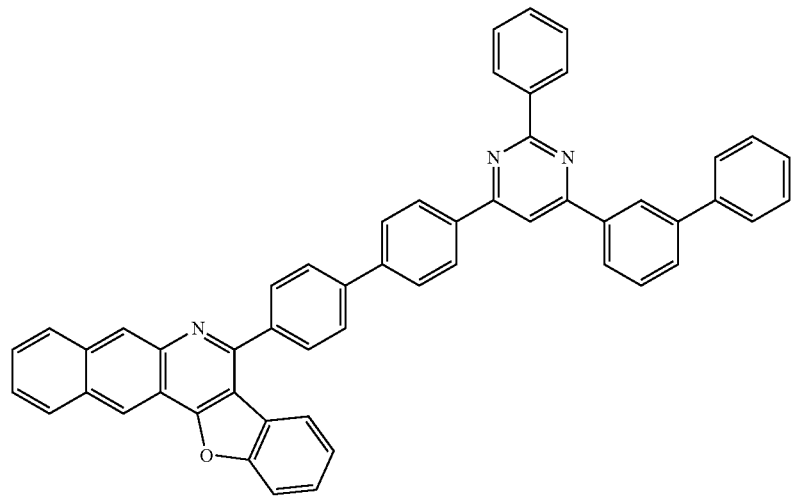
126
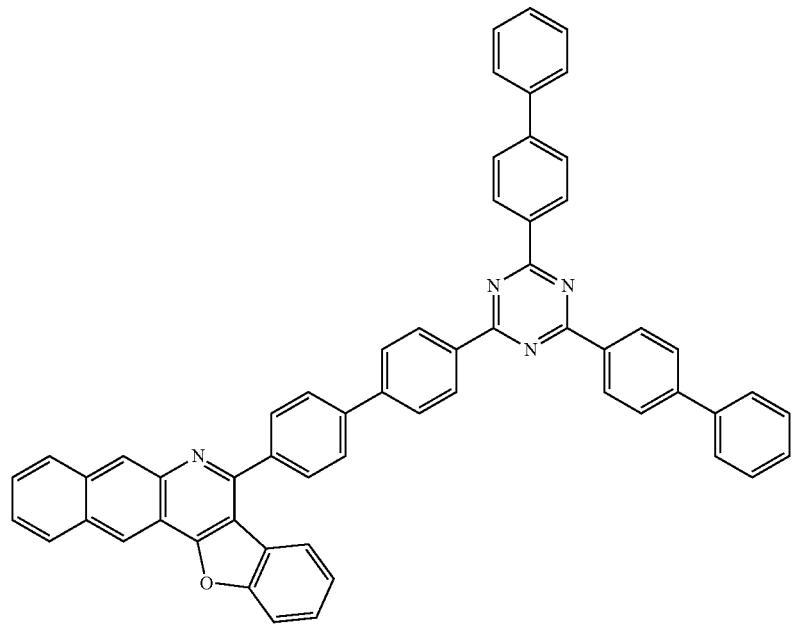
127

128
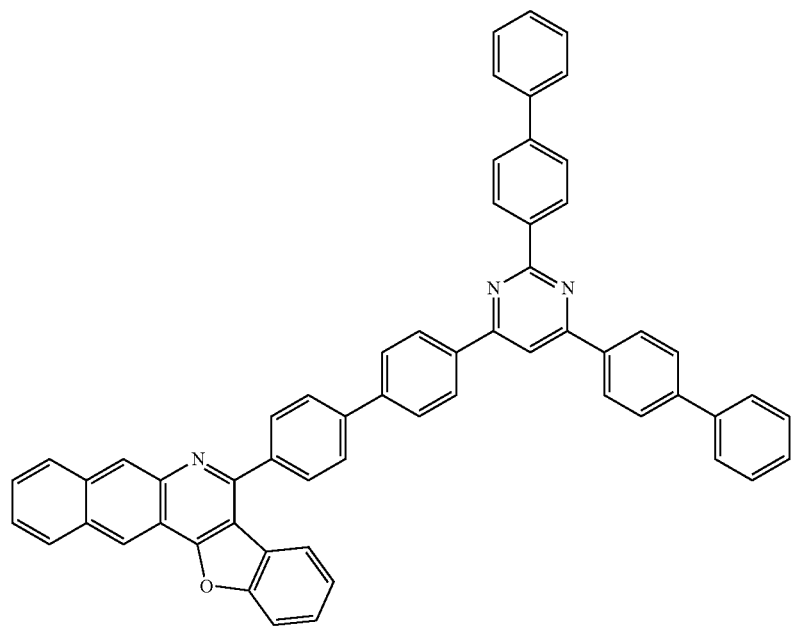
129
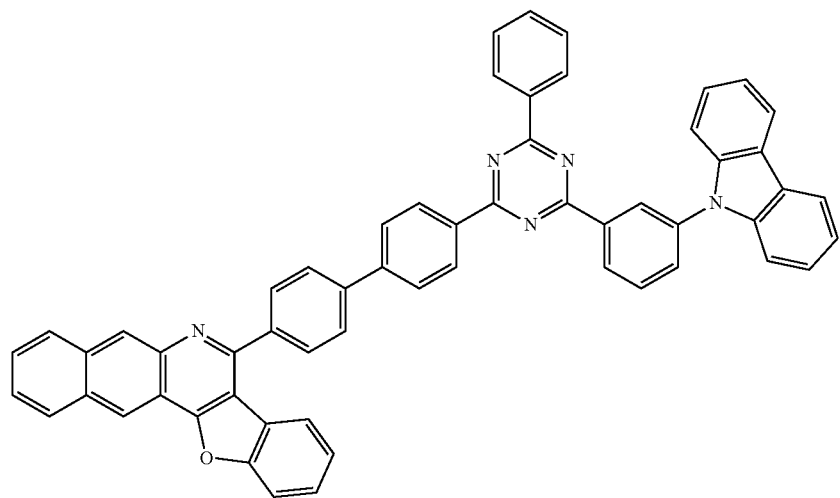
130
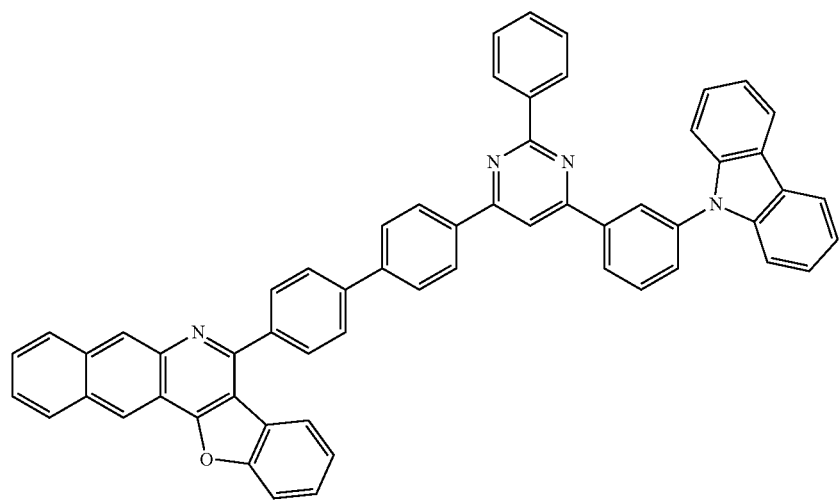

-continued
131
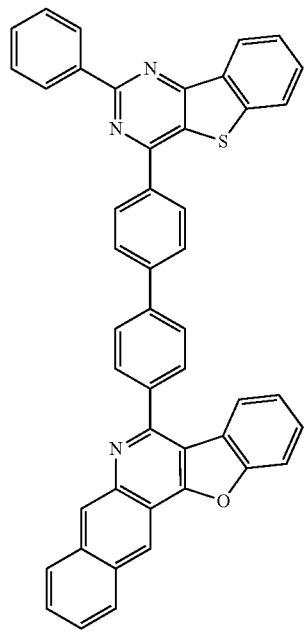
132
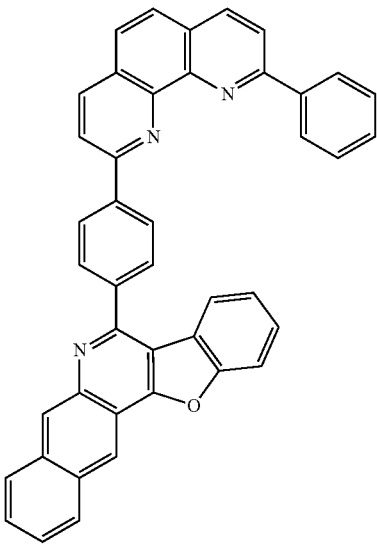
133
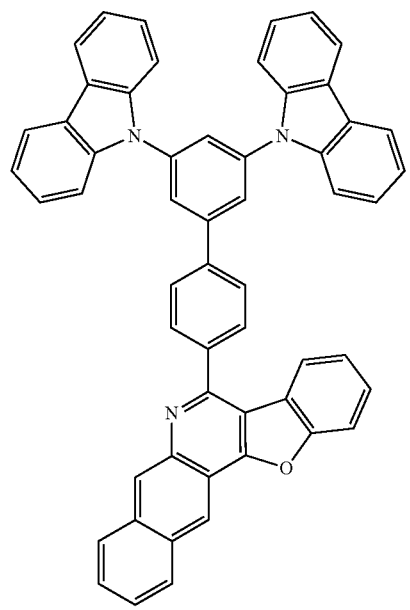
134
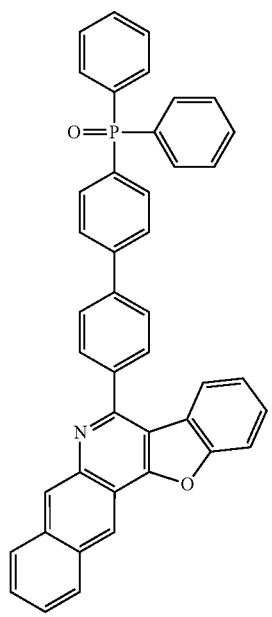

-continued
135 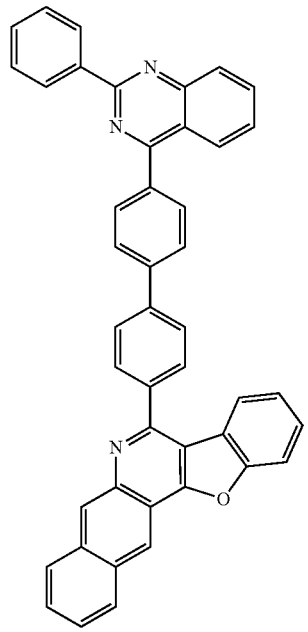
136 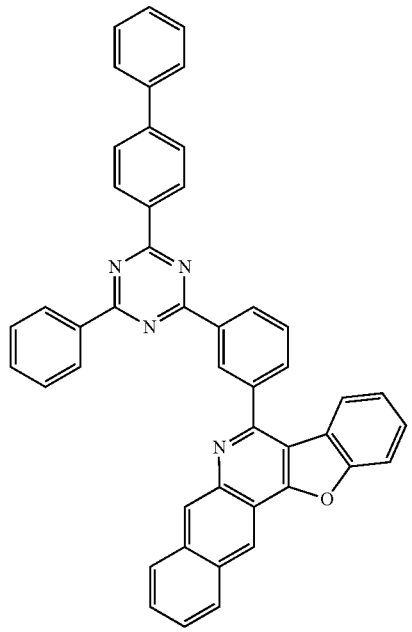
137 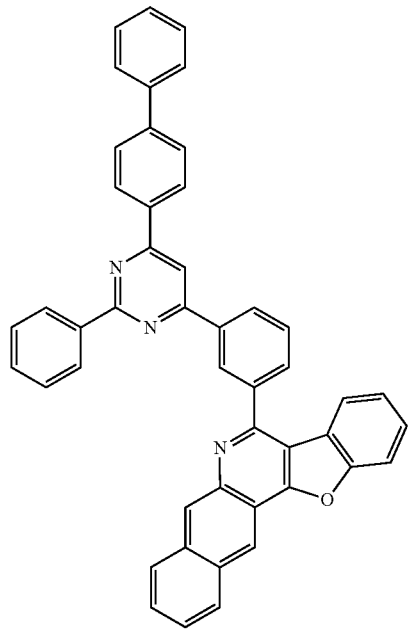
138 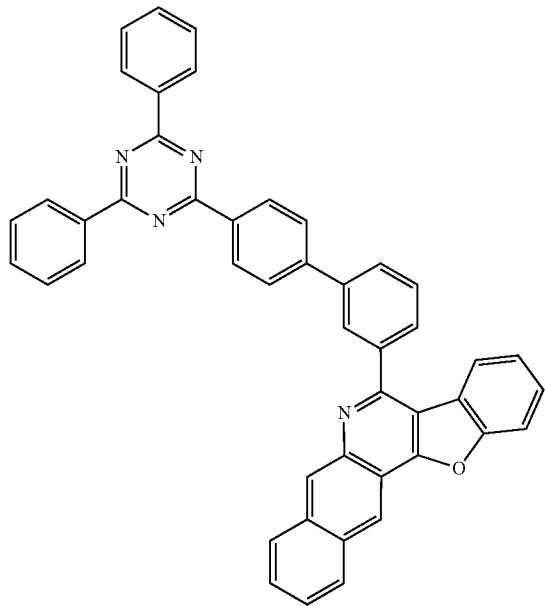

-continued
139
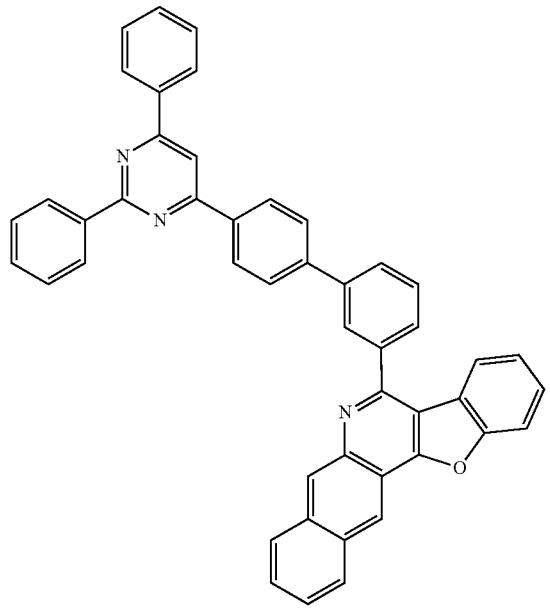
140
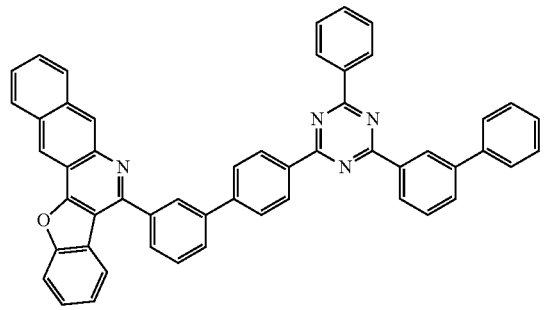
141
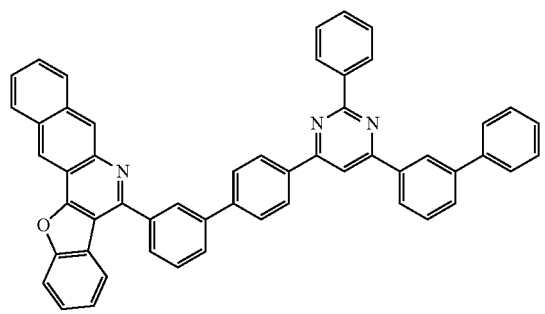
142
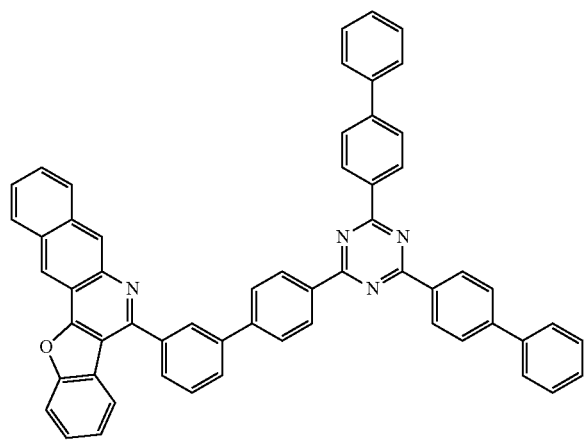
143
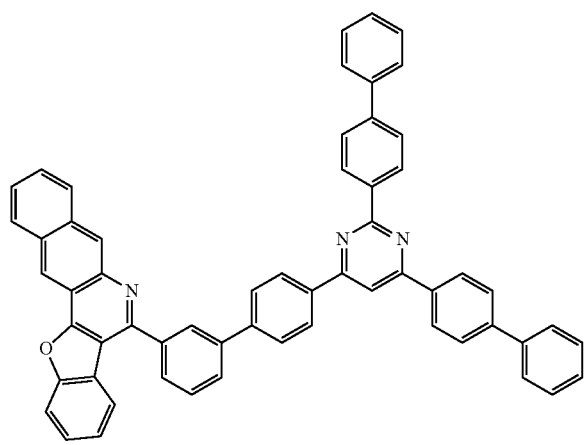
144
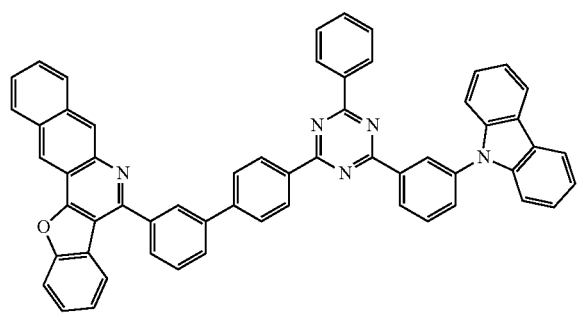

-continued
145
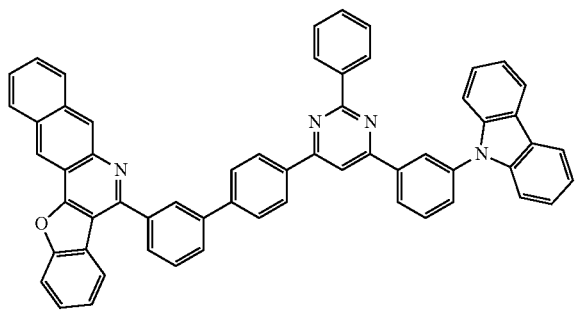
146
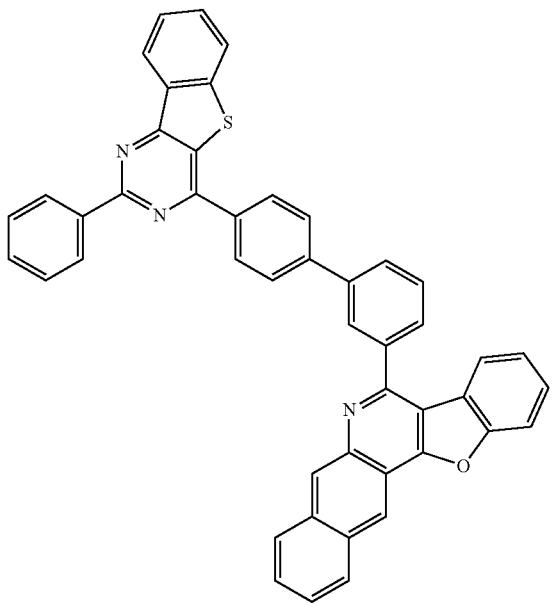
147
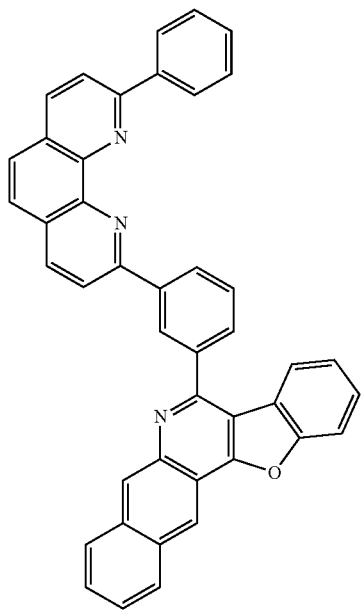
148
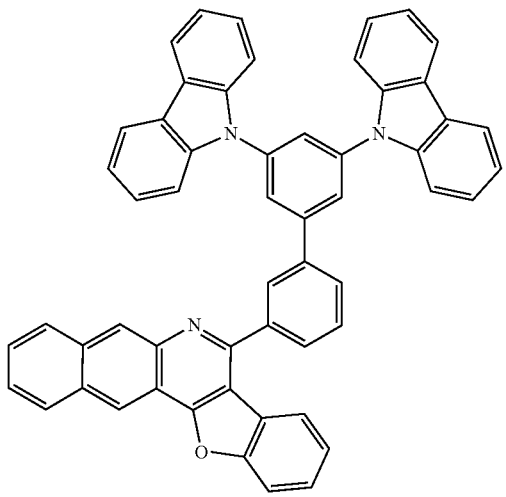

-continued
149
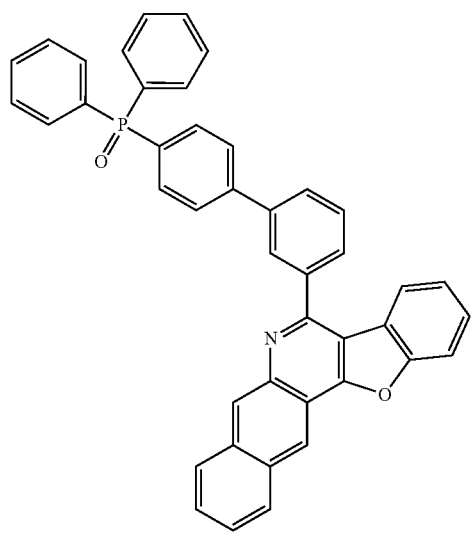
150
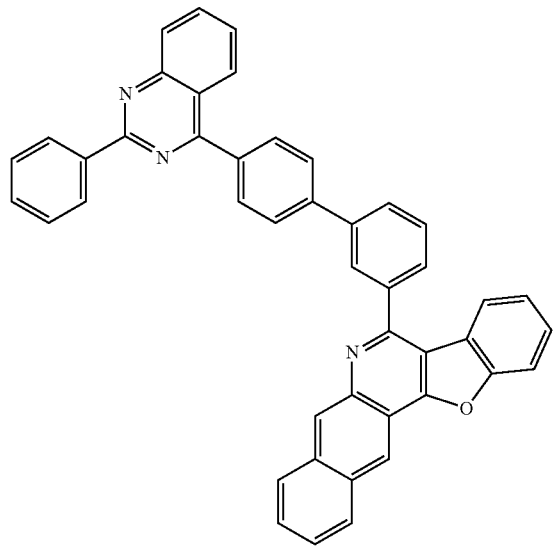
151
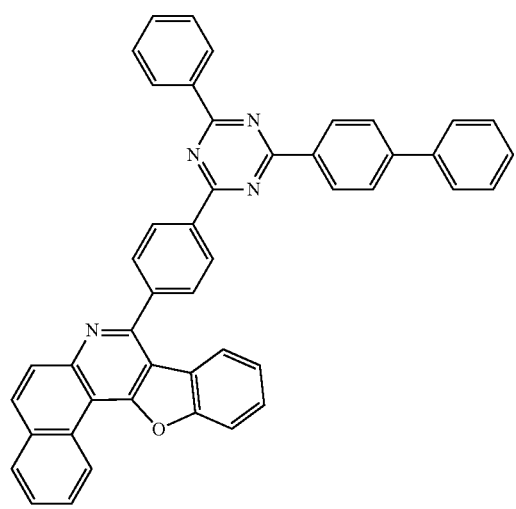
152
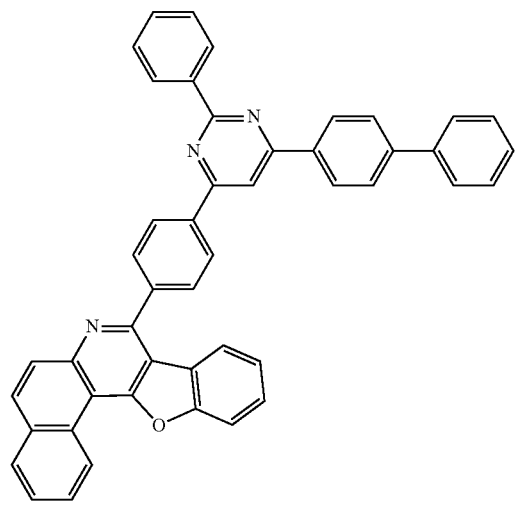
153
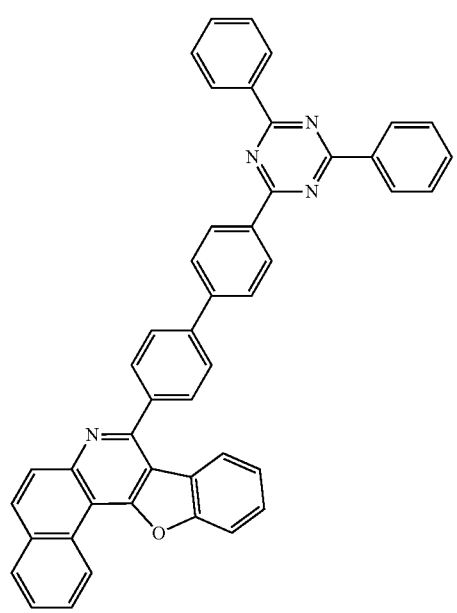
154
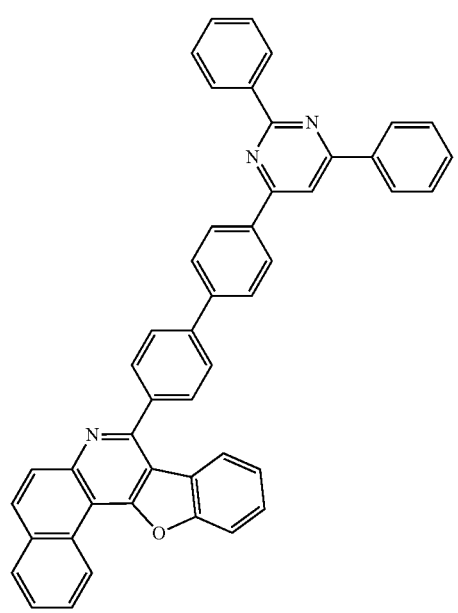

155
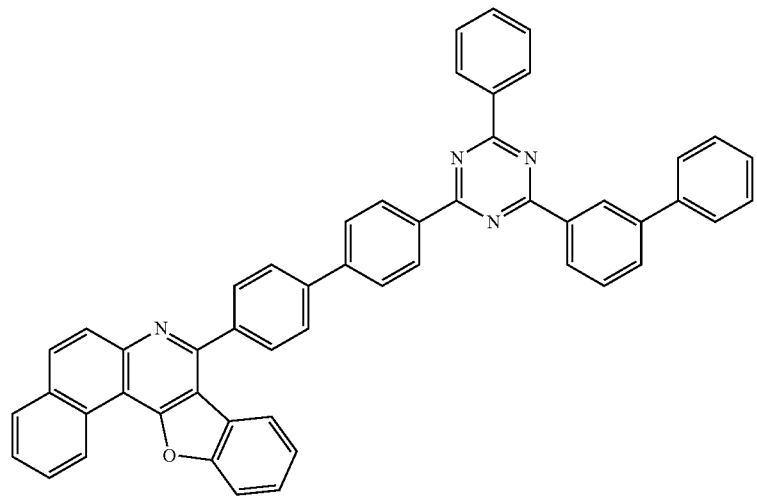
156
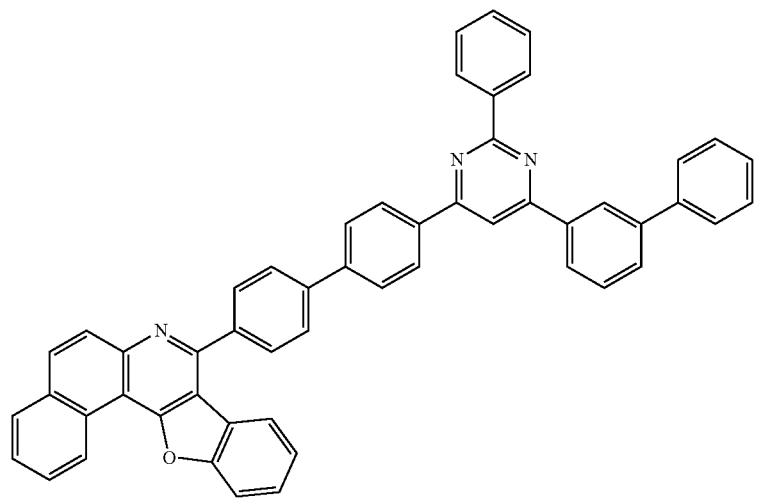
157
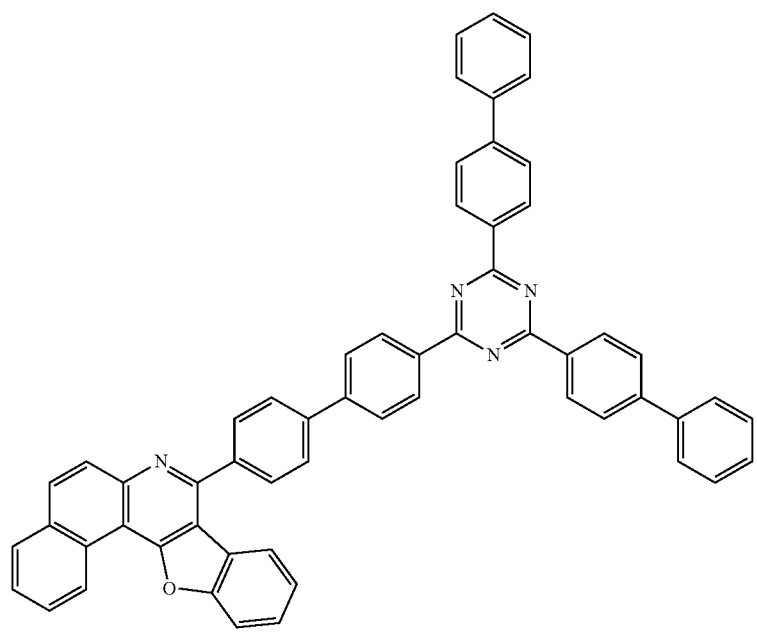

-continued
158
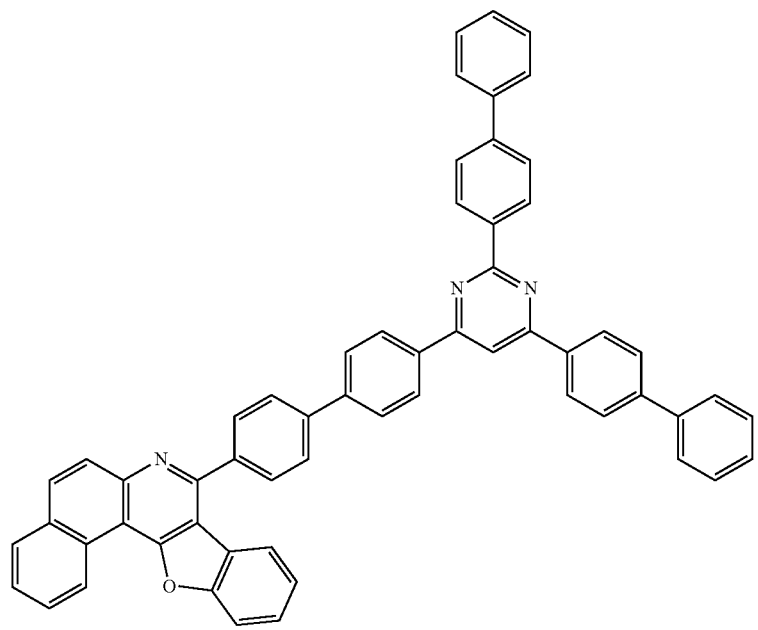
159
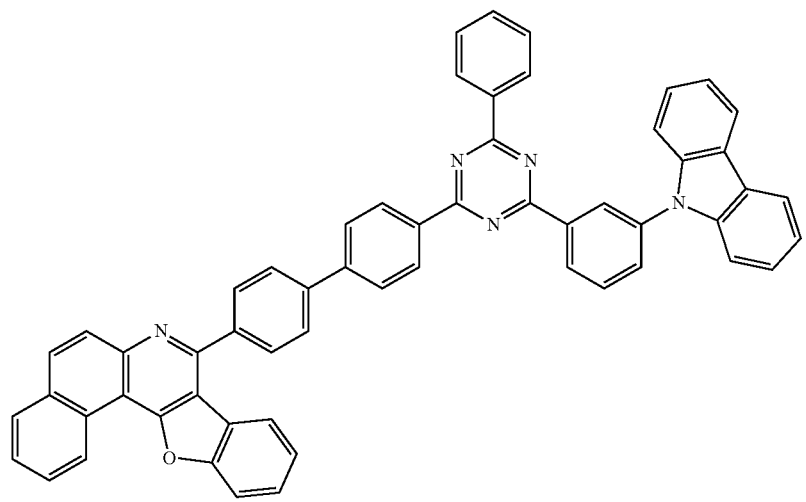
160
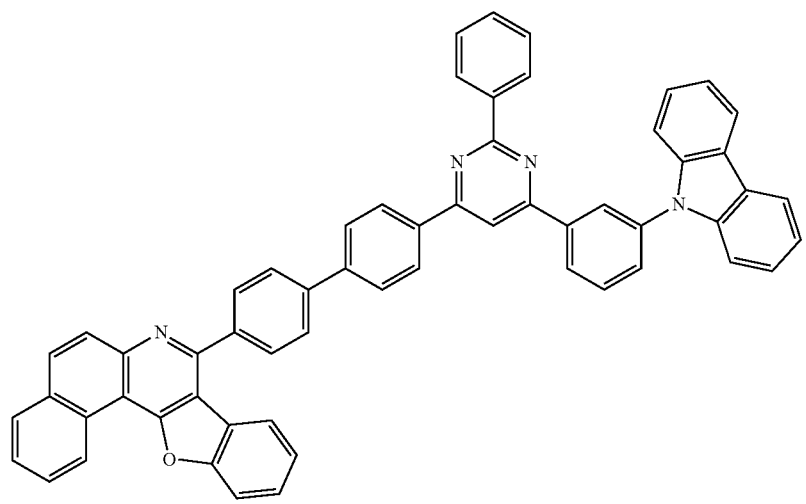

-continued
161
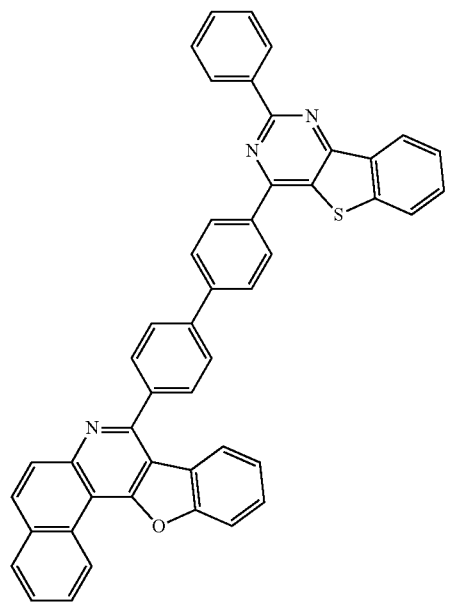
162
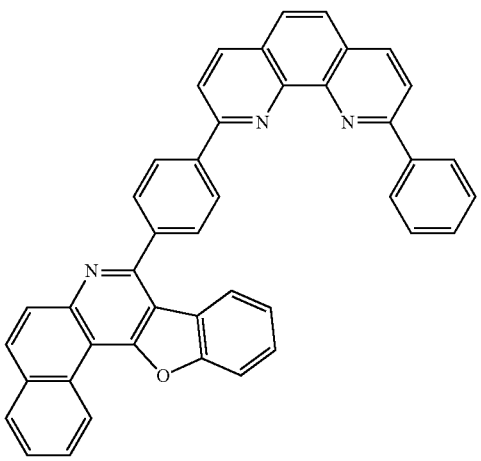
163
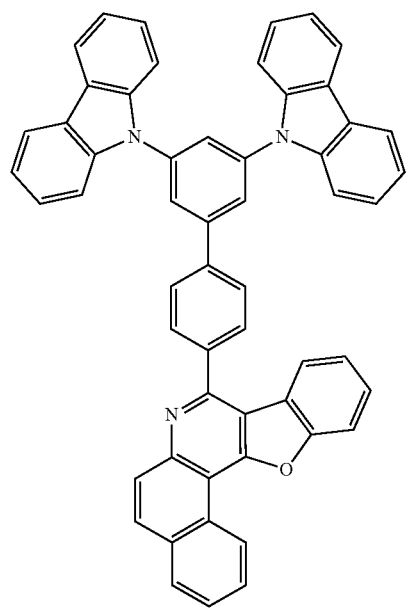
164
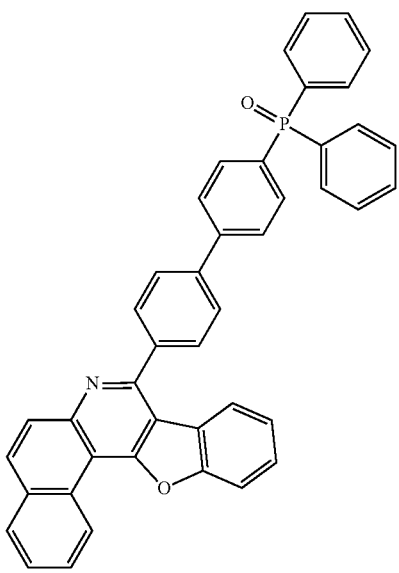

-continued
165 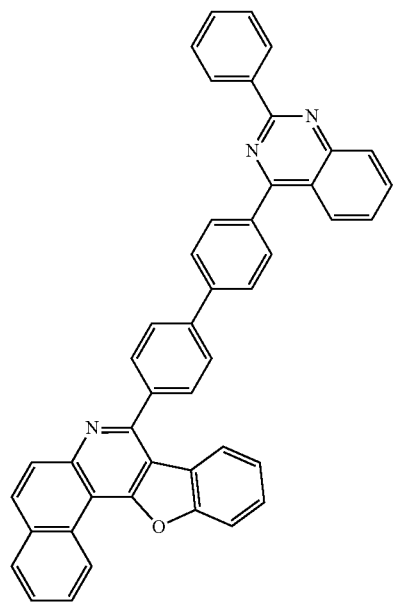
166 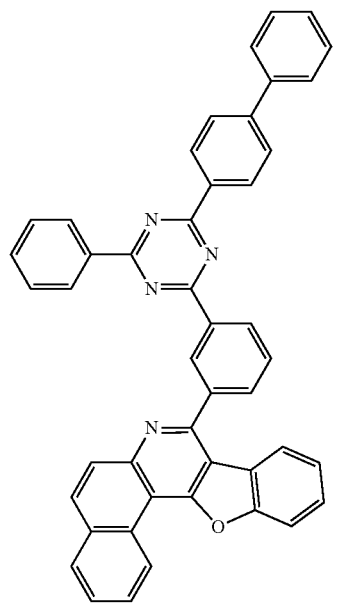
167 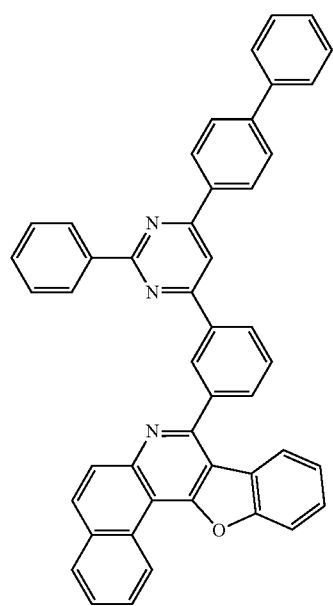
168 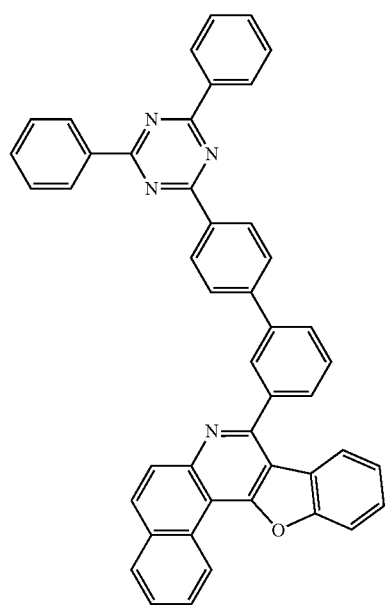

-continued
169
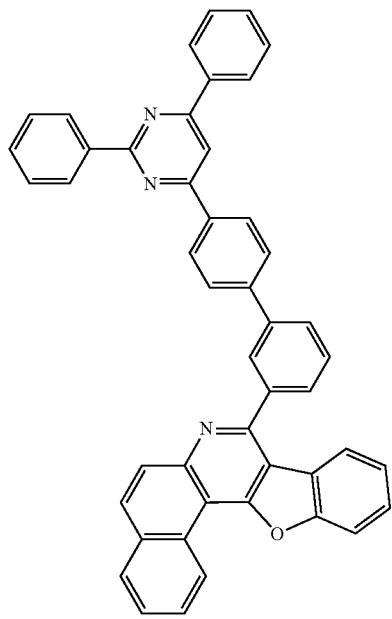
170
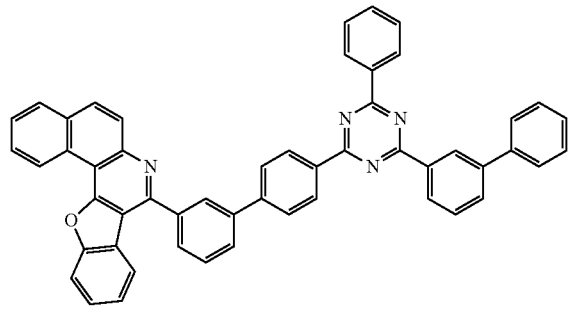
171
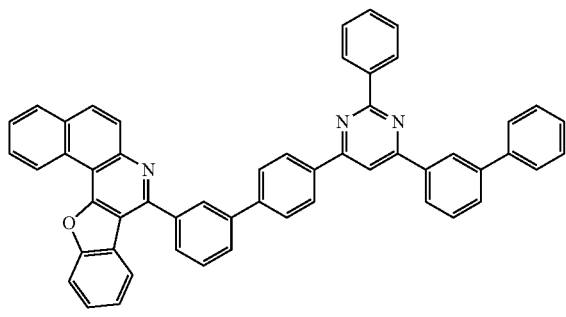
172
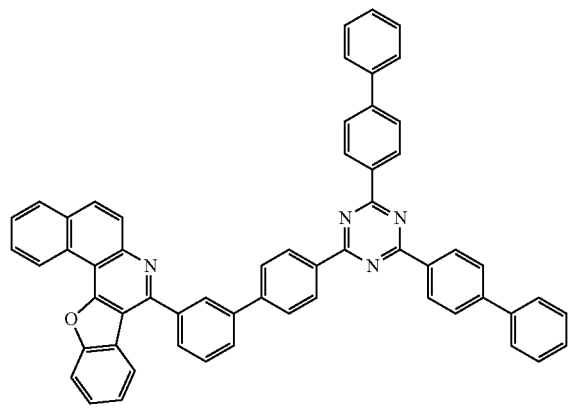
173
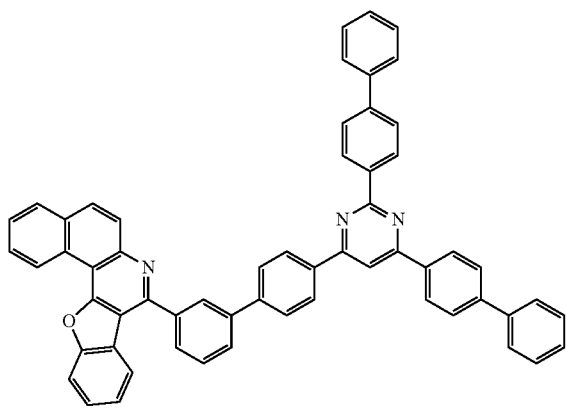

174
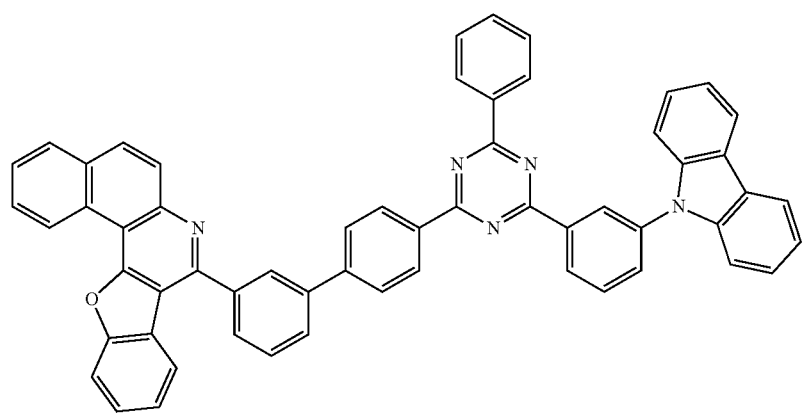
175
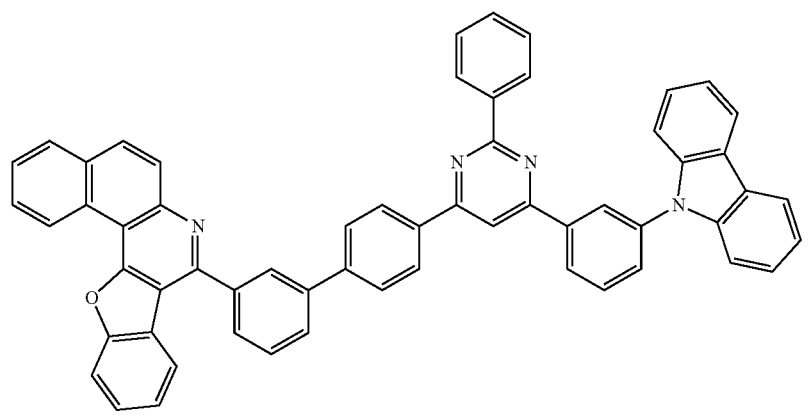
176
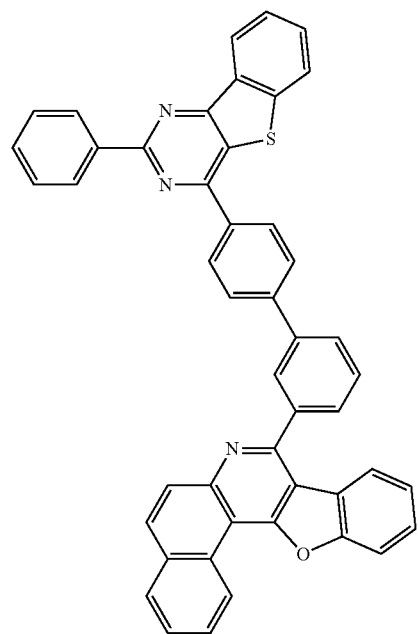
177
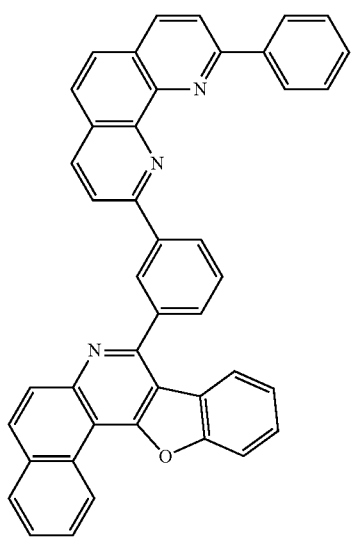

-continued
178
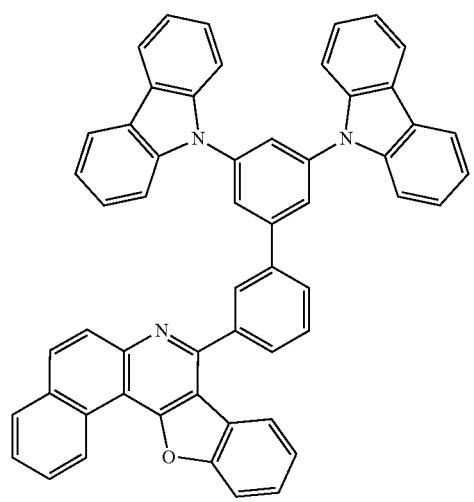
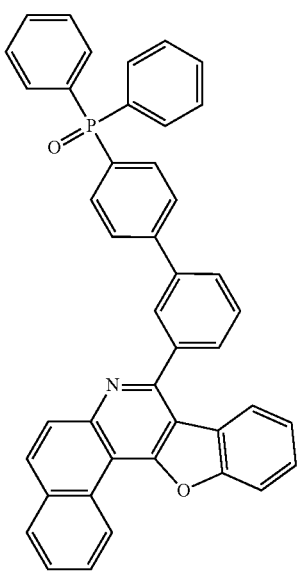
179
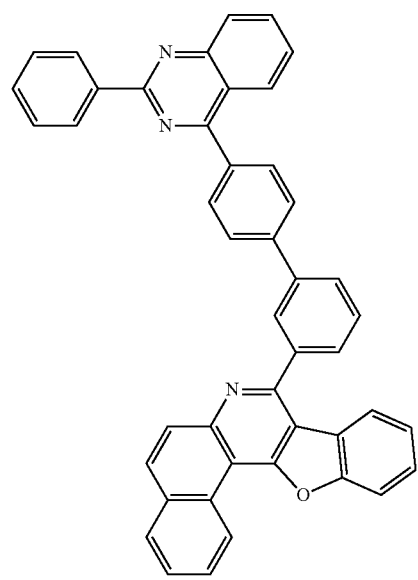
180

105 106
181
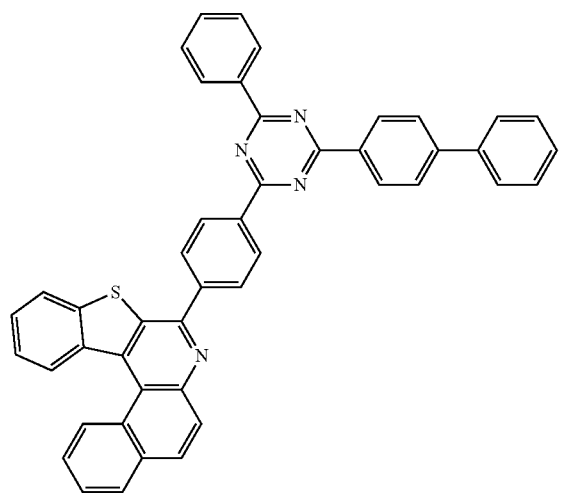
182
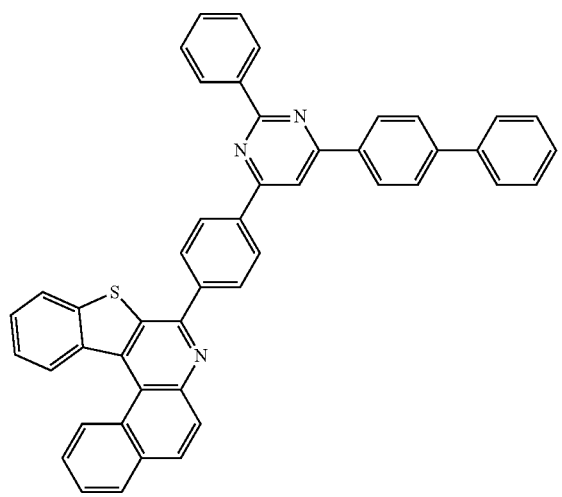
183
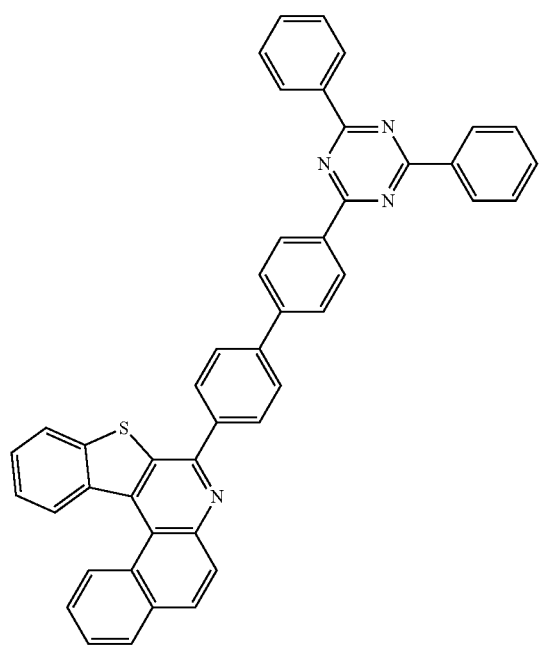 [SMILES: c1ccc(-c2cc(-c3ccc(-c4ccc(-c5nc6ccc7ccccc7c6c6c5oc5ccccc56)cc4)cc3)nc(-c3ccccc3)n2)cc1]
184
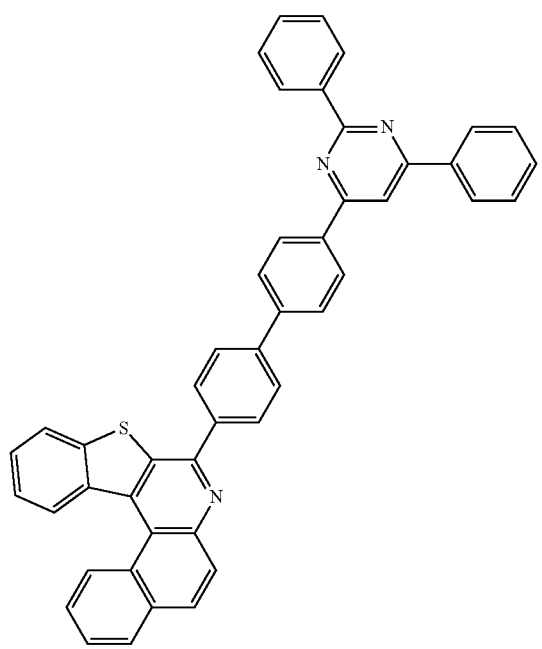
185
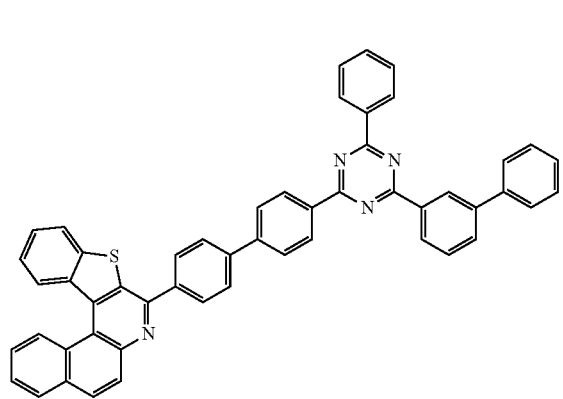
186
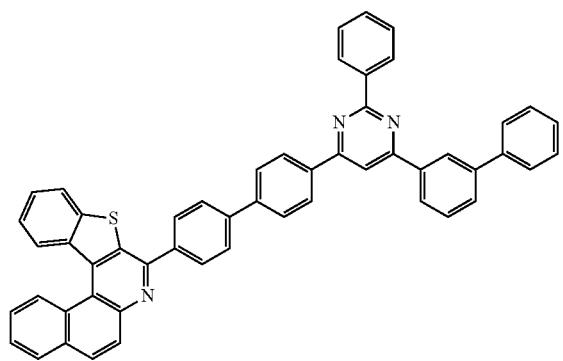

187
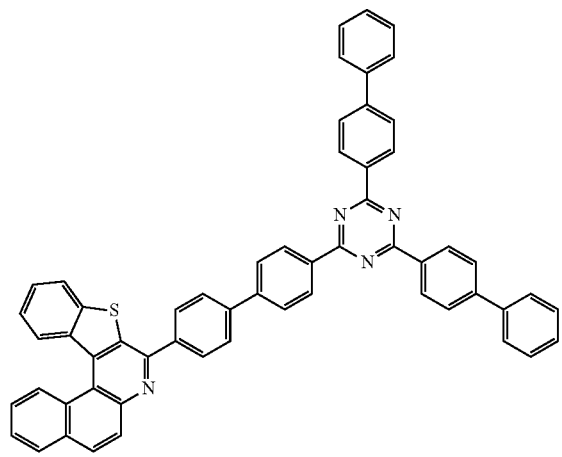
188
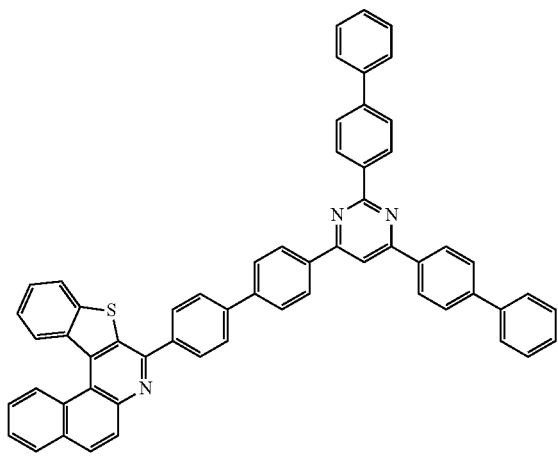
189
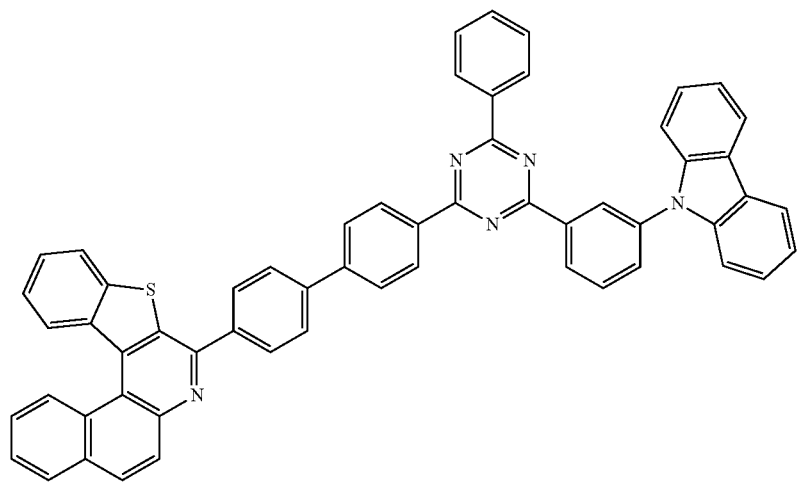
190
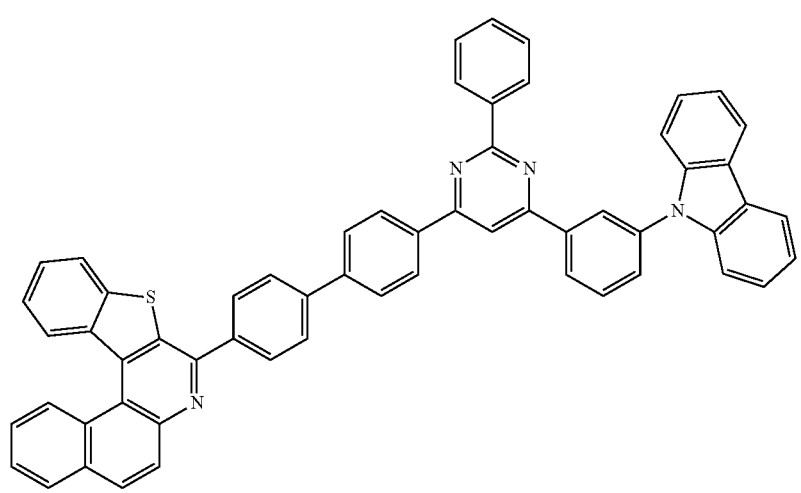

-continued
191
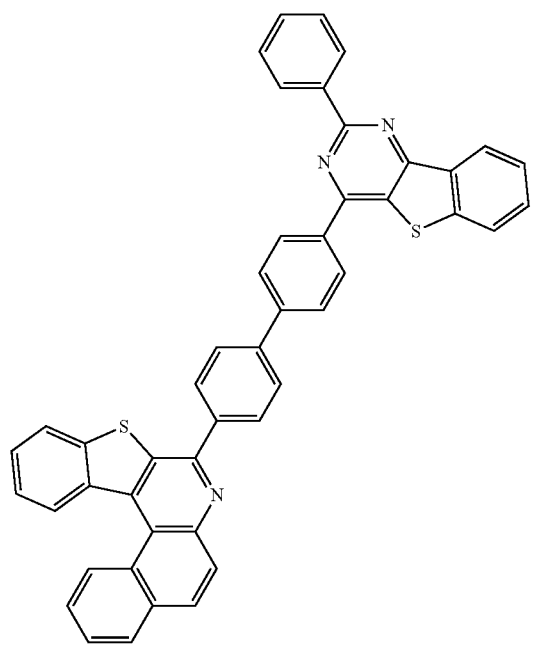
192
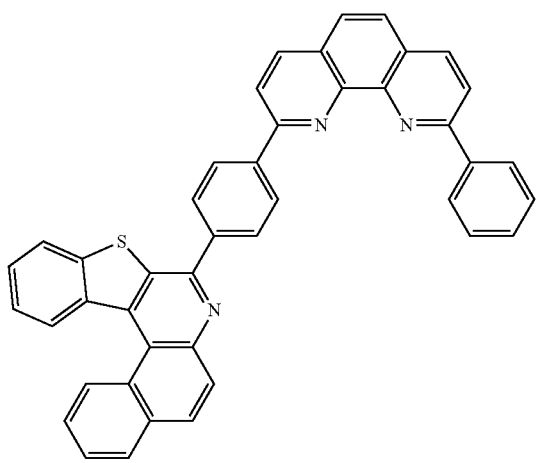
193
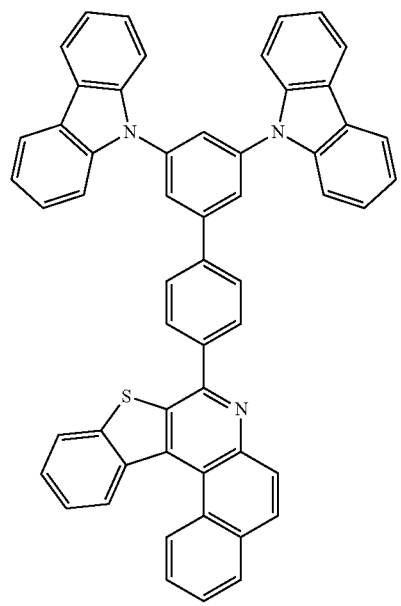
194
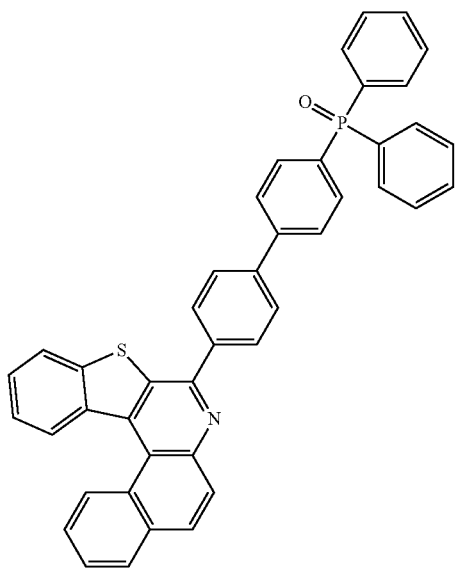

-continued
195
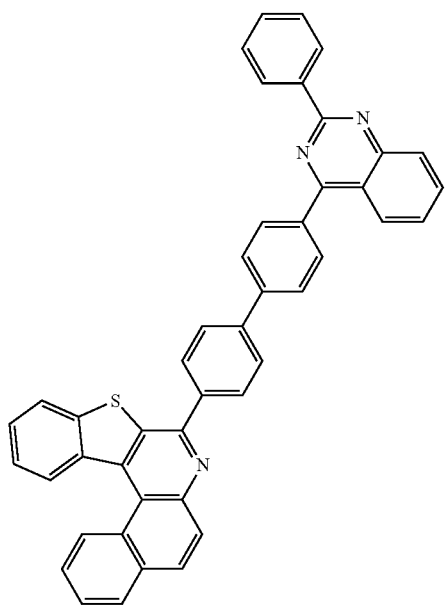
196
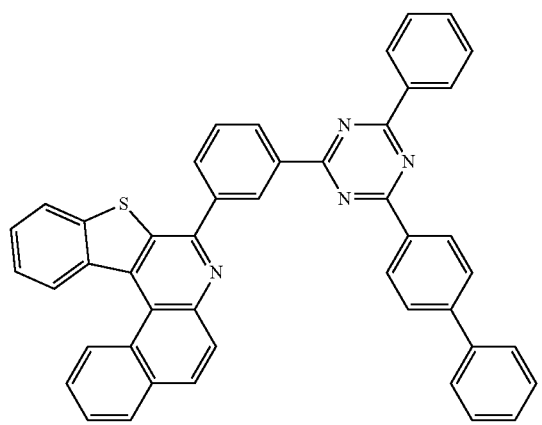
197
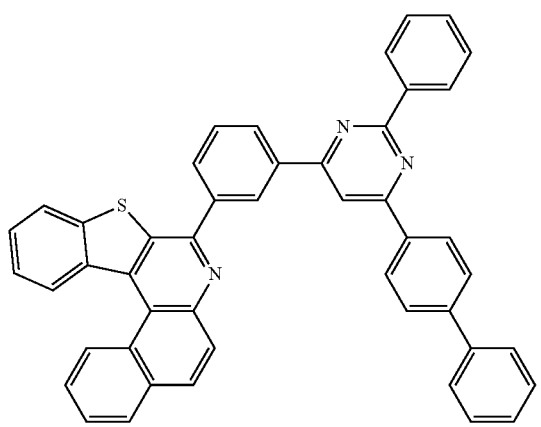
198
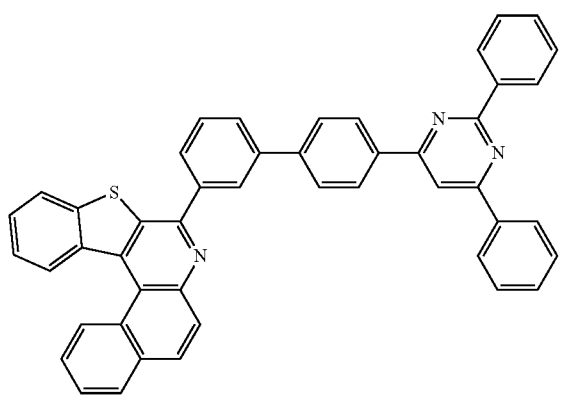
199
200
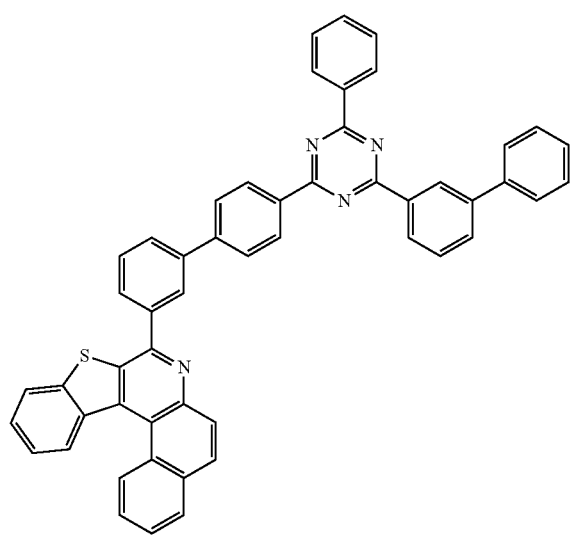

-continued
201
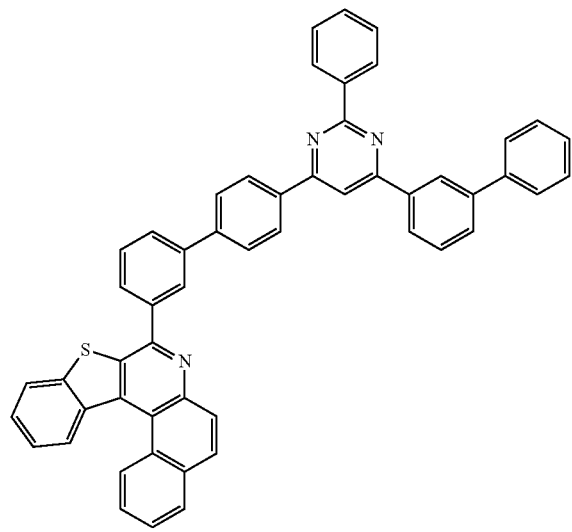
202
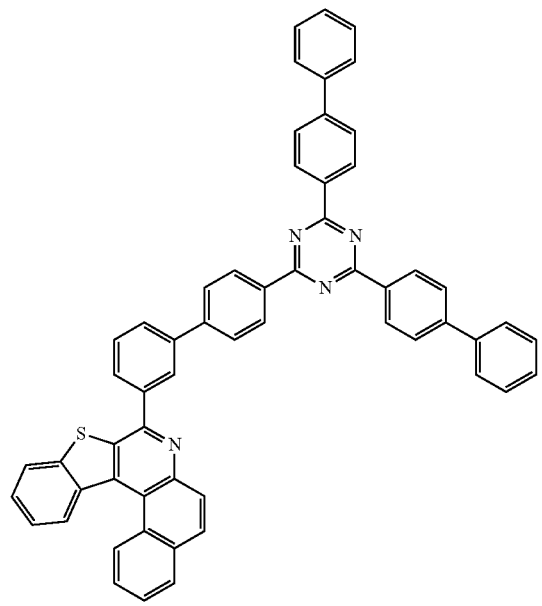 [SMILES: c1ccc(-c2ccc(-c3cc(-c4ccc(-c5cccc(-c6nc7ccc8ccccc8c7c7c6oc6ccccc67)c5)cc4)nc(-c4ccc(-c5ccccc5)cc4)n3)cc2)cc1]
203
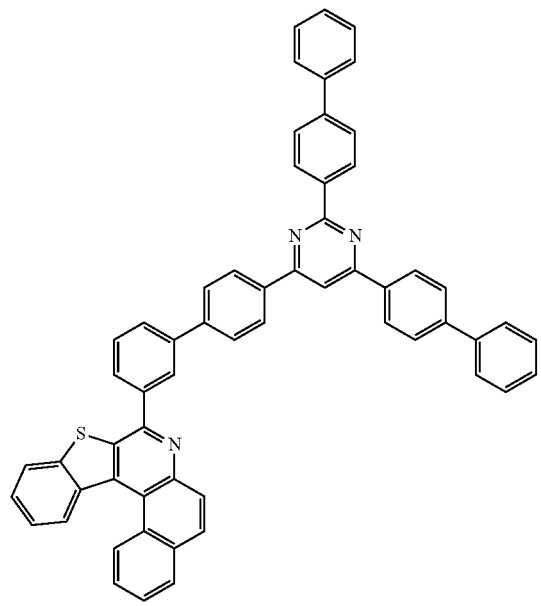
204
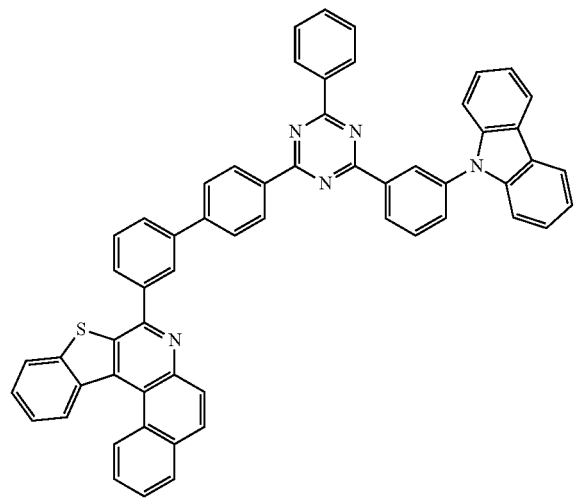

-continued
205
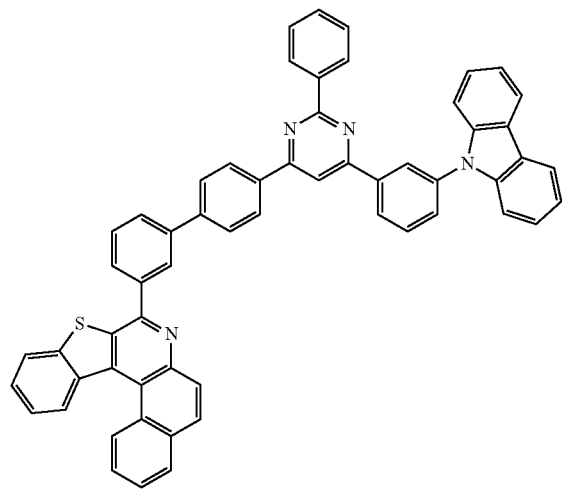
206
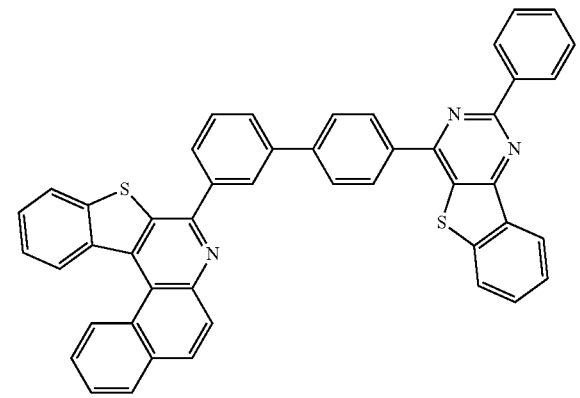
207
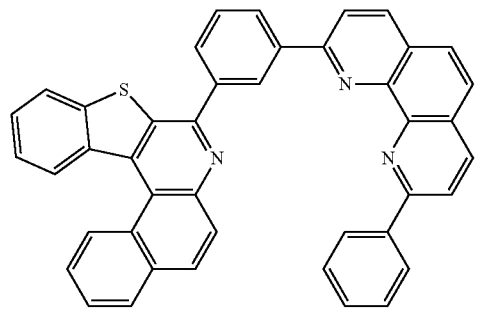
208
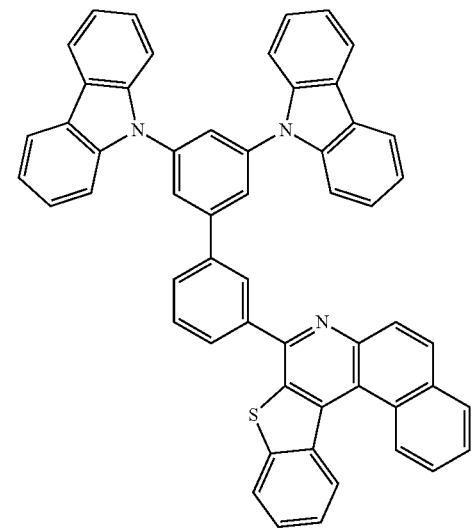
209
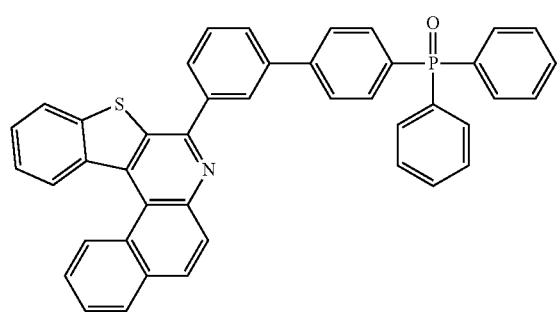
210
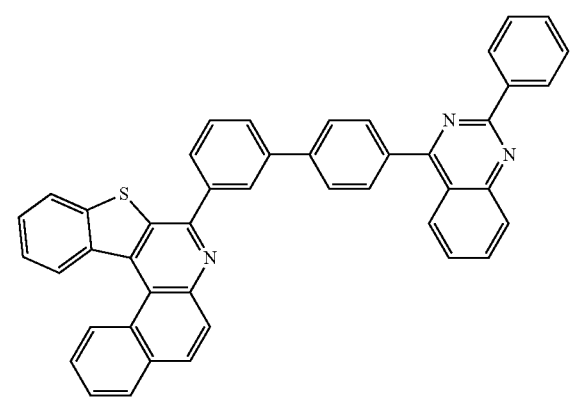

211
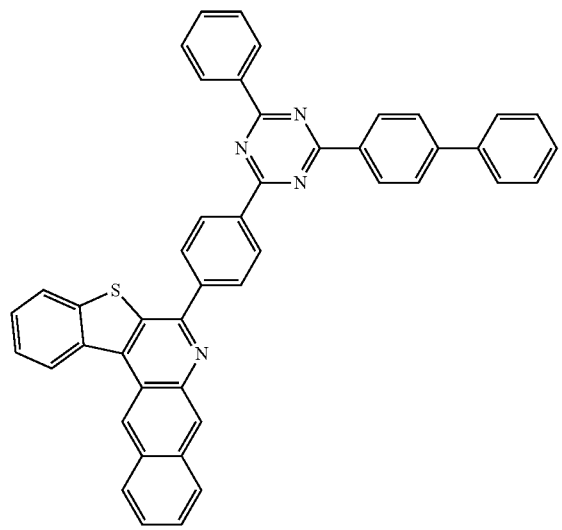
212
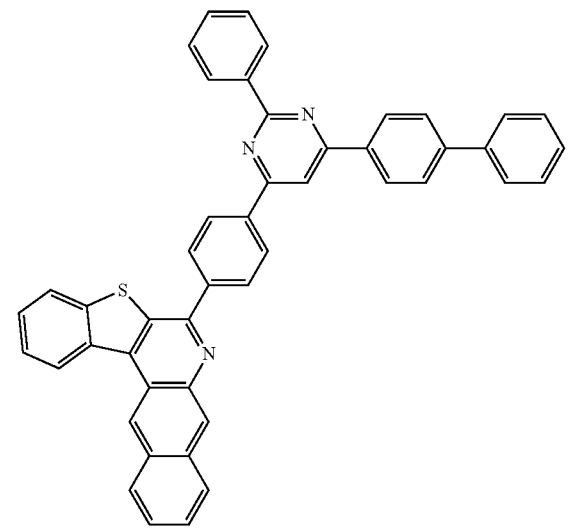
213
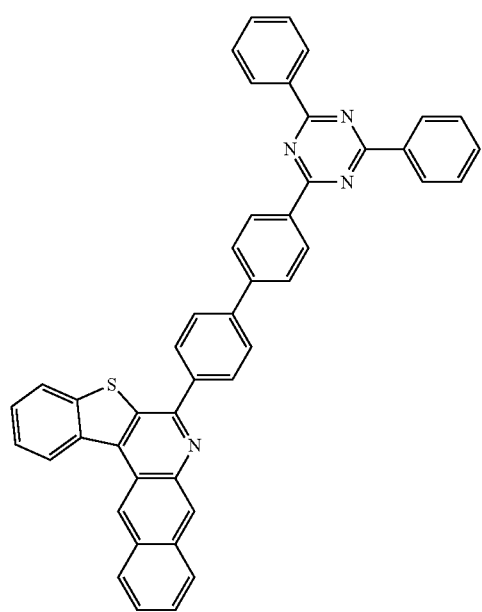
214
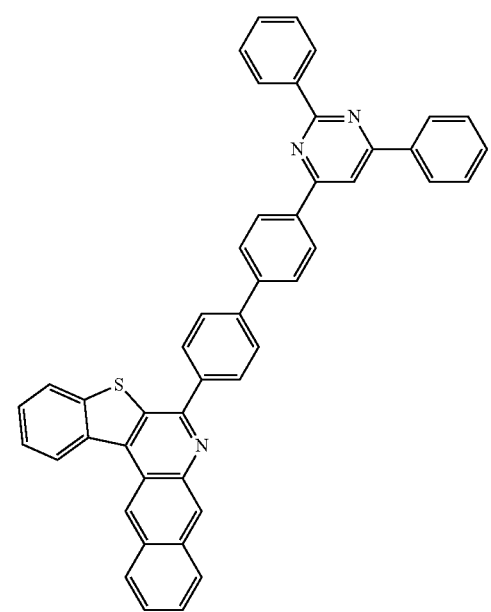
215
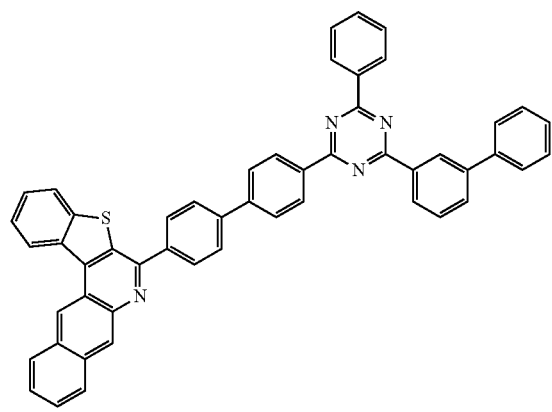
216
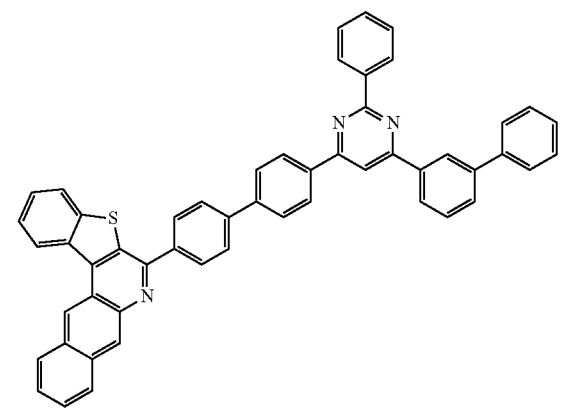

-continued
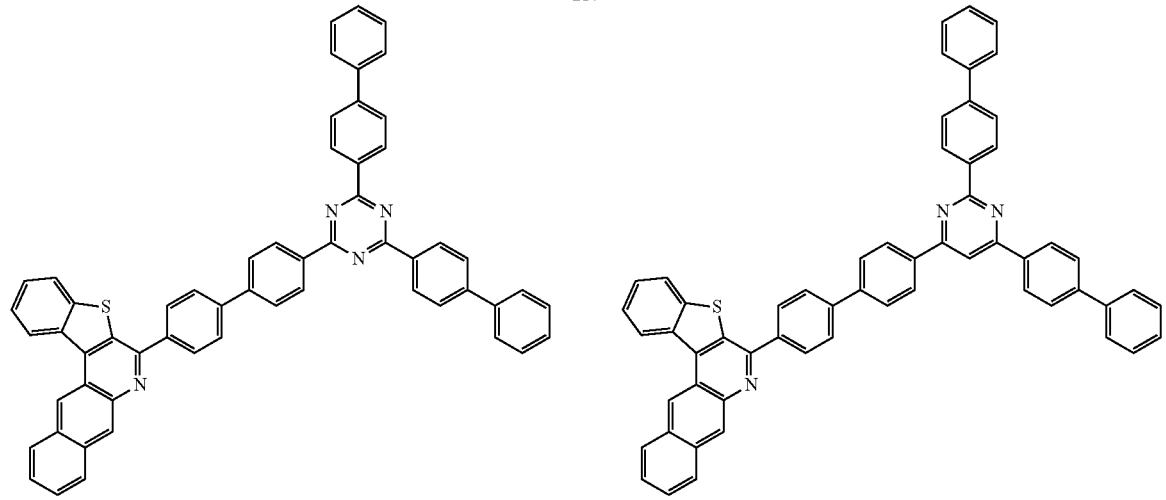
217
218
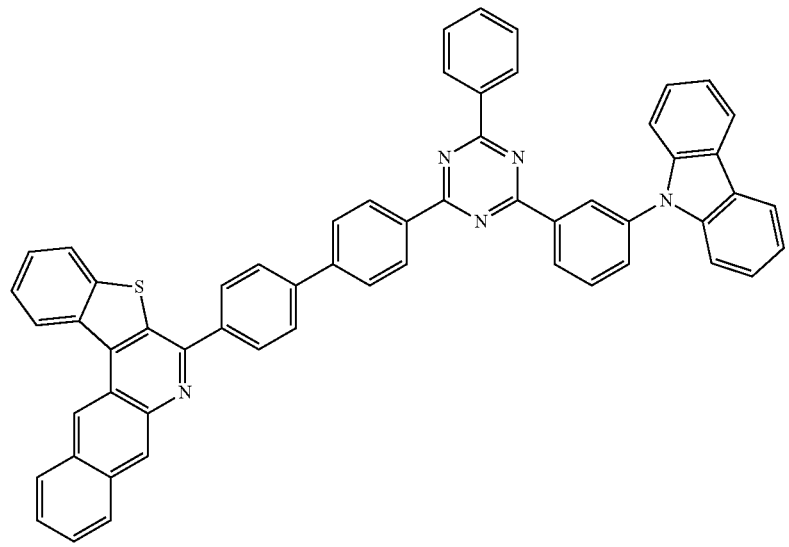
219
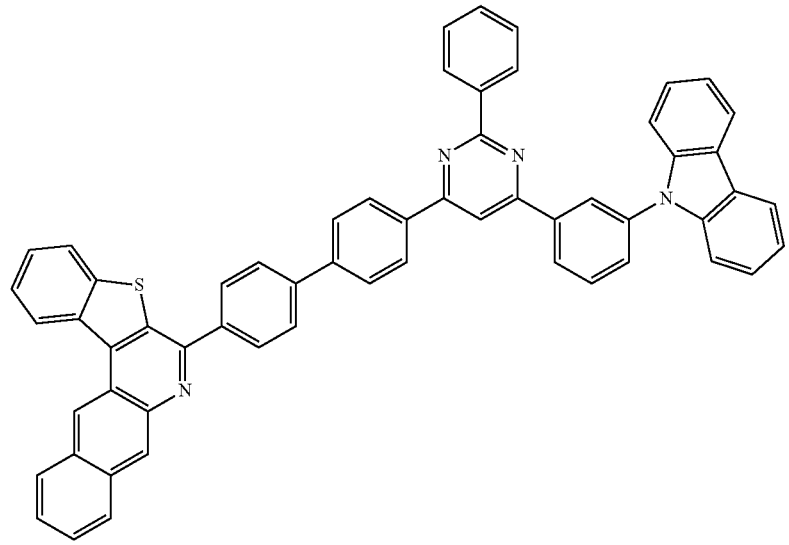
220

-continued
121
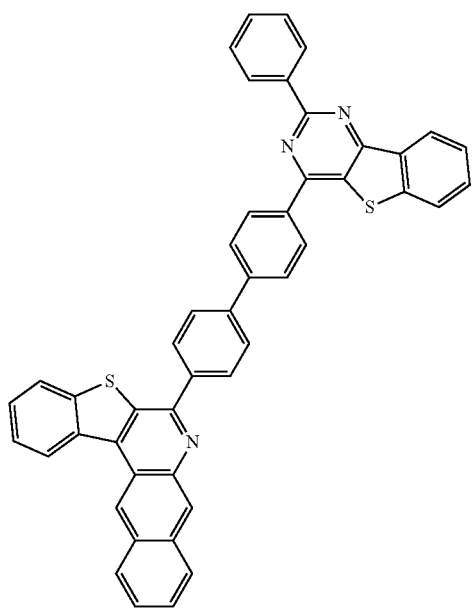
122
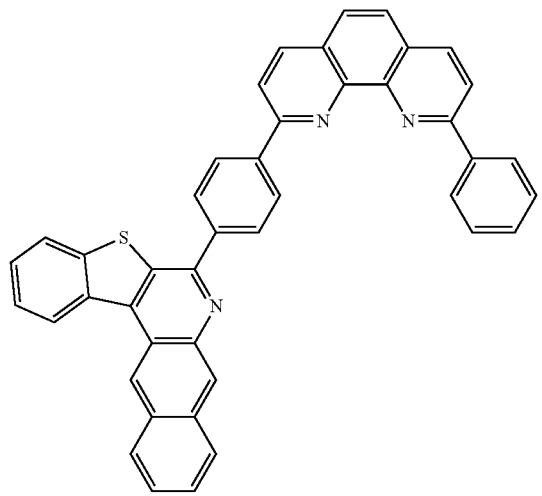
221
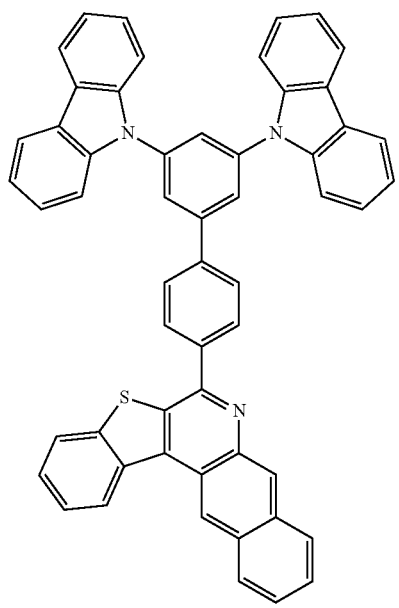
222
223
224
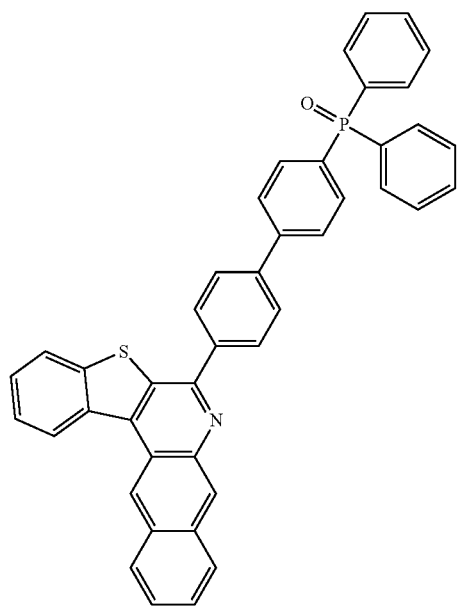

-continued
225
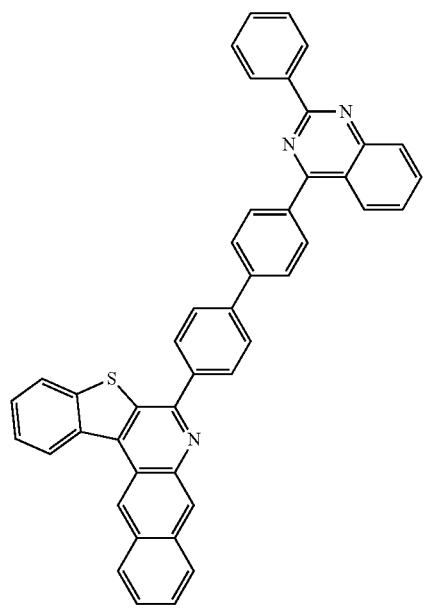
226
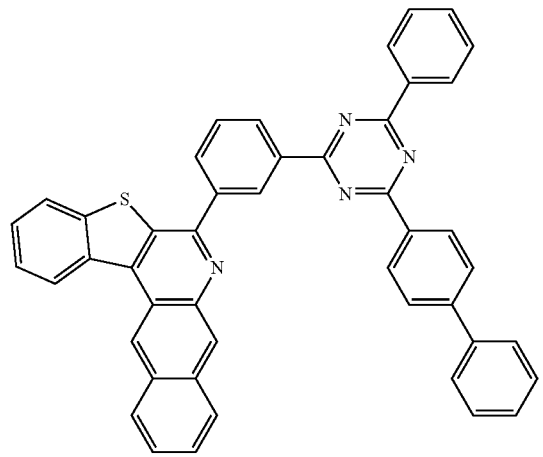
227 228
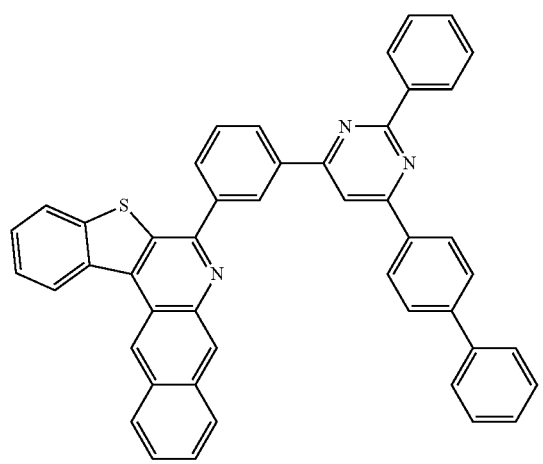
229 230
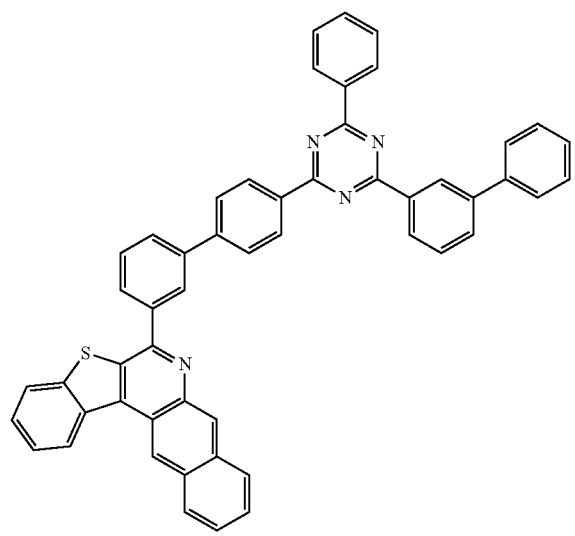

-continued
231
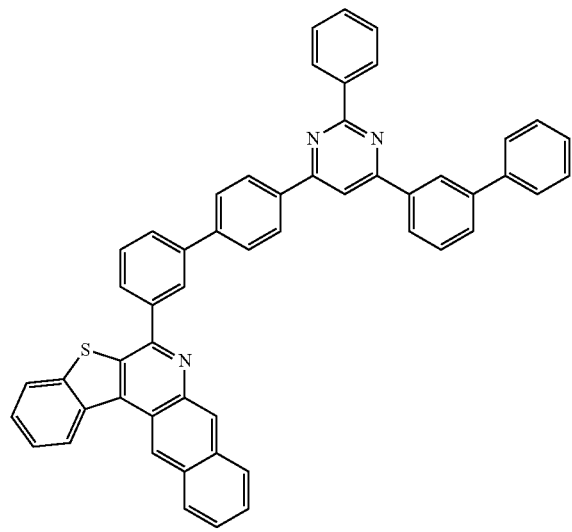
232
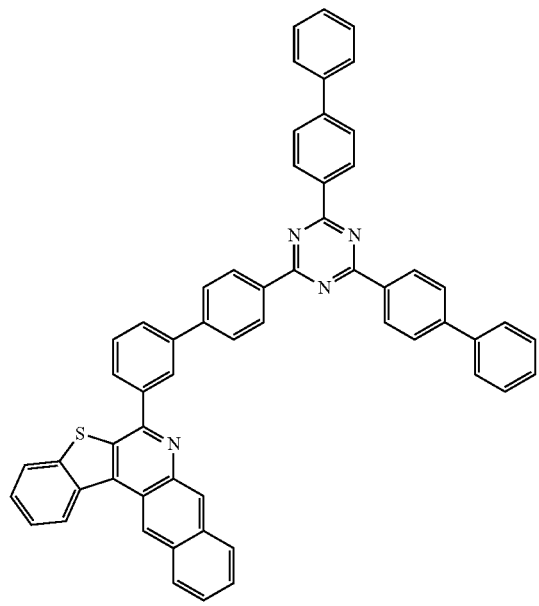
233
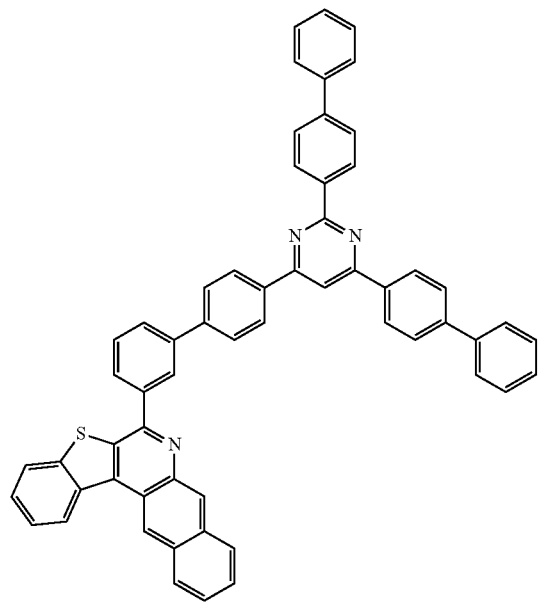
234
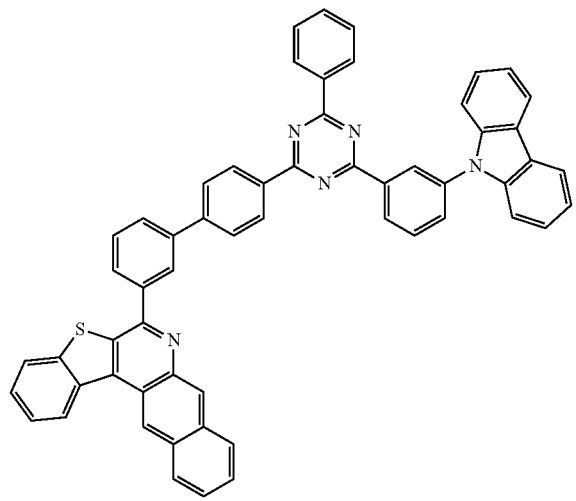

-continued
235
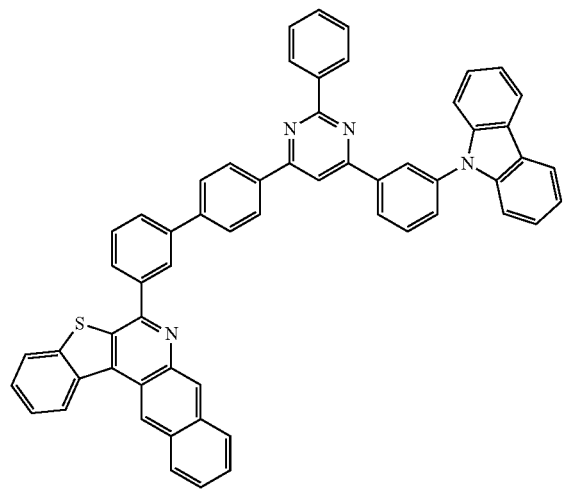
236
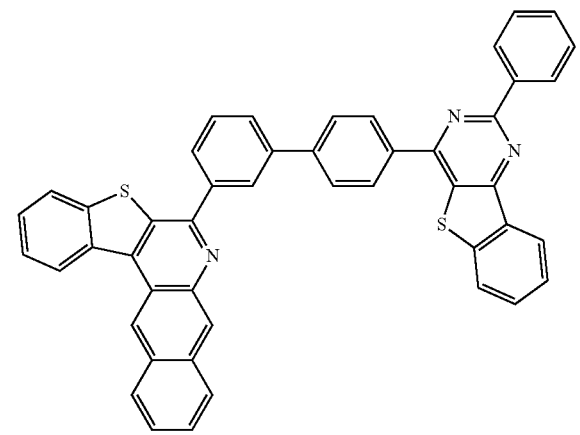
237
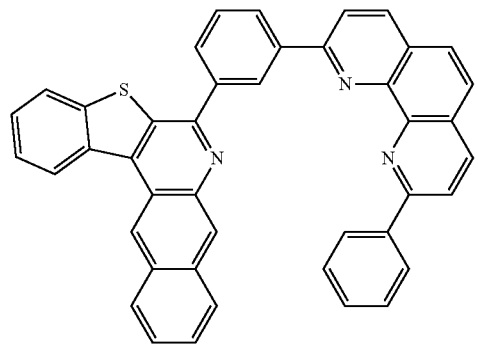
238
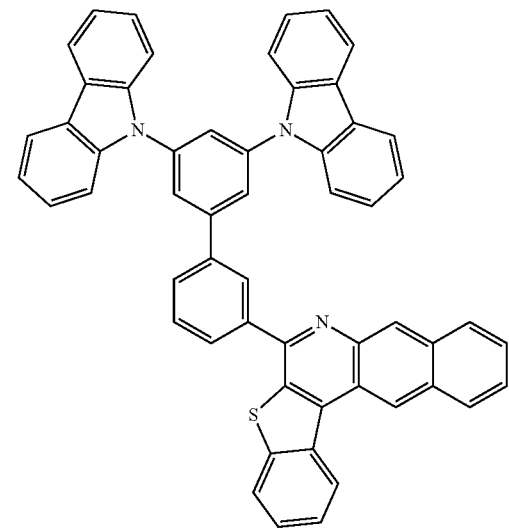
239
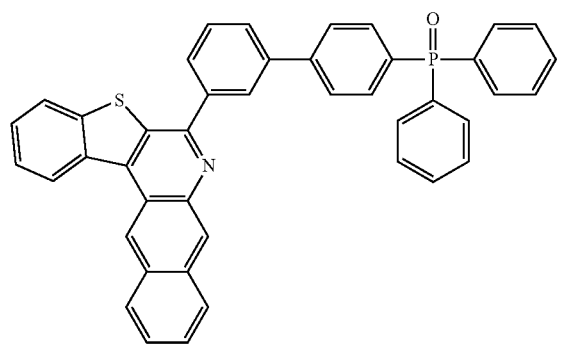
240
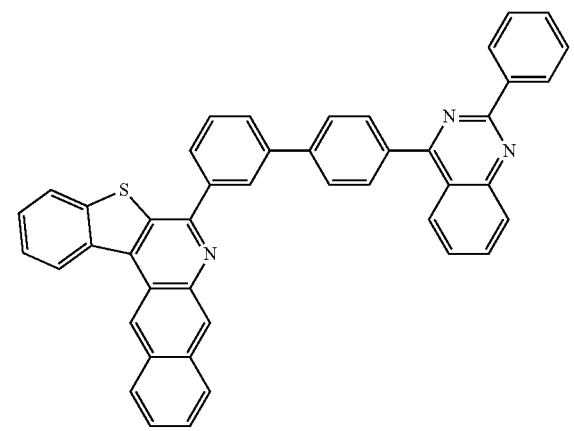

241
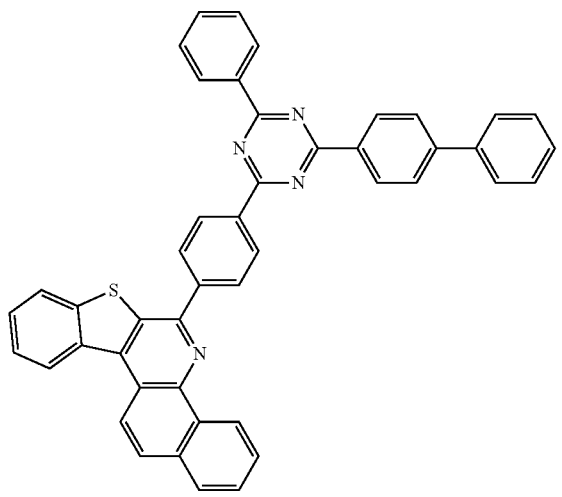
242
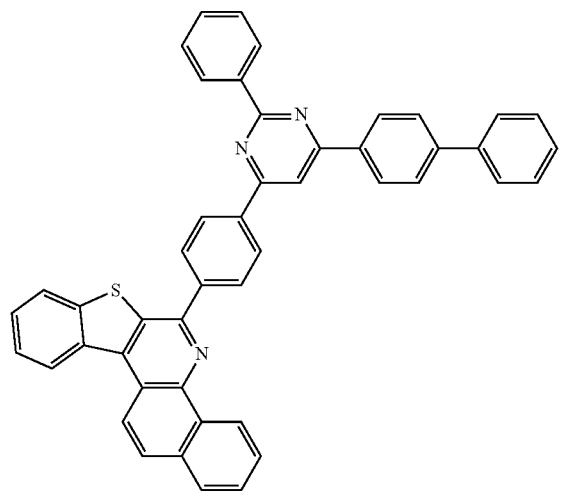
243
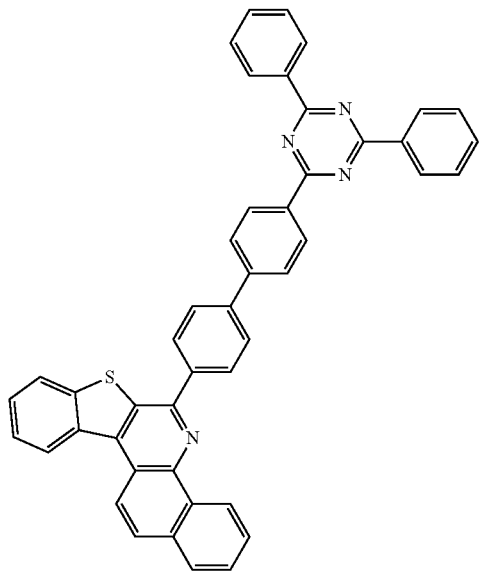
244
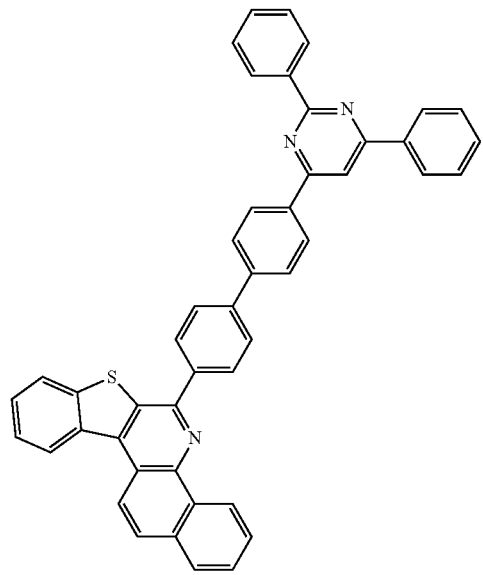
245
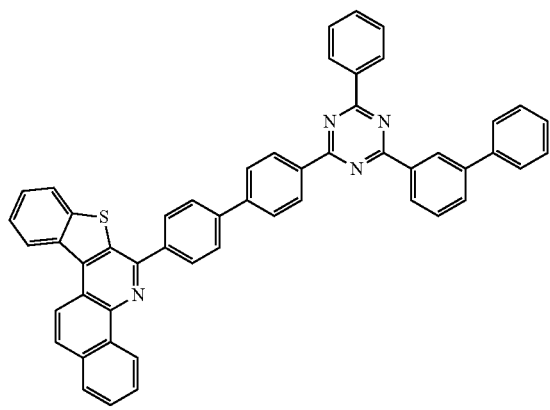
246
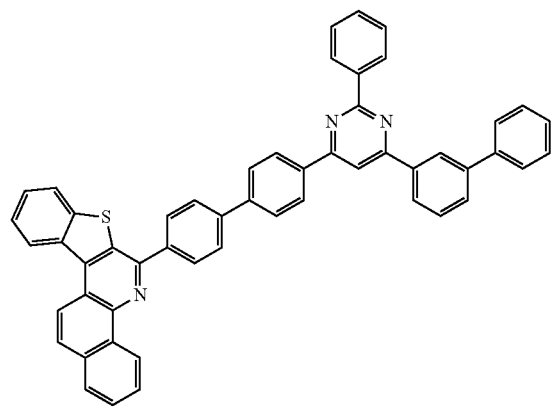

-continued
247
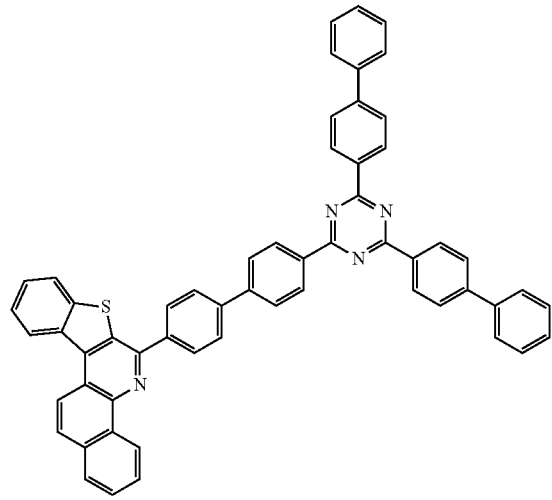
248
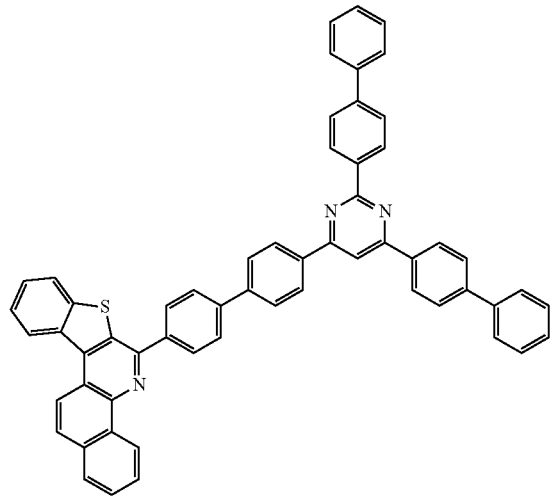
249
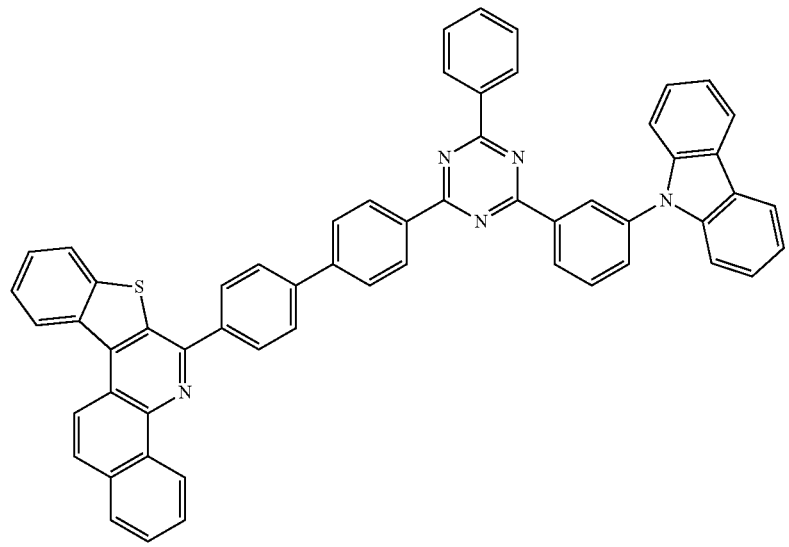
250
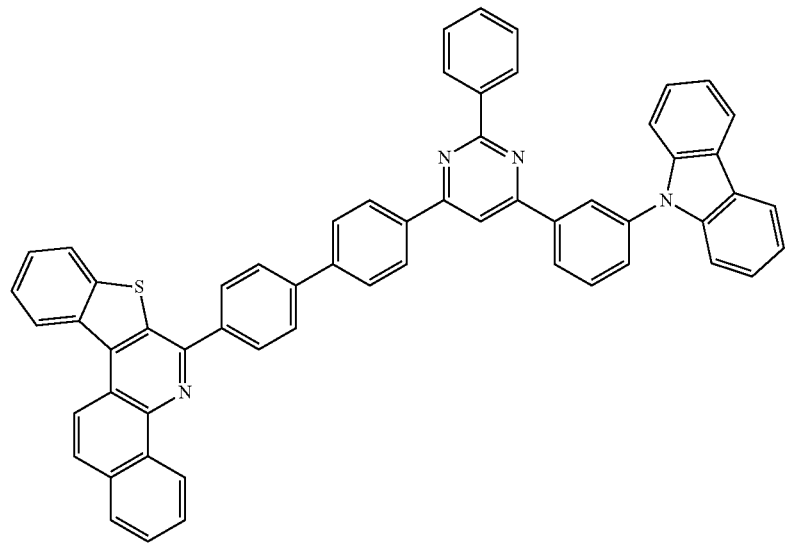

-continued
251 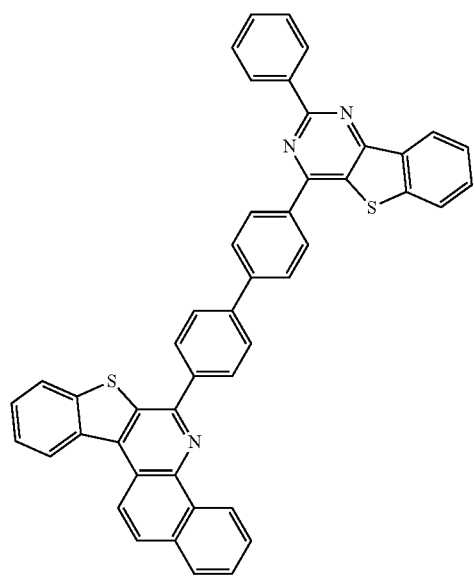
252 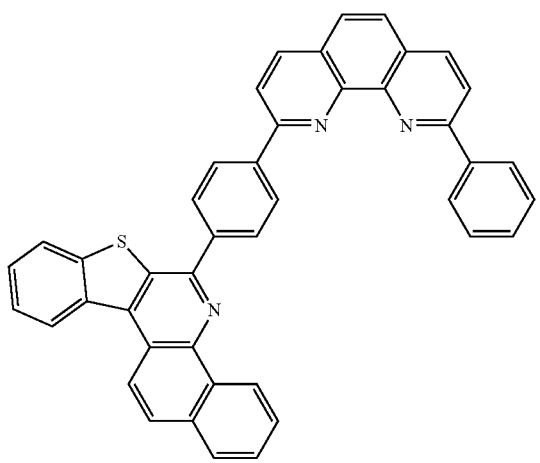
253 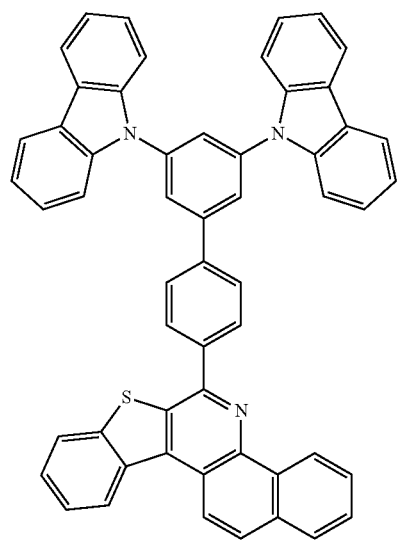
254 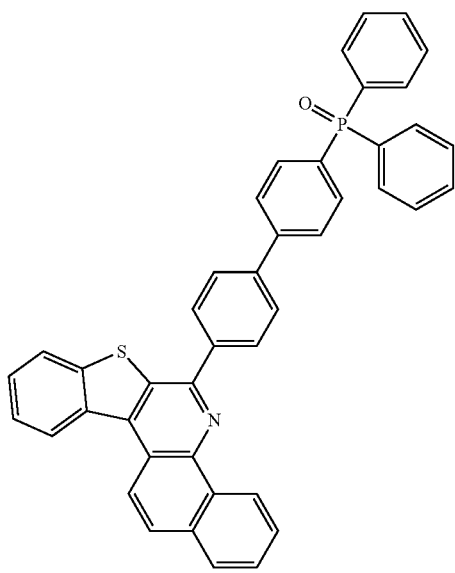

-continued
255
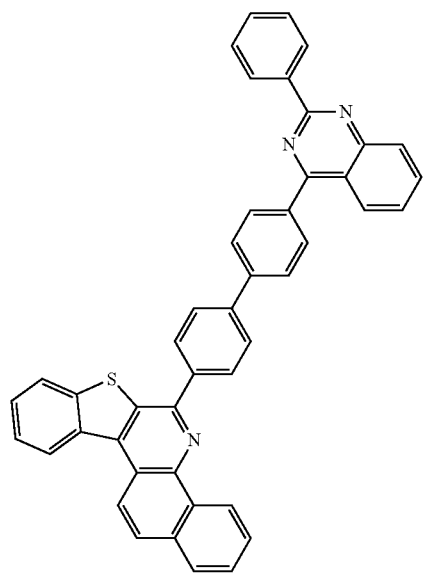
256
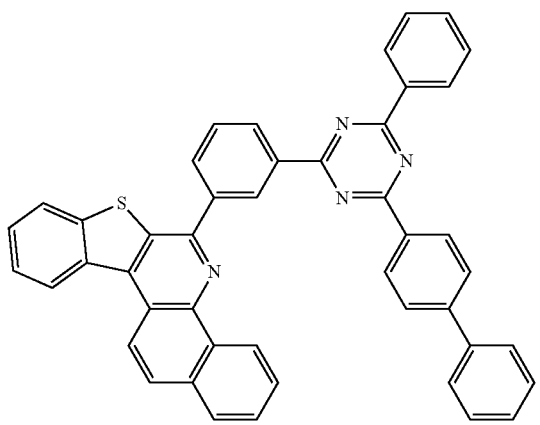
257
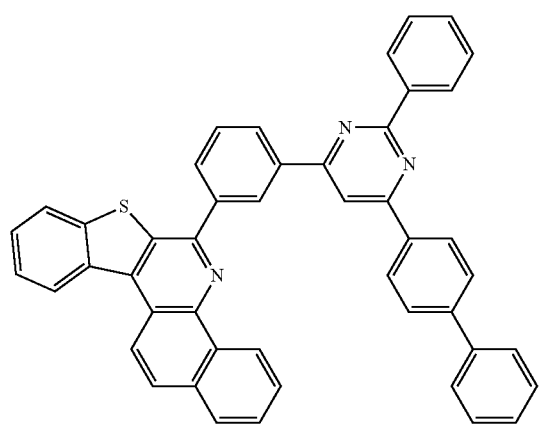
258
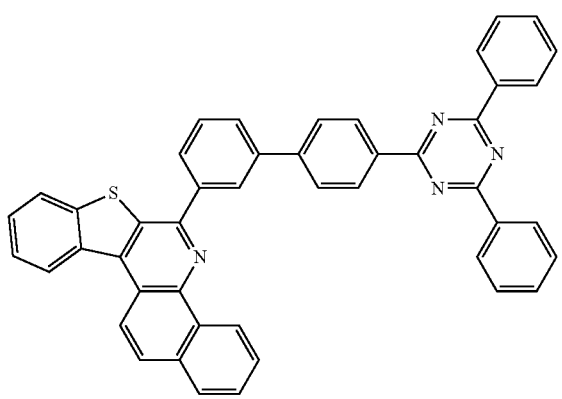
259
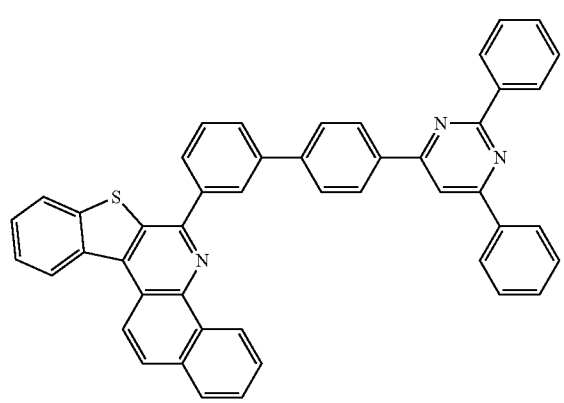
260
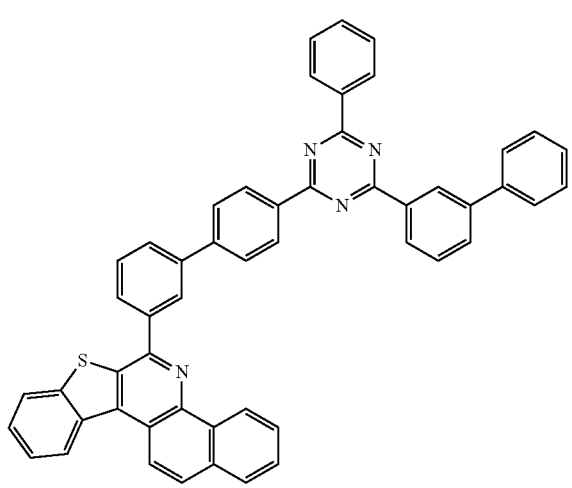

-continued
261
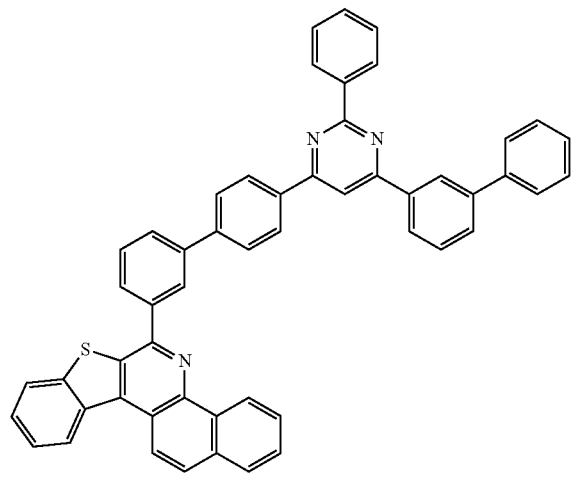
262
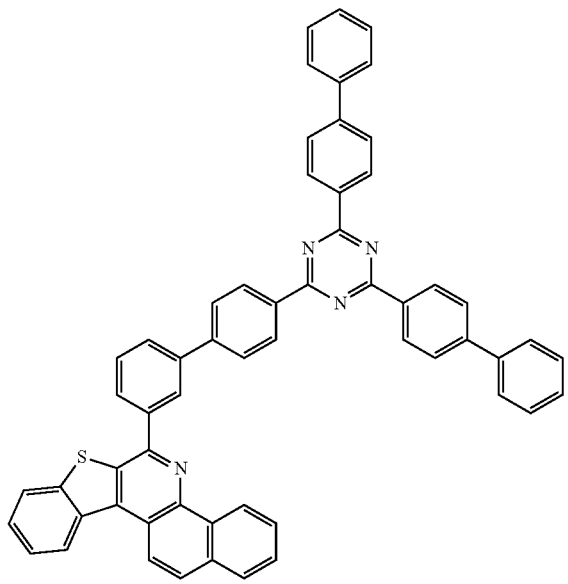
263
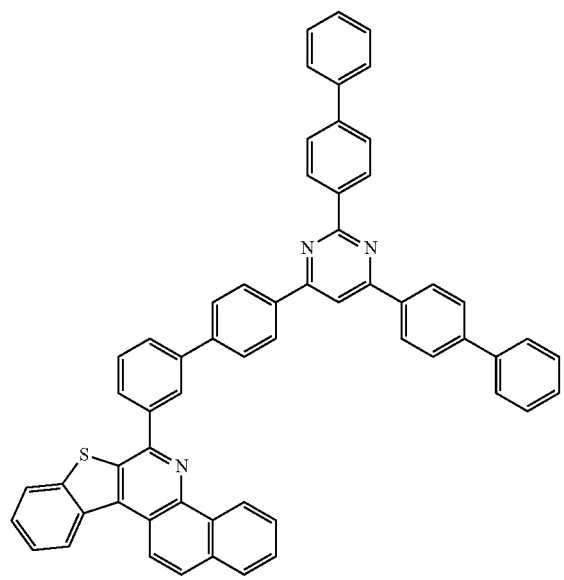
264
265
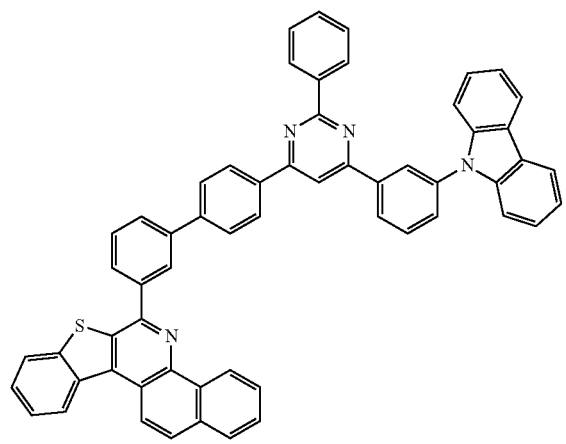
266
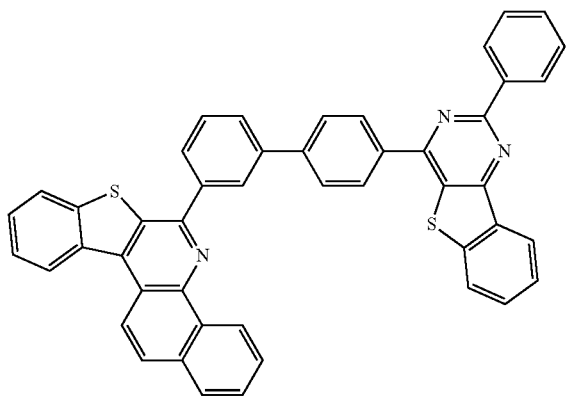

-continued
267
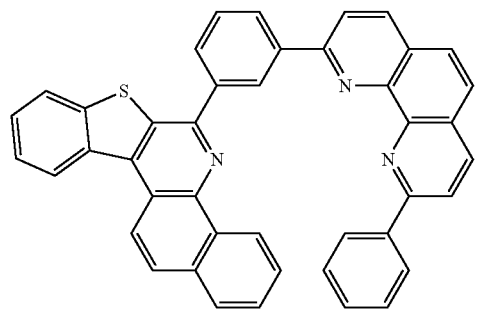
268
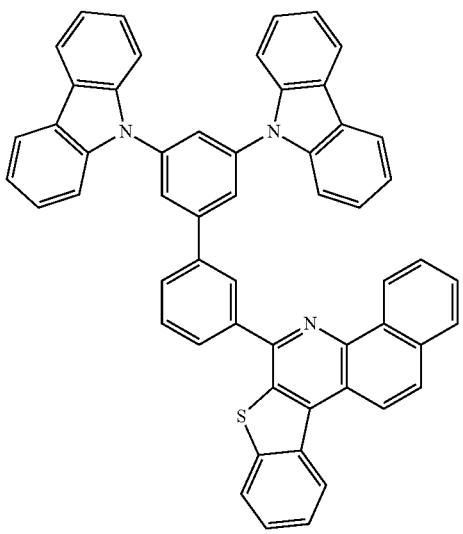
269
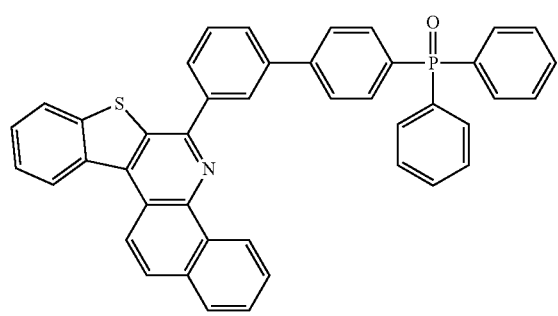
270
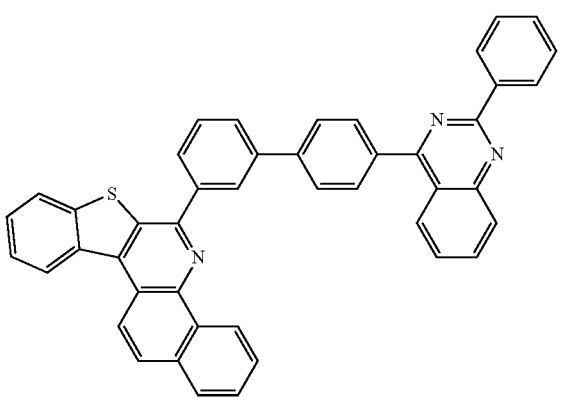
271
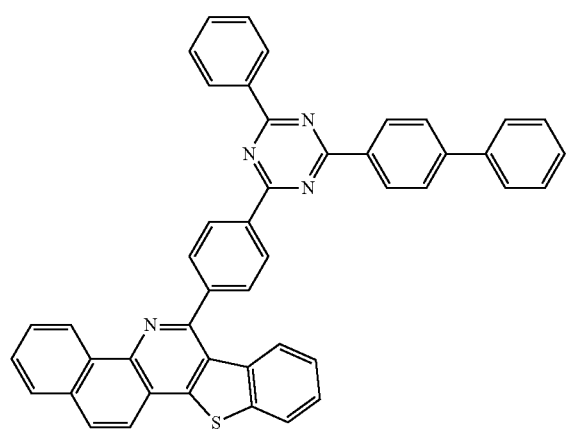
272
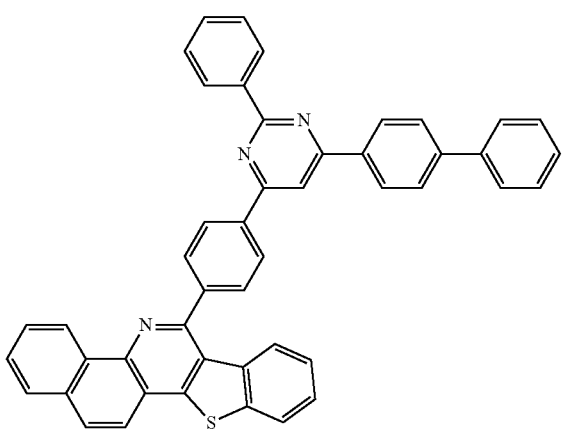

-continued
273
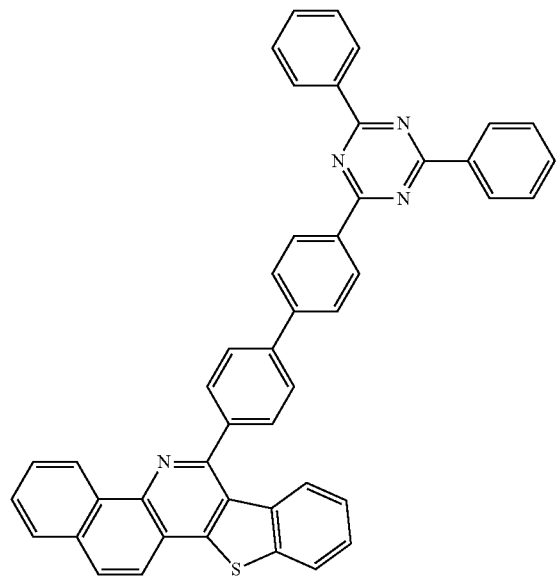
274
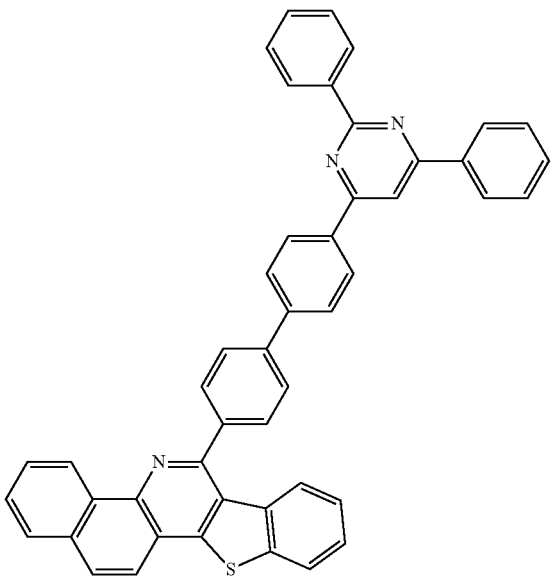
275
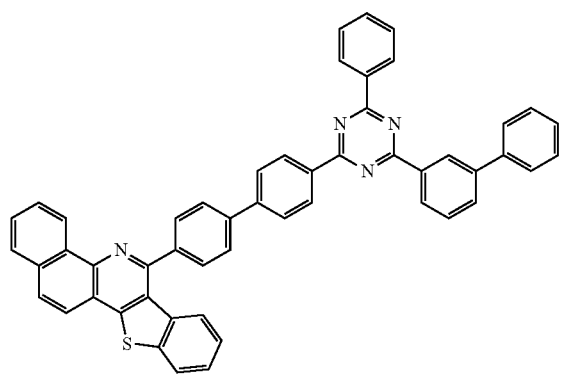
276
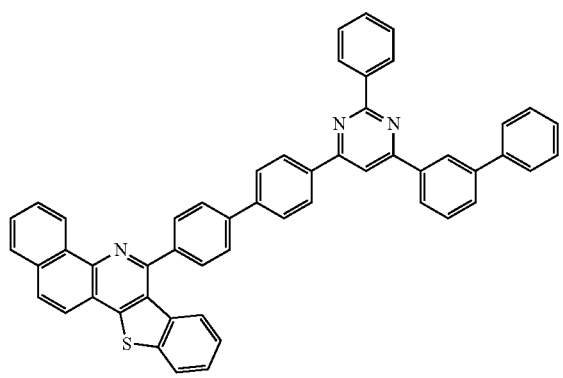
277
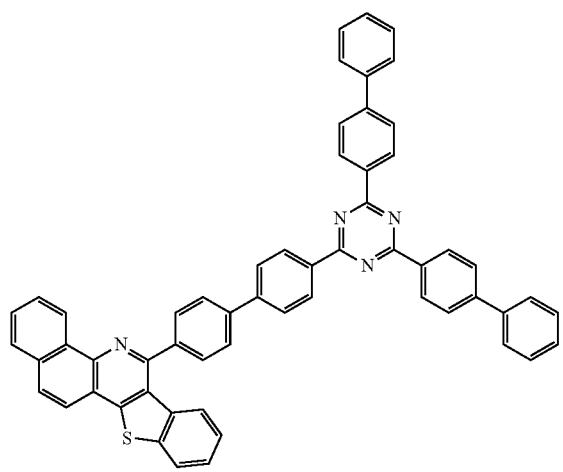
278
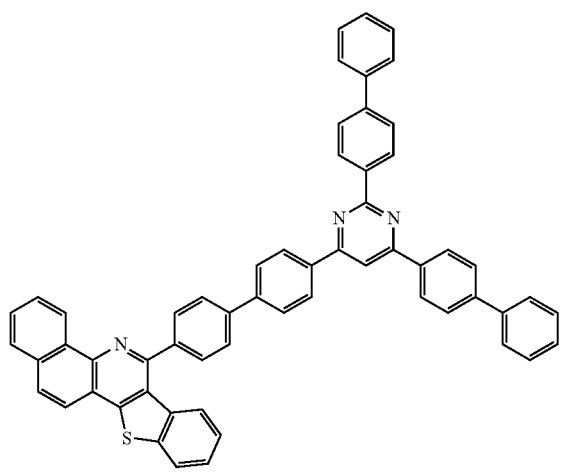

279
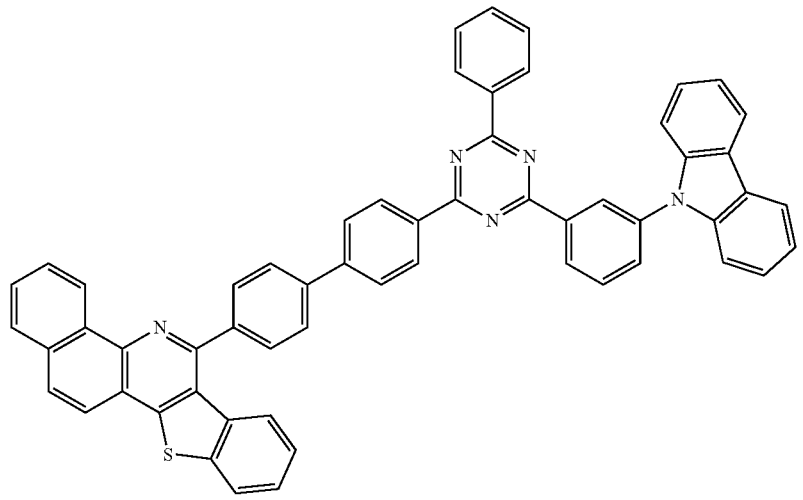
280
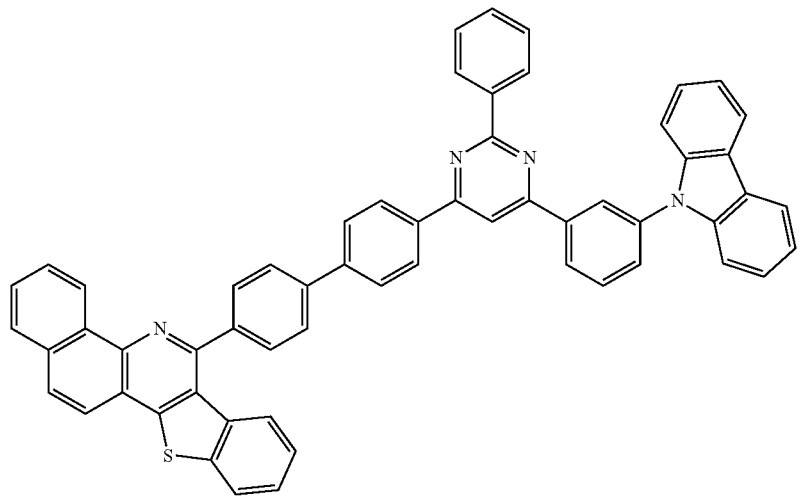
281
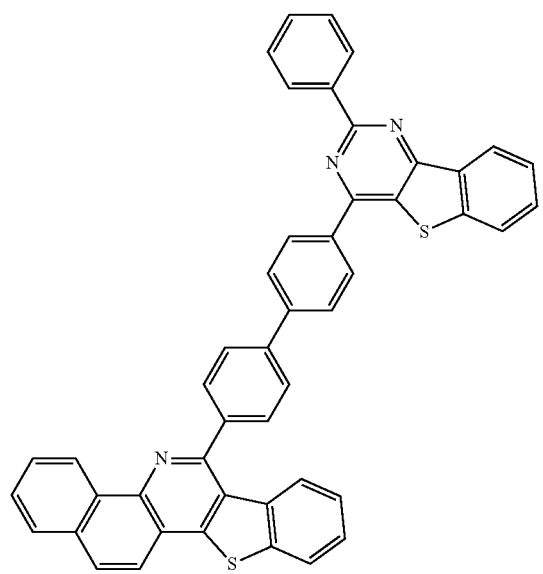
282
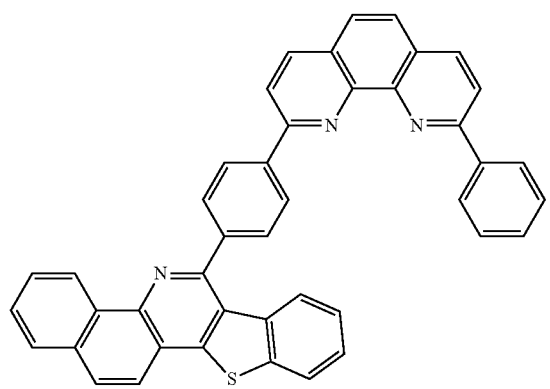

-continued
283
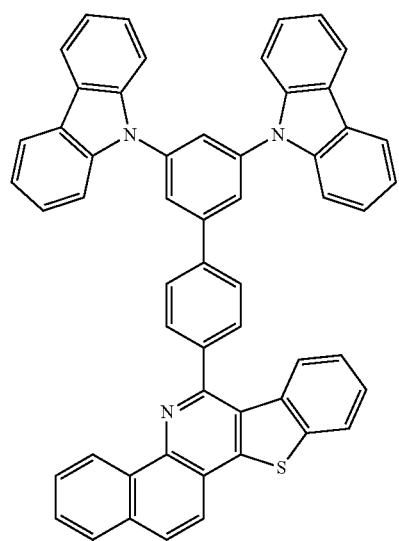
284
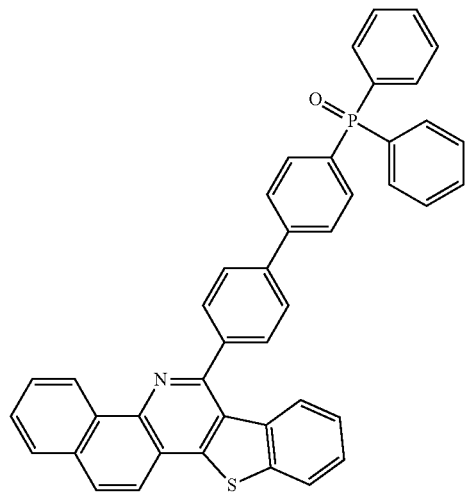
285
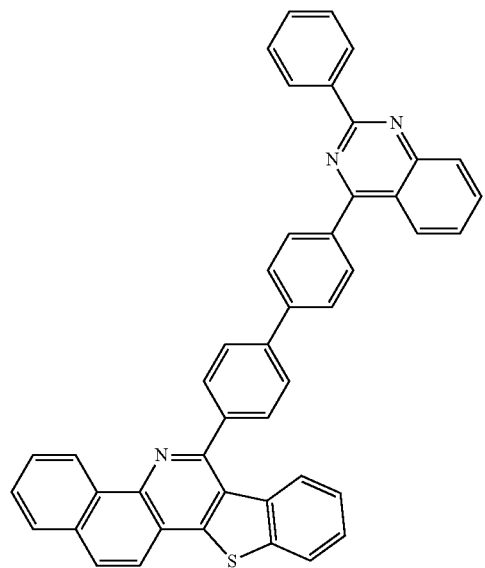
286
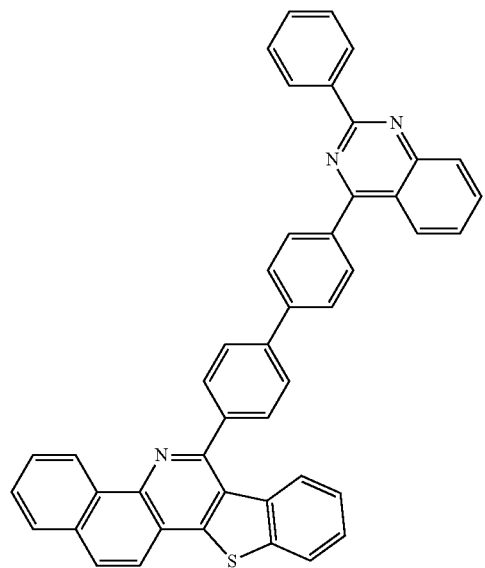
287
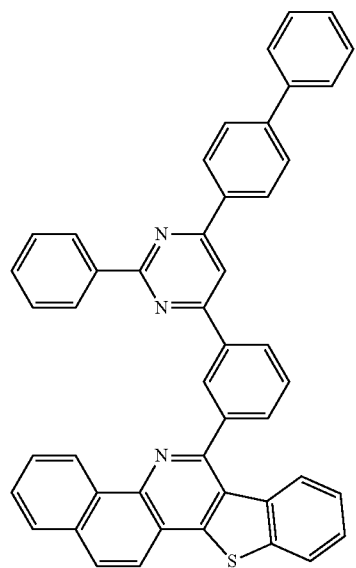
288
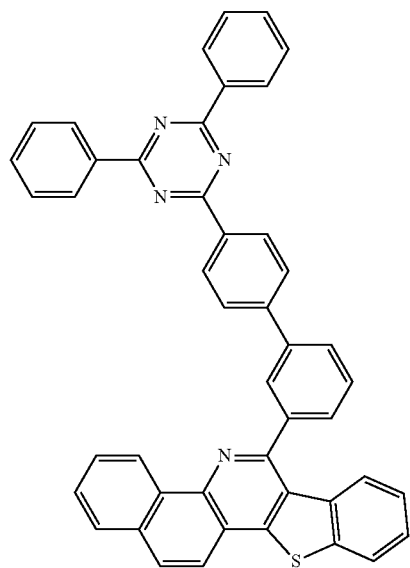

289
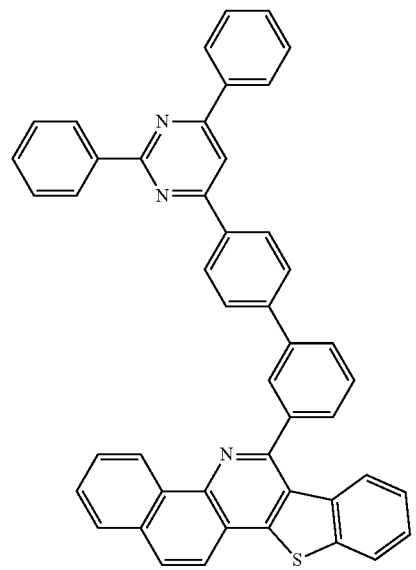
290
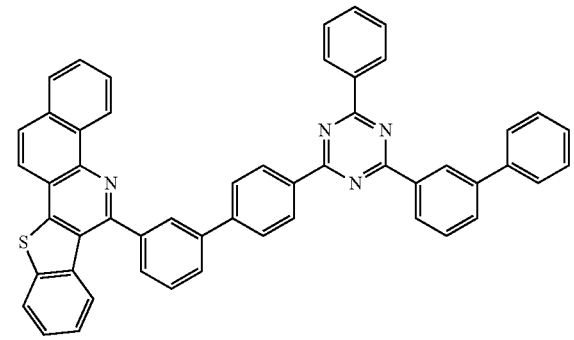
291
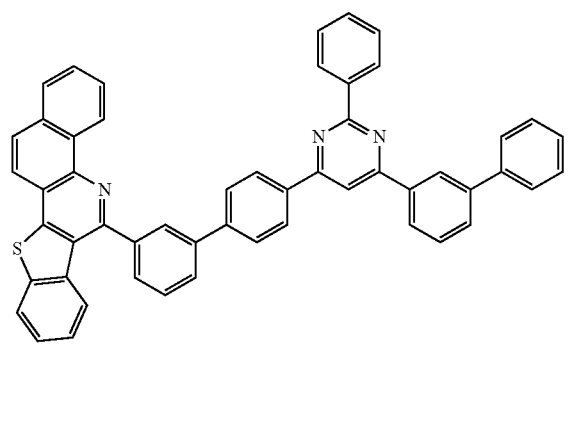
292
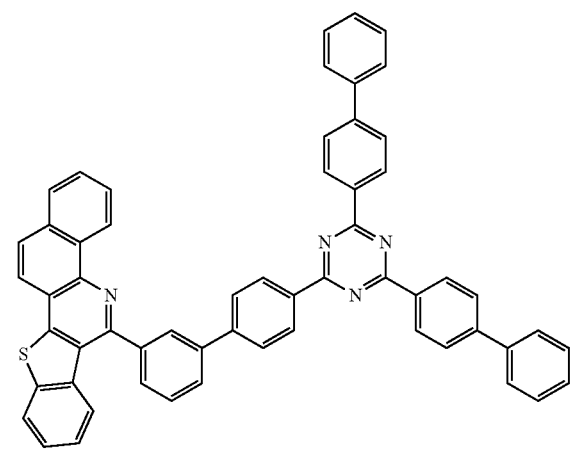
293
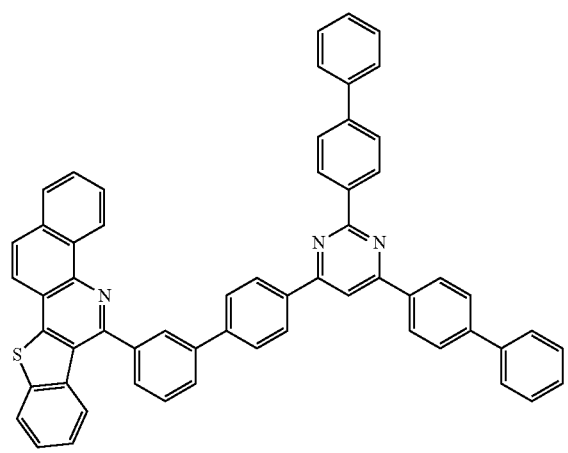
294
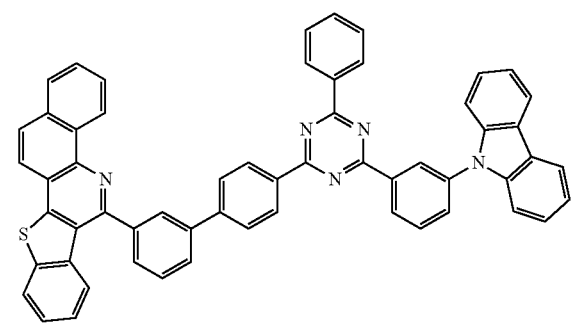

-continued
295
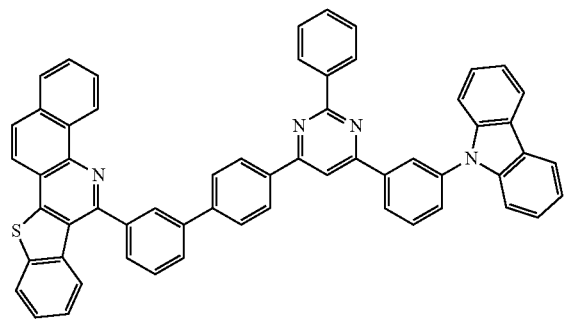
296
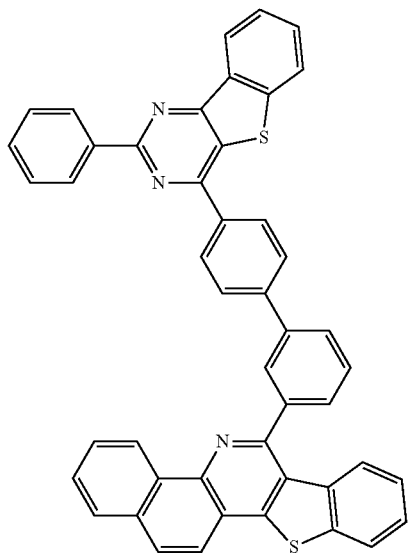
297
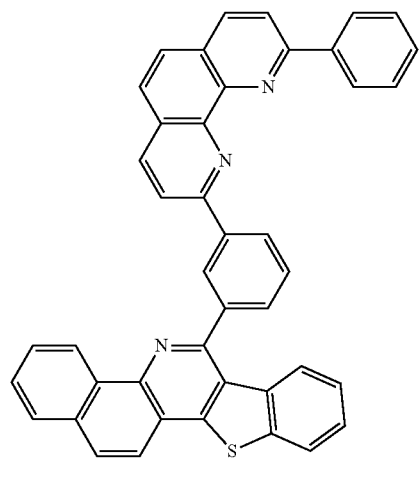
298
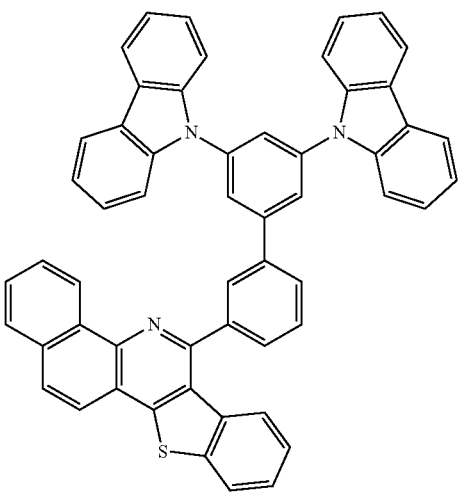
299
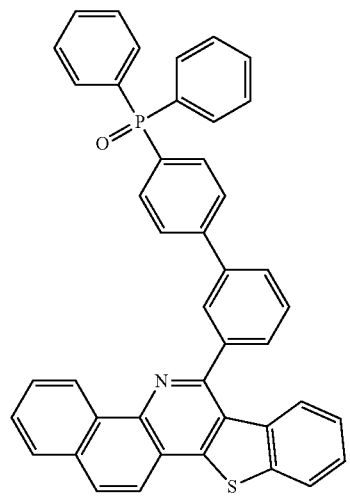
300
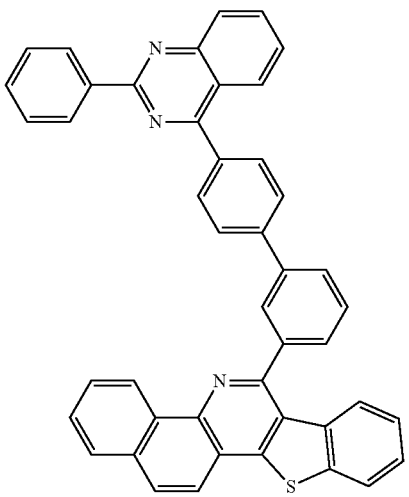

-continued
301
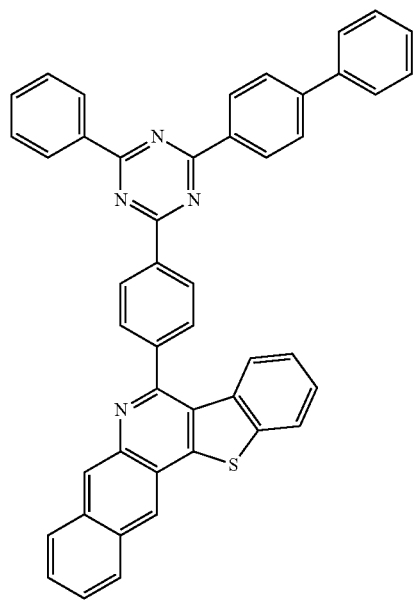
302
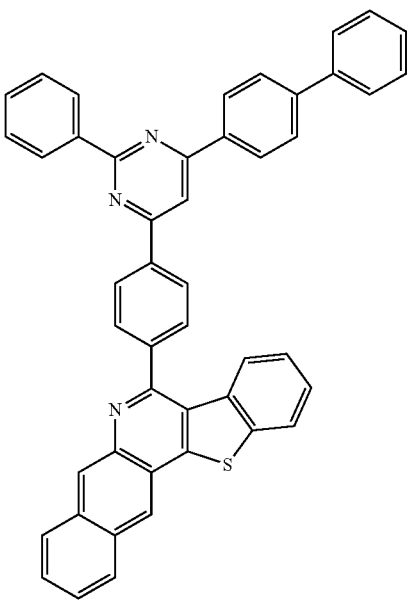
303
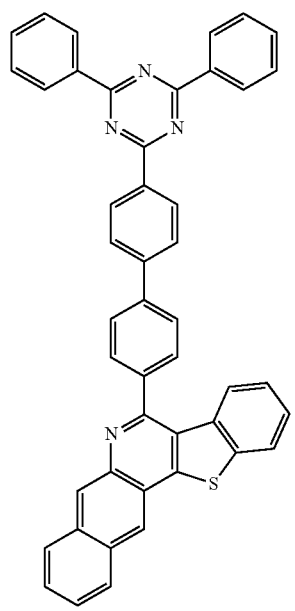
304
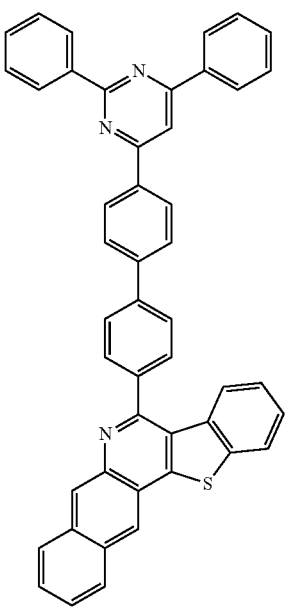

305
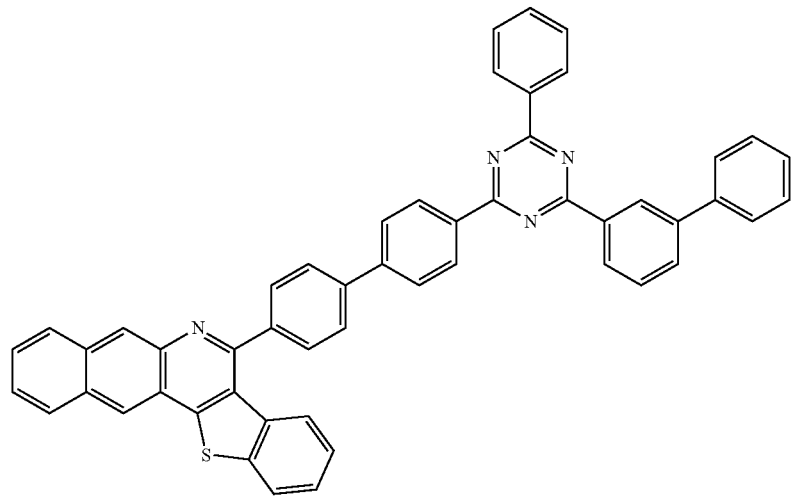
306
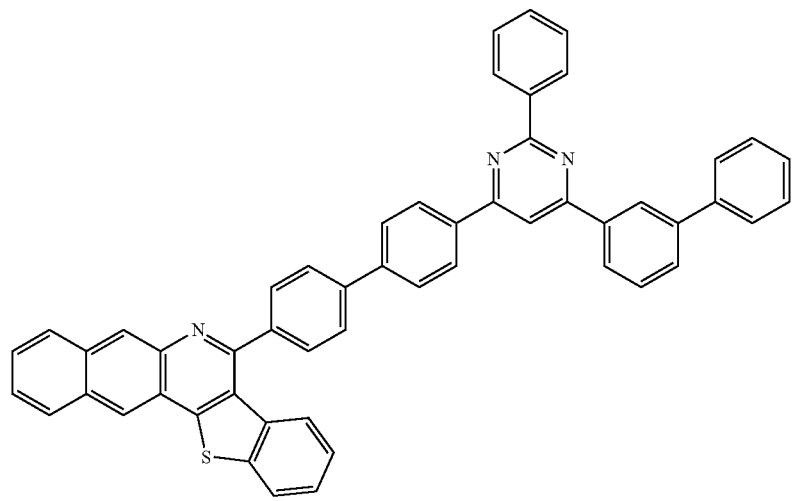
307
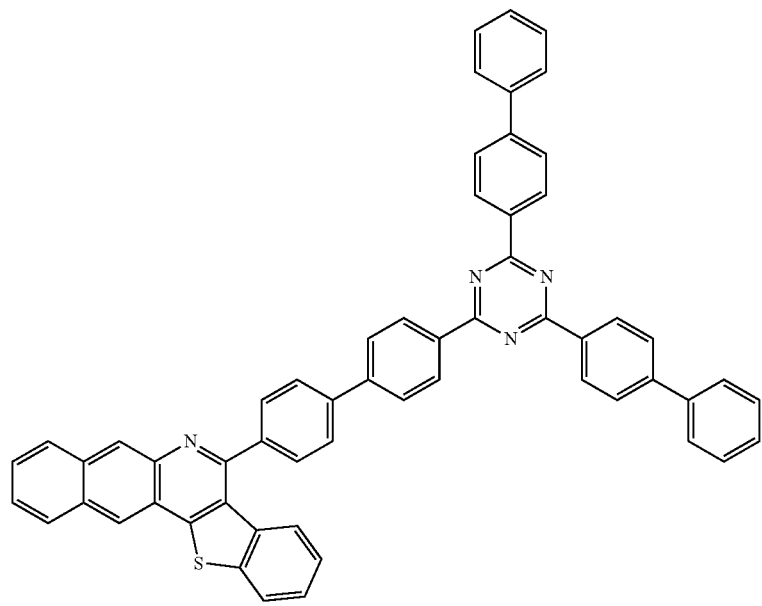

308
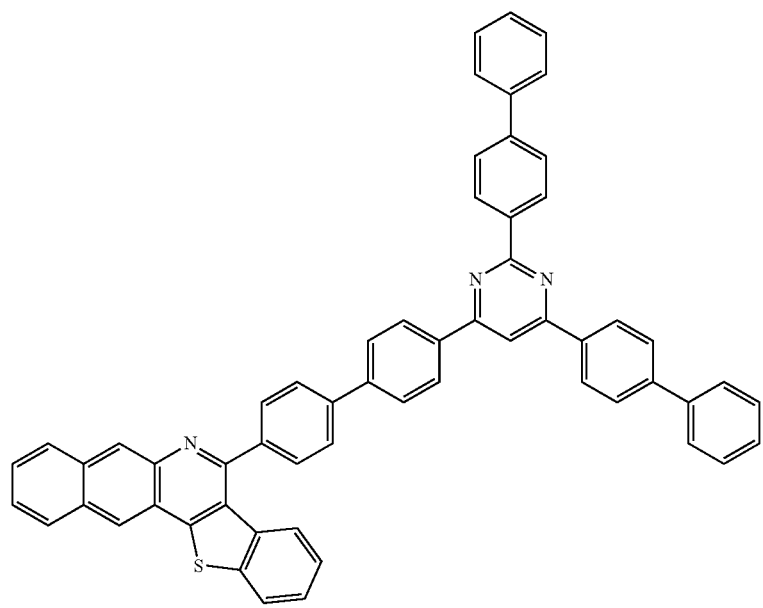
309
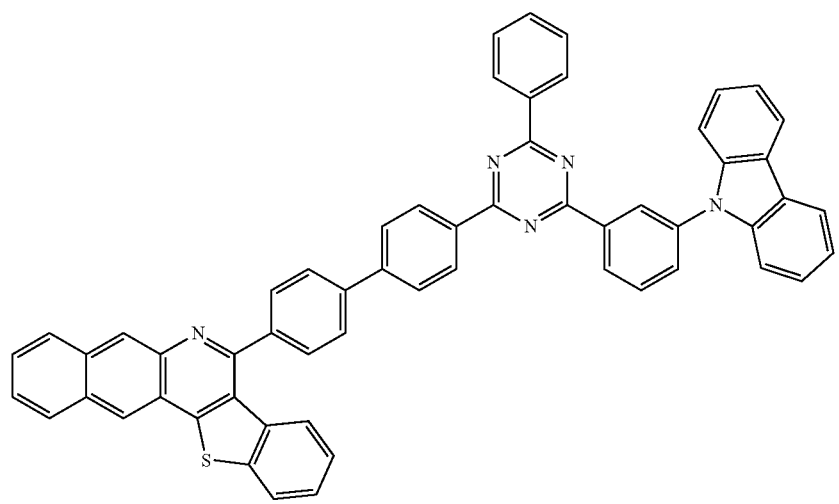
310
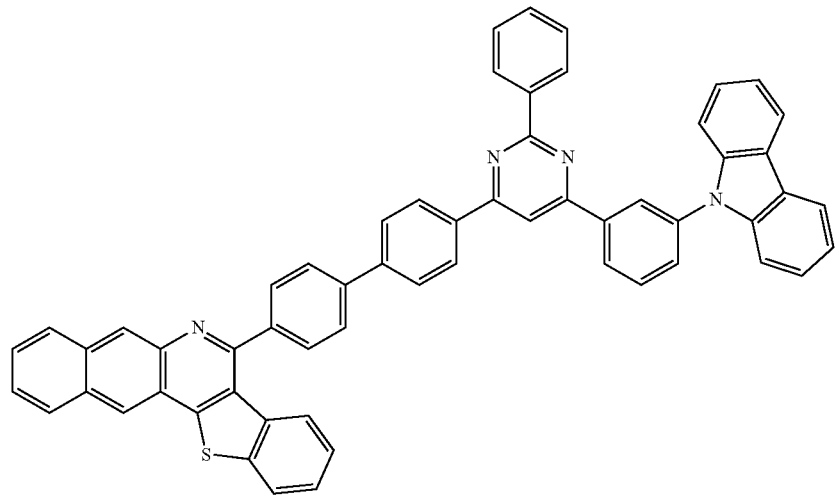

-continued
311 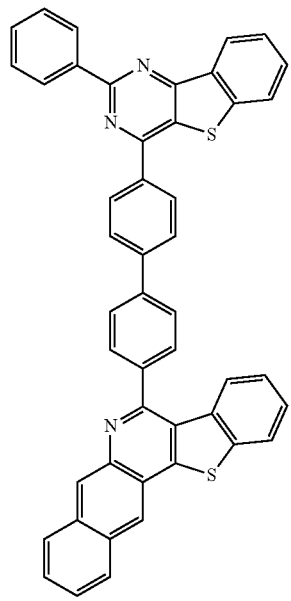 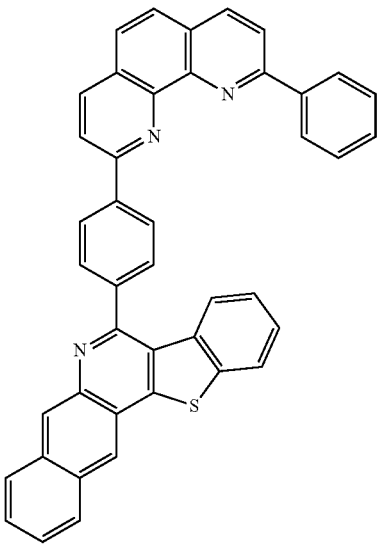 312
313 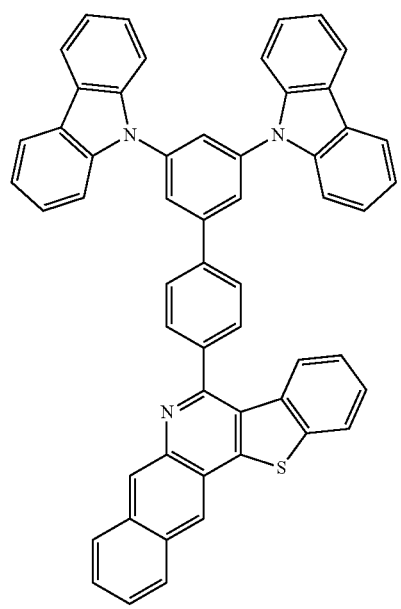 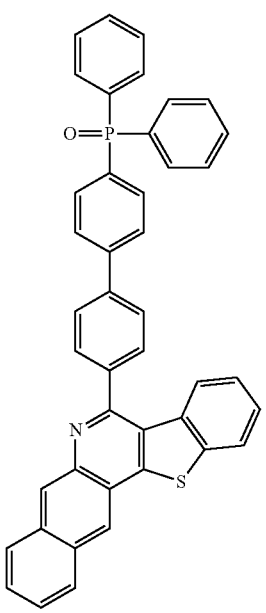 314

-continued
315 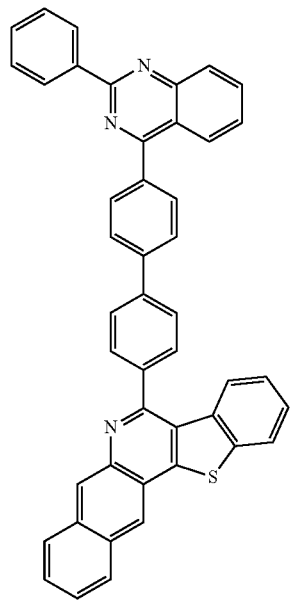
316 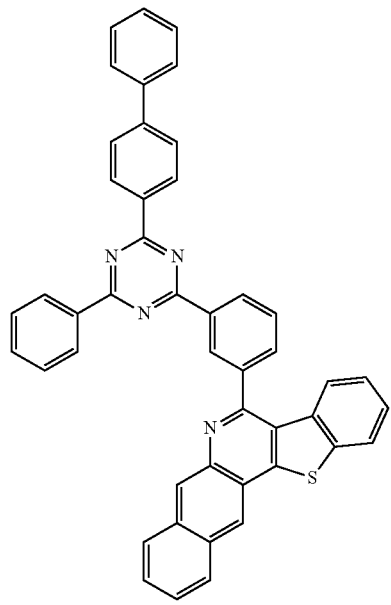
317 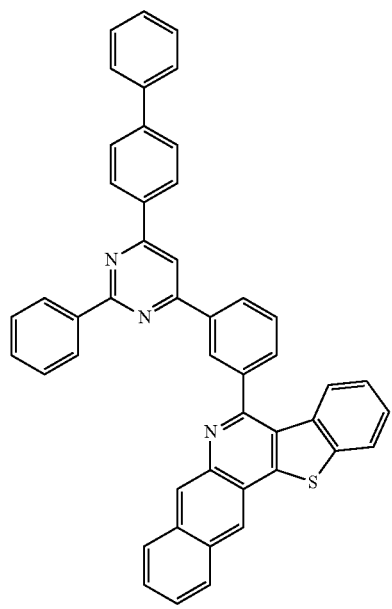
318 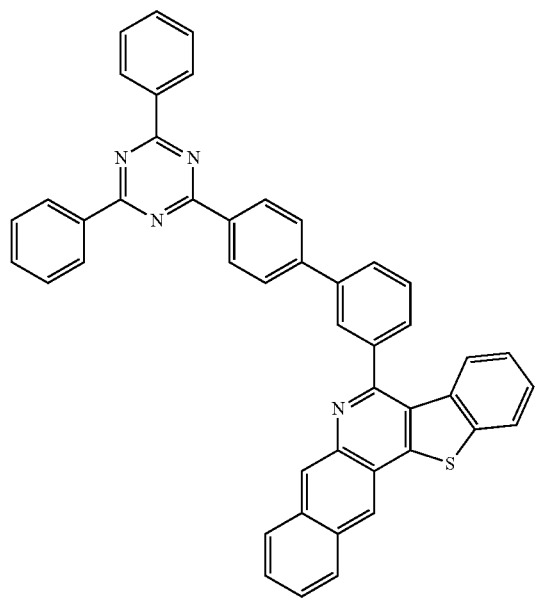

-continued
319
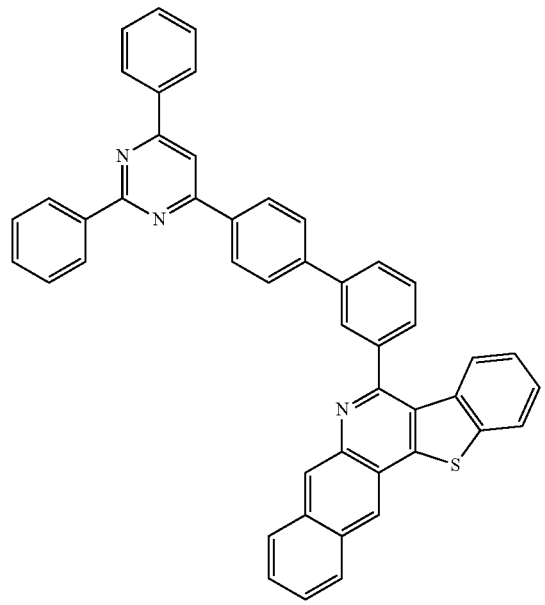
320
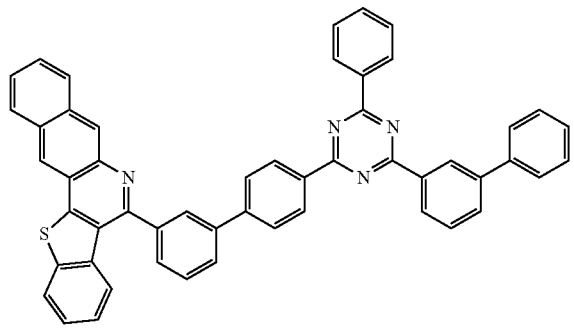
321
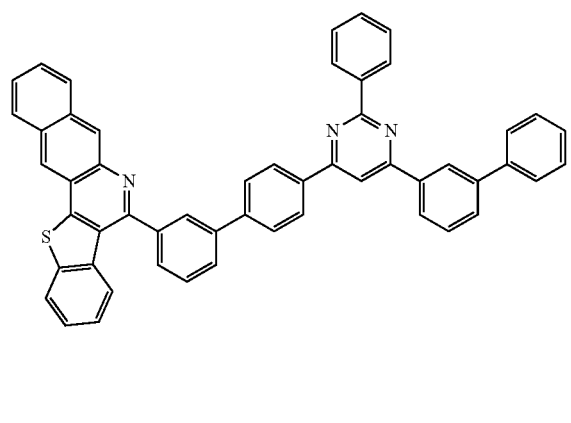
322
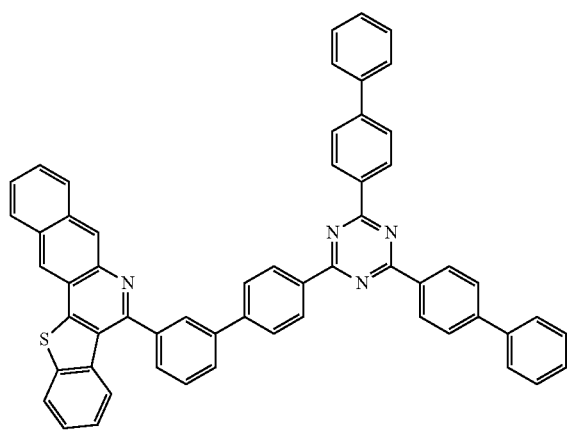
323
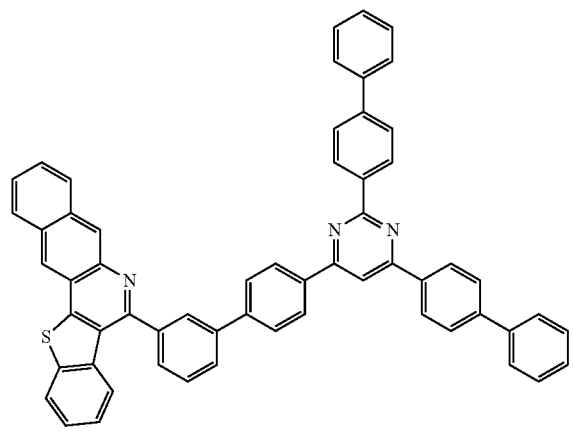
324
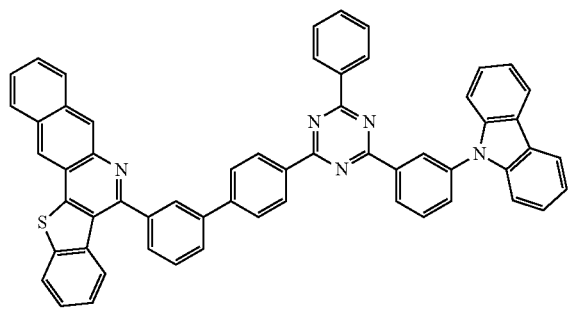

-continued
325 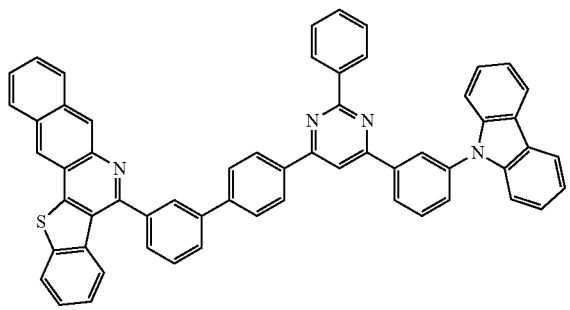
326 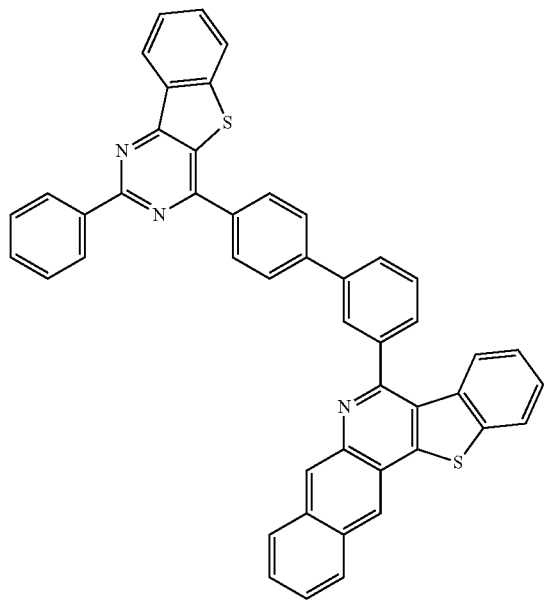
327 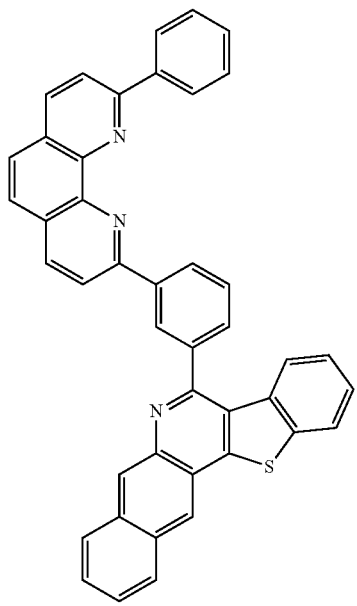
328 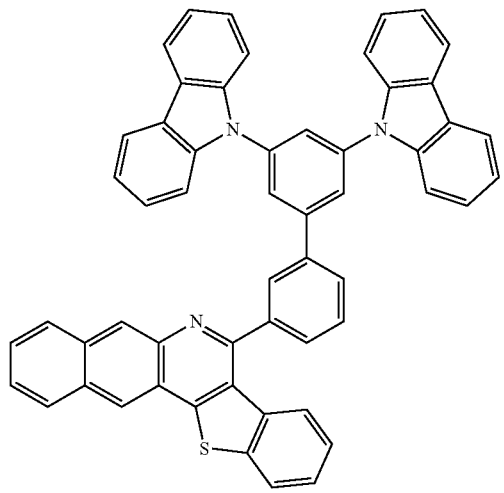

-continued
329
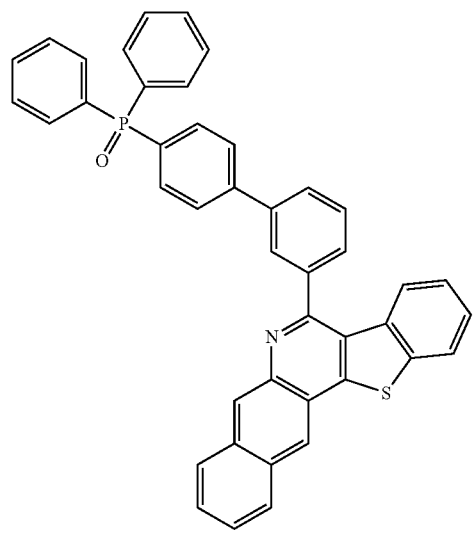
330
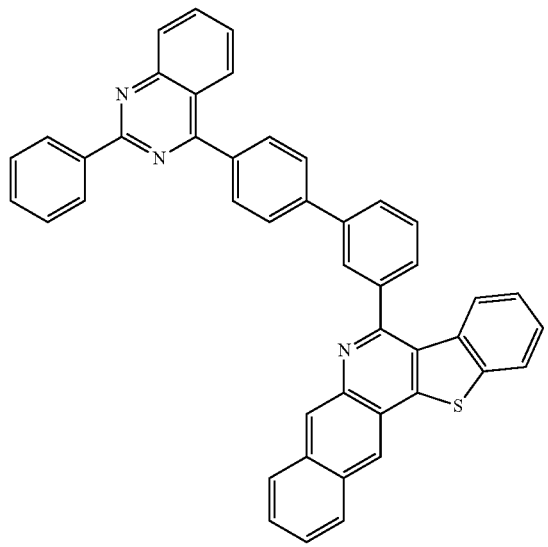
331
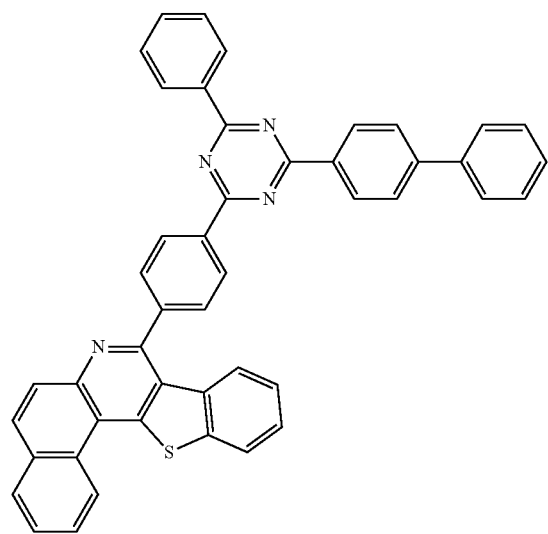
332
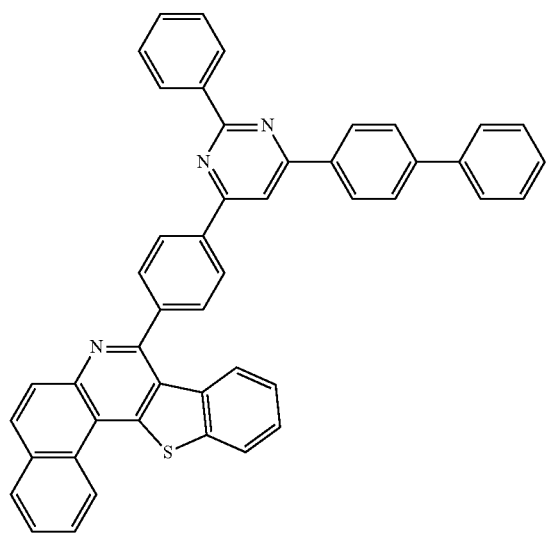

-continued
333
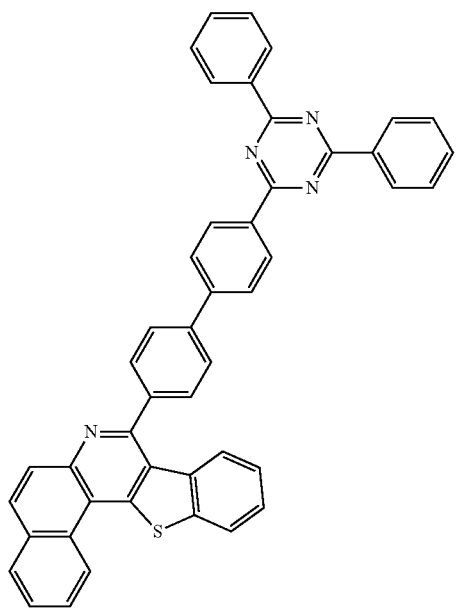
334
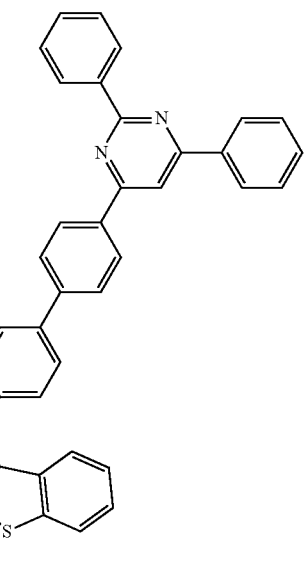
335
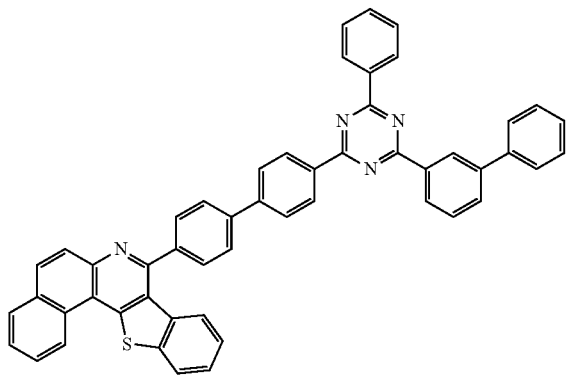
336
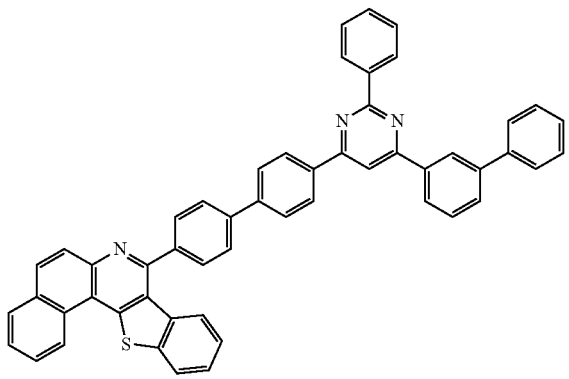
337
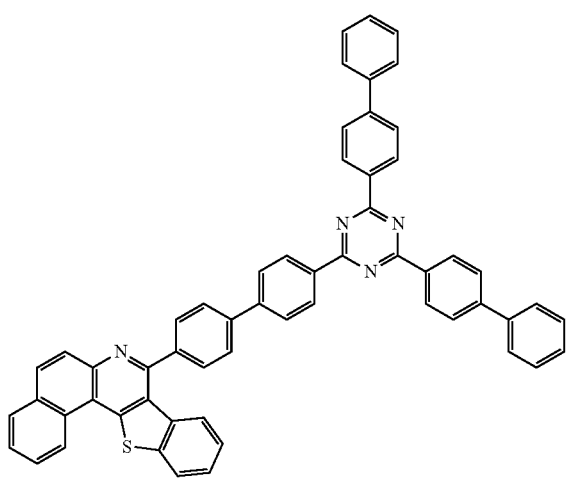
338
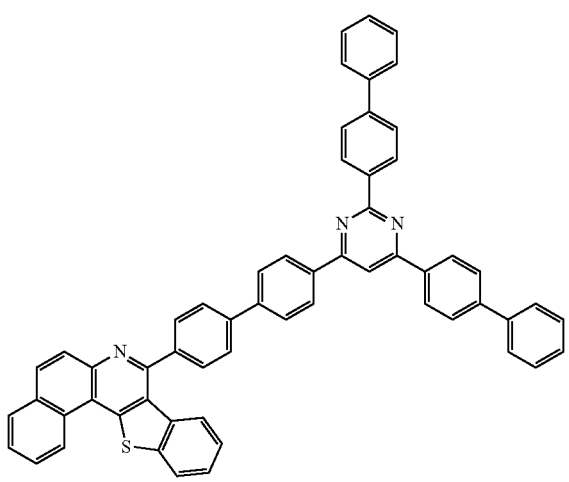

339
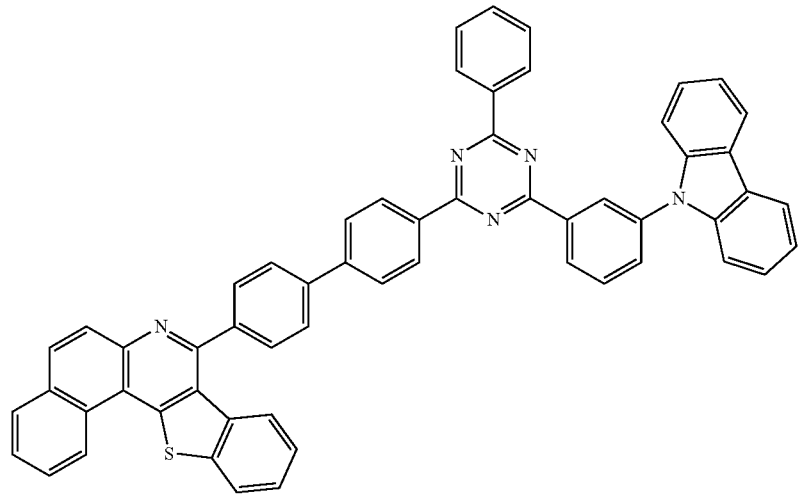
340
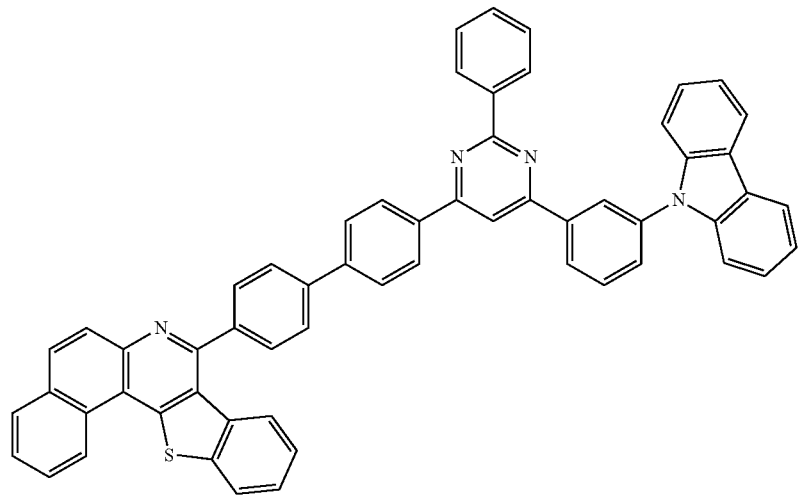
341
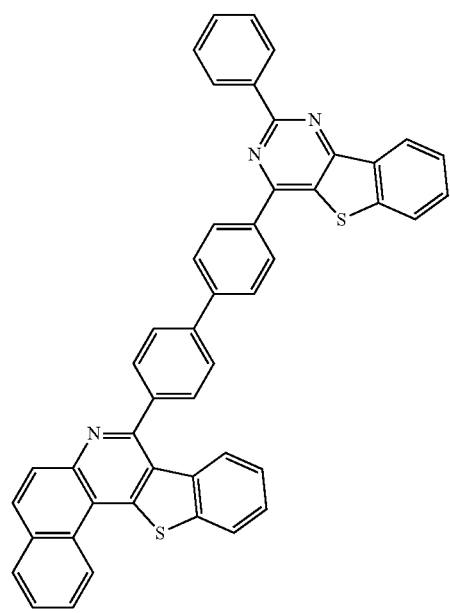
342
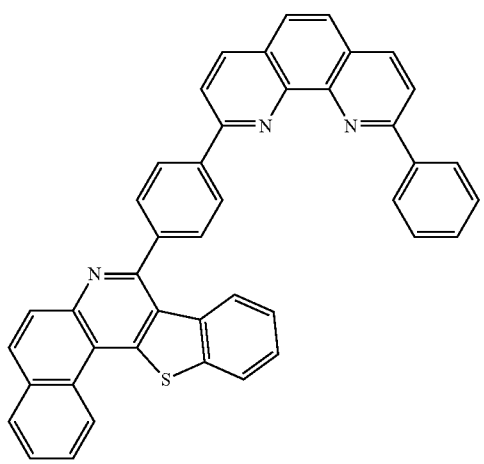

171
172
-continued
343 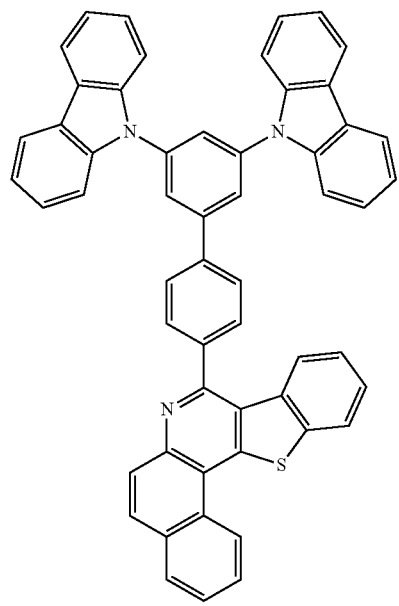 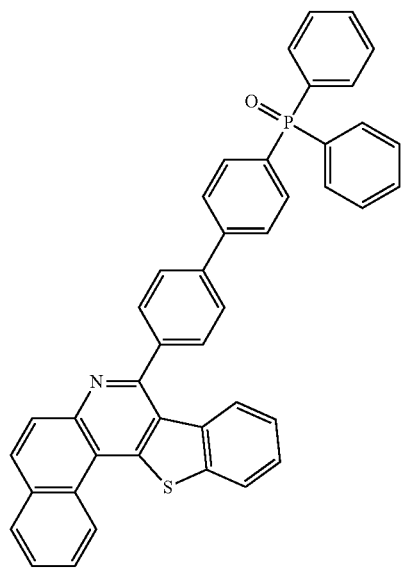 344
345 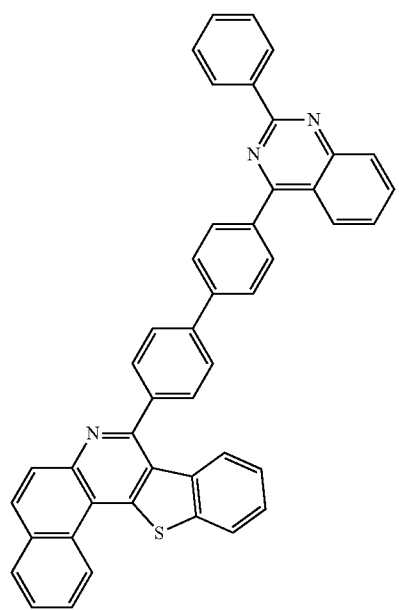 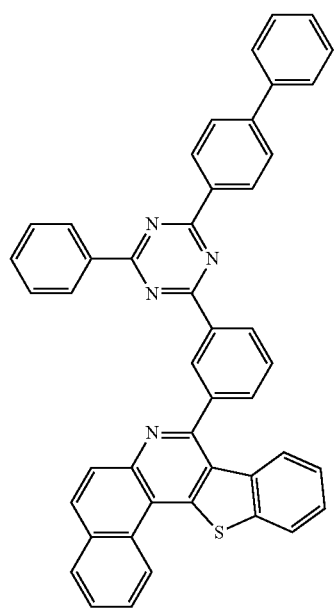 346

-continued
347
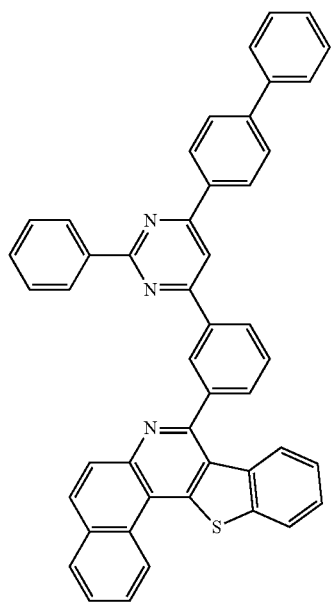
348
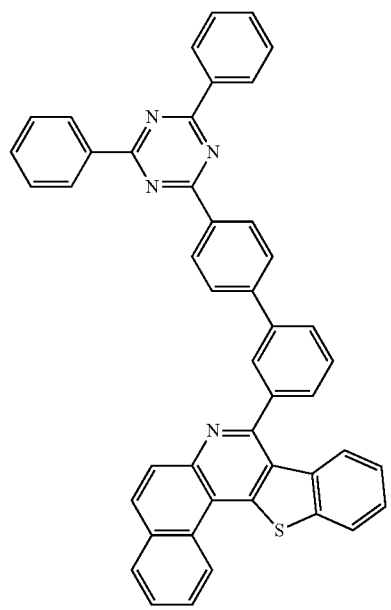
349
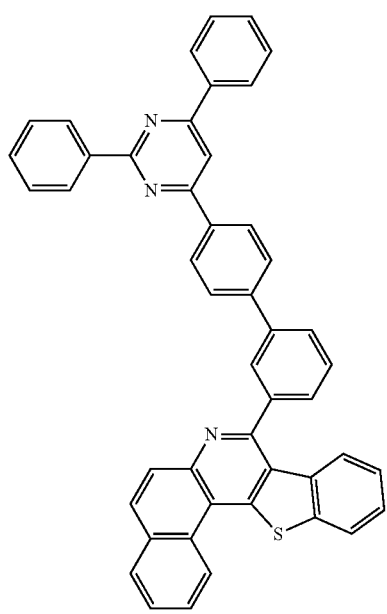
350
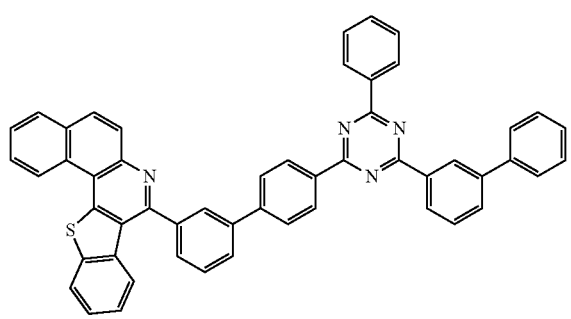
351
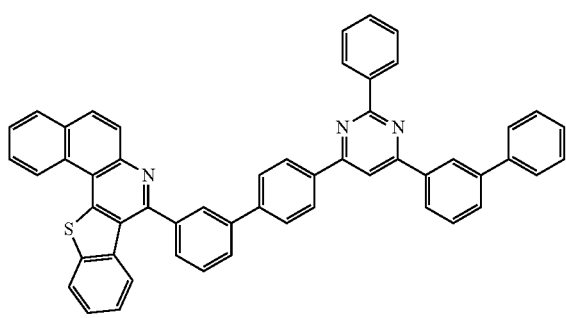
352
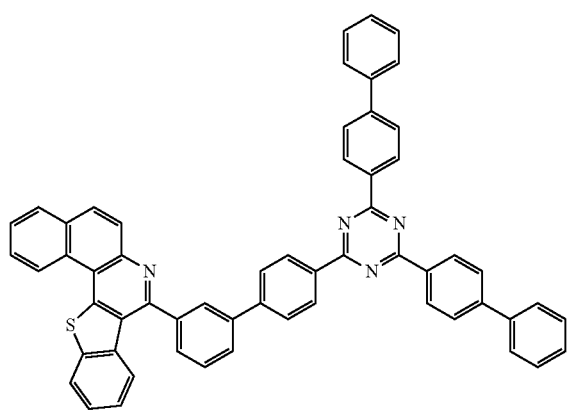

353
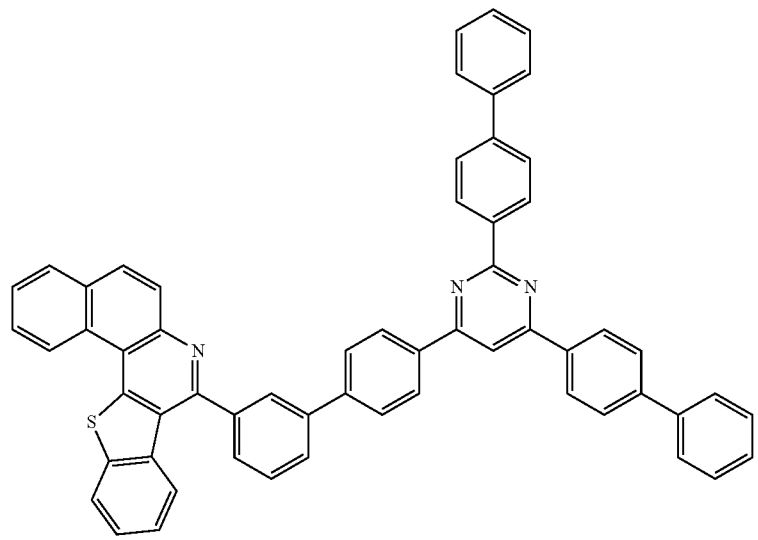
354
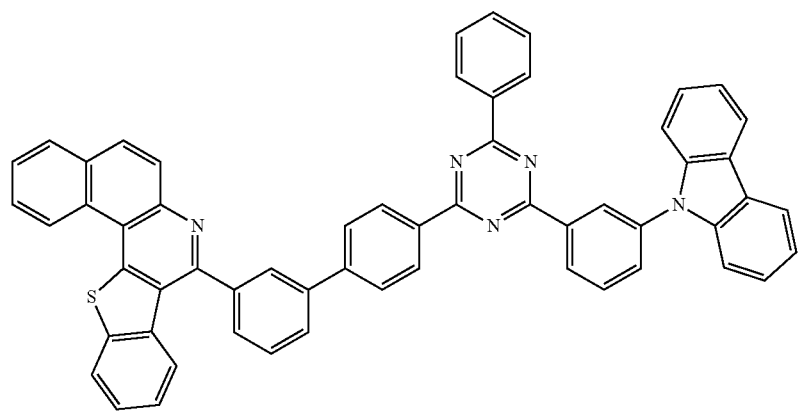
355
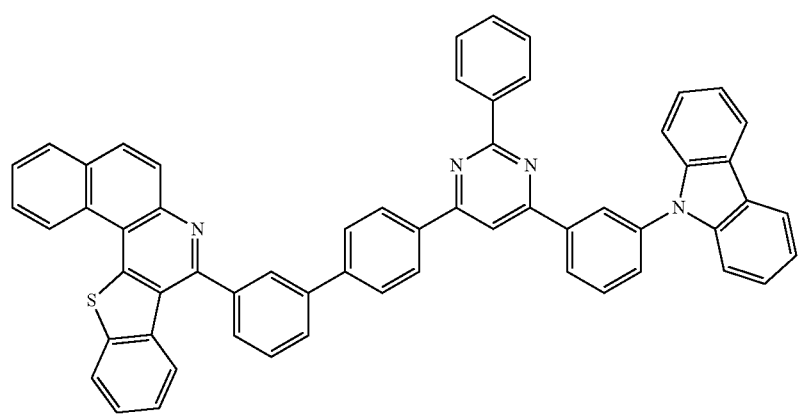

-continued
356
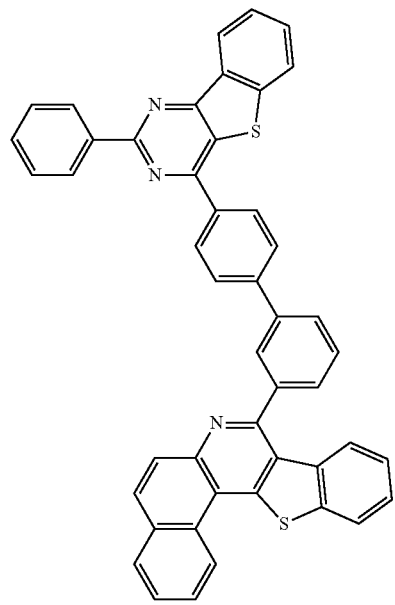
357
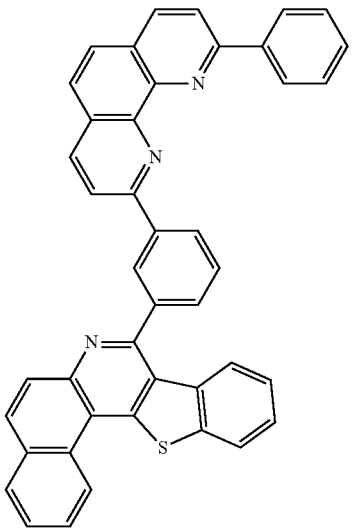
358
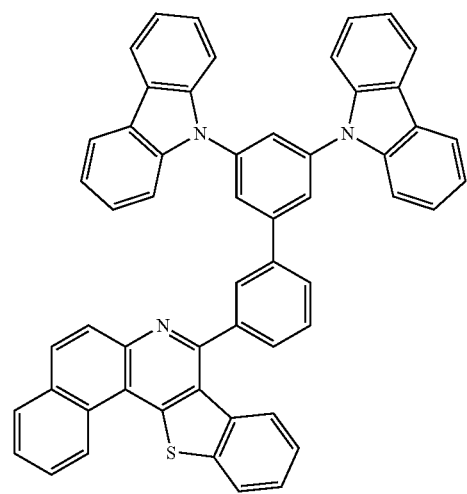
359
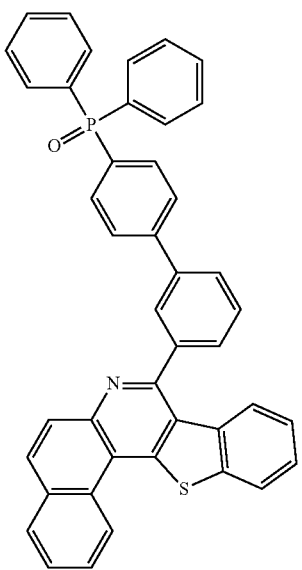

-continued

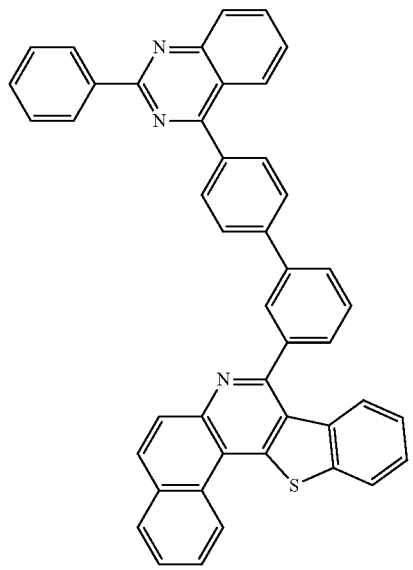

360

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device including a first electrode; a second electrode provided opposite to the first electrode; and one or more organic material layers provided between the first electrode and the second electrode, wherein one or more layers of the organic material layers include the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In the organic light emitting device of the present disclosure, the organic material layer includes an electron injection layer or an electron transfer layer, and the electron injection layer or the electron transfer layer may include the heterocyclic compound.

In the organic light emitting device of the present disclosure, the organic material layer includes an electron transfer layer, and the electron transfer layer may include the heterocyclic compound.

In another organic light emitting device, the organic material layer includes an electron blocking layer or a hole blocking layer, and the electron blocking layer or the hole blocking layer may include the heterocyclic compound.

In another organic light emitting device, the organic material layer includes a hole blocking layer, and the hole blocking layer may include the heterocyclic compound.

In another organic light emitting device, the organic material layer includes an electron transfer layer, a light emitting layer or a hole blocking layer, and the electron transfer layer, the light emitting layer or the hole blocking layer may include the heterocyclic compound.

The organic light emitting device of the present disclosure may further include one, two or more layers selected from the group consisting of a light emitting layer, a hole injection layer, a hole transfer layer, an electron injection layer, an electron transfer layer, an electron blocking layer and a hole blocking layer.

FIGS. 1 to 4 illustrate a lamination order of electrodes and organic material layers of an organic light emitting device according to one embodiment of the present application.

However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100).

However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 includes a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer including the compound of Chemical Formula 1 may further include other materials as necessary.

In addition, the organic light emitting device according to one embodiment of the present application includes an anode, a cathode, and two or more stacks provided between the anode and the cathode, and the two or more stacks each independently include a light emitting layer, a charge generation layer is included between the two or more stacks, and the charge generation layer includes the heterocyclic compound represented by Chemical Formula 1.

In addition, the organic light emitting device according to one embodiment of the present application includes an anode, a first stack provided on the anode and including a first light emitting layer, a charge generation layer provided on the first stack, a second stack provided on the charge generation layer and including a second light emitting layer, and a cathode provided on the second stack. Herein, the charge generation layer may include the heterocyclic compound represented by Chemical Formula 1. In addition, the first stack and the second stack may each independently further include one or more types of the hole injection layer, the hole transfer layer, the hole blocking layer, the electron transfer layer, the electron injection layer and the like described above.

The charge generation layer may be an N-type charge generation layer, and the charge generation layer may further include a dopant known in the art in addition to the heterocyclic compound represented by Chemical Formula 1.

As the organic light emitting device according to one embodiment of the present application, an organic light emitting device having a 2-stack tandem structure is schematically illustrated in the following FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having relatively small work function may be used, and metals, metal oxides, conductive polymers or the like may be used. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature[Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed.

For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device including an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 2

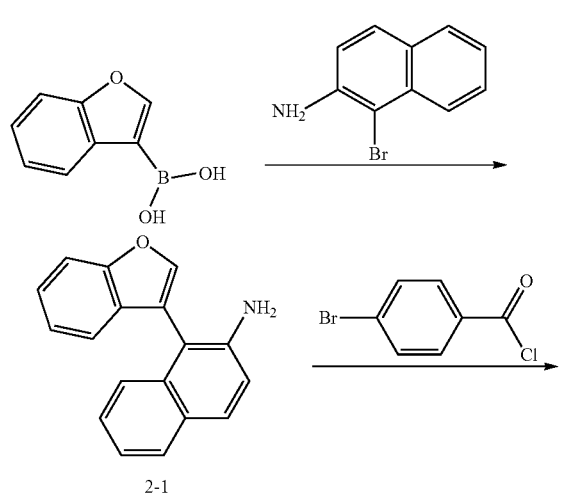

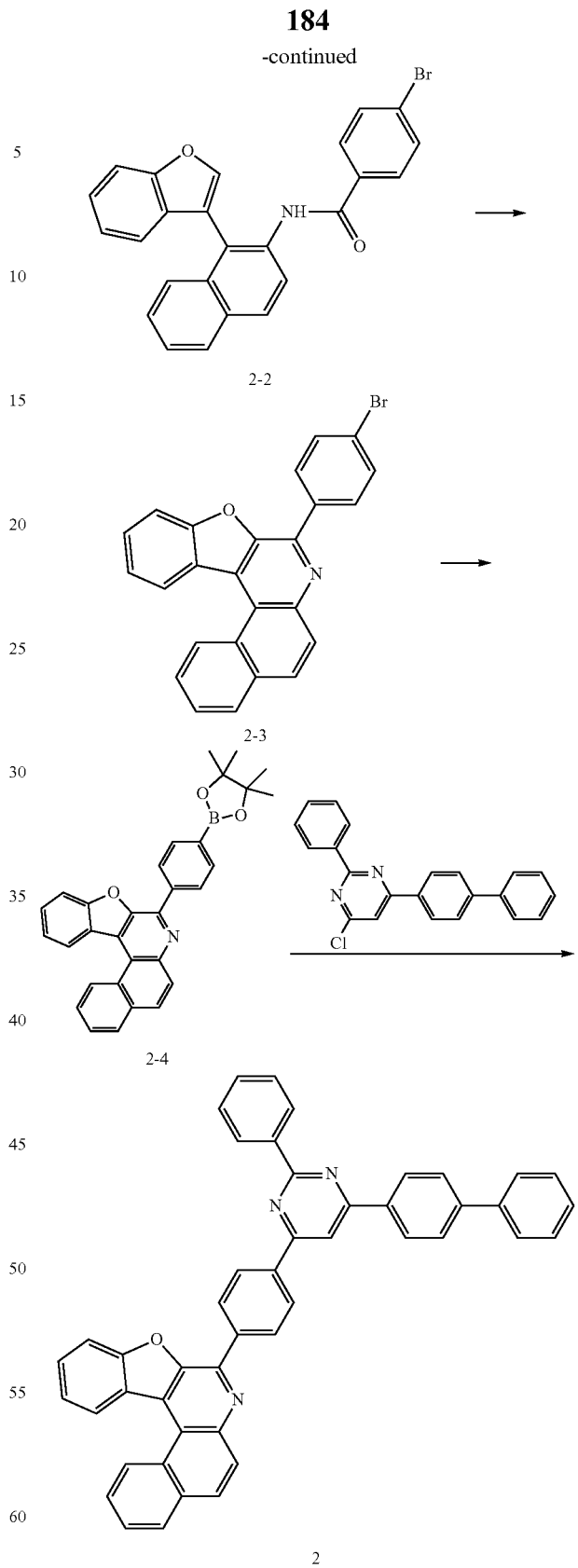

Preparation of Compound 2-1

After dissolving benzofuran-3-ylboronic acid (20 g, 123.49 mmol) and 1-bromonaphthalen-2-amine (27.43 g, 123.49 mmol) in THF (200 ml) and H$_2$O (40 ml), (N$_2$ condition) Pd (PPh$_3$) 4 (7.14 g, 6.17 mmol) and K$_3$PO$_4$ (78.64 g, 370.48 mmol) were introduced thereto, and the result was stirred for 24 hours under reflux. After the reaction was completed, methylene chloride (MC) was introduced to dissolve the reaction solution, and then the result was extracted with distilled water. The organic layer was dried with anhydrous MgSO$_4$, and, after removing the solvent using a rotary evaporator, purified with column chromatography using dichloromethane and hexane as a developing solvent to obtain Compound 2-1 (28 g, 87%).

Preparation of Compound 2-2

After dissolving Compound 2-1 (28 g, 107.98 mmol) in MC (280 ml), triethanolamine (TEA) (32.78 g, 323.95 mmol) was introduced thereto. The temperature was lowered from room temperature to 0° C., and 4-bromobenzoyl chloride (26.07 g, 118.78 mmol) dissolved in MC was slowly added dropwise thereto. After the reaction was completed, the result was extracted with MC and distilled water. The organic layer was dried with anhydrous MgSO$_4$, and, after removing the solvent using a rotary evaporator, purified with column chromatography using dichloromethane and hexane as a developing solvent to obtain Compound 2-2 (37 g, 77%).

Preparation of Compound 2-3

After dissolving Compound 2-2 (37 g, 83.65 mmol) in nitrobenzene (370 ml), POCl$_3$ (14.11, 92.02 mmol) was slowly added dropwise thereto, and the result was stirred for 3 hours at 150° C. After the reaction was completed, the result was extracted with MC and distilled water. The organic layer was dried with anhydrous MgSO$_4$, and, after removing the solvent using a rotary evaporator, purified with column chromatography using dichloromethane and hexane as a developing solvent to obtain Compound 2-3 (33 g, 92%).

Preparation of Compound 2-4

After dissolving Compound 2-3 (33 g, 77.78 mmol) and bis(pinacolato)diboron (29.63 g, 116.67 mmol) in 1,4-dioxane (330 ml), (N$_2$ condition) Pd(dppf)Cl$_2$ (2.85 g, 3.89 mmol) and KOAc (22.90 g, 233.33 mmol) were introduced thereto, and the result was stirred for 18 hours under reflux. After the reaction was completed, the result was extracted with MC and water. The organic layer was dried with anhydrous MgSO$_4$, and then silica gel filtered. The result was precipitated using MC/MeOH, and the precipitates were filtered to obtain Compound 2-4 (30 g, 81%).

Preparation of Compound 2

After dissolving Compound 2-4 (7 g, 14.85 mmol) and 4-([1,1'-biphenyl]-4-yl)-6-chloro-2-phenylpyrimidine (5.35 g, 15.59 mmol) in toluene (100 ml), EtOH (20 ml) and H$_2$O (20 ml), (N$_2$ condition) Pd(PPh$_3$)$_4$ (0.86 g, 0.74 mmol) and K$_3$PO$_4$ (9.46 g, 44.55 mmol) were introduced thereto, and the result was stirred for 16 hours under reflux. After the reaction was completed, the result was cooled to room temperature, and produced solids were filtered and then washed with ethyl acetate (EA) and MeOH. After that, the solids were all dissolved in an excess amount of dichloromethane, and then silica gel filtered to obtain Compound 2 (6.6 g, 68%).

Target compounds were synthesized in the same manner as in Preparation Example 1 except that Intermediate A of the following Table 1 was used instead of benzofuran-3-ylboronic acid, Intermediate B of the following Table 1 was used instead of 1-bromonaphthalen-2-amine, Intermediate C of the following Table 1 was used instead of 4-bromobenzoyl chloride, and Intermediate D of the following Table 1 was used instead of 4-([1,1'-biphenyl]-4-yl)-6-chloro-2-phenylpyrimidine.

| Compound | Intermediate A | Intermediate B | Intermediate C | Intermediate D | Target Compound | Yield |
|---|---|---|---|---|---|---|
| 3 | 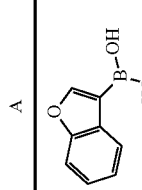 |  | 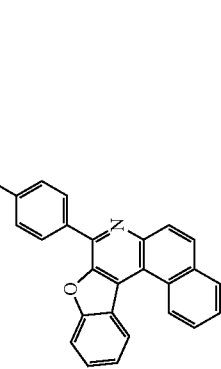 | 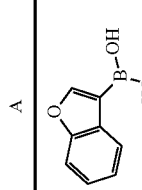 |  | 74% |
| 4 | 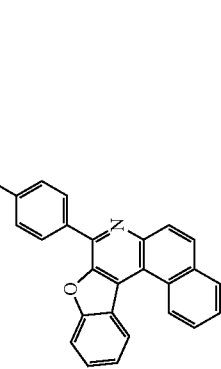 | | | | | 72% |

| Compound | Intermediate A | Intermediate B | Intermediate C | Intermediate D | Target Compound | Yield |
|---|---|---|---|---|---|---|
| 23 | 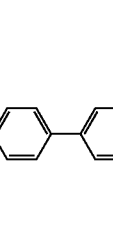 | 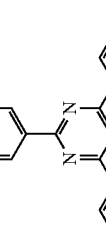 | 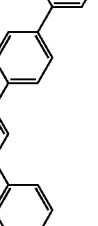 |  | 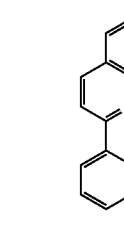 | 81% |
| 27 |  |  | 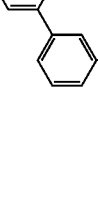 | 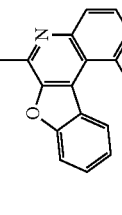 | 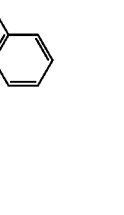 | 77% |

-continued

| Compound | Intermediate A | Intermediate B | Intermediate C | Intermediate D | Target Compound | Yield |
|---|---|---|---|---|---|---|
| 28 | | | | | | 72% |
| 51 | | | | | | 67% |

-continued
| Compound | Intermediate A | Intermediate B | Intermediate C | Intermediate D | Target Compound | Yield |
|---|---|---|---|---|---|---|
| 70 |  | 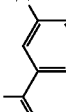 |  |  | 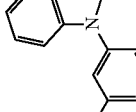 | 64% |
| 85 |  | 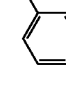 |  | 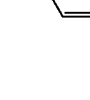 | 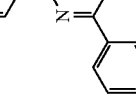 | 69% |
| 87 |  |  | 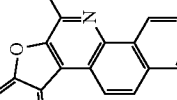 | 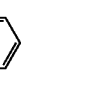 |  | 75% |

-continued

| Compound | Intermediate A | Intermediate B | Intermediate C | Intermediate D | Target Compound | Yield |
|---|---|---|---|---|---|---|
| 88 | | | | | | 77% |
| 89 | | | | | | 70% |
| 91 | | | | | | 68% |

-continued

| Compound | Intermediate A | Intermediate B | Intermediate C | Intermediate D | Target Compound | Yield |
|---|---|---|---|---|---|---|
| 96 | benzofuran-2-boronic acid | 2-bromo-1-naphthylamine | 4-bromobenzoyl chloride | | | 82% |
| 117 | benzofuran-2-boronic acid | 2-bromo-1-naphthylamine | 3-bromobenzoyl chloride | | | 77% |

-continued

| Compound | Intermediate A | Intermediate B | Intermediate C | Intermediate D | Target Compound | Yield |
|---|---|---|---|---|---|---|
| 153 | benzofuran-2-boronic acid | 1-bromo-2-aminonaphthalene | 4-bromobenzoyl chloride | 2-(4-bromophenyl)-4,6-diphenyl-1,3,5-triazine | (structure) | 62% |
| 154 | benzofuran-2-boronic acid | 1-bromo-2-aminonaphthalene | 4-bromobenzoyl chloride | 2-(4-bromophenyl)-4,6-diphenylpyrimidine | (structure) | 66% |

-continued
| Compound | Intermediate A | Intermediate B | Intermediate C | Intermediate D | Target Compound | Yield |
|---|---|---|---|---|---|---|
| 163 | 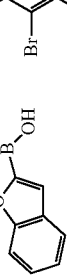 | 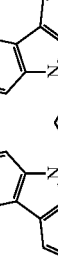 | 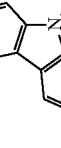 |  | 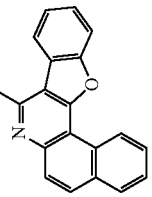 | 72% |
| 168 | 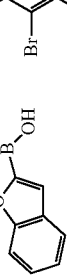 | 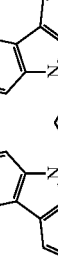 | 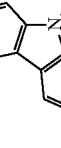 |  | 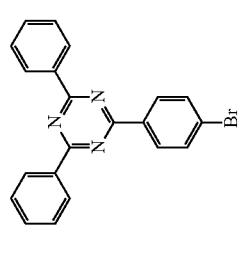 | 66% |

-continued

| Compound | Intermediate A | Intermediate B | Intermediate C | Intermediate D | Target Compound | Yield |
|---|---|---|---|---|---|---|
| 169 | benzofuran-2-boronic acid | 1-bromo-2-aminonaphthalene | 3-bromobenzoyl chloride | 4-bromophenyl-(2,6-diphenylpyrimidin-4-yl) | | 70% |
| 179 | benzofuran-2-boronic acid | 1-bromo-2-aminonaphthalene | 3-bromobenzoyl chloride | (4-bromophenyl)diphenylphosphine oxide | | 59% |

-continued

| Compound | Intermediate A | Intermediate B | Intermediate C | Intermediate D | Target Compound | Yield |
|---|---|---|---|---|---|---|
| 181 | | | | | | 62% |
| 198 | | | | | | 64% |
| 199 | | | | | | 64% |

-continued
| Compound | Intermediate A | Intermediate B | Intermediate C | Intermediate D | Target Compound | Yield |
|---|---|---|---|---|---|---|
| 203 | 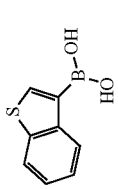 |  |  |  | 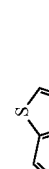 | 71% |
| 244 | 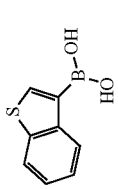 |  |  |  | 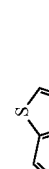 | 73% |

| Compound | Intermediate A | Intermediate B | Intermediate C | Intermediate D | Target Compound | Yield |
|---|---|---|---|---|---|---|
| 250 | 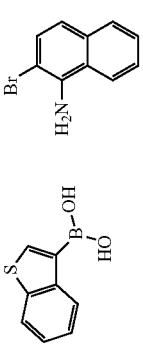 |  | 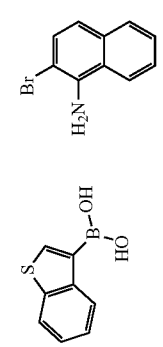 | 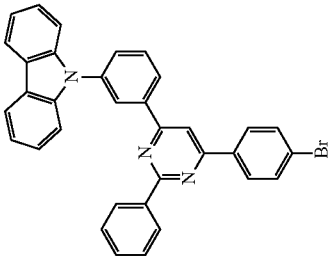 | 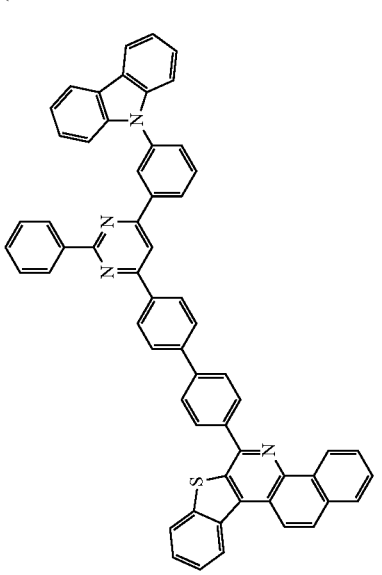 | 77% |
| 257 | 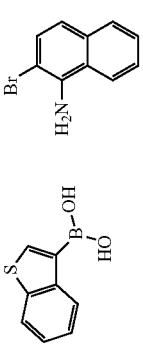 |  | 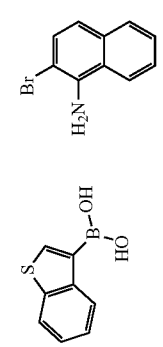 | 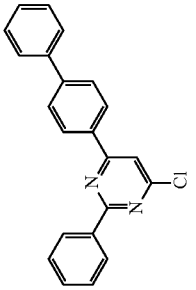 | 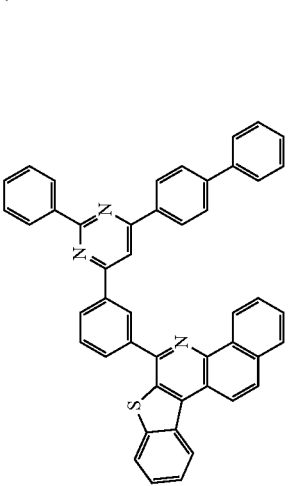 | 75% |

-continued
| Compound | Intermediate A | Intermediate B | Intermediate C | Intermediate D | Target Compound | Yield |
|---|---|---|---|---|---|---|
| 263 | 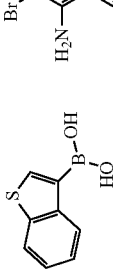 | 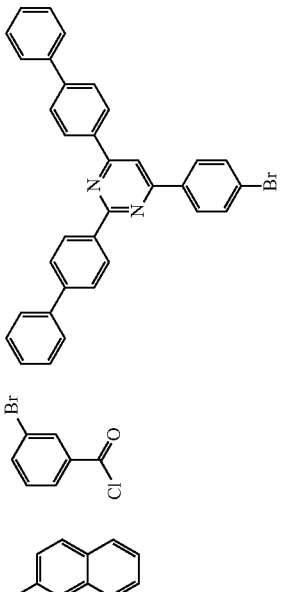 | 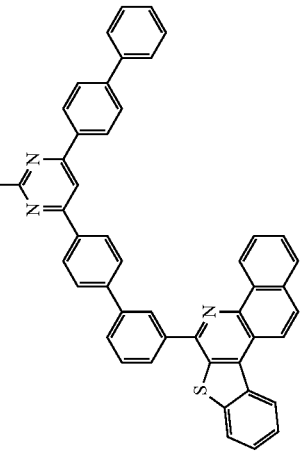 | 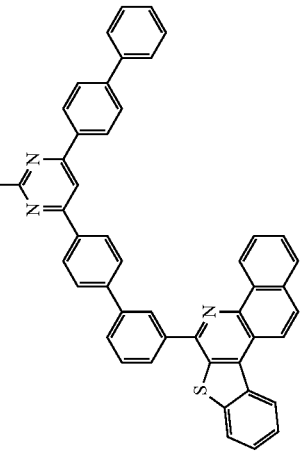 | 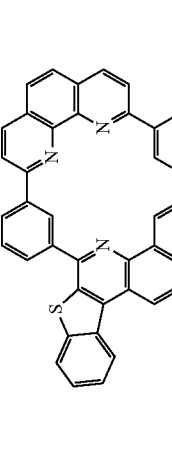 | 65% |
| 267 | 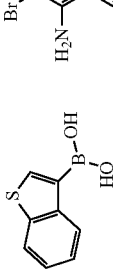 | 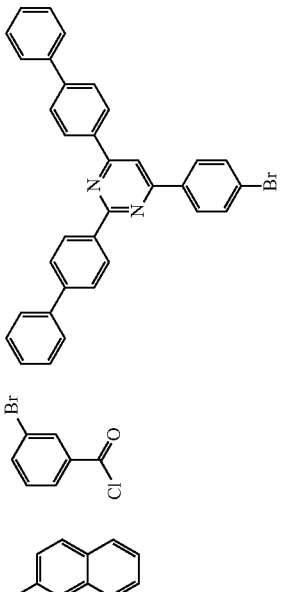 | 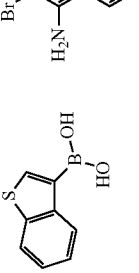 | 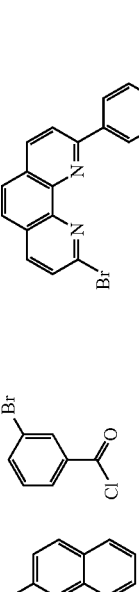 | 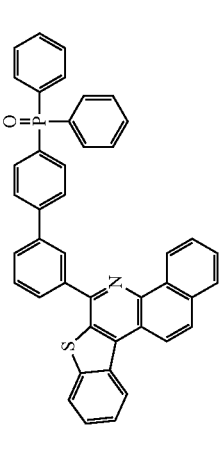 | 72% |
| 269 | 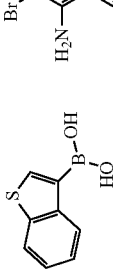 | 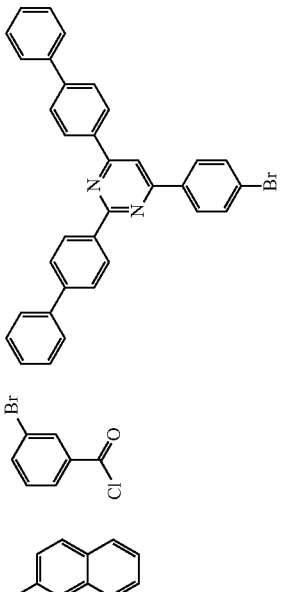 | 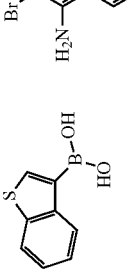 | 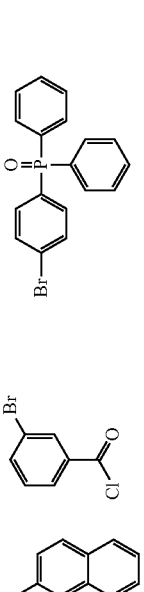 | 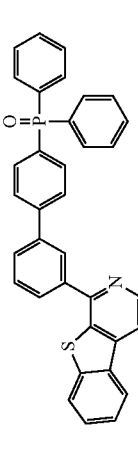 | 78% |

| Compound | Intermediate A | Intermediate B | Intermediate C | Intermediate D | Target Compound | Yield |
|---|---|---|---|---|---|---|
| 281 | | | | | | 69% |
| 297 | | | | | | 67% |

-continued

| Compound | Intermediate A | Intermediate B | Intermediate C | Intermediate D | Target Compound | Yield |
|---|---|---|---|---|---|---|
| 313 | | | | | | 69% |
| 332 | | | | | | 70% |

-continued
| Compound | Intermediate A | Intermediate B | Intermediate C | Intermediate D | Target Compound | Yield |
|---|---|---|---|---|---|---|
| 353 | 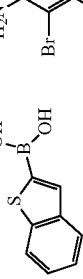 | 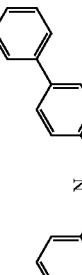 | 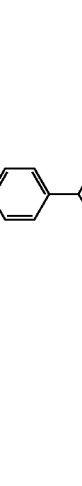 | 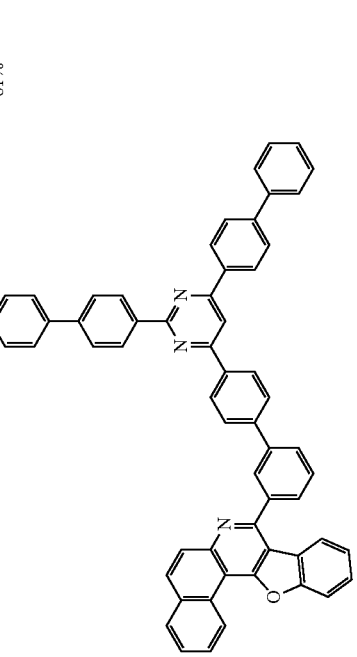 | 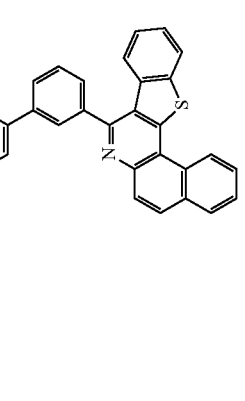 | 81% |
| 356 | 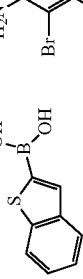 | 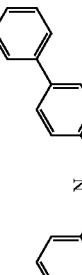 | 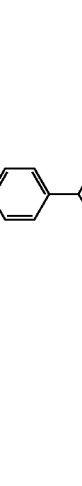 | 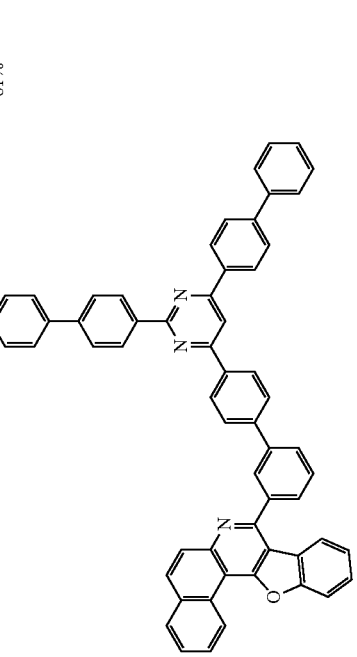 | 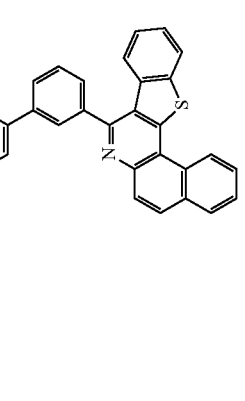 | 79% |

TABLE 2

| NO | ¹H NMR(CDCl₃, 300 Mz) |
|---|---|
| 2 | 8.69(2H, d), 8.54(1H, d), 8.36-8.22(7H, m), 8.16(1H, d), 7.99-7.98(2H, m), 7.85(2H, d), 7.75(2H, d), 7.61-7.31(11H, m) |
| 3 | 8.69(2H, d), 8.54(1H, d), 8.38-8.34(4H, m), 8.25(2H, d), 8.16(1H, d), 8.00-7.97(2H, m), 7.85(2H, d), 7.75(1H, d), 7.62-7.49(9H, m), 7.40-7.24(4H, m) |
| 4 | 8.69(2H, d), 8.54(1H, d), 8.36-8.29(4H, m), 8.23(1H, s), 8.16(1H, d), 8.00-7.84(8H, m), 7.75(1H, d), 7.62-7.30(11H, m) |
| 23 | 8.54(1H, d), 8.30-8.16(8H, m), 7.99-7.98(2H, m), 7.87-7.85(7H, m), 7.67-7.32(19H, m) |
| 27 | 8.72(1H, s), 8.54(1H, d), 8.32-8.30(3H, m), 8.16-7.98(6H, m), 7.89-7.81(2H, m), 7.67-7.32(11H, m) |
| 28 | 8.55-8.54(3H, m), 8.26-8.09(7H, m), 7.99-7.89(5H, m), 7.67-7.50(9H, m), 7.38-7.25(9H, m) |
| 51 | 8.30-8.16(9H, m), 8.05(1H, d), 7.89-7.85(3H, m), 7.68-7.32(m, 20H, m) |
| 70 | 8.81(2H, d), 8.55-8.51(2H, m), 8.30-8.06(9H, m), 7.94-7.79(8H, m), 7.67-7.63(4H, m), 7.51-7.25(11H, m) |
| 85 | 8.55-8.51(2H, m), 8.30-8.06(11H, m), 7.94-7.79(6H, m), 7.67-7.32(17H, m) |
| 87 | 8.72(1H, s), 8.51(1H, d), 8.32-8.30(4H, m), 8.16-8.06(5H, m), 7.89-7.81(3H, m), 7.67-7.32(11H, m) |
| 88 | 8.55-8.51(3H, m), 8.26-8.06(8H, m), 7.89-7.94(3H, m), 7.81(1H, d), 7.67-7.50(9H, m), 7.40-7.25(9H, m) |
| 89 | 8.51(1H, d), 8.26-8.16(3H, m), 8.06(1H, d), 7.83-7.32(23H, m) |
| 91 | 8.81(2H, d), 8.51(1H, d), 8.28(2H, d), 8.16(1H, d), 8.06(1H, d), 7.89-7.85(6H, m), 7.67-7.66(3H, m), 7.66-7.32(12H, m) |
| 96 | 8.81(2H, d), 8.51(1H, d), 8.30-8.23(5H, m), 8.16(1H, d), 8.06(1H, d), 7.89-7.66(11H, m), 7.57-7.32(12H, m) |
| 117 | 8.72(1H, s), 8.51(1H, d), 8.32-8.30(4H, m), 8.16-8.06(5H, m), 7.89-7.81(3H, m), 7.67-7.32(11H, m) |
| 153 | 8.81(2H, d), 8.54(1H, d), 8.28(4H, d), 8.16(1H, d), 7.99-7.98(2H, m), 7.89-7.85(5H, m), 7.67-7.66(3H, m), 7.51-7.25(10H, m) |
| 154 | 8.81(2H, d), 8.54(1H, d), 8.30-8.16(6H, m), 7.99-7.98(2H, m), 7.89-7.79(7H, m), 7.67-7.66(3H, m), 7.51-7.32(8H, m) |
| 163 | 8.81(2H, d), 8.55-8.54(3H, m), 8.16-8.09(5H, m), 7.99-7.88(7H, m), 7.67-7.63(5H, m), 7.50(2H, t), 7.40-7.25(9H, m) |
| 168 | 8.54(1H, d), 8.28-8.16(7H, m), 7.99-7.98(2H, m), 7.89-7.85(3H, m), 7.67-7.41(15H, m) |
| 169 | 8.54(1H, d), 8.30-8.16(8H, m), 7.99-7.98(2H, m), 7.89-7.79(5H, m), 7.67-7.41(13H, m) |
| 179 | 8.54(1H, d), 8.26-8.16(3H, m), 7.99-7.98(2H, m), 7.83-7.32(22H, m) |
| 181 | 8.81(2H, d), 8.54(1H, d), 8.45(1H, d), 8.29(2H, d), 8.16(1H, d), 7.99-7.98(3H, m), 7.88-7.85(4H, m), 7.67(2H, m), 7.52-7.41(10H, m), 7.25(2H, d) |
| 198 | 8.54(1H, d), 8.45(1H, d), 8.28-8.16(7H, m), 7.99-7.98(3H, m), 7.85(2H, d), 7.67-7.41(12H, m), 7.25(2H, d) |
| 199 | 8.54(1H, d), 8.45(1H, d), 8.30-8.16(8H, m), 7.99-7.98(3H, m), 7.85-7.79(4H, m), 7.67-7.41(12H, m) |
| 203 | 8.54(1H, d), 8.45(1H, d), 8.30-8.16(8H, m), 7.99-7.98(3H, m), 7.85(6H, d), 7.67-7.41(16H, m), 7.25(2H, d) |
| 244 | 8.81(2H, d), 8.51-8.41(2H, m), 8.30-8.23(5H, m), 8.16(1H, d), 8.06(1H, d), 7.98(1H, d), 7.88-7.79(7H, m), 7.67(2H, d), 7.52-7.41(8H, m) |
| 250 | 8.81(2H, d), 8.55-8.45(3H, m), 8.30-8.06(9H, m), 7.98-7.79(8H, m), 7.67-7.63(3H, m), 7.52-7.25(11H, m) |
| 257 | 8.51-8.45(2H, m), 8.30-8.16(8H, m), 8.06(1H, d), 7.98(1H, d), 7.85-7.81(4H, m), 7.67-7.41(13H, m) |
| 263 | 8.51-8.45(2H, m), 8.30-8.16(8H, m), 8.06(1H, d), 7.98(1H, d), 7.85-7.81(7H, m), 7.67-7.41(16H, m), 7.25(2H, d) |
| 267 | 8.72(1H, s), 8.51-8.45(2H, m), 8.32-8.30(4H, m), 8.16-7.98(6H, m), 7.81(2H, d), 7.67-7.50(8H, m), 7.35(2H, d) |
| 269 | 8.51-8.45(2H, m), 8.26-8.16(3H, m), 8.06(1H, d), 7.98(1H, d), 7.83-7.77(9H, m), 7.67-7.45(12H, m) |
| 281 | 8.81(2H, d), 8.51-8.45(2H, m), 8.30-8.28(4H, m), 8.16(1H, d), 8.06-7.98(4H, m), 7.88-7.81(5H, m), 7.67(2H, d), 7.52-7.41(7H, m) |
| 297 | 8.72(1H, s), 8.51-8.45(2H, m), 8.32-8.30(4H, m), 8.16-7.98(6H, m), 7.81(2H, d), 7.67-7.47(8H, m), 7.35(2H, d) |
| 313 | 8.81(2H, d), 8.55(2H, d), 8.45(1H, s), 8.16-7.94(12H, m), 7.68-7.63(5H, m), 7.50(4H, m), 733-7.25(7H, m) |
| 332 | 8.81(2H, d), 8.54(1H, d), 8.45(1H, d), 8.33-8.23(7H, m), 8.16(1H, d), 7.99-7.98(3H, m), 7.85(2H, d), 7.67(2H, d), 7.52-7.50(10H, m) |
| 353 | 8.54(1H, d), 8.45(1H, d), 8.30-8.16(8H, m), 7.99-7.98(3H, m), 7.85(6H, d), 7.67-7.41(16H, m), 7.25(2H, d) |
| 356 | 8.54(1H, d), 8.45(1H, d), 8.30-8.16(7H, m), 8.05-7.98(5H, m), 7.85(2H, d), 7.67-7.41(11H, m) |

TABLE 3

| Compound | FD-MS | Compound | FD-MS |
|---|---|---|---|
| 2 | m/z = 651.75 (C49H27N3O = 651.23) | 3 | m/z = 652.74 (C46H28N4O = 652.23) |
| 4 | m/z = 651.75 (C49H27N3O = 651.23) | 23 | m/z = 803.94 (C59H37N3O = 803.29) |
| 27 | m/z = 599.68 (C43H25N3O = 599.20) | 28 | m/z = 751.87 (C55H33N3O = 751.26) |
| 51 | m/z = 727.85 (C53H33N3O = 727.26) | 70 | m/z = 816.94 (C59H39N4O = 816.29) |
| 85 | m/z = 816.94 (C59H39N4O = 816.29) | 87 | m/z = 599.68 (C43H25N3O = 599.20) |
| 88 | m/z = 751.87 (C55H33N3O = 751.26) | 89 | m/z = 621.66 (C43H28NO2P = 621.19) |
| 91 | m/z = 652.74 (C46H28N4O = 652.23) | 96 | m/z = 727.85 (C53H33N3O = 727.26) |
| 117 | m/z = 599.68 (C43H25N3O = 599.20) | 153 | m/z = 652.74 (C46H28N4O = 652.23) |
| 154 | m/z = 651.75 (C49H27N3O = 651.23) | 163 | m/z = 751.87 (C55H33N3O = 751.26) |
| 168 | m/z = 652.74 (C46H28N4O = 652.23) | 169 | m/z = 651.75 (C49H27N3O = 651.23) |
| 179 | m/z = 621.66 (C43H28NO2P = 621.19) | 181 | m/z = 668.81 (C46H28N4S = 668.20) |
| 198 | m/z = 668.81 (C46H28N4S = 668.20) | 199 | m/z = 667.82 (C47H29N3S = 667.21) |
| 203 | m/z = 820.01 (C59H37N3S = 819.27) | 244 | m/z = 667.82 (C47H29N3S = 667.21) |
| 250 | m/z = 833.01 (C59H36N4S = 832.27) | 257 | m/z = 667.82 (C47H29N3S = 667.21) |
| 263 | m/z = 820.01 (C59H37N3S = 819.27) | 267 | m/z = 615.74 (C43H25N3S = 615.18) |
| 269 | m/z = 673.73 (C43H28NOPS = 637.16) | 281 | m/z = 699.88 (C47H29N3S2 = 699.18) |
| 297 | m/z = 615.74 (C43H25N3S = 615.18) | 313 | m/z = 767.94 (C55H33N3S = 767.24) |
| 332 | m/z = 667.82 (C47H29N3S = 667.21) | 353 | m/z = 820.01 (C59H37N3S = 819.27) |
| 356 | m/z = 699.88 (C47H29N3S2 = 699.18) | | |

EXPERIMENTAL EXAMPLE

Experimental Example 1

1) Manufacture of Organic Light Emitting Device

A transparent indium tin oxide electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

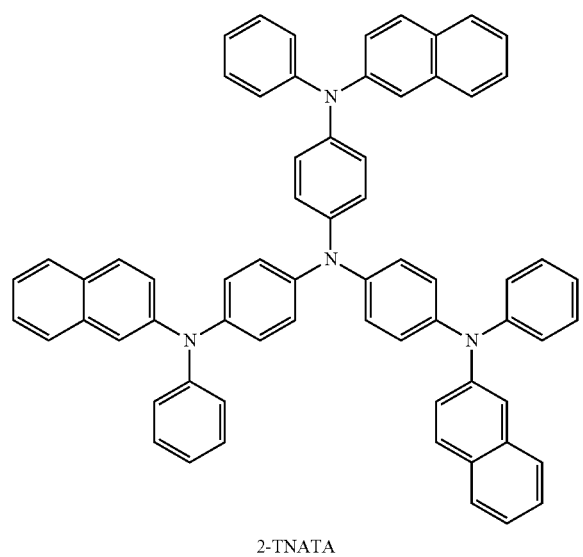

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

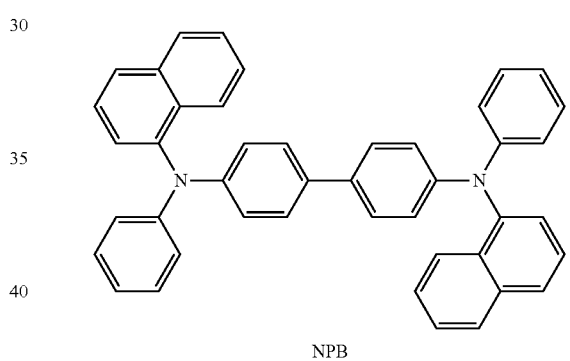

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

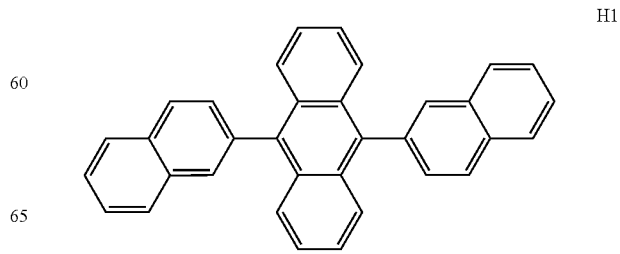

H1

-continued

D1

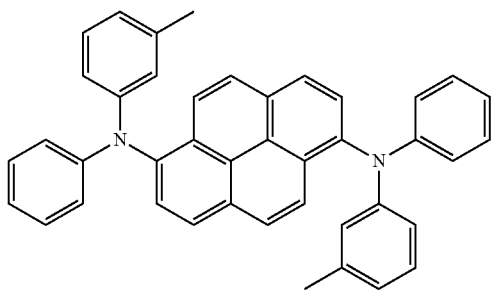

Subsequently, a compound of the following Table 4 was deposited to a thickness of 300 Å as an electron transfer layer.

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electrolumine scent (EL) properties were measured using M7000 manufactured by McScience Inc., and with the measurement results, T95 when standard luminance was 700 cd/m² was measured using a lifetime measurement system (M6000) manufactured by McScience Inc. Results of measuring driving voltage, light emission efficiency, external quantum efficiency and color coordinate (CIE) of the white organic light emitting devices manufactured according to the present disclosure are as shown in Table 4.

TABLE 4

| Compound | | Driving Voltage (v) | Light Emission Efficiency (cd/A) | CIE (x,y) | Lifetime (T95) |
|---|---|---|---|---|---|
| Example 1 | 2 | 5.51 | 6.55 | (0.134,0.101) | 32 |
| Example 2 | 3 | 4.76 | 6.44 | (0.134,0.102) | 47 |
| Example 3 | 4 | 4.64 | 5.99 | (0.134,0.101) | 36 |
| Example 4 | 23 | 5.38 | 6.20 | (0.134,0.103) | 35 |
| Example 5 | 51 | 5.60 | 6.12 | (0.134,0.102) | 34 |
| Example 6 | 70 | 4.65 | 7.14 | (0.134,0.101) | 48 |
| Example 7 | 85 | 4.72 | 6.22 | (0.134,0.102) | 30 |
| Example 8 | 89 | 5.32 | 6.33 | (0.134,0.101) | 29 |
| Example 9 | 91 | 5.40 | 6.13 | (0.134,0.101) | 31 |
| Example 10 | 96 | 4.40 | 6.92 | (0.134,0.100) | 45 |
| Example 11 | 117 | 5.37 | 6.35 | (0.134,0.101) | 32 |
| Example 12 | 153 | 5.38 | 6.41 | (0.134,0.100) | 30 |
| Example 13 | 154 | 4.47 | 7.42 | (0.134,0.100) | 51 |
| Example 14 | 168 | 5.48 | 6.21 | (0.134,0.100) | 32 |
| Example 15 | 169 | 4.72 | 7.39 | (0.134,0.100) | 49 |
| Example 16 | 179 | 5.45 | 6.68 | (0.134,0.100) | 34 |
| Example 17 | 181 | 5.22 | 6.28 | (0.134,0.102) | 37 |
| Example 18 | 198 | 5.12 | 6.20 | (0.134,0.101) | 32 |
| Example 19 | 199 | 5.39 | 6.77 | (0.134,0.102) | 30 |
| Example 20 | 203 | 5.42 | 6.88 | (0.134,0.100) | 25 |
| Example 21 | 244 | 5.21 | 5.45 | (0.134,0.103) | 37 |
| Example 22 | 250 | 5.38 | 6.66 | (0.134,0.100) | 35 |
| Example 23 | 257 | 5.40 | 6.36 | (0.134,0.102) | 32 |
| Example 24 | 263 | 5.42 | 6.26 | (0.134,0.101) | 48 |
| Example 25 | 269 | 5.39 | 6.19 | (0.134,0.100) | 31 |
| Example 26 | 281 | 5.55 | 6.27 | (0.134,0.102) | 31 |

TABLE 4-continued

| Compound | | Driving Voltage (v) | Light Emission Efficiency (cd/A) | CIE (x,y) | Lifetime (T95) |
|---|---|---|---|---|---|
| Example 27 | 297 | 5.18 | 6.20 | (0.134,0.103) | 30 |
| Example 28 | 332 | 5.41 | 6.19 | (0.134,0.100) | 32 |
| Example 29 | 353 | 4.75 | 7.28 | (0.134,0.103) | 41 |
| Example 30 | 356 | 5.29 | 6.41 | (0.134,0.102) | 33 |
| Comparative Example 1-1 | E1 | 5.56 | 5.91 | (0.134,0.100) | 28 |
| Comparative Example 1-2 | BBQB | 5.50 | 6.10 | (0.134,0.101) | 30 |
| Comparative Example 1-3 | TBQB | 5.51 | 6.15 | (0.134,0.102) | 29 |
| Comparative Example 1-4 | E2 | 5.65 | 5.82 | (0.134,0.101) | 28 |
| Comparative Example 1-5 | E3 | 5.52 | 6.05 | (0.134,0.102) | 27 |

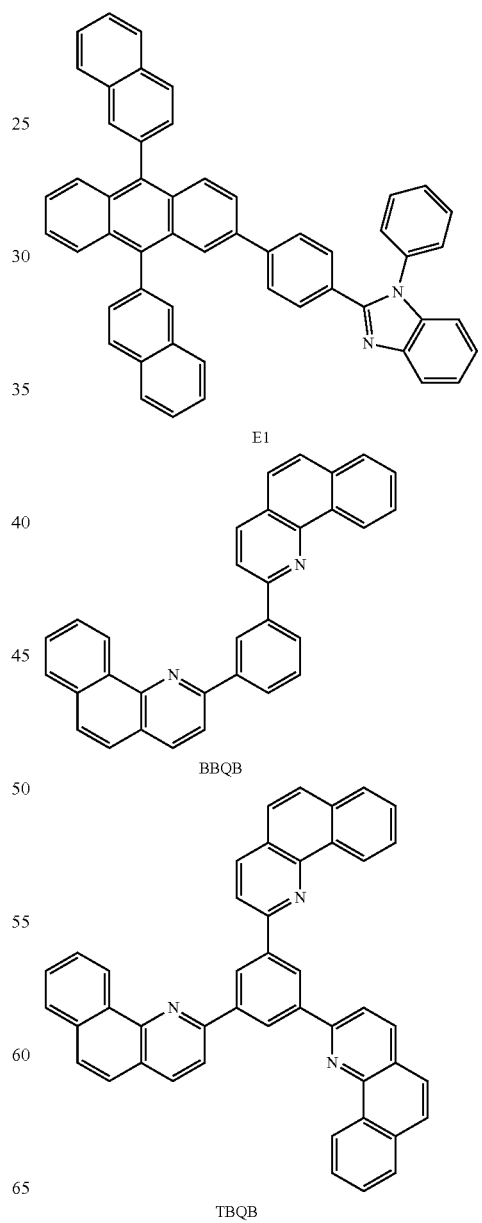

E1

BBQB

TBQB

TABLE 4-continued

| Compound | Driving Voltage (v) | Light Emission Efficiency (cd/A) | CIE (x,y) | Lifetime (T95) |
|---|---|---|---|---|

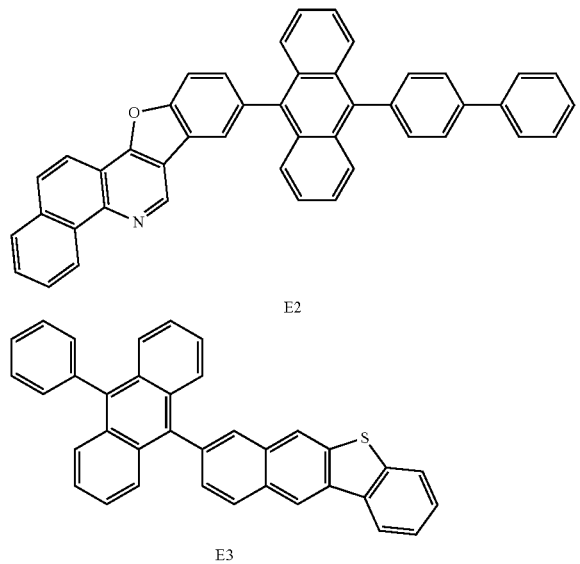

E2

E3

As seen from the results of Table 4, the organic light emitting device using the electron transfer layer material of the blue organic light emitting device of the present disclosure had lower driving voltage and significantly improved light emission efficiency and lifetime compared to the comparative examples. Particularly, it was identified that Compounds 70, 96, 154, 169 and 353 were superior in all aspects of driving voltage, efficiency and lifetime.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, those that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

Experimental Example 2

Comparative Example 2

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris(N,N-(2-naphthyl)-phenylamino)triphenylamine (2-TNATA) was deposited on a cell in the vacuum deposition apparatus.

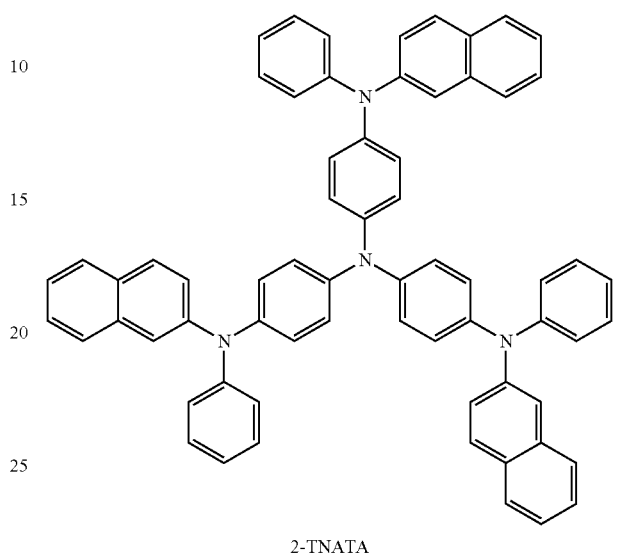

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

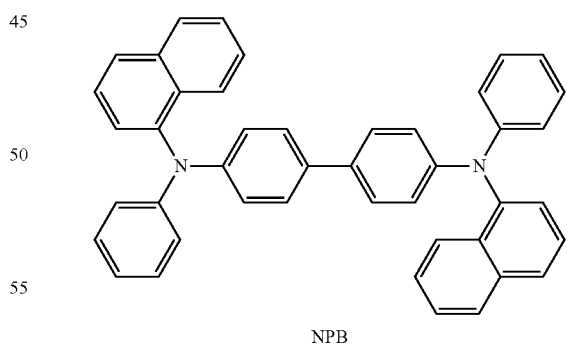

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

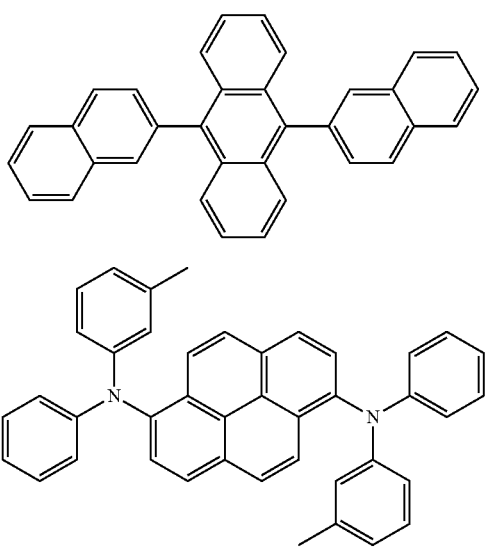

H1

D1

Subsequently, a compound of the following structural formula E1 was deposited to a thickness of 300 Å as an electron transfer layer.

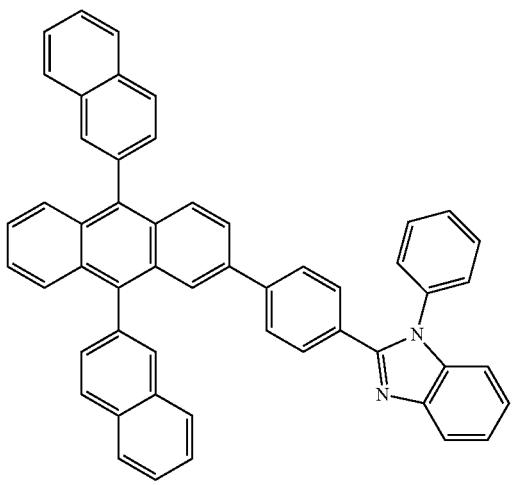

E1

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 31 to 34

Organic electroluminescent devices were manufactured in the same manner as in Comparative Example 2 except that the electron transfer layer E1 was formed to a thickness of 250 Å, and then a hole blocking layer was formed on the electron transfer layer using a compound presented in the following Table 5 to a thickness of 50 Å.

Results of measuring driving voltage, light emission efficiency, color coordinate (CIE) and lifetime of the blue organic light emitting devices manufactured according to the present disclosure are as shown in the following Table 5.

TABLE 5

| Compound | Driving Voltage (V) | Light Emission Efficiency (cd/A) | CIE (x, y) | Lifetime (T95) |
|---|---|---|---|---|
| Comparative Example 2 | — | 5.51 | 5.54 | (0.134, 0.100) | 31 |
| Example 31 | 28 | 4.77 | 6.17 | (0.134, 0.101) | 52 |
| Example 32 | 88 | 4.83 | 6.59 | (0.134, 0.102) | 54 |
| Example 33 | 163 | 5.11 | 6.62 | (0.134, 0.101) | 44 |
| Example 34 | 313 | 4.89 | 6.51 | (0.134, 0.103) | 47 |

As seen from the results of Table 5, the organic electroluminescent device using the hole blocking layer material of the blue organic electroluminescent device of the present disclosure had lower driving voltage and significantly improved light emission efficiency and lifetime compared to Comparative Example 2.

Experimental Example 3

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was 8% doped with FIrpic, a blue phosphorescent dopant, and deposited to 300 Å. After forming an electron transfer layer to 400 Å using TmPyPB, the compound described in the following Table 6 was 20% doped with $Cs_2CO_3$ to form a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to TAPC and then depositing TAPC to 300 Å. A light emitting layer was formed by 8% doping Ir(ppy)$_3$, a green phosphorescent dopant, to TCz1, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-6}$ torr to $10^{-8}$ torr for each material to be used in the OLED manufacture.

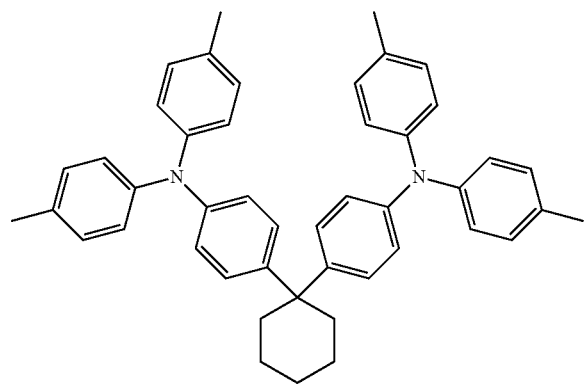

TAPC

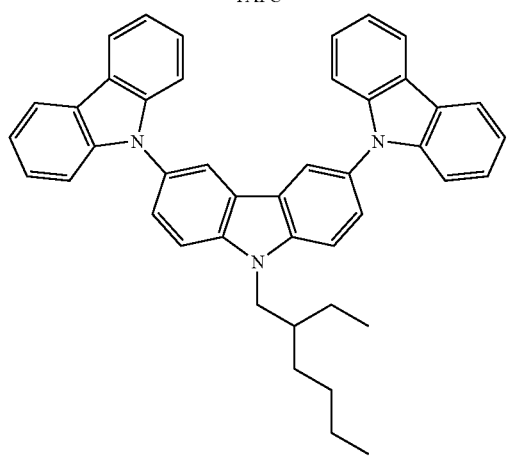

TCz1

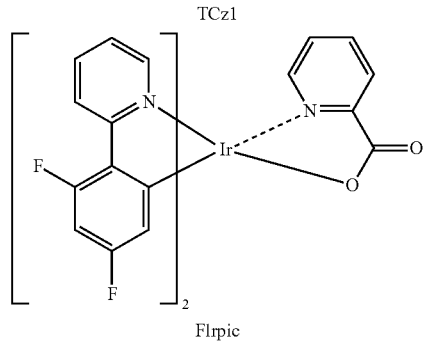

FIrpic

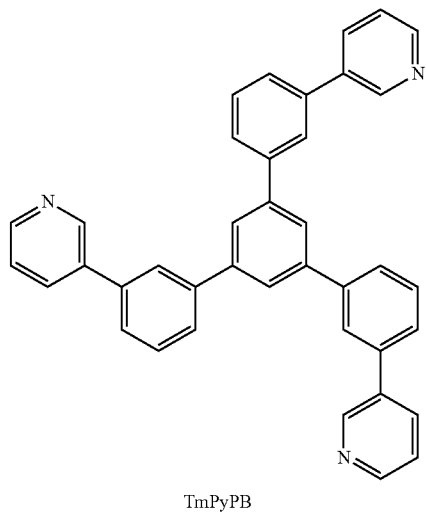

TmPyPB

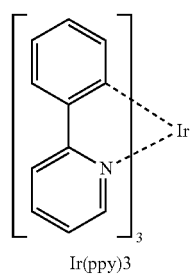

Ir(ppy)3

Results of measuring driving voltage, light emission efficiency, color coordinate (CIE) and lifetime of the white organic light emitting devices manufactured according to the present disclosure are as shown in the following Table 6.

TABLE 6

| Compound | | Driving Voltage (V) | Light Emission Efficiency (cd/A) | CIE (x, y) | Lifetime (T95) |
| --- | --- | --- | --- | --- | --- |
| Comparative Example 3 | TBQB | 7.54 | 54.23 | (0.213, 0.430) | 25 |
| Example 35 | 27 | 6.34 | 65.44 | (0.212, 0.421) | 40 |
| Example 36 | 87 | 6.44 | 66.32 | (0.211, 0.433) | 39 |
| Example 37 | 117 | 5.89 | 74.68 | (0.217, 0.439) | 50 |
| Example 38 | 267 | 5.87 | 73.99 | (0.212, 0.424) | 53 |
| Example 39 | 297 | 6.12 | 69.52 | (0.211, 0.435) | 41 |

As seen from the results of Table 6, the organic electroluminescent device using the charge generation layer material of the 2-stack white organic electroluminescent device of the present disclosure had lower driving voltage and improved light emission efficiency compared to Comparative Example 6.

Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and efficiency and lifetime were improved in the organic light emitting device.

The invention claimed is:
1. A heterocyclic compound represented by any one of the following Chemical Formula 4 to Chemical Formula 6:

[Chemical Formula 4]

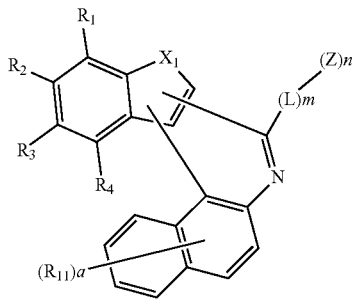

[Chemical Formula 5]

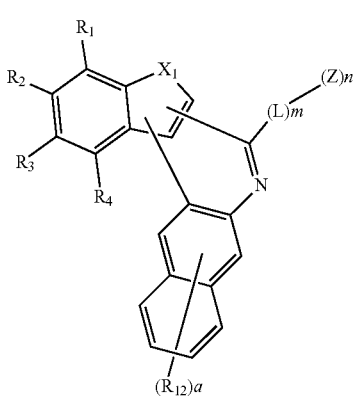

[Chemical Formula 6]

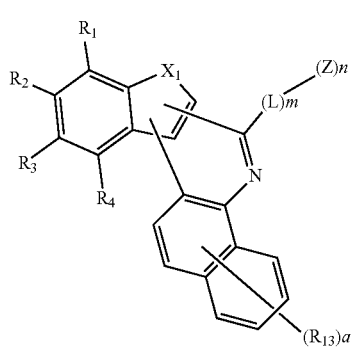

in Chemical Formulae 4 to 6, $X_1$ is O; or S;

$R_1$ to $R_4$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring;

L is a direct bond; a substituted or unsubstituted arylene group; or a substituted or unsubstituted heteroatylene group;

Z is selected from the group consisting of deuterium; —CN; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group;

$R_{11}$ to $R_{13}$ are the same as or different from each other, and each independently selected from the group consisting of hydrogen; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aromatic hydrocarbon ring or a substituted or unsubstituted heteroring;

R, R' and R" are the same as or different from each other, and each independently, hydrogen; a substituted or unsubstituted alkyl group; a substituted or unsubstituted aryl group; or a substituted or unsubstituted heteroaryl group;

a is an integer of 0 to 6, m is an integer of 0 to 5; and n is an integer of 1 to 6.

2. The heterocyclic compound of claim 1, wherein the "substituted or unsubstituted" means being substituted or unsubstituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R" have the same definitions as in Chemical Formulas 4-6.

3. A heterocyclic compound represented by any one of the following compounds:
1
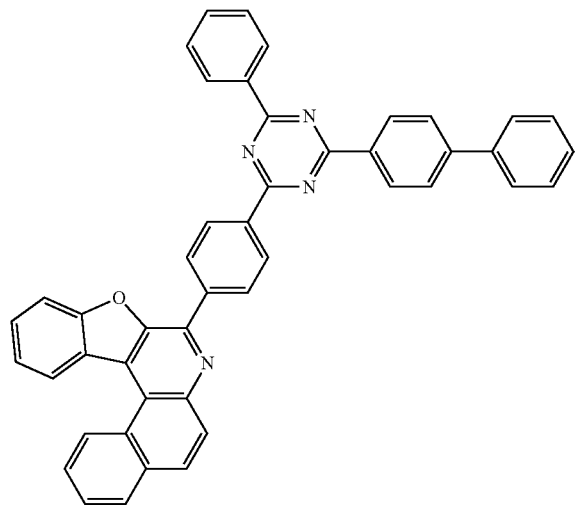
2
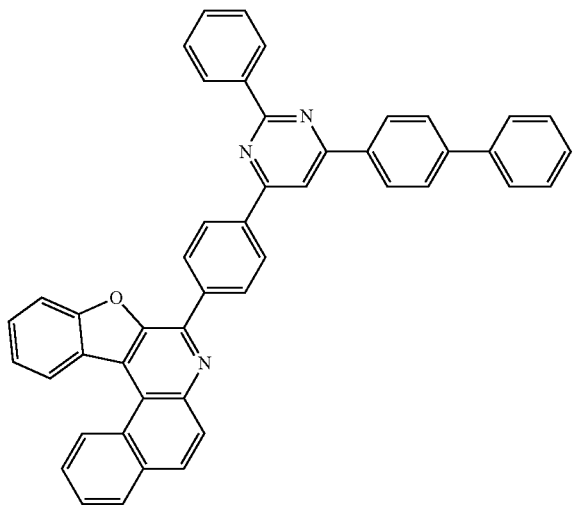
3
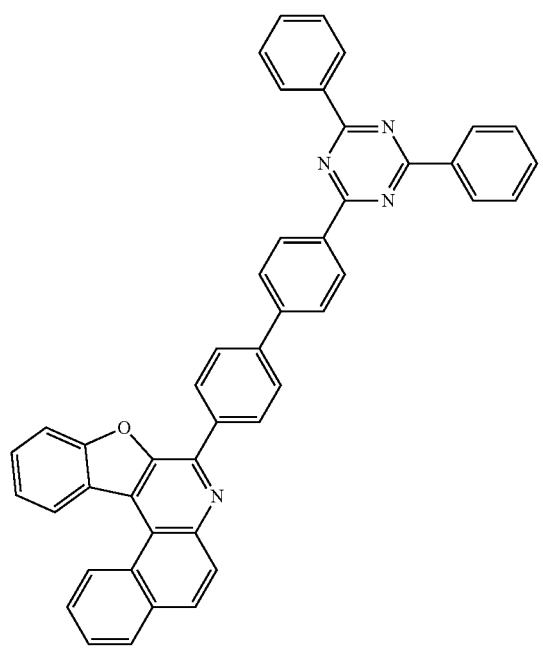
4
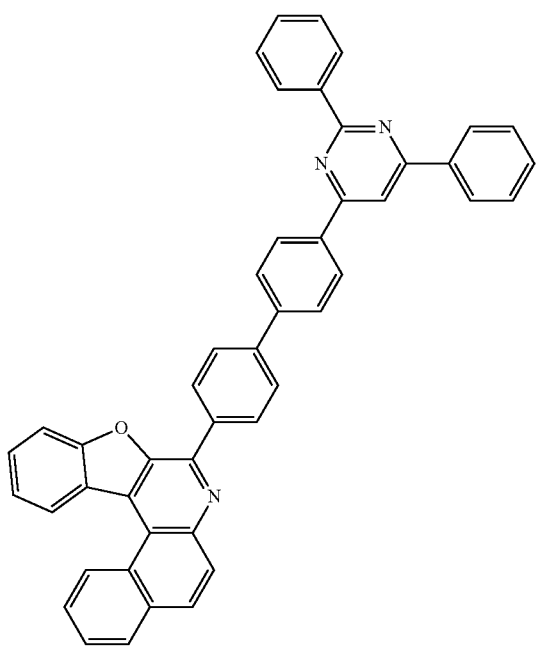
5
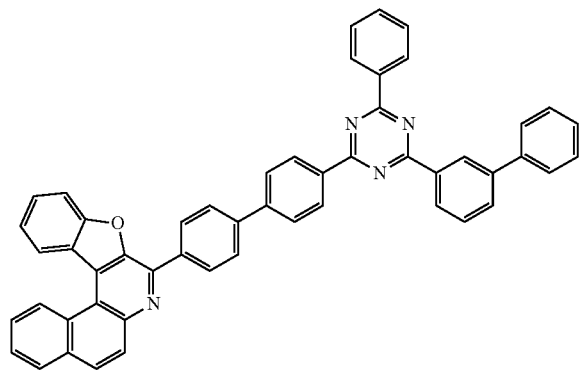
6
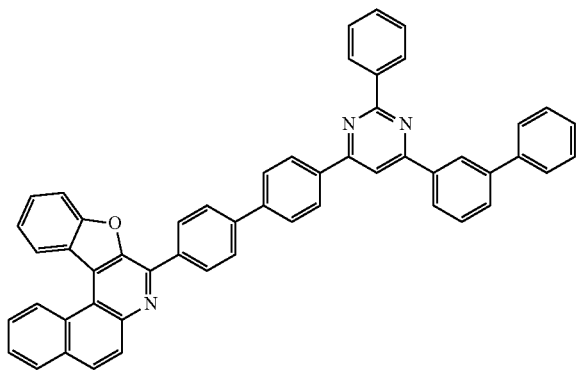

-continued
7
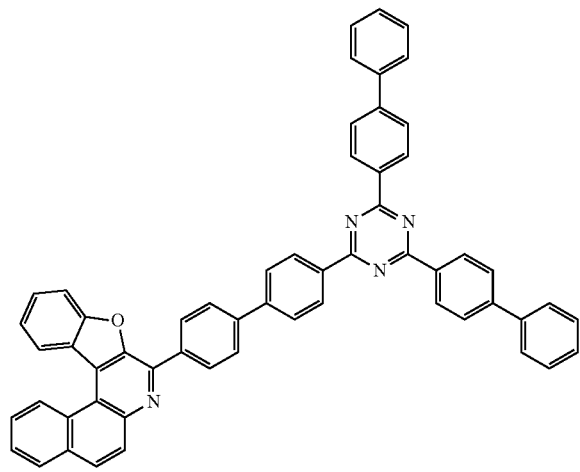
8
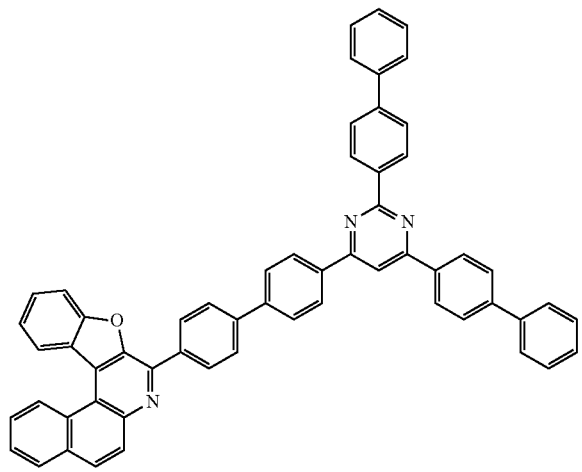
9
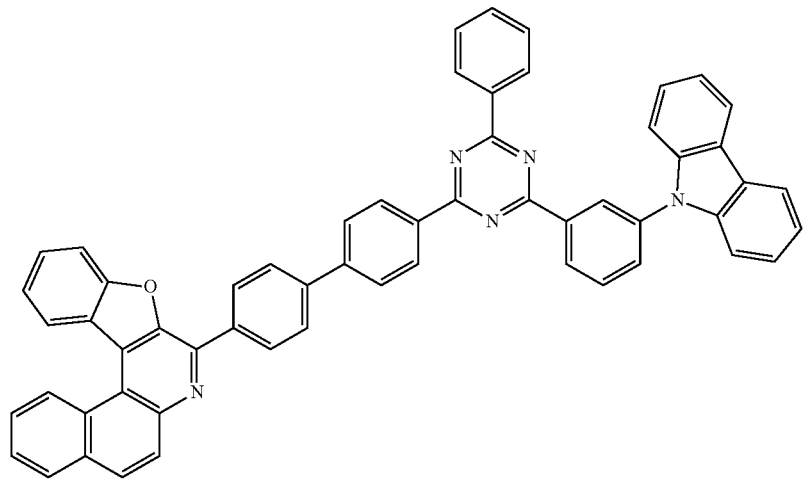
10
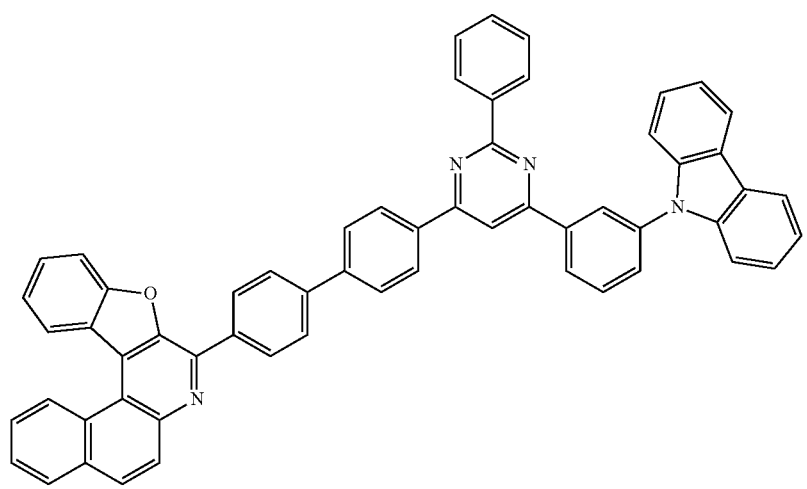

-continued
11
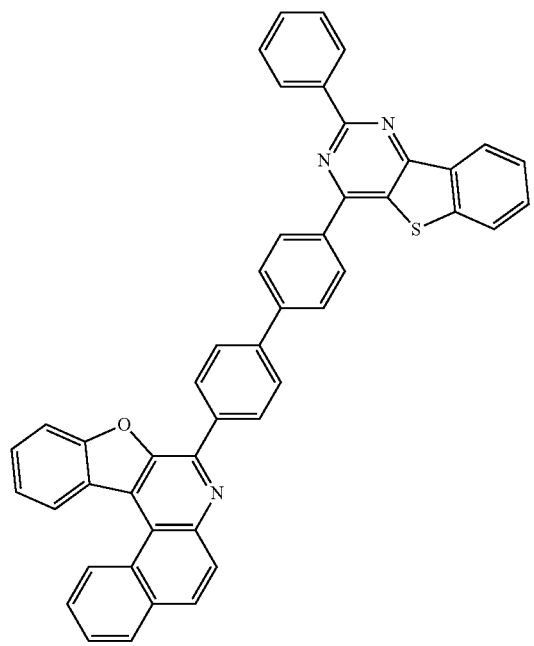
12
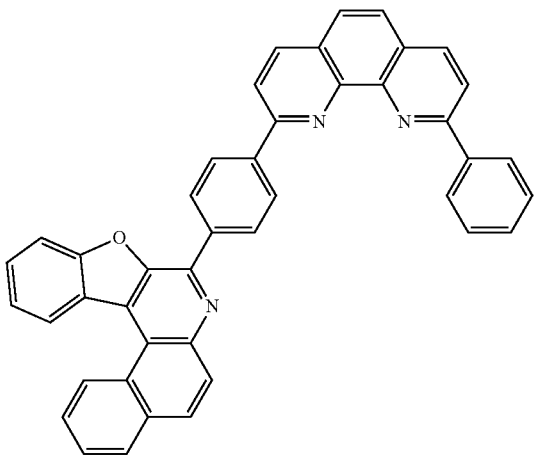
13
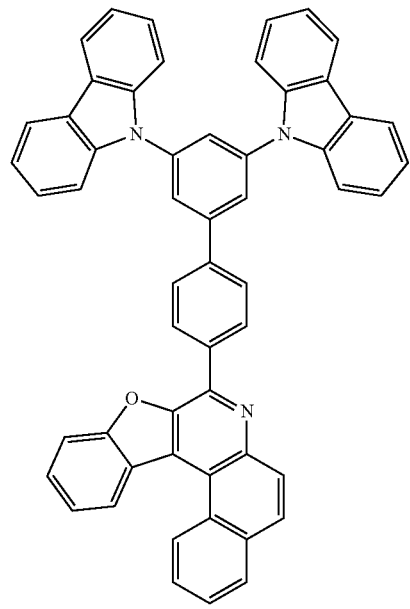
14
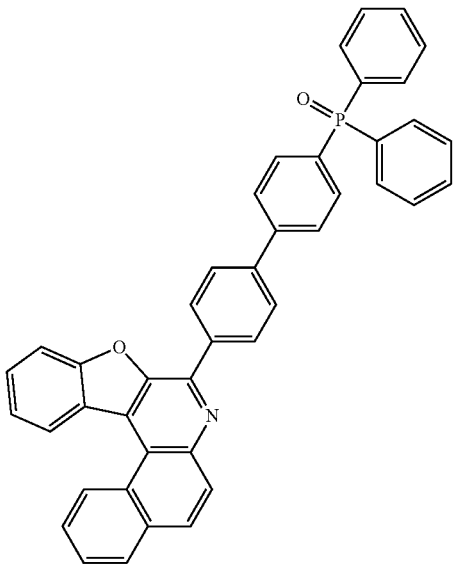

-continued
15
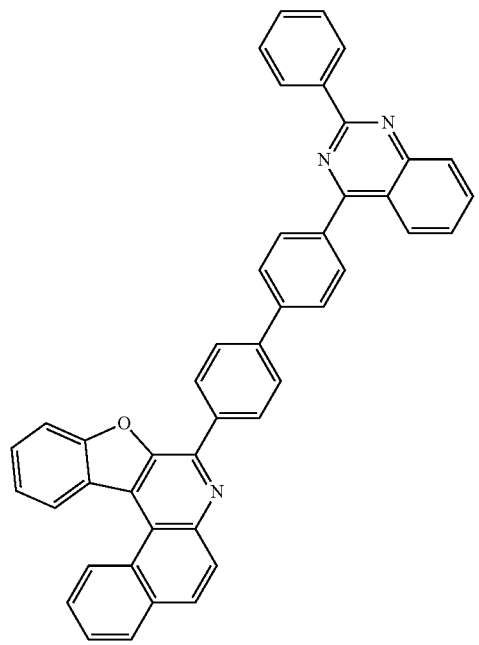
16
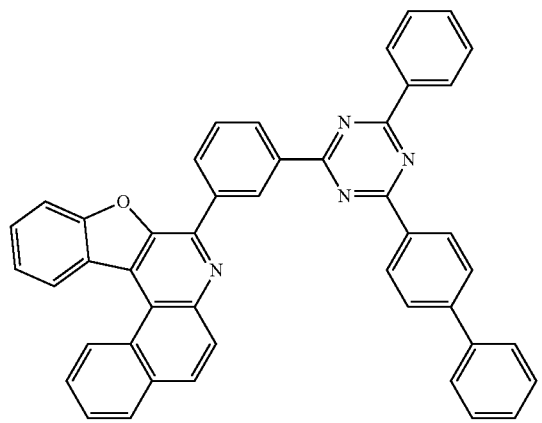
17
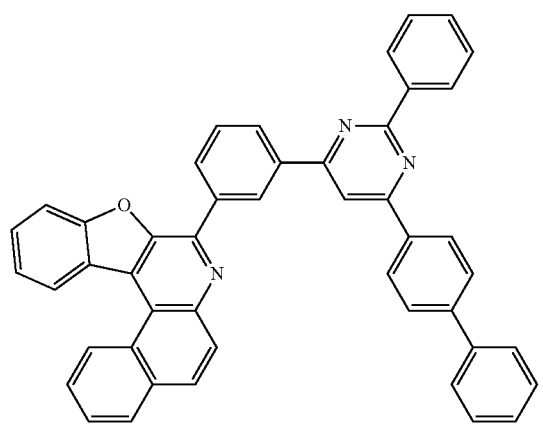
18
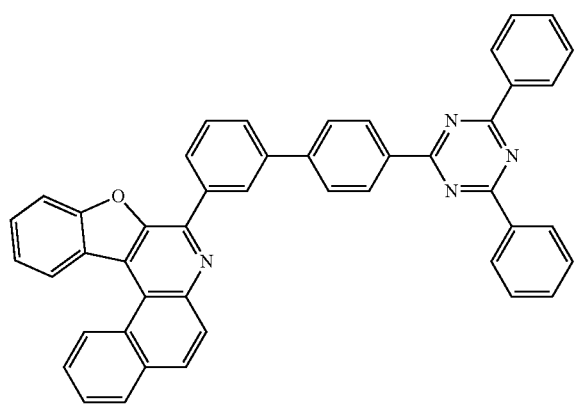
19
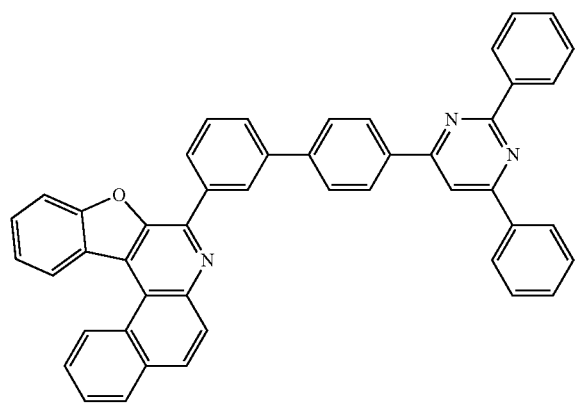
20
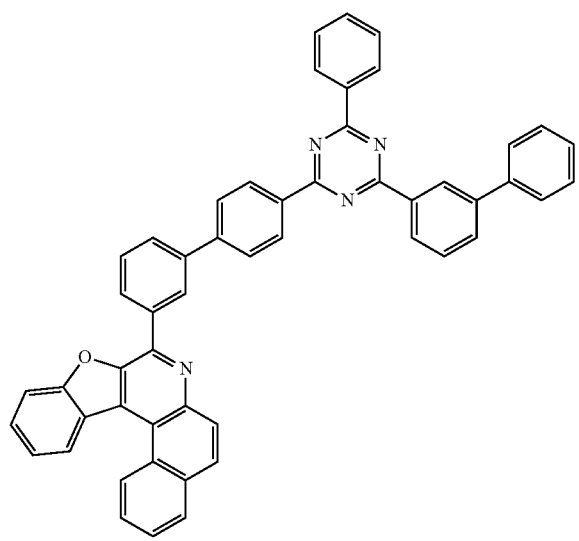

-continued
21
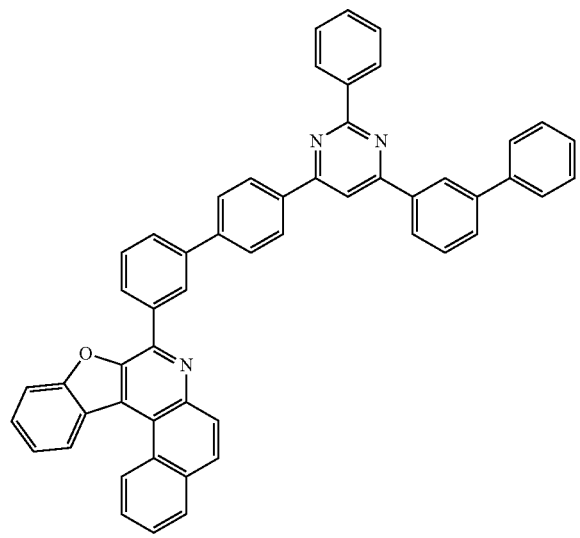
22
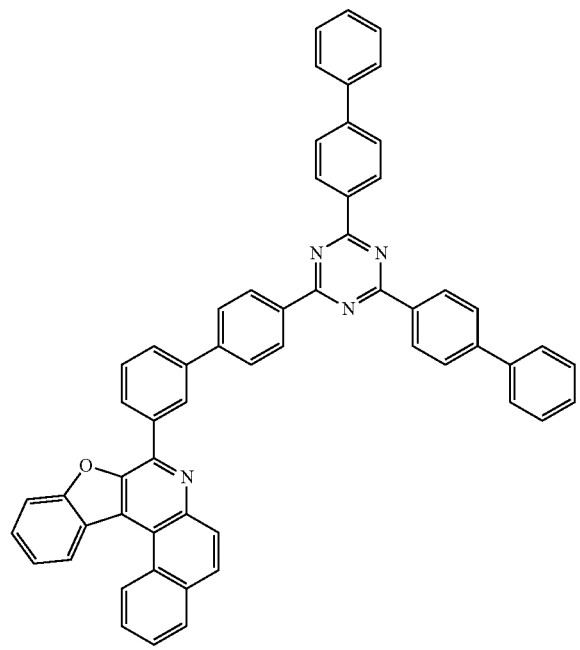
23
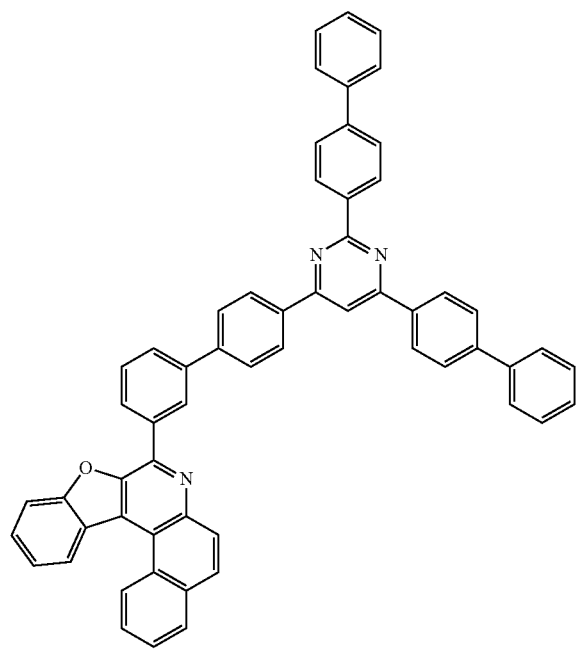
24
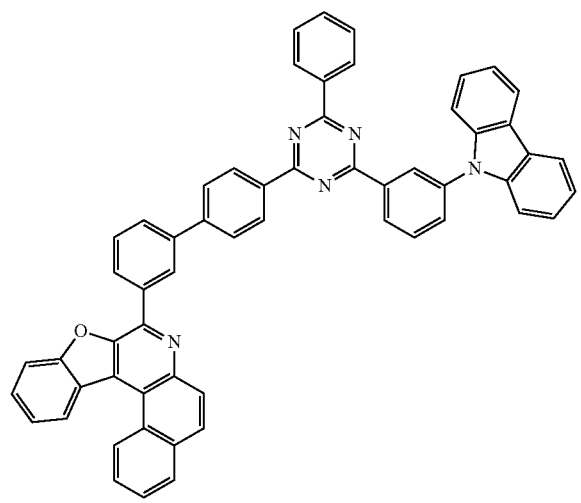

25
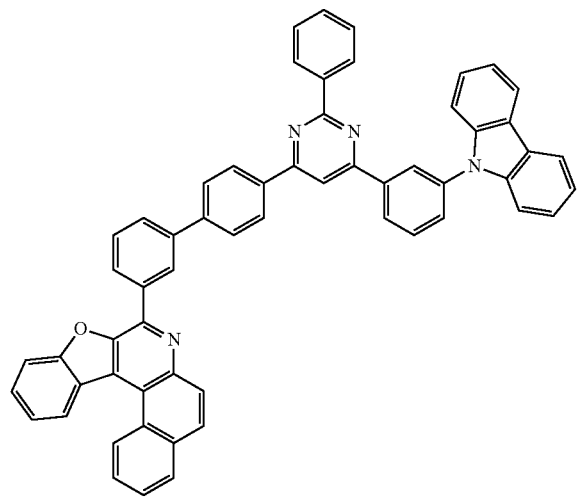
26
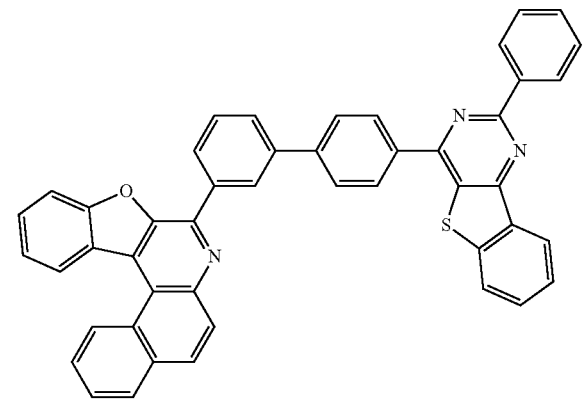
27
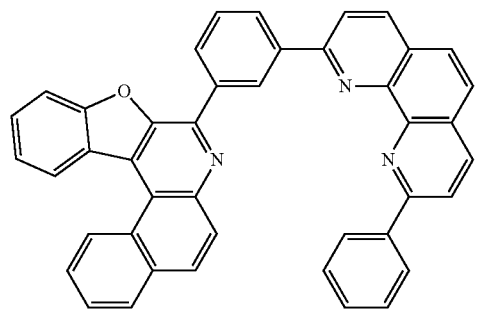 [SMILES: c1ccc(-c2ccc3ccc4ccc(-c5cccc(-c6nc7ccc8ccccc8c7c7c6oc6ccccc67)c5)nc4c3n2)cc1]
28
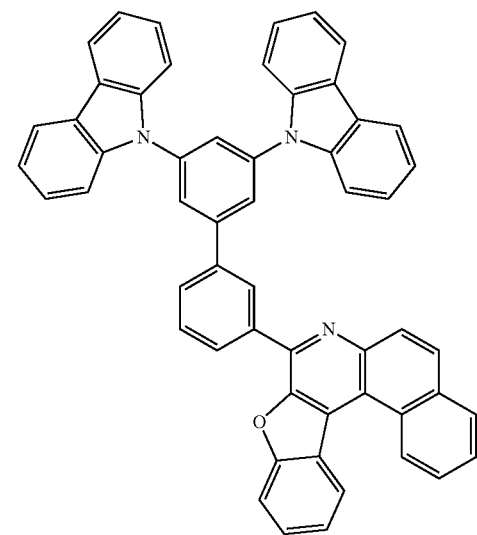 [SMILES: c1cc(-c2cc(-n3c4ccccc4c4ccccc43)cc(-n3c4ccccc4c4ccccc43)c2)cc(-c2nc3ccc4ccccc4c3c3c2oc2ccccc23)c1]
29
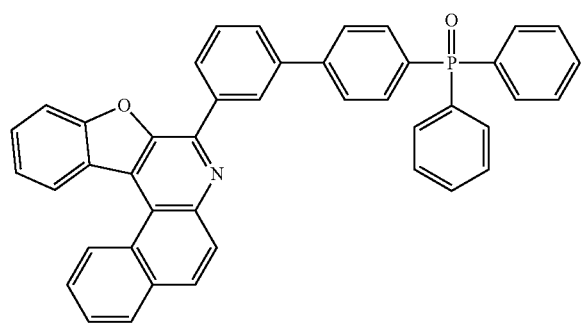
30
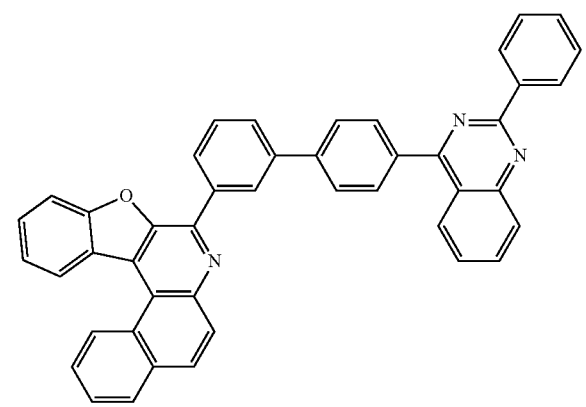

31
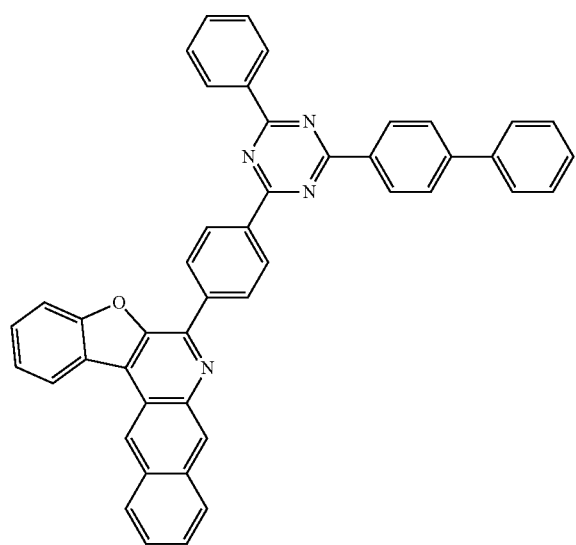
32
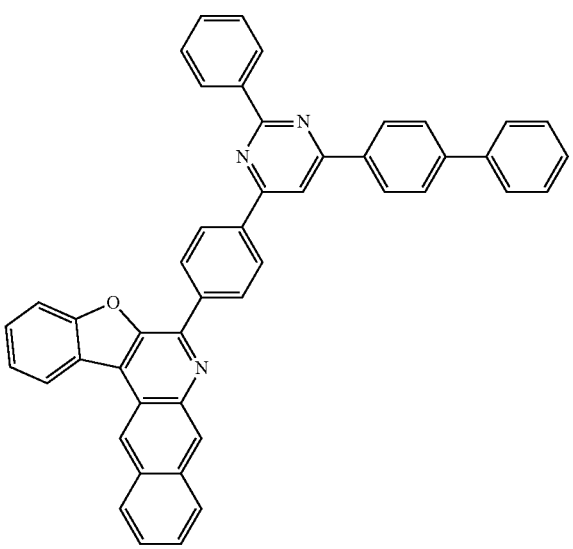
33
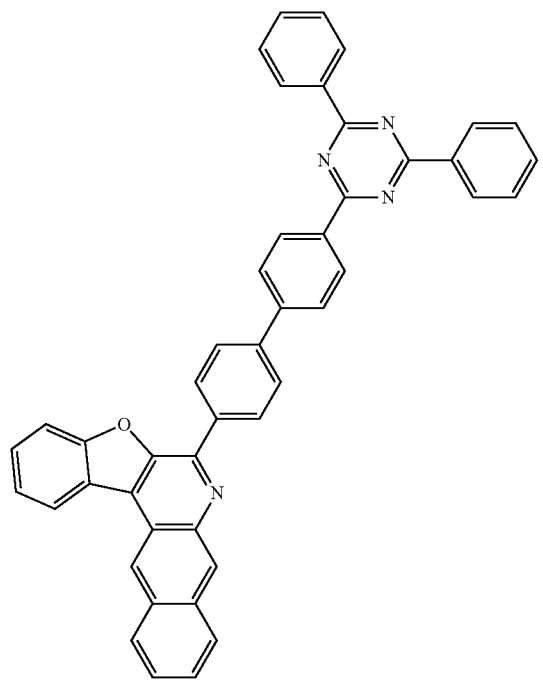
34
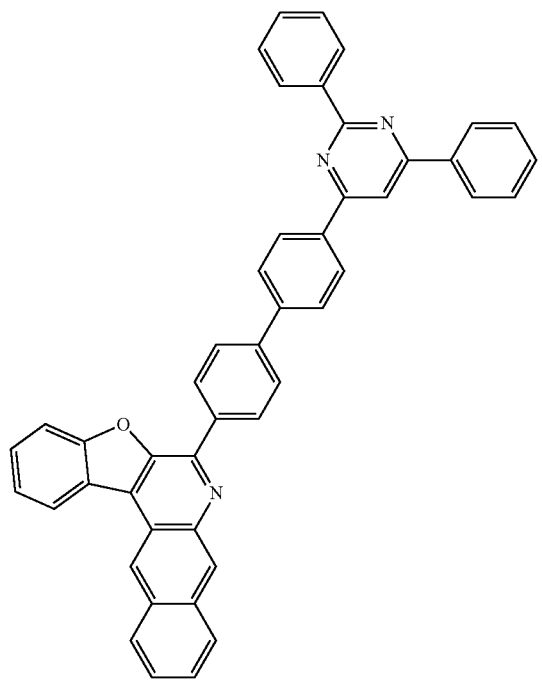

35
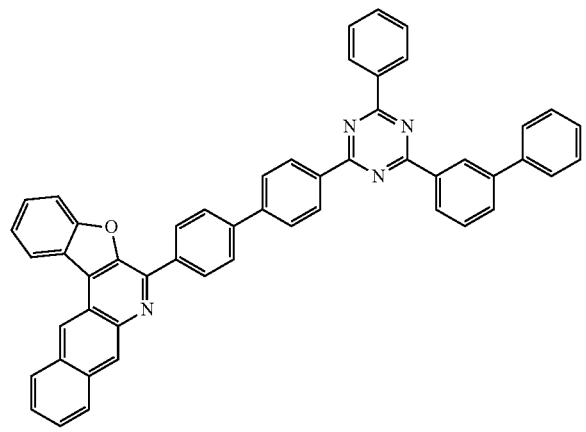
36
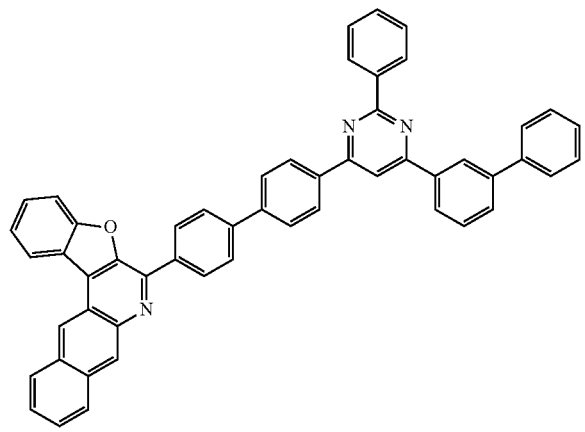
37
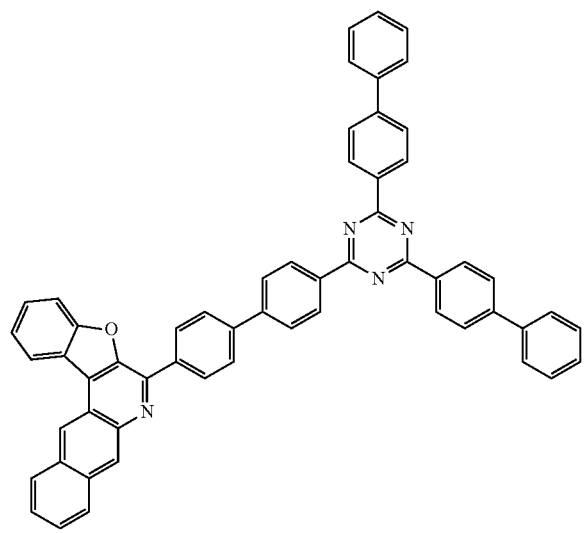
38
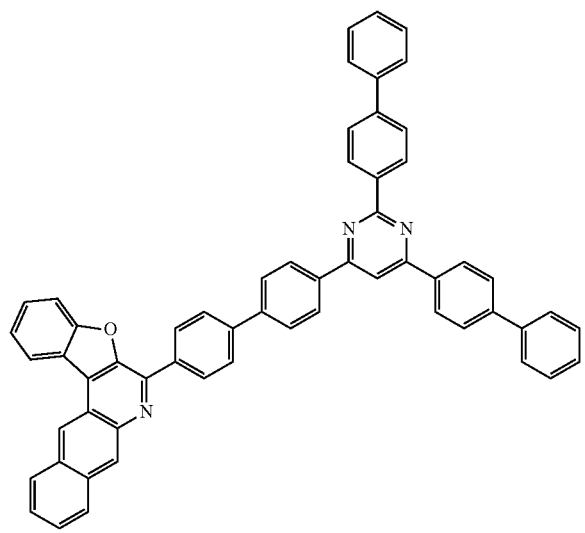
39
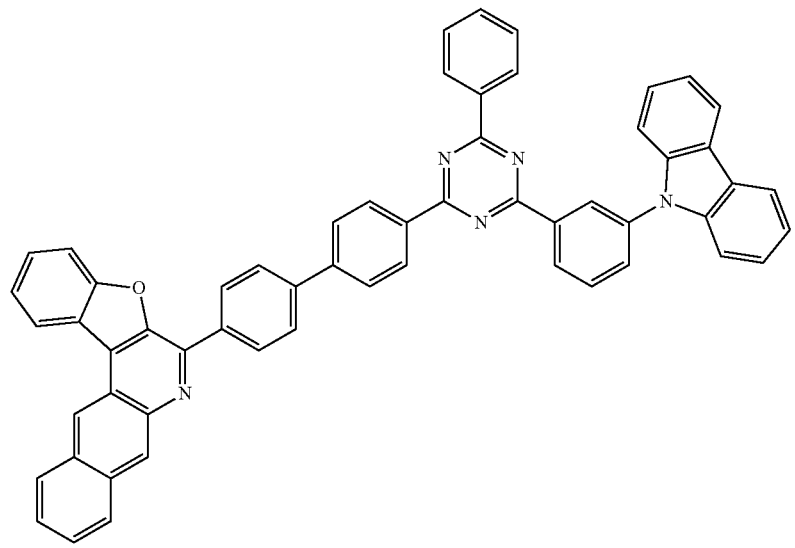

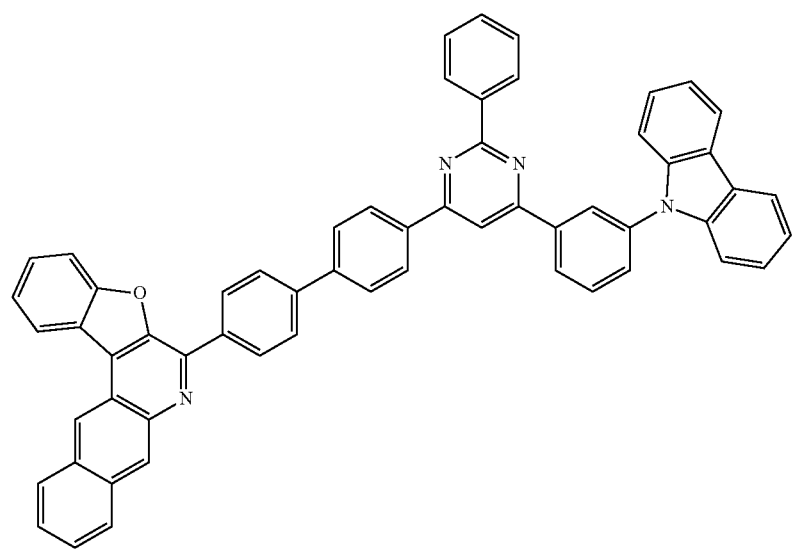
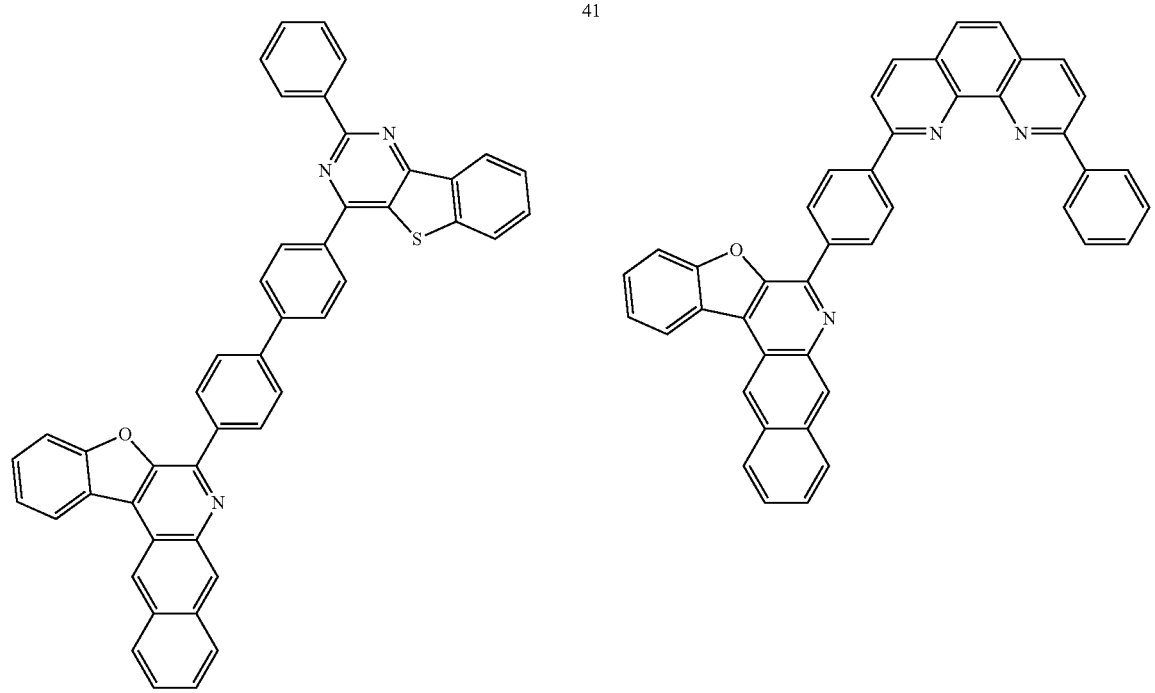

43
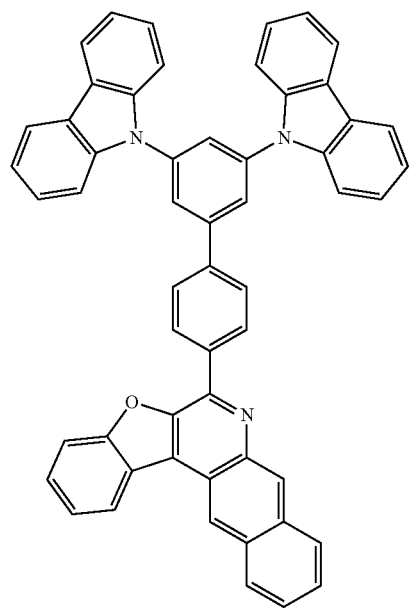
44
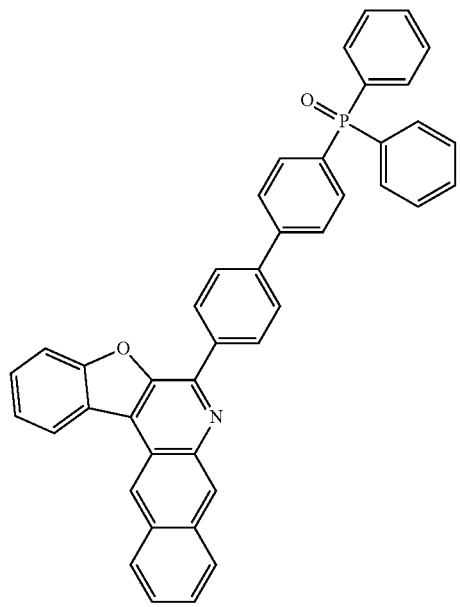
45
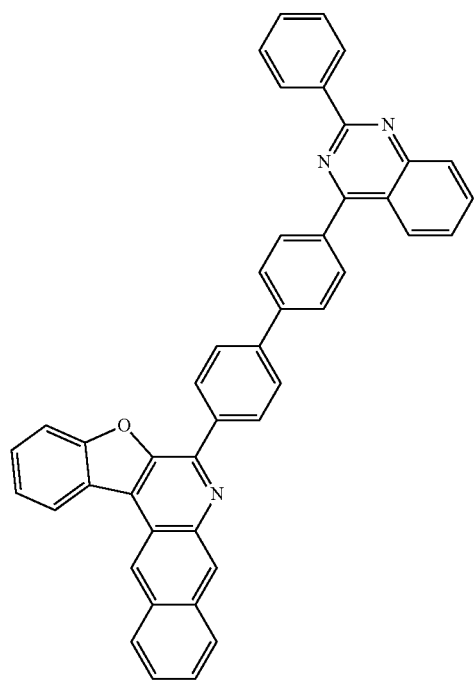
46
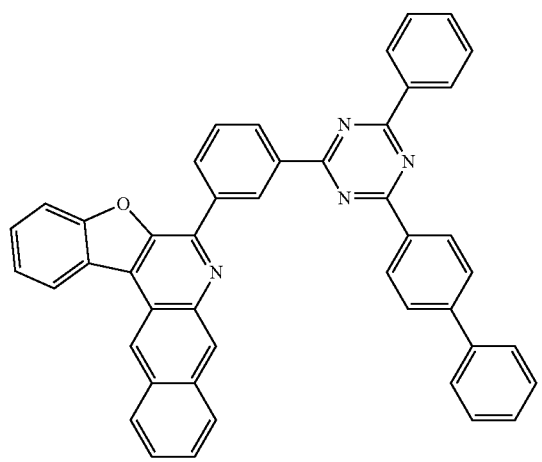

47
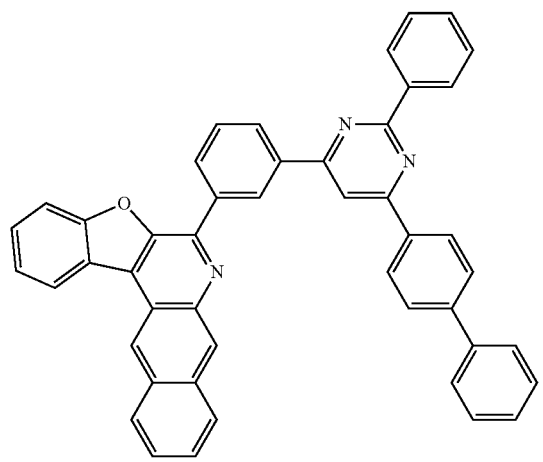
48
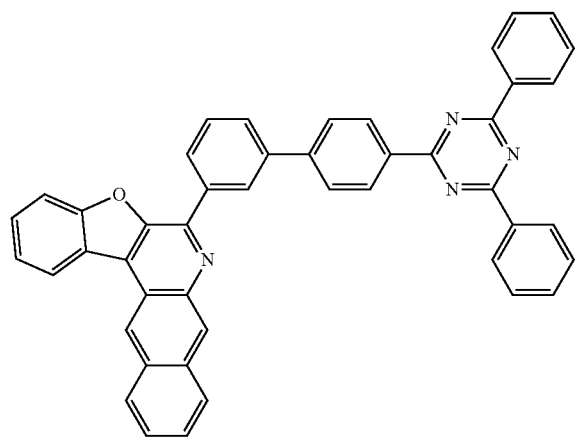
49
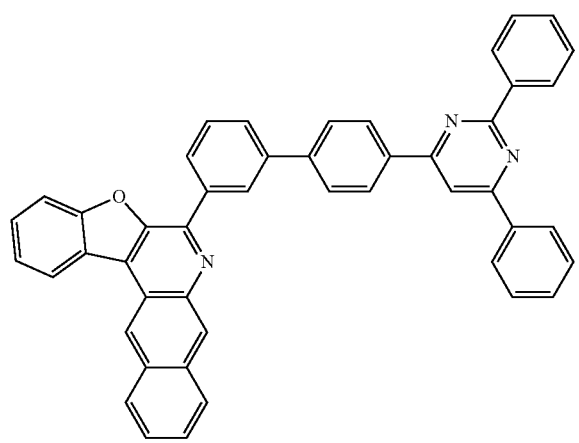
50
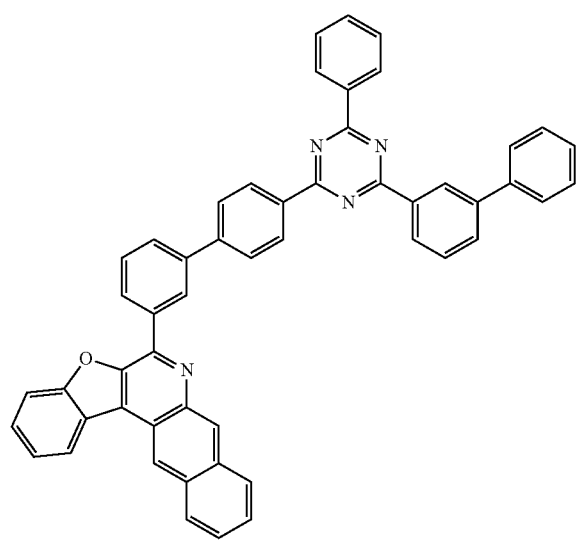

-continued
51
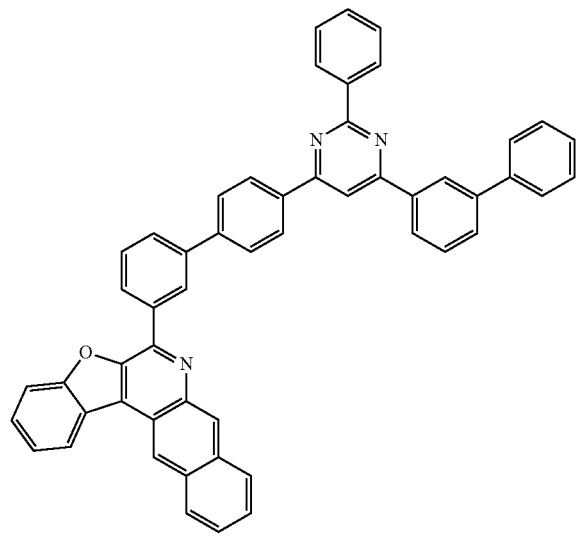 [SMILES: c1ccc(-c2cccc(-c3cc(-c4ccc(-c5cccc(-c6nc7cc8ccccc8cc7c7c6oc6ccccc67)c5)cc4)nc(-c4ccccc4)n3)c2)cc1]
52
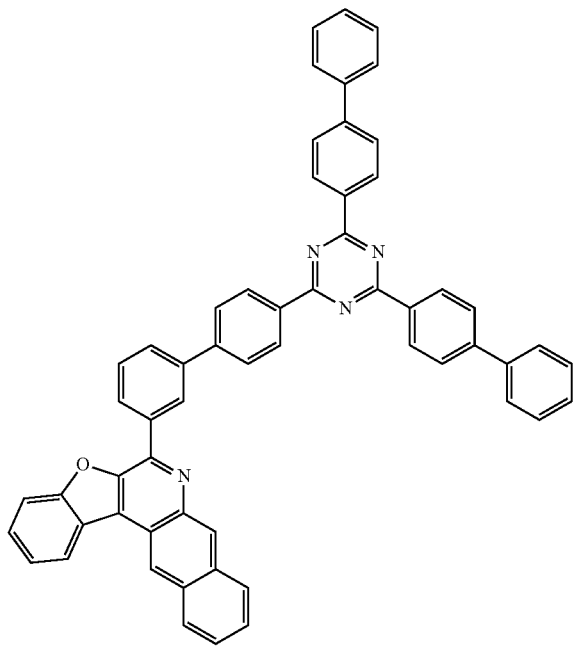
53
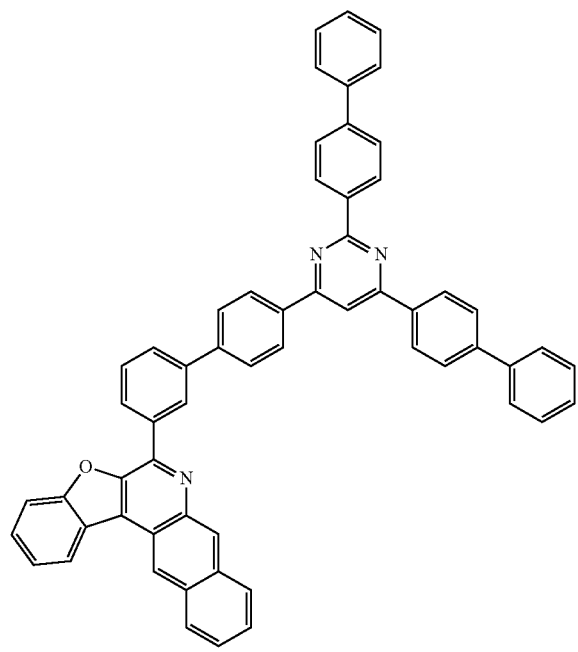
54
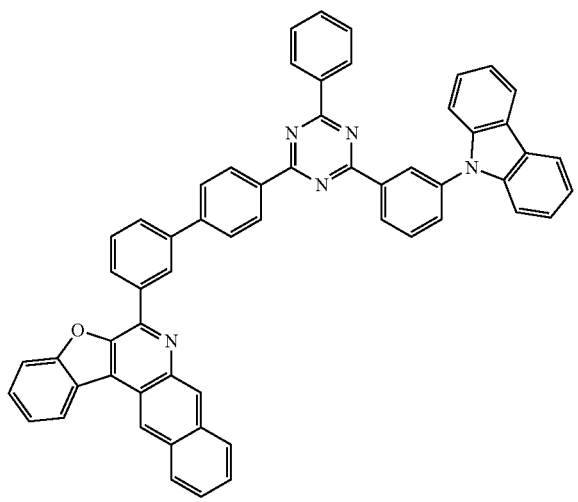

55
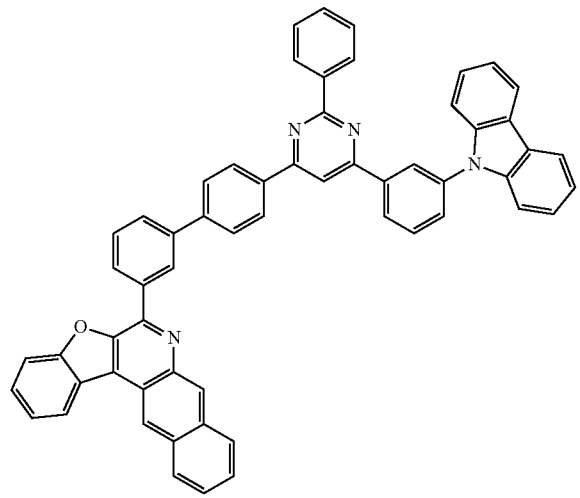
56
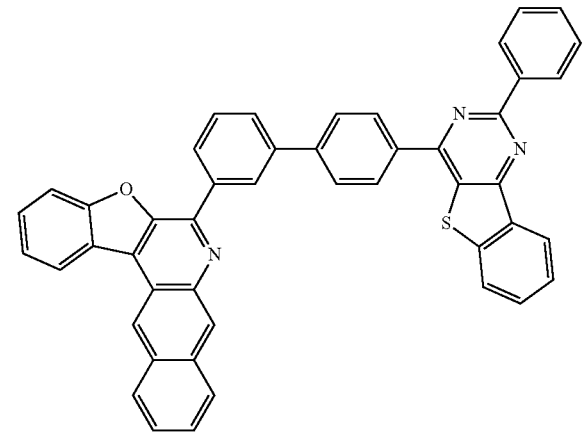
57
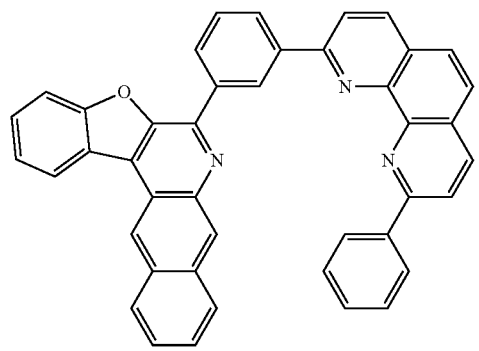
58
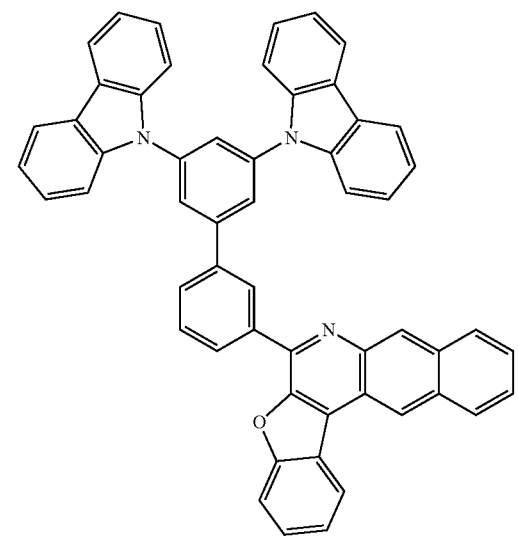
59
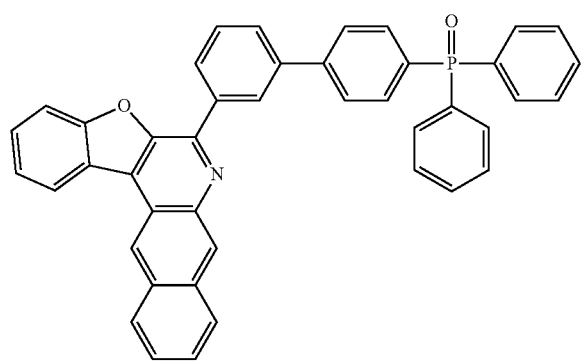
60
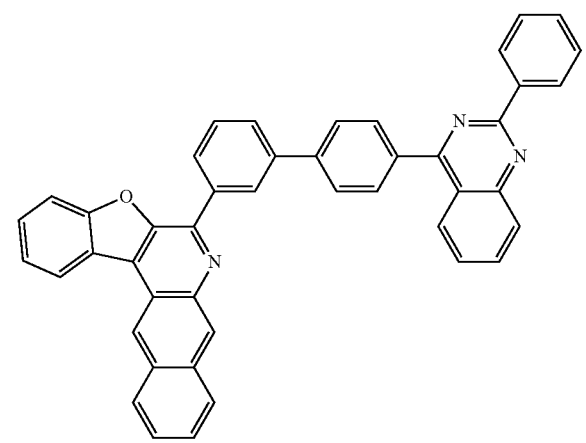

-continued
61
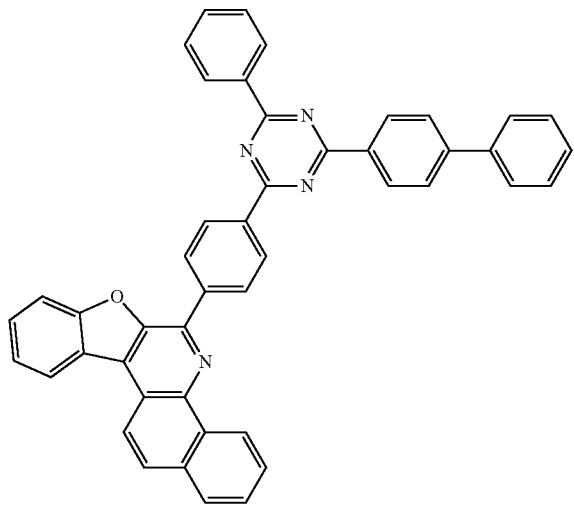
62
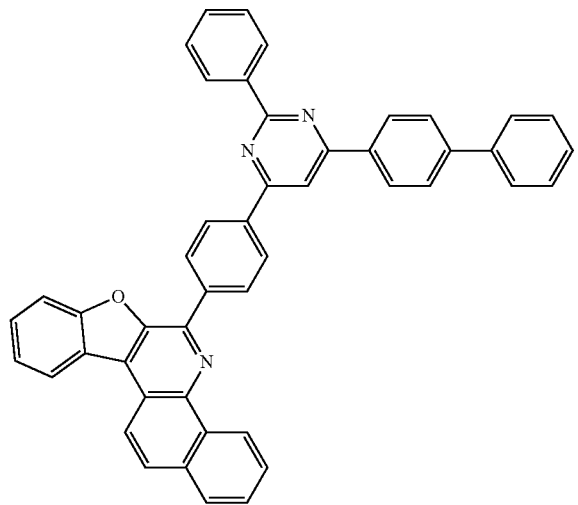
63
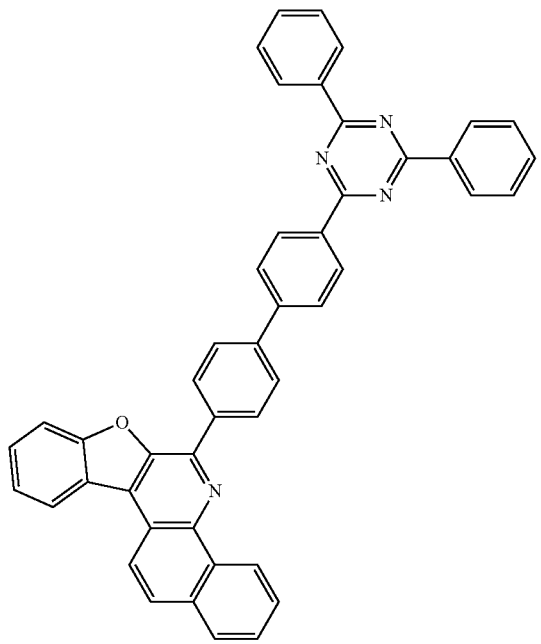
64
65
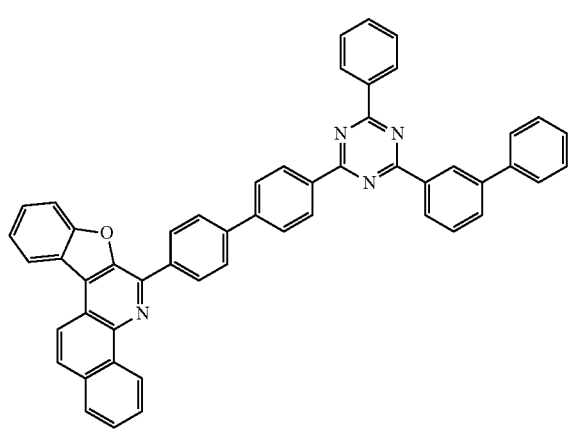
66
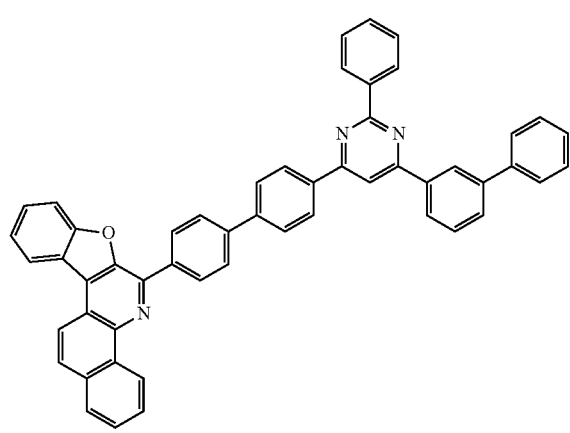

67
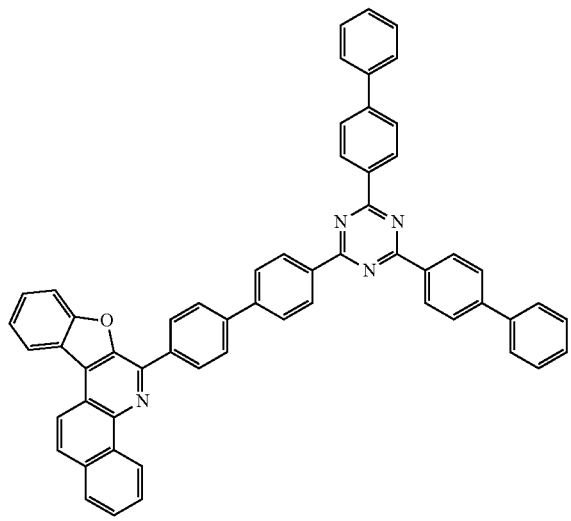
68
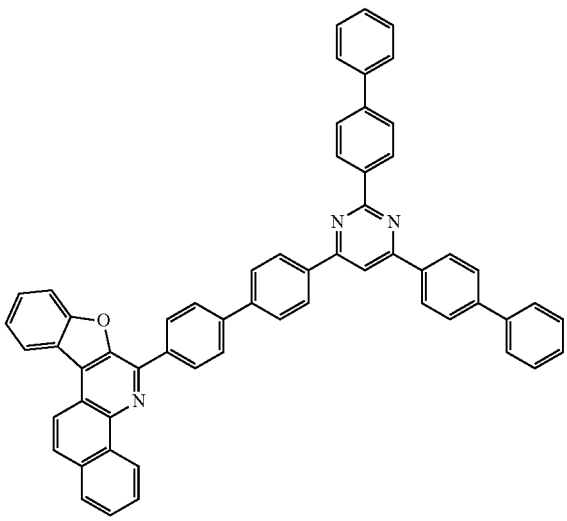
69
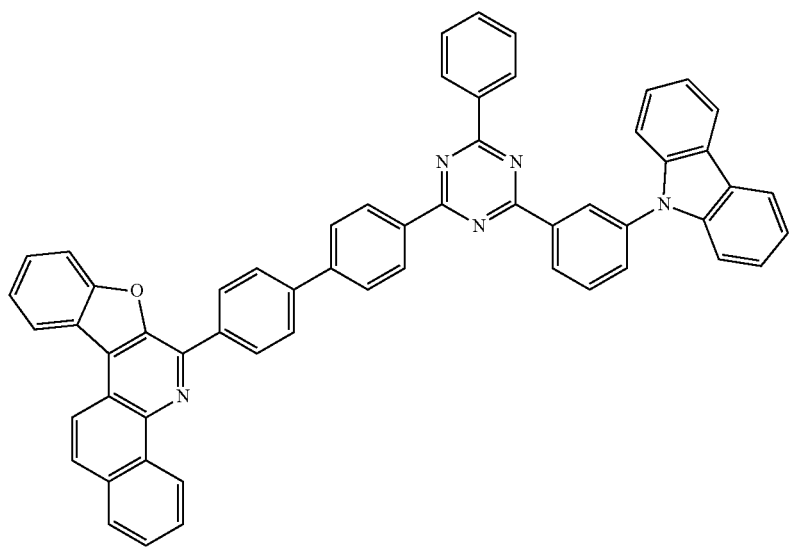 [SMILES: c1ccc(-c2nc(-c3ccc(-c4ccc(-c5nc6c7ccccc7ccc6c6c5oc5ccccc56)cc4)cc3)cc(-c3cccc(-n4c5ccccc5c5ccccc54)c3)n2)cc1]
70
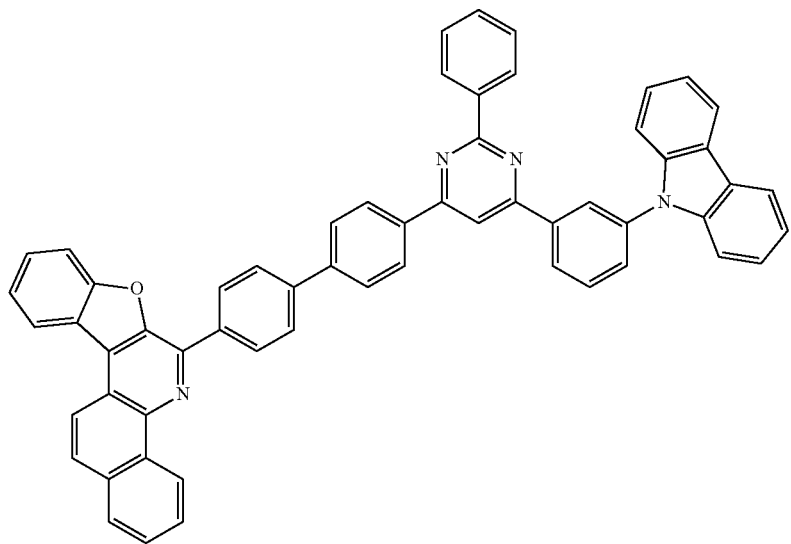

-continued
263
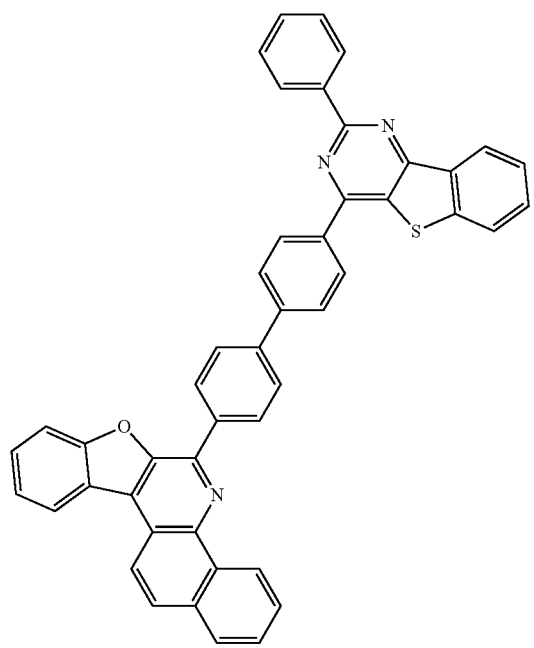
71
264
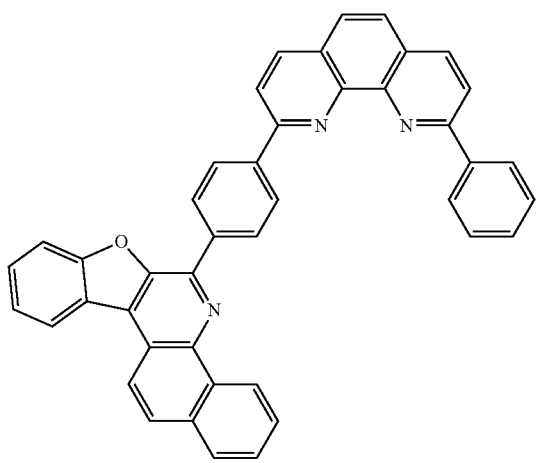
72
73
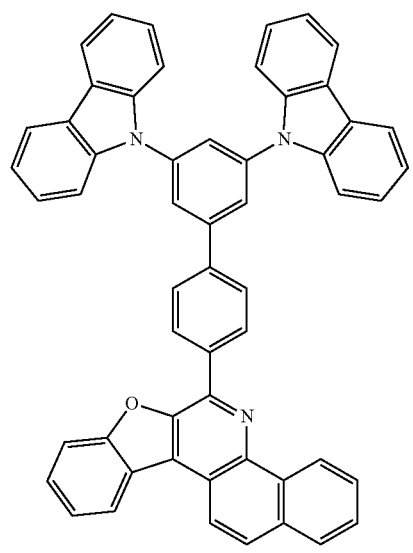
74
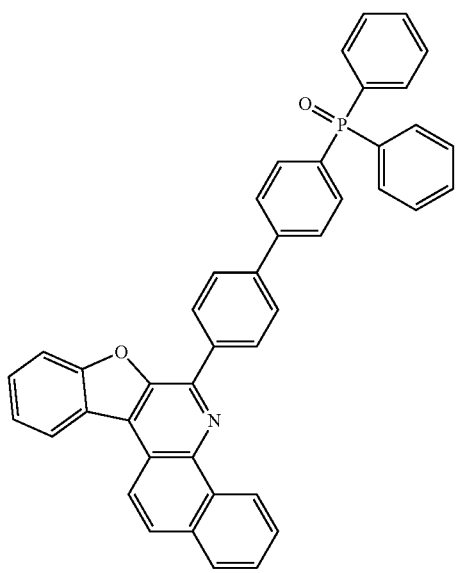

75
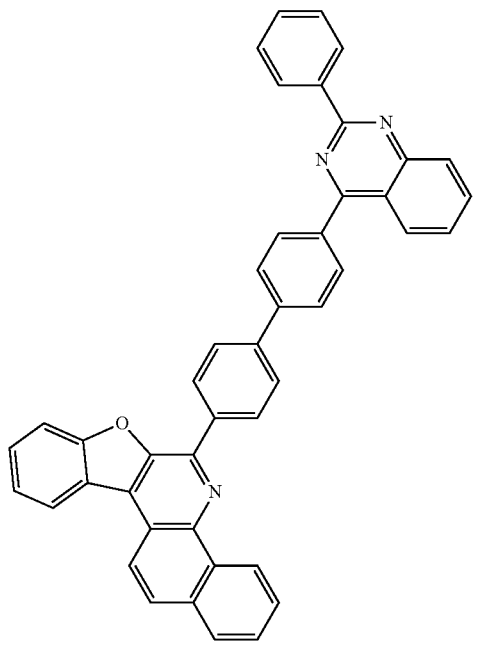
76
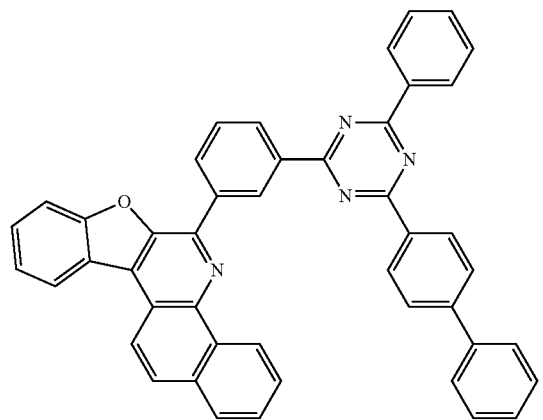
77
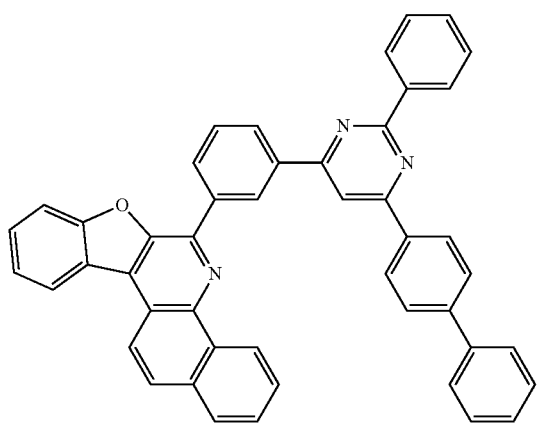
78
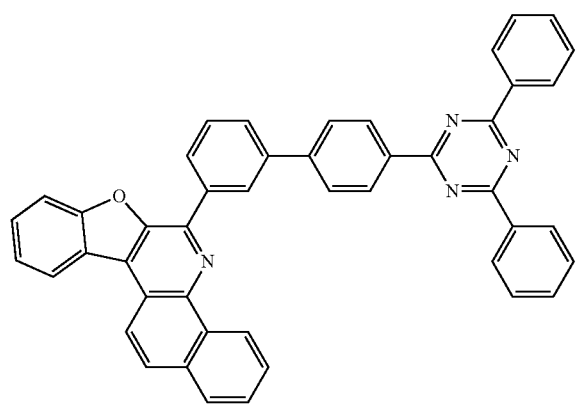
79
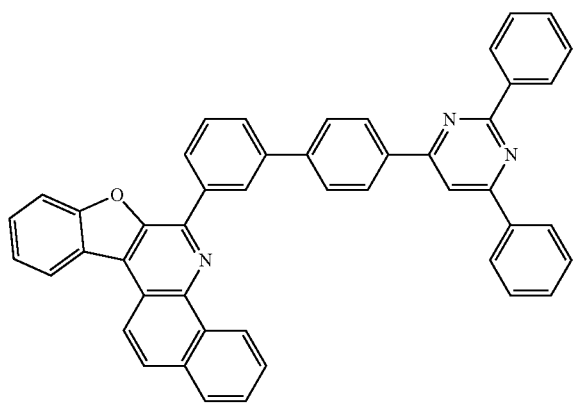
80
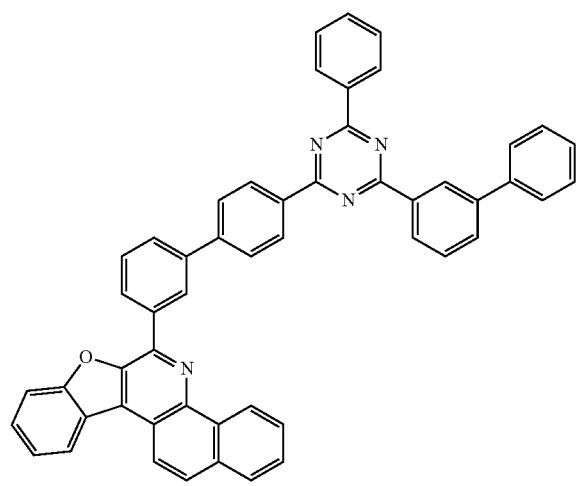

81
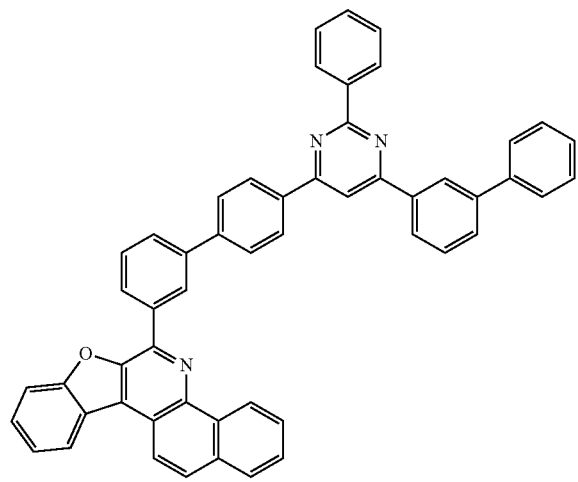
82
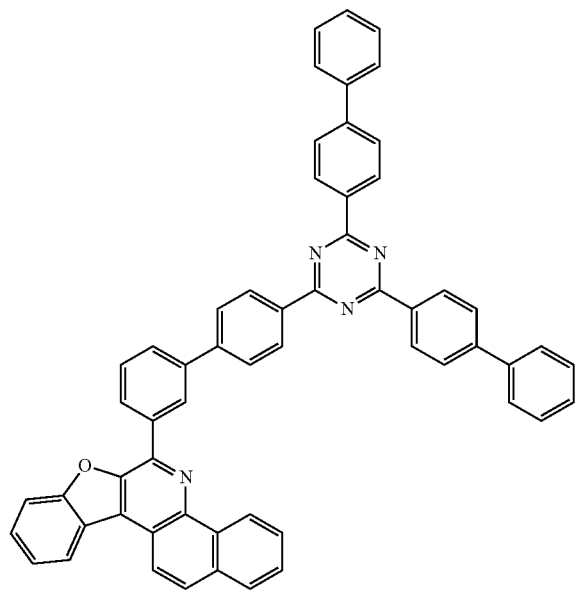
83
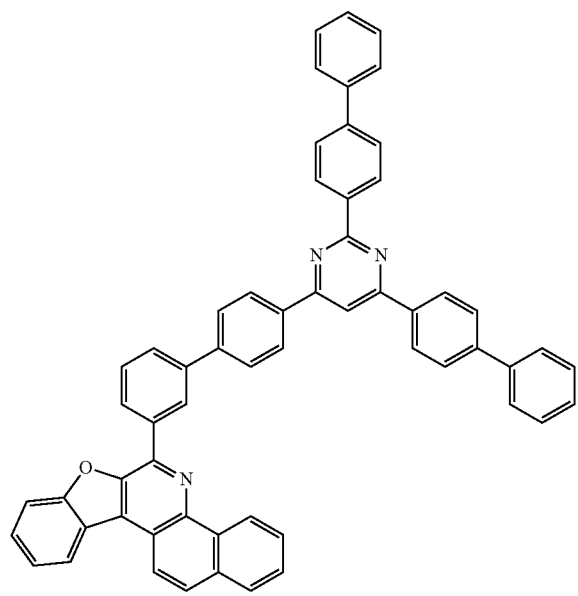
84
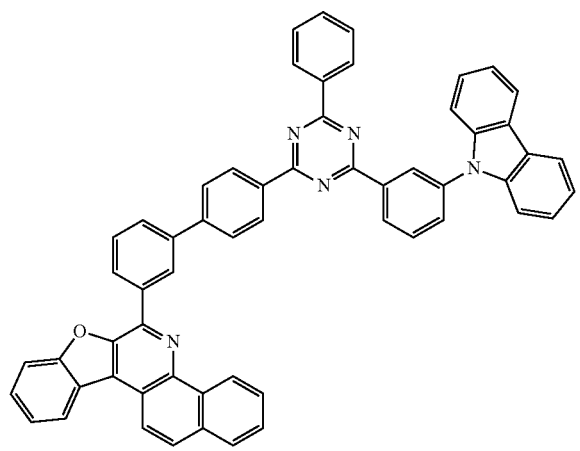 [SMILES: c1ccc(-c2nc(-c3ccc(-c4cccc(-c5nc6c7ccccc7ccc6c6c5oc5ccccc56)c4)cc3)cc(-c3cccc(-n4c5ccccc5c5ccccc54)c3)n2)cc1]

-continued
85
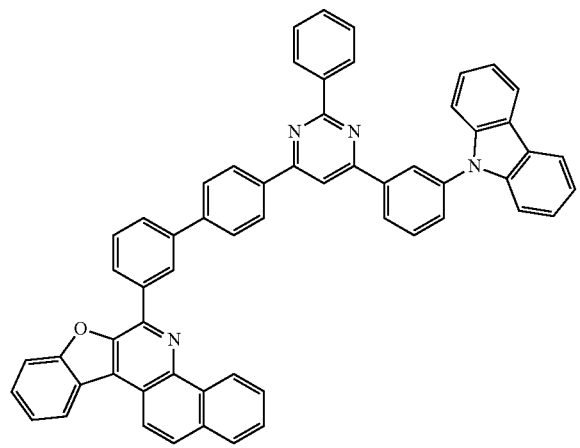
86
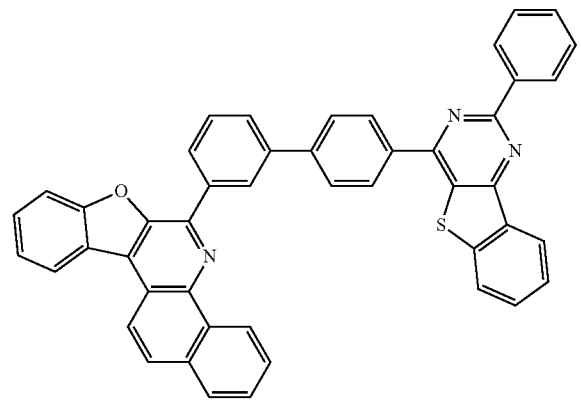
87
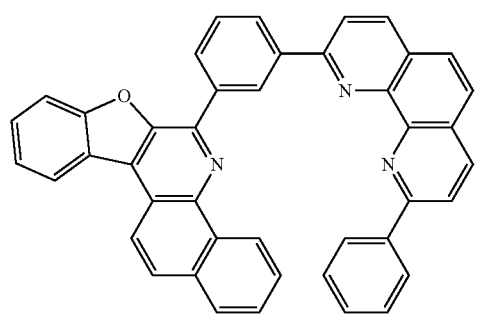
88
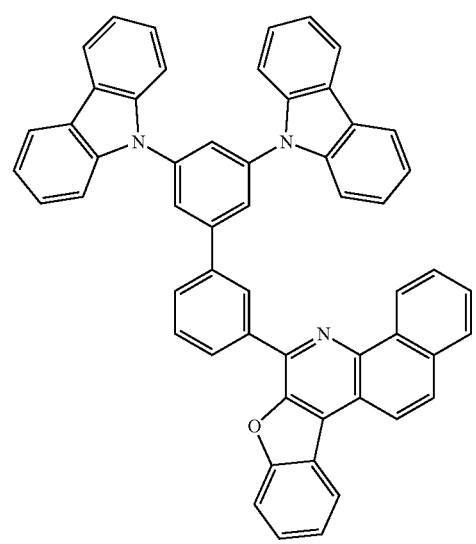 [SMILES: c1cc(-c2cc(-n3c4ccccc4c4ccccc43)cc(-n3c4ccccc4c4ccccc43)c2)cc(-c2nc3c4ccccc4ccc3c3c2oc2ccccc23)c1]
89
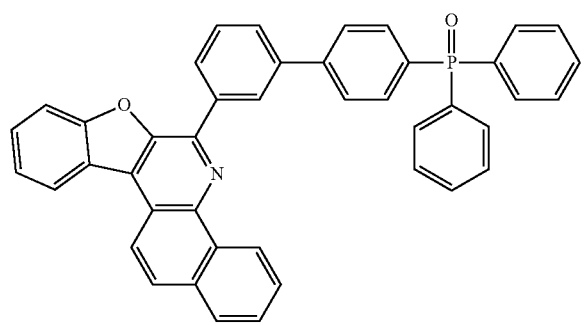
90
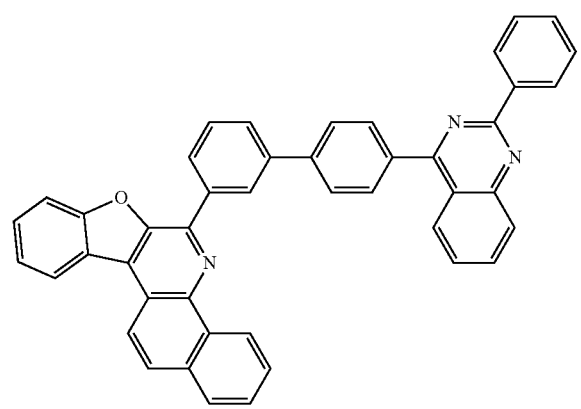

-continued
91
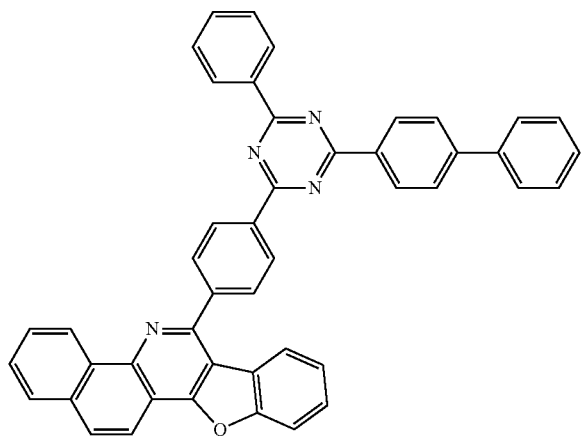 [SMILES: c1ccc(-c2ccc(-c3nc(-c4ccccc4)nc(-c4ccc(-c5nc6c7ccccc7ccc6c6oc7ccccc7c56)cc4)n3)cc2)cc1]
92
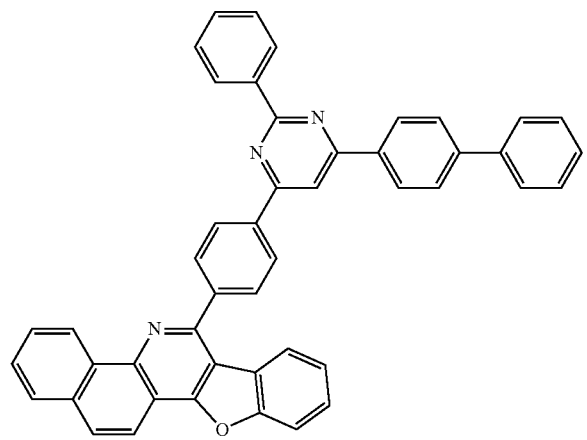
93
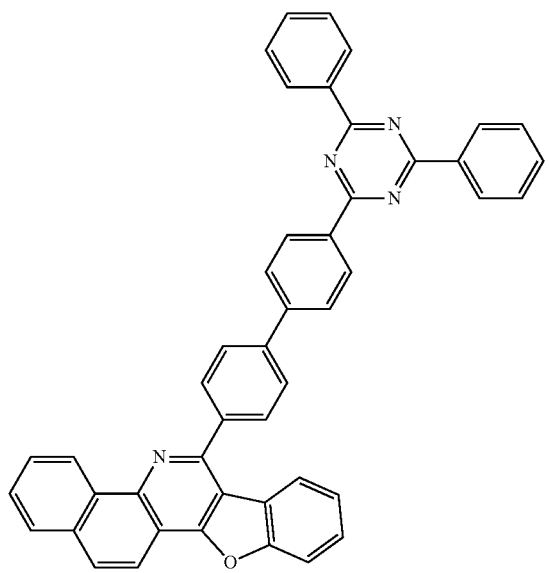
94
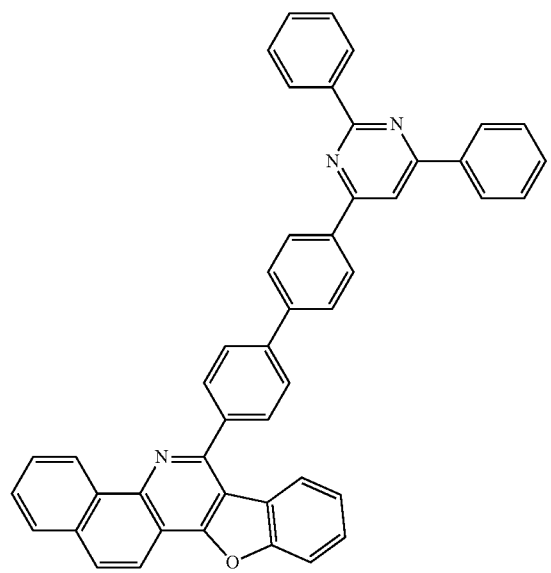
95
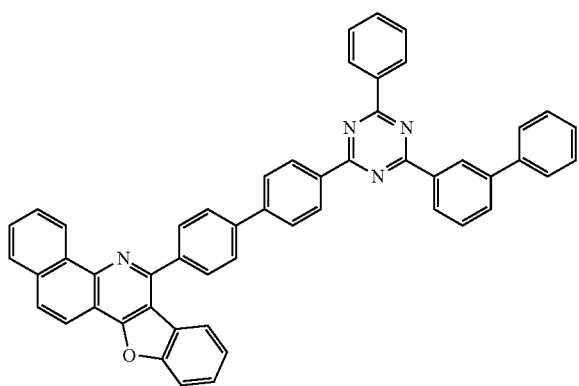
96
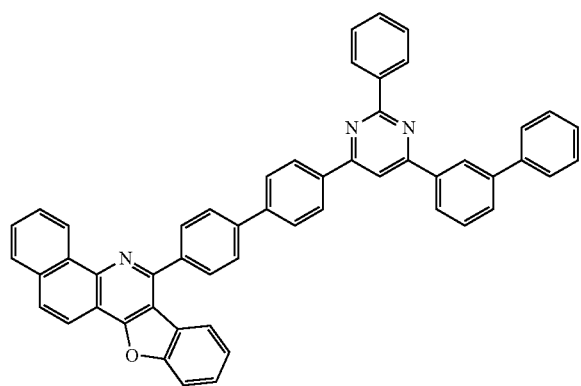 [SMILES: c1ccc(-c2cccc(-c3cc(-c4ccc(-c5ccc(-c6nc7c8ccccc8ccc7c7oc8ccccc8c67)cc5)cc4)nc(-c4ccccc4)n3)c2)cc1]

97
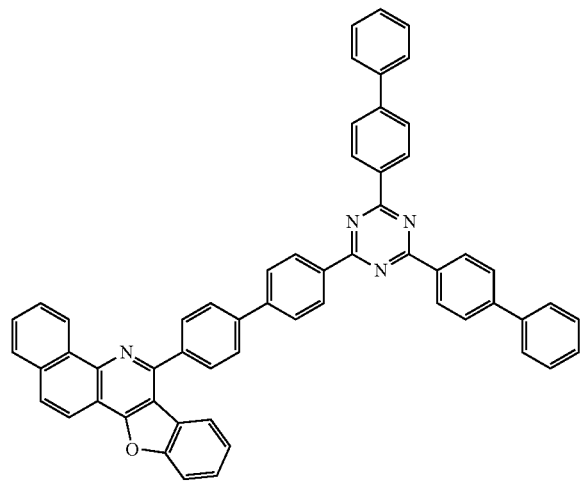
98
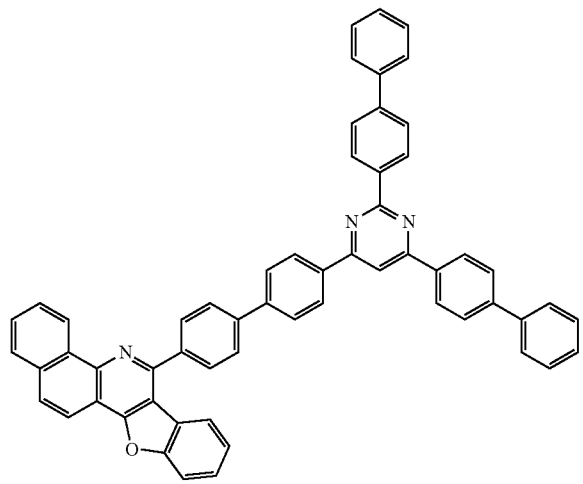
99
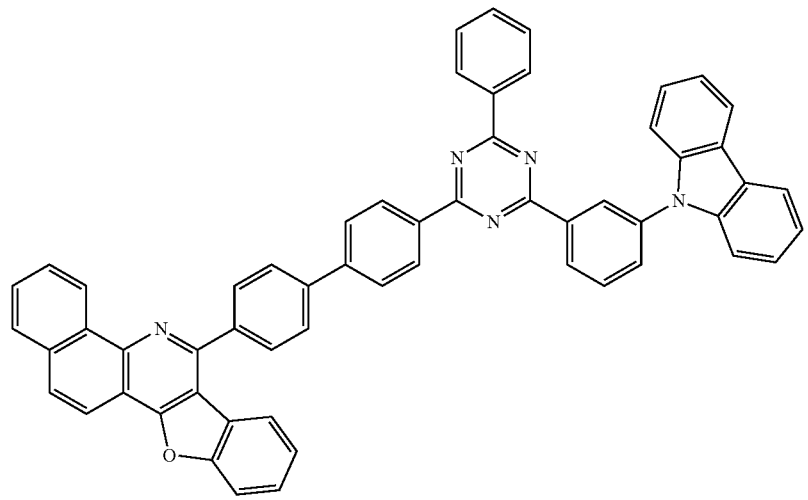
100
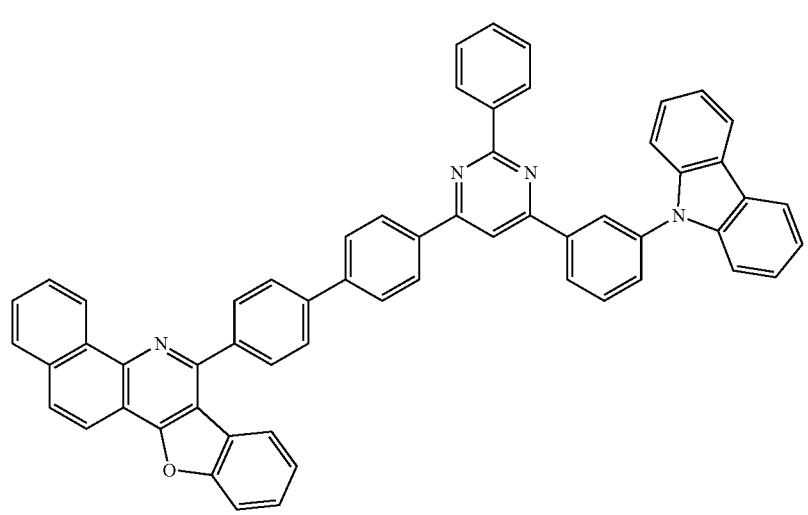

-continued
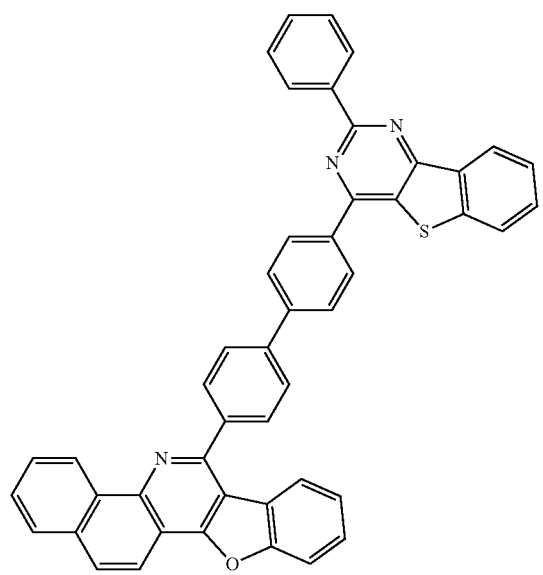
101
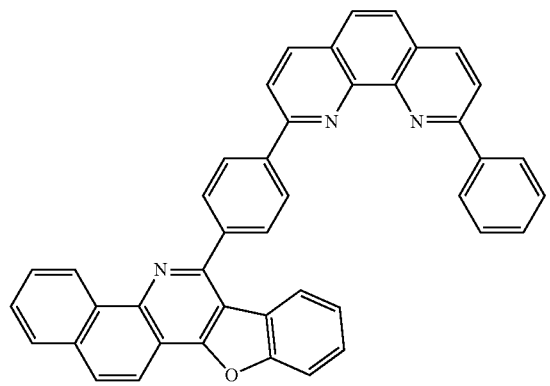
102
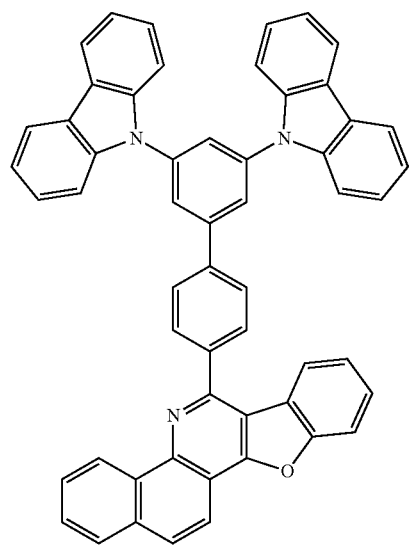
103
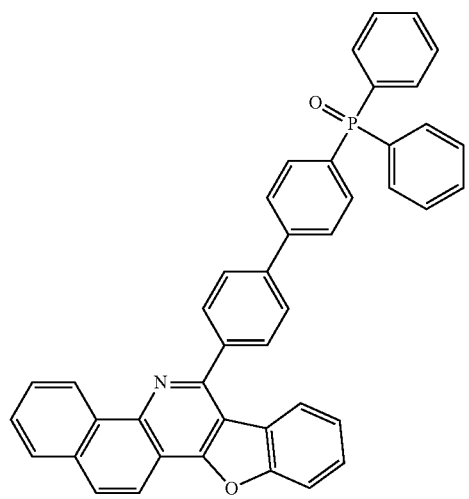
104

-continued
277
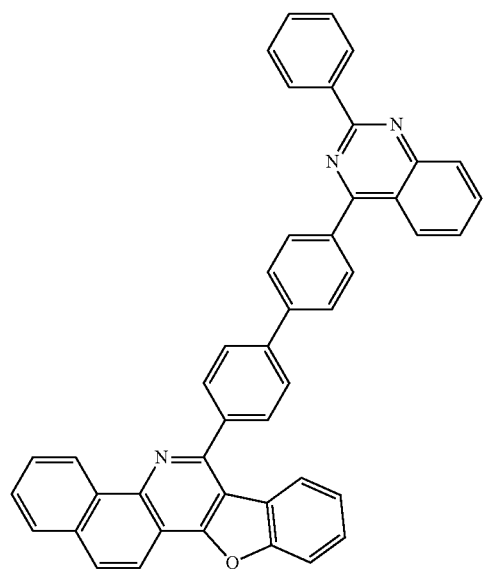
278
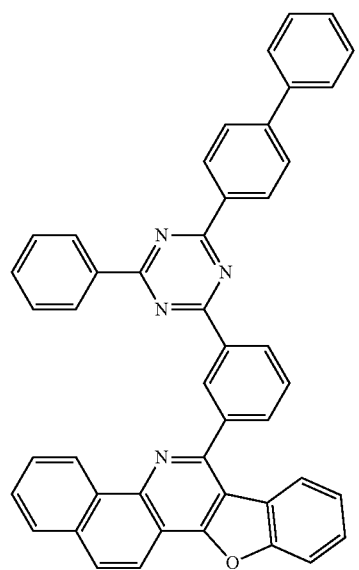
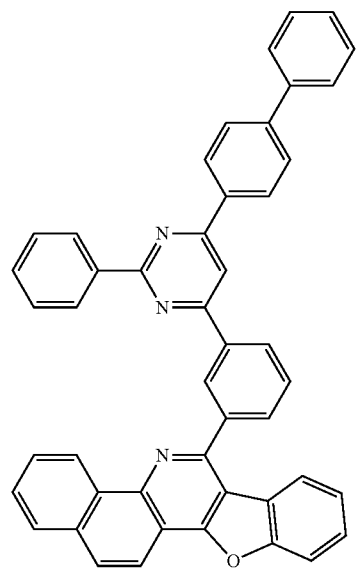
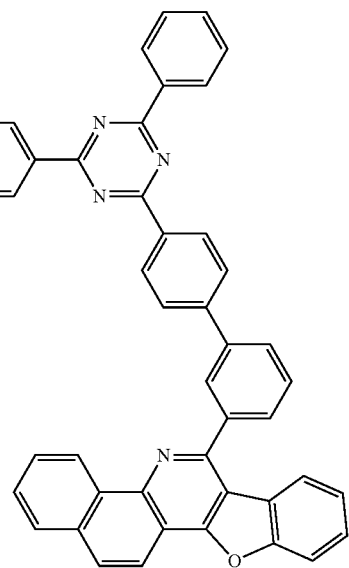

-continued
109
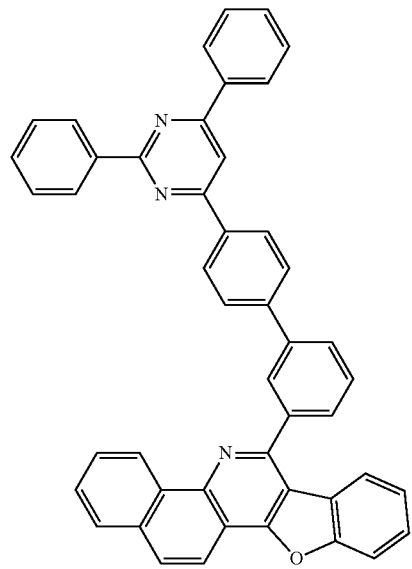
110
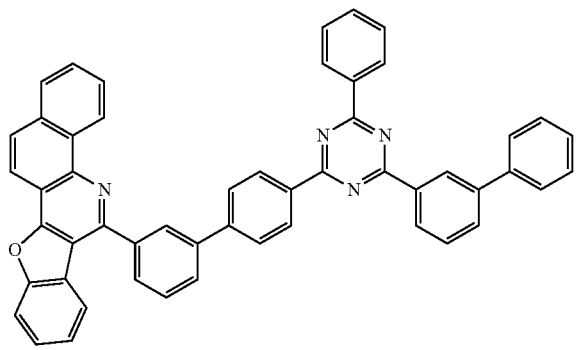
111
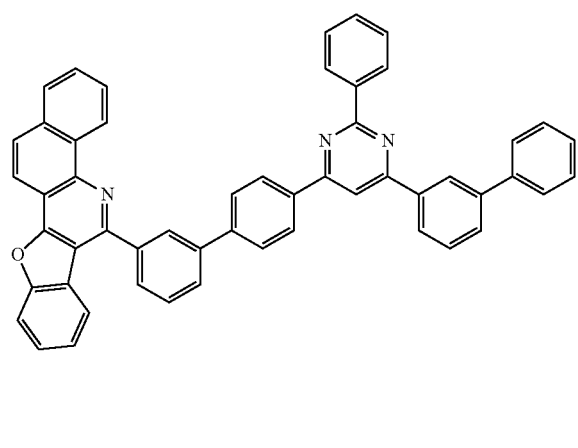
112
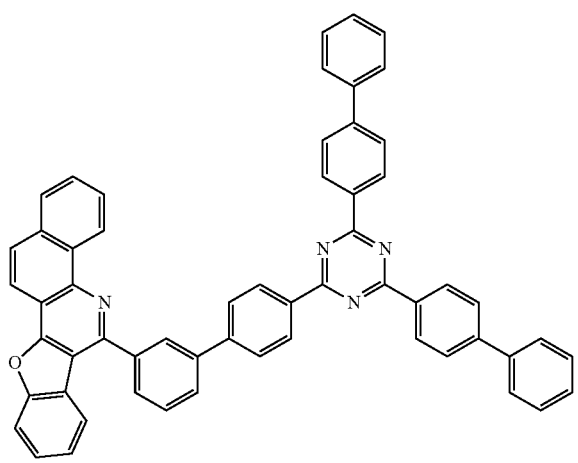
113
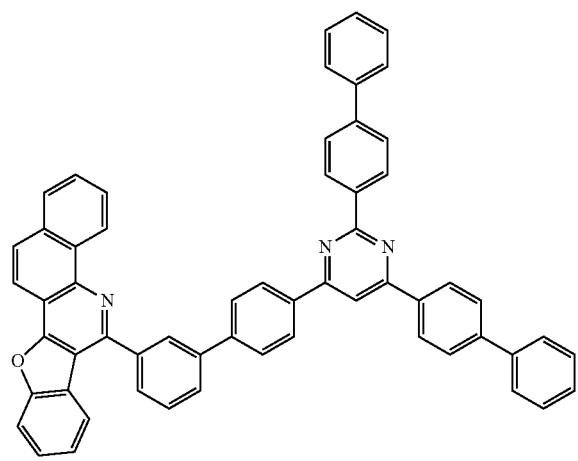
114
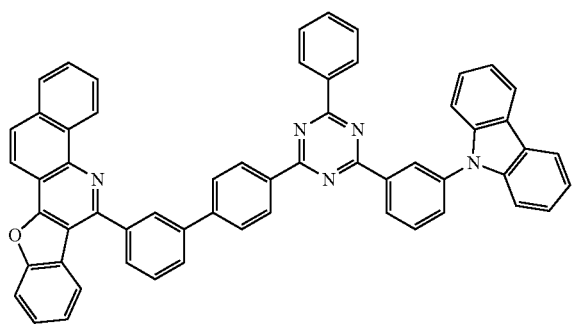

115
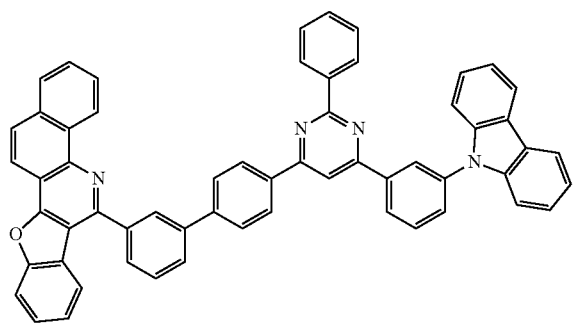
116
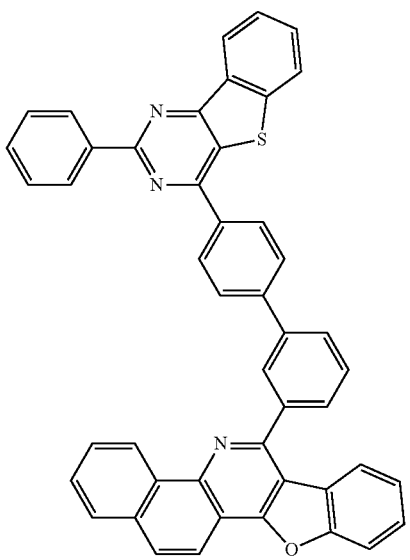
117
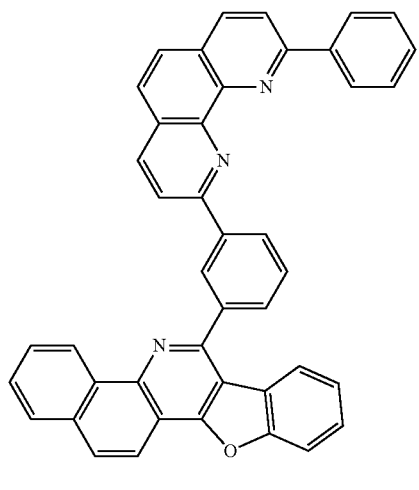
118
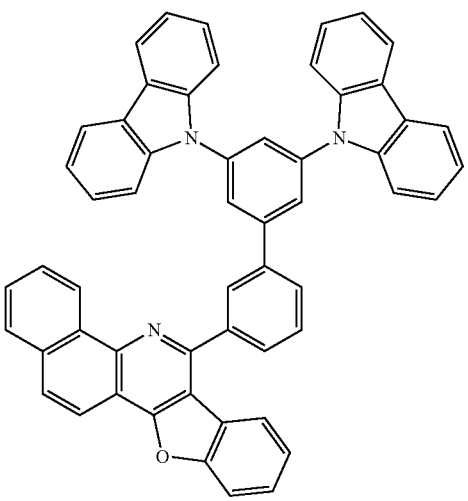
119
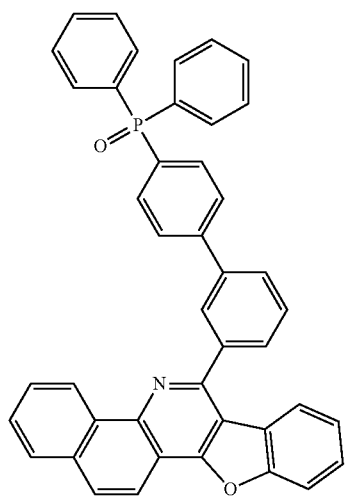
120
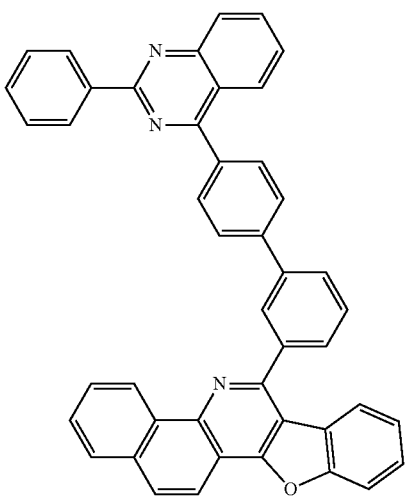

-continued
121
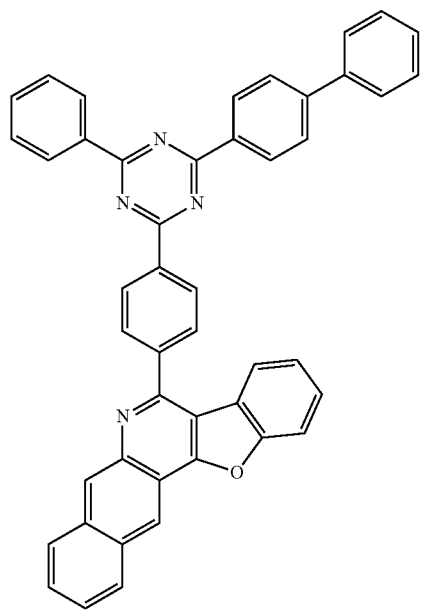
122
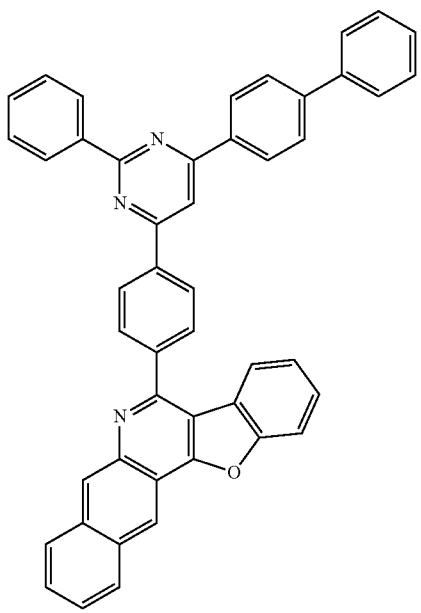
123
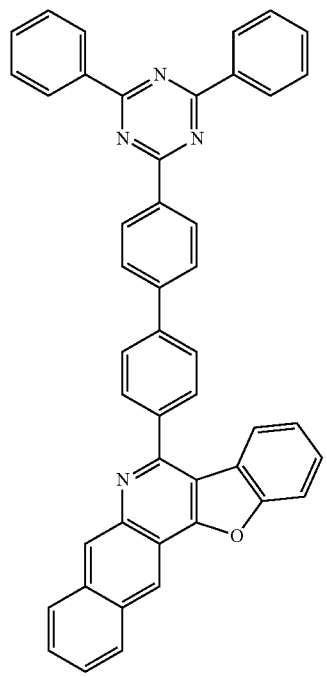
124
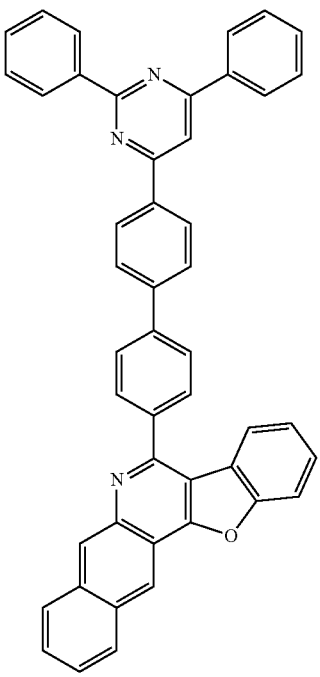

125
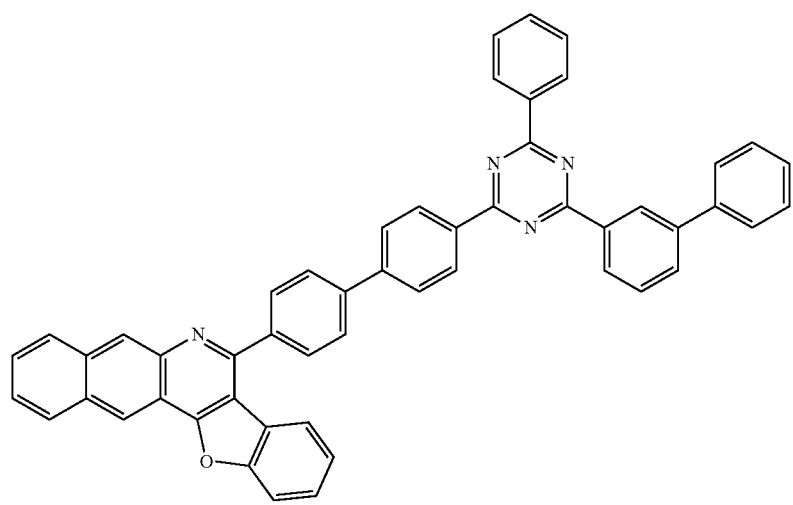
126
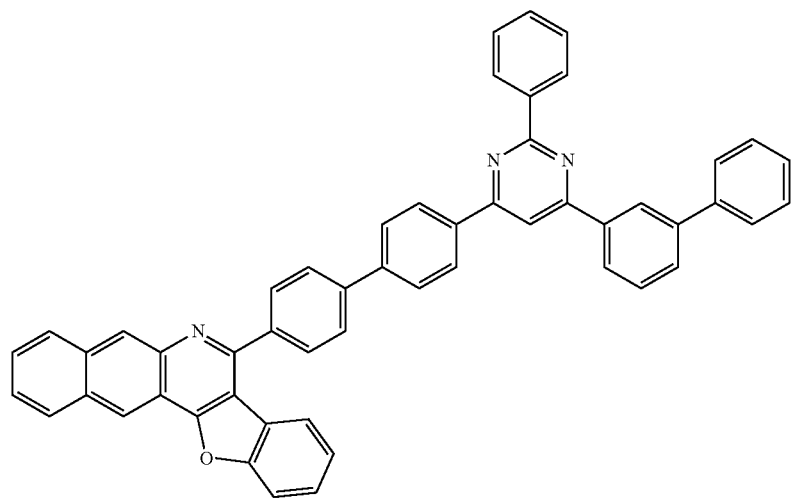
127
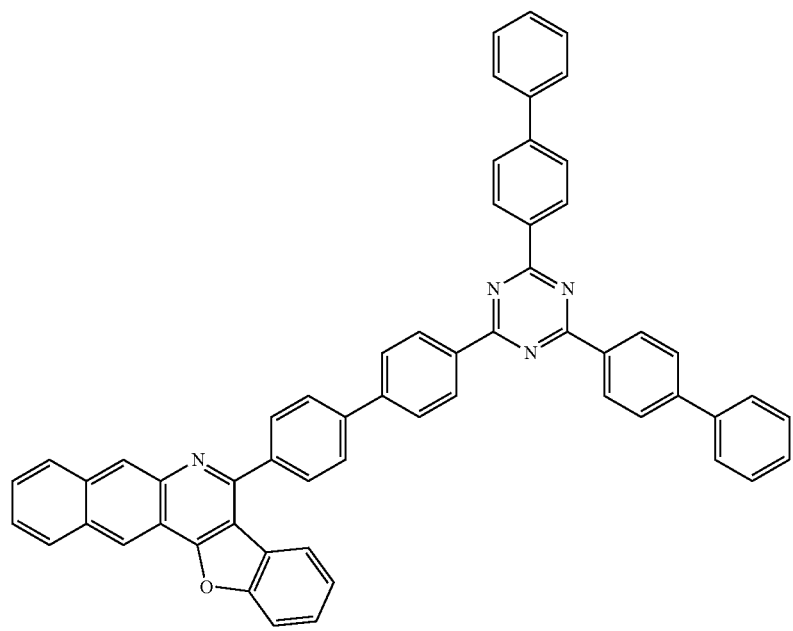

128
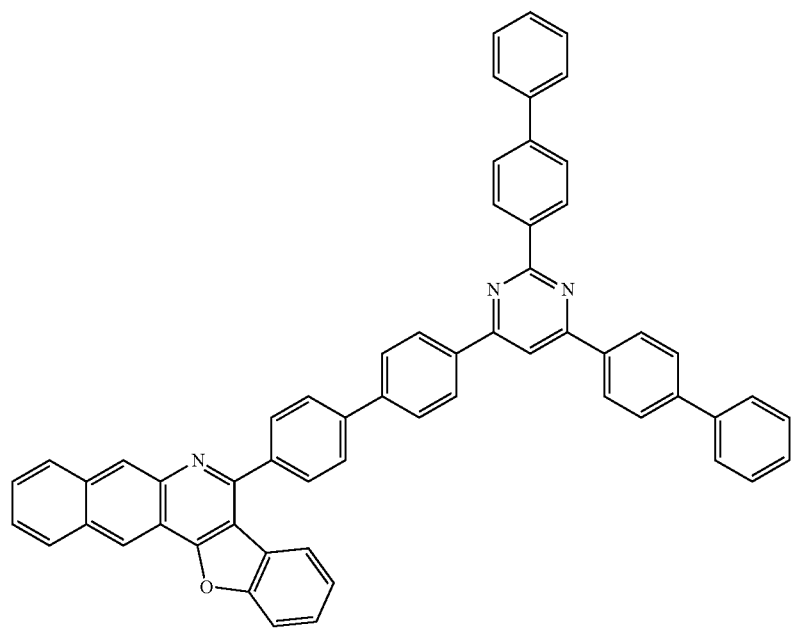
129
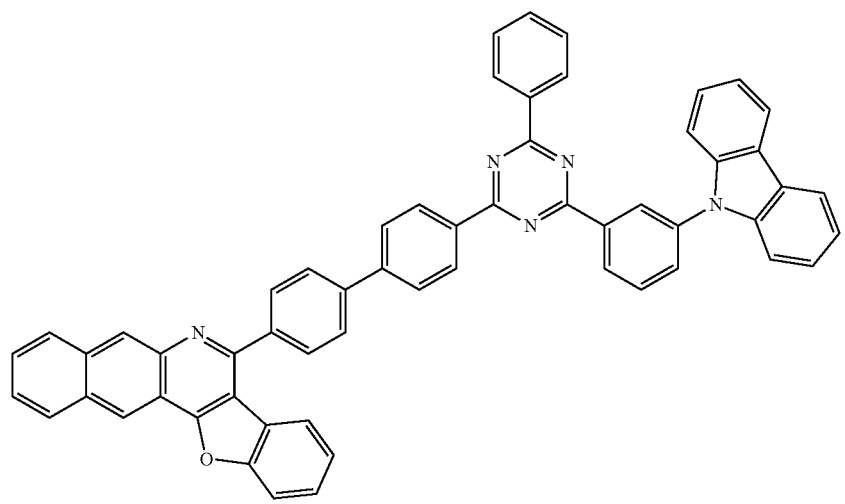
130
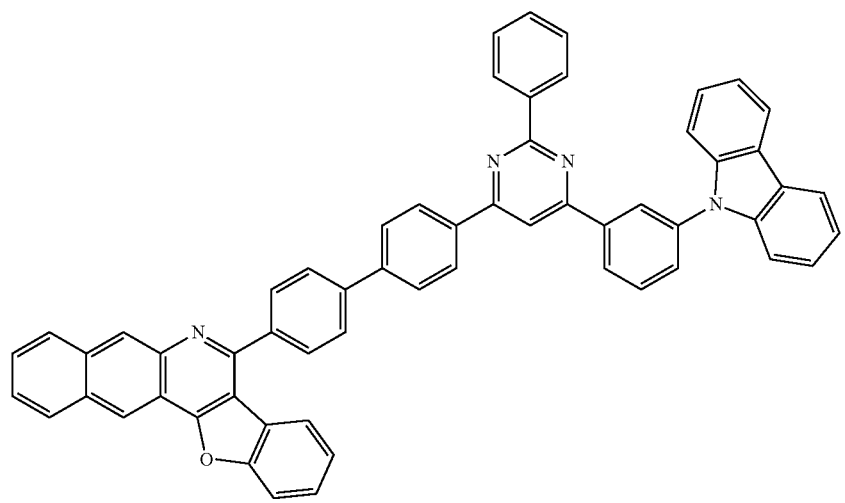

-continued
131
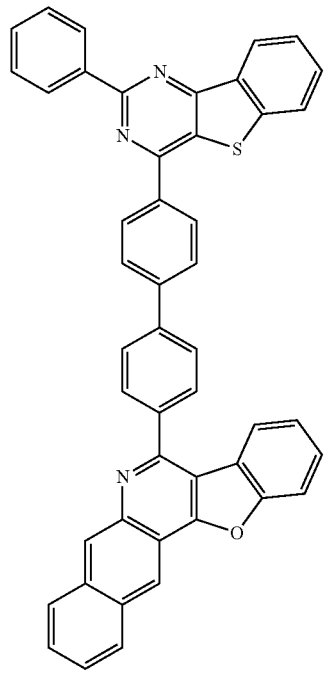
132
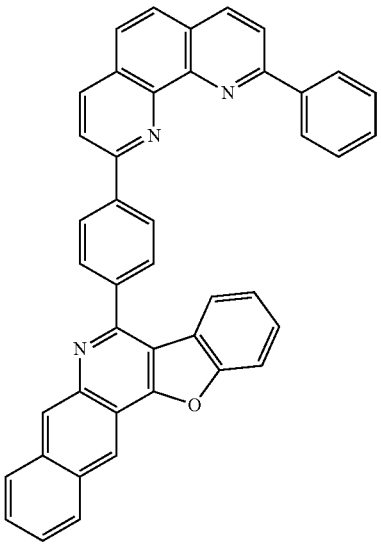
133
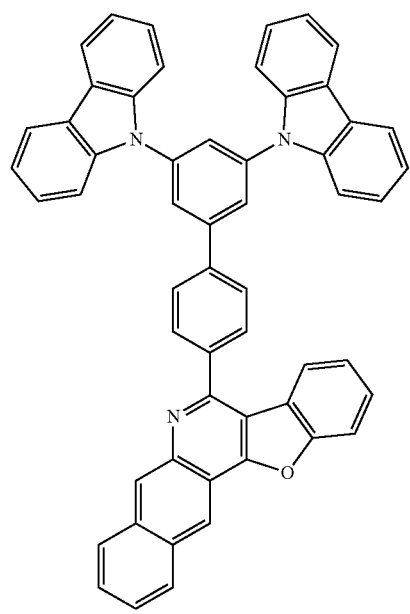
134
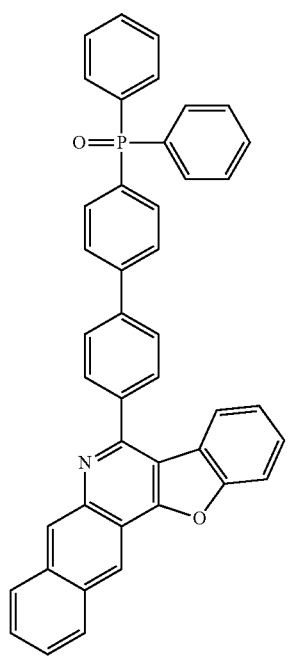

135
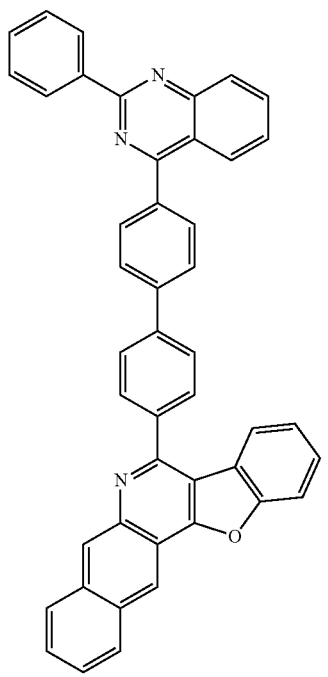
136
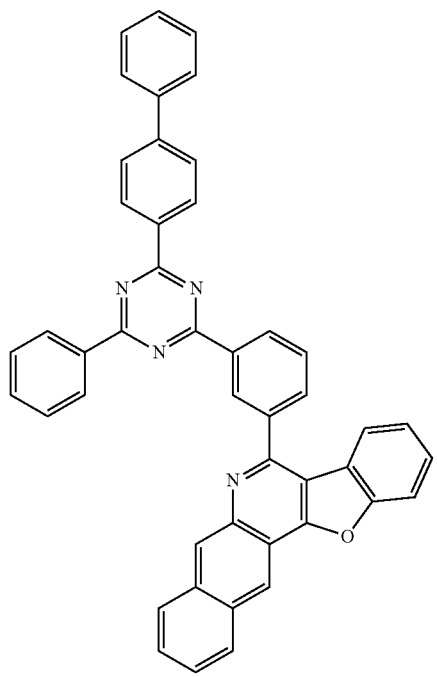
137
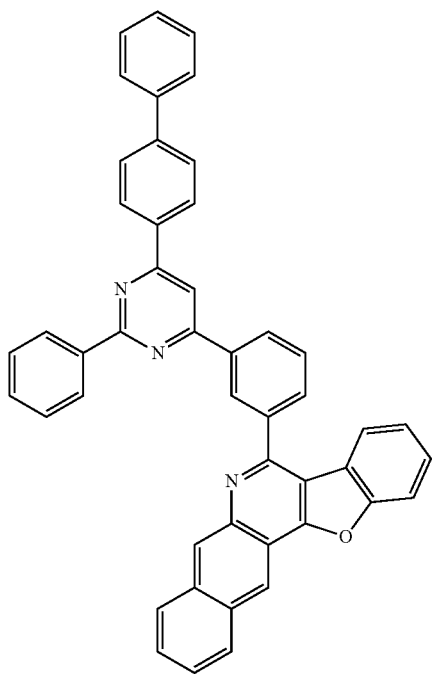
138
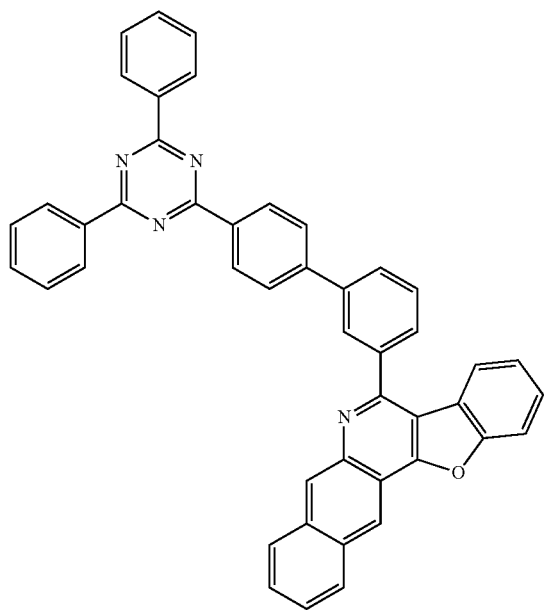

-continued
139
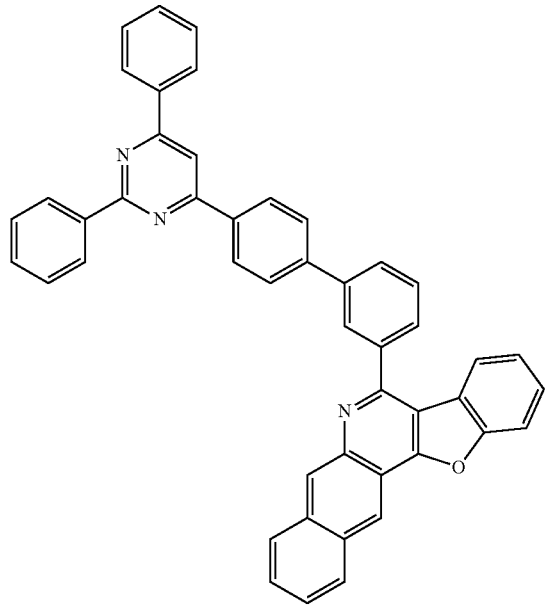
140
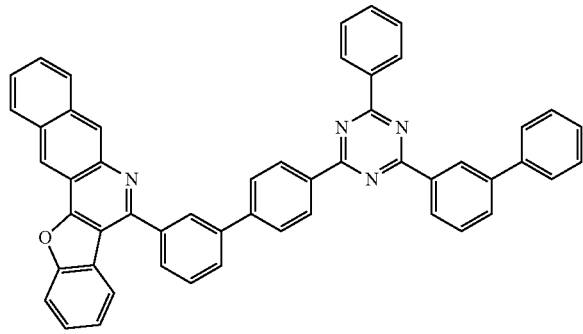
141
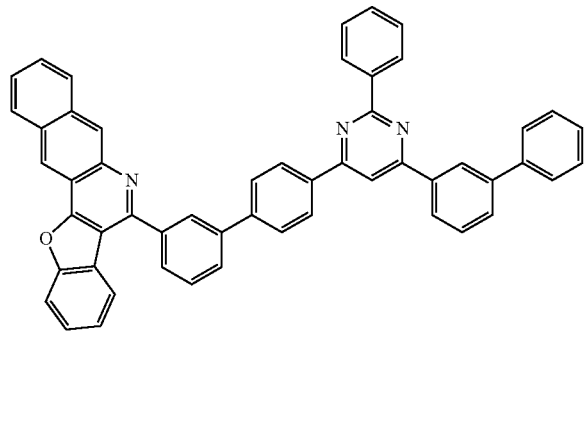
142
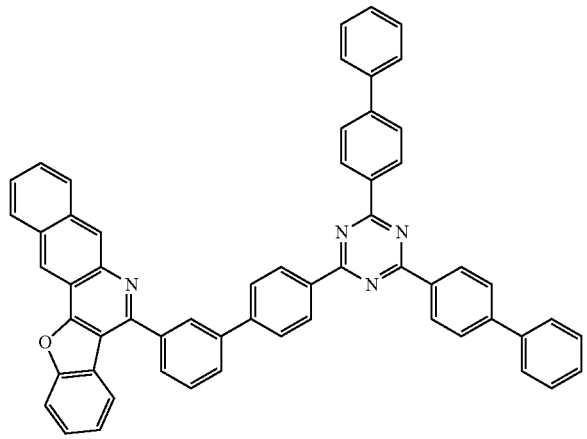
143
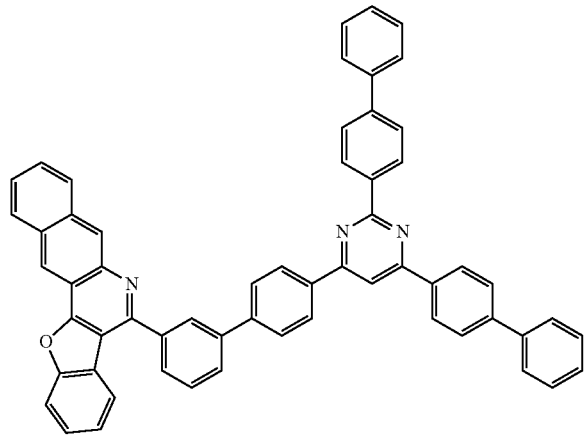
144
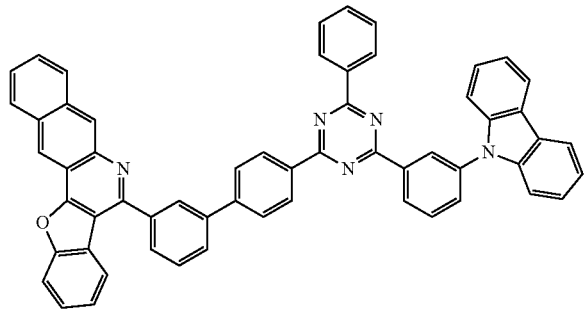

145
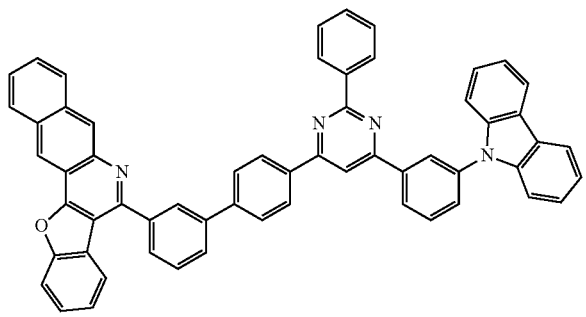
146
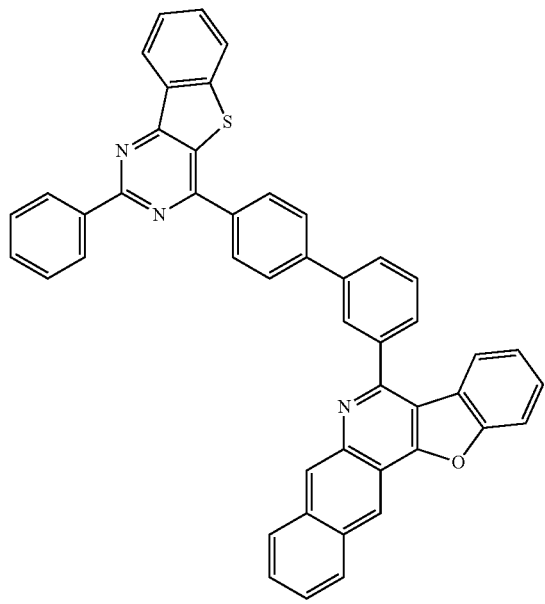
147
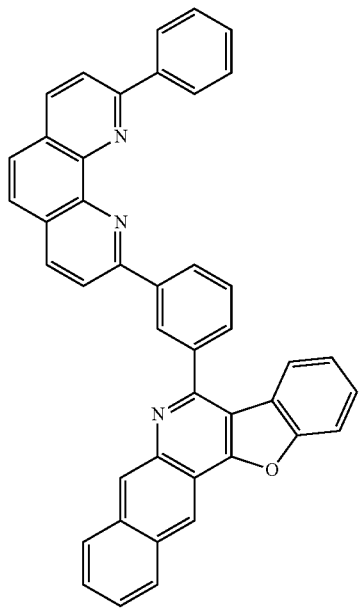
148
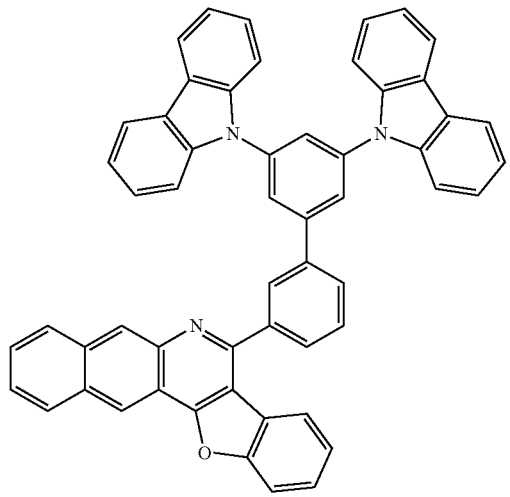

-continued
149
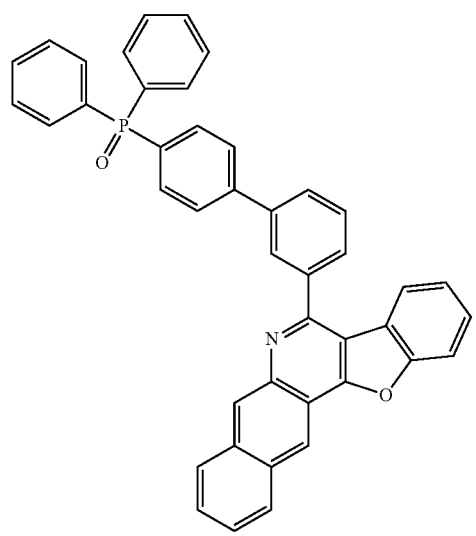
150
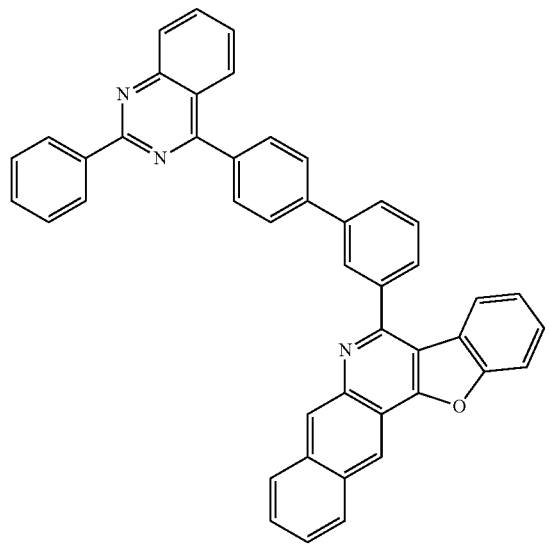
151
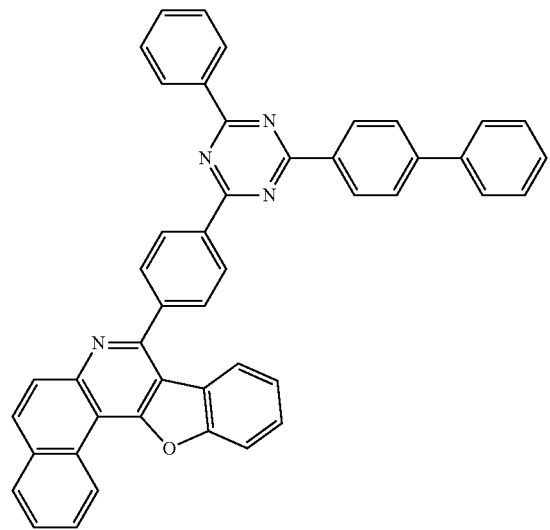
152
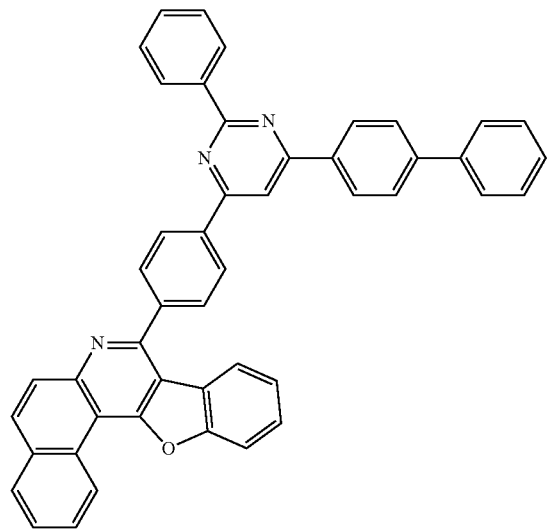

-continued
153
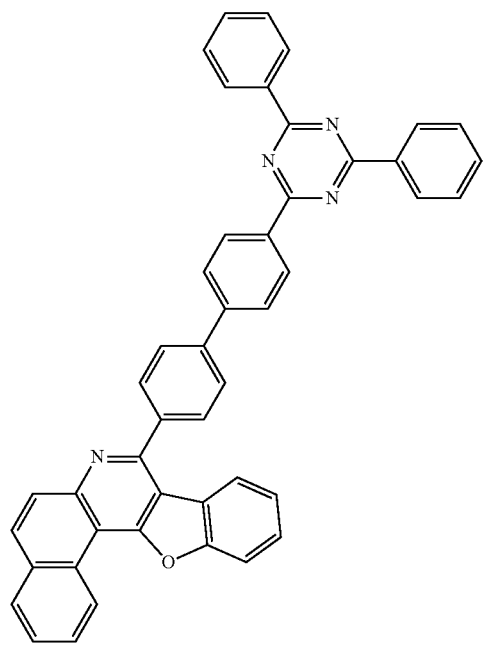 [SMILES: c1ccc(-c2nc(-c3ccccc3)nc(-c3ccc(-c4ccc(-c5nc6ccc7ccccc7c6c6oc7ccccc7c56)cc4)cc3)n2)cc1]
154
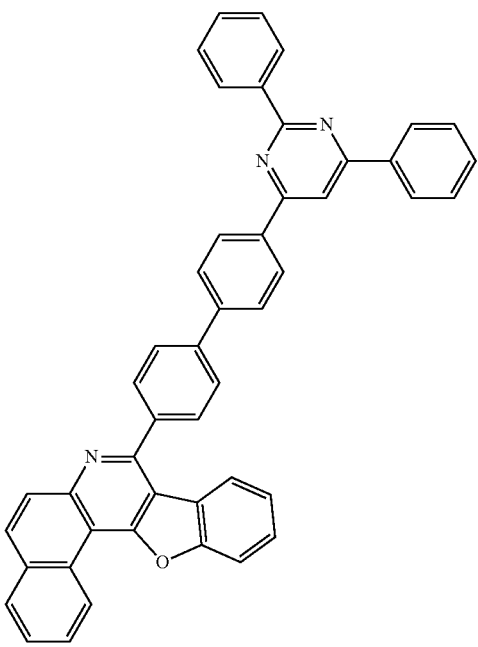 [SMILES: c1ccc(-c2cc(-c3ccc(-c4ccc(-c5nc6ccc7ccccc7c6c6oc7ccccc7c56)cc4)cc3)nc(-c3ccccc3)n2)cc1]
155
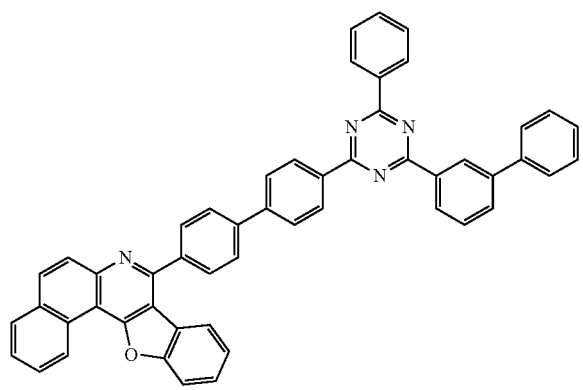
156
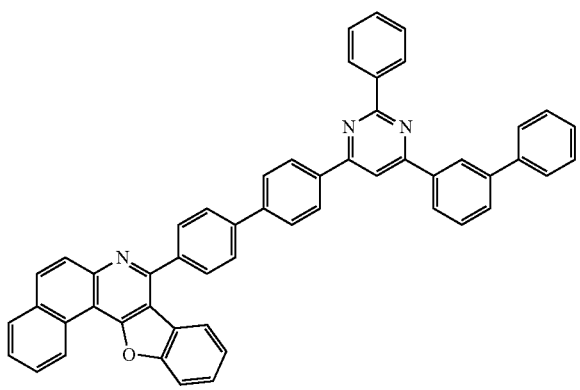
157
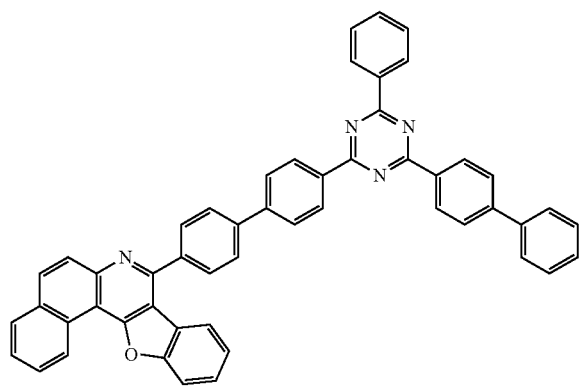
158
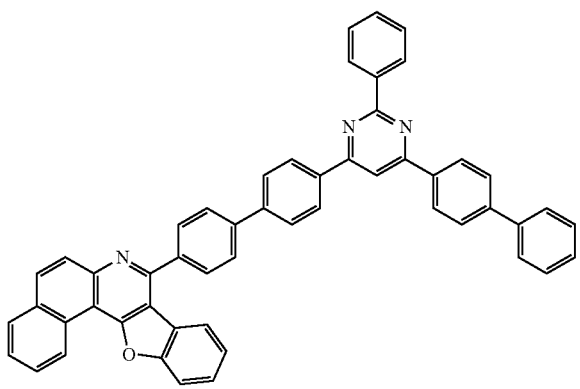

-continued
159
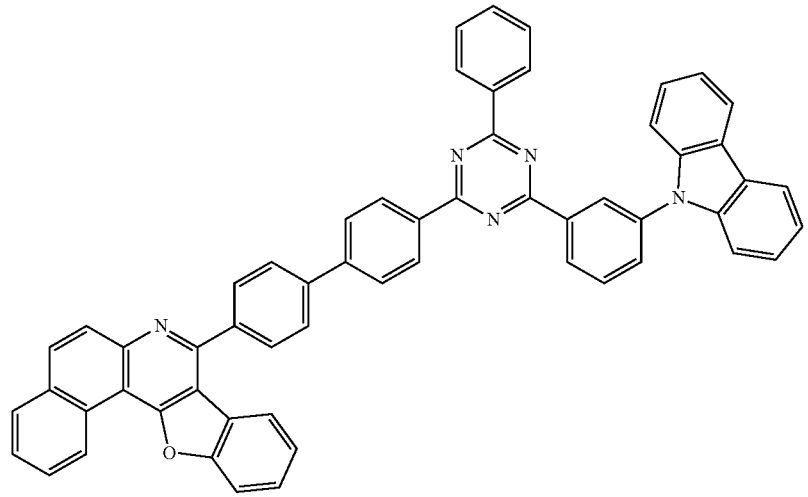
160
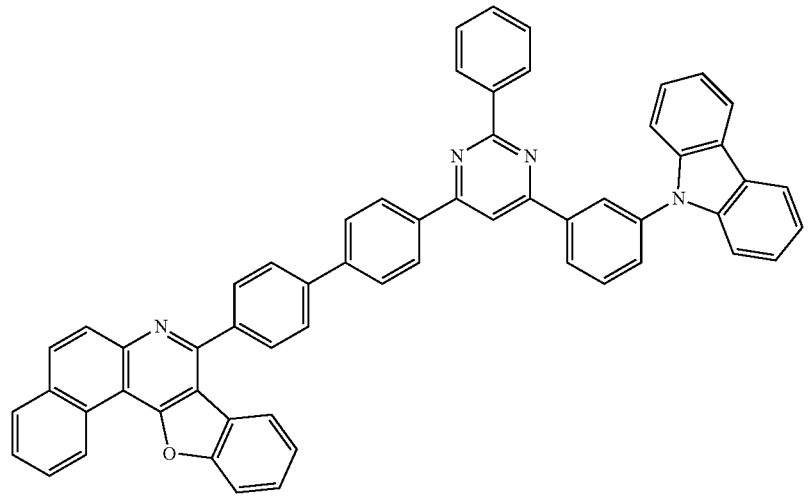
161
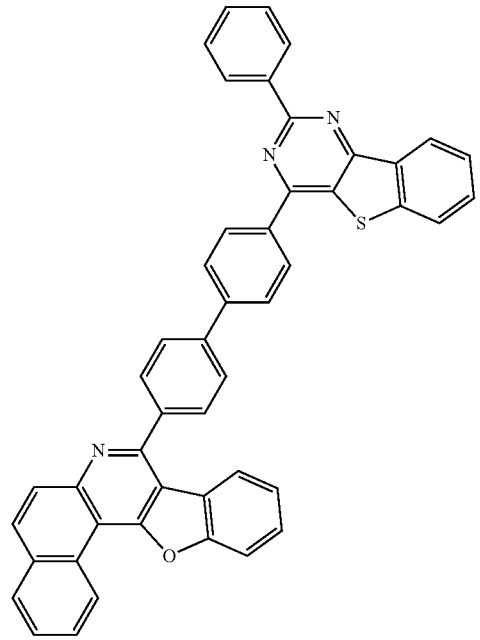
162
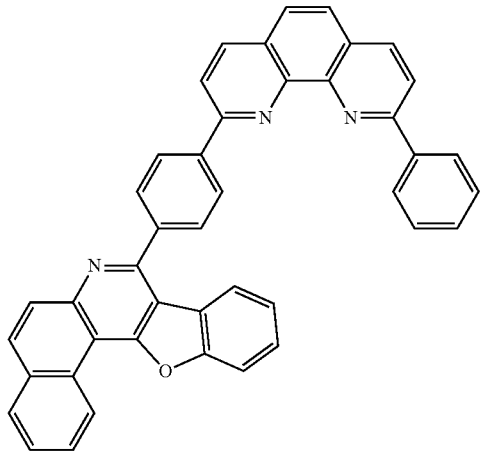

303
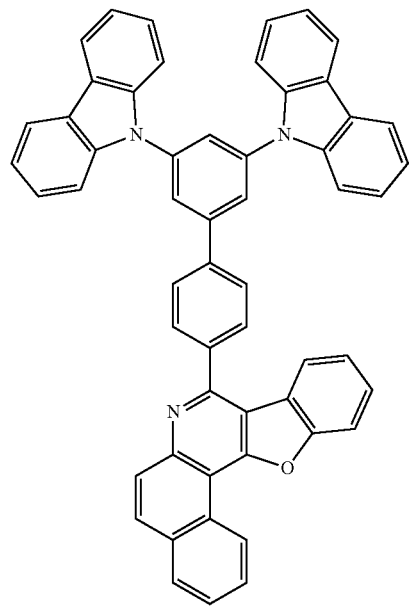 [SMILES: c1ccc2c(c1)ccc1nc(-c3ccc(-c4cc(-n5c6ccccc6c6ccccc65)cc(-n5c6ccccc6c6ccccc65)c4)cc3)c3c4ccccc4oc3c12]
304
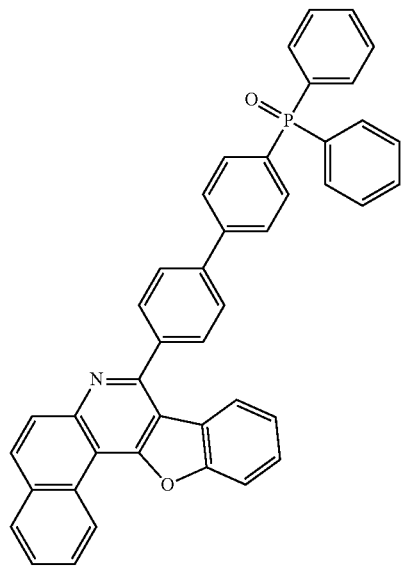
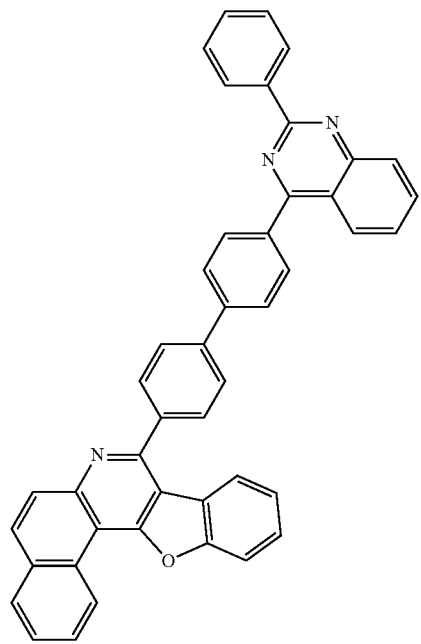
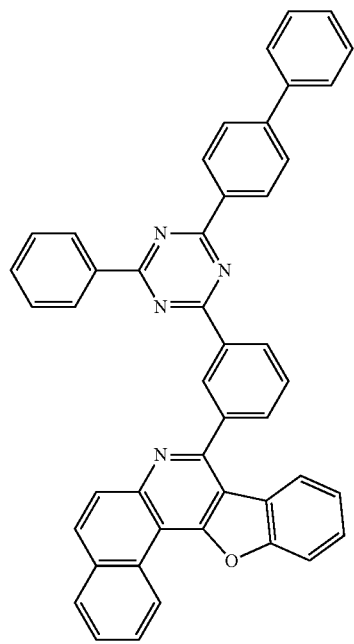

167
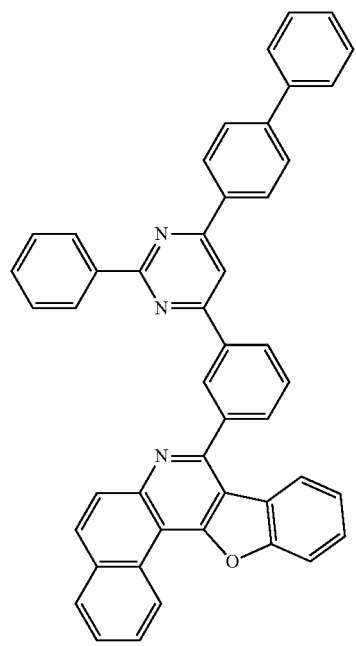
168
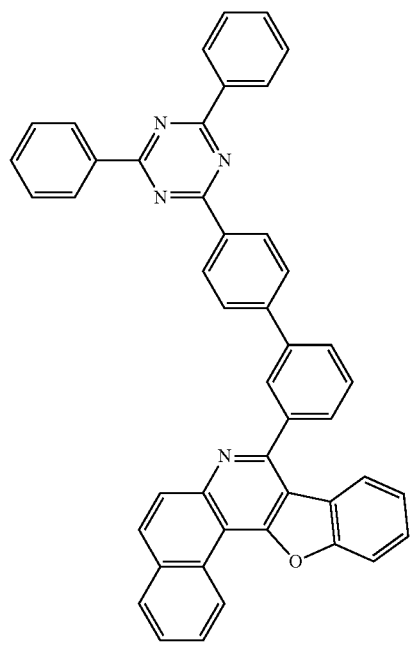
169
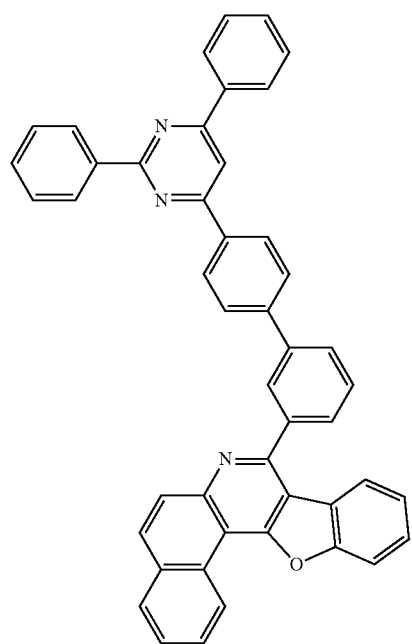 [SMILES: c1ccc(-c2cc(-c3ccc(-c4cccc(-c5nc6ccc7ccccc7c6c6oc7ccccc7c56)c4)cc3)nc(-c3ccccc3)n2)cc1]
170
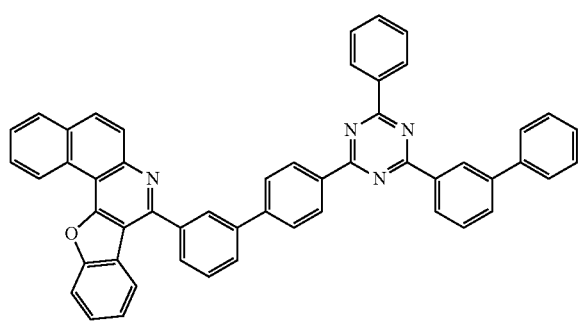

-continued
171
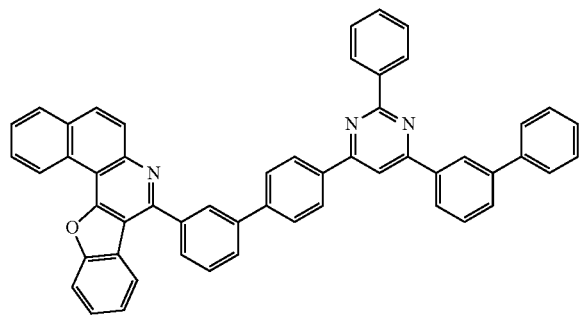
172
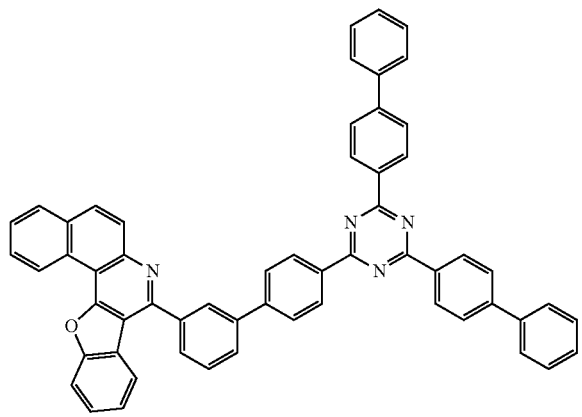
173
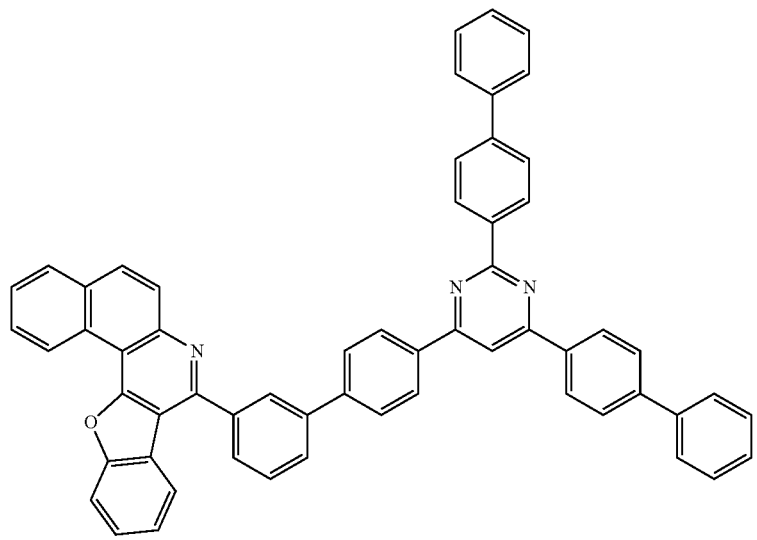
174
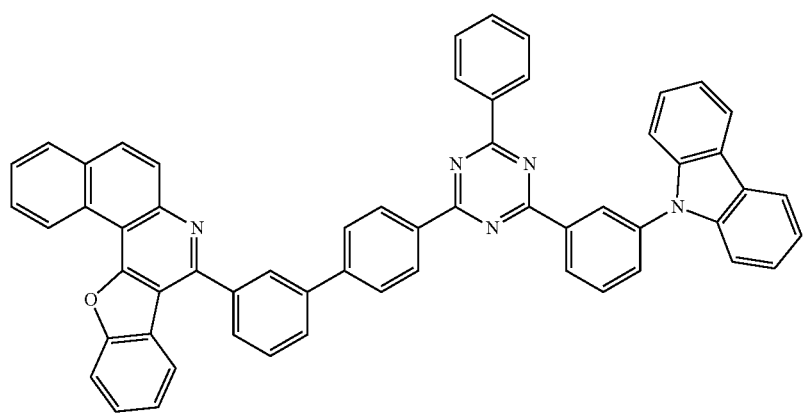

175
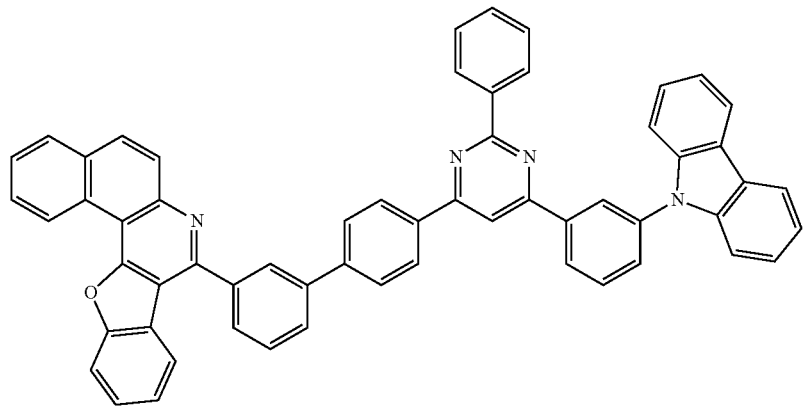
176
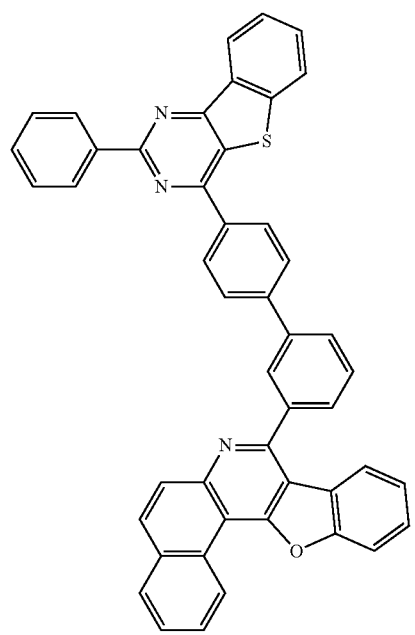
177
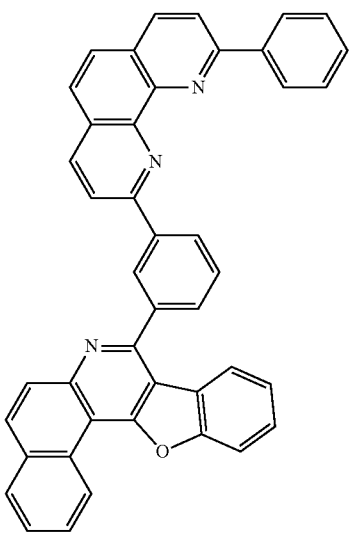
178
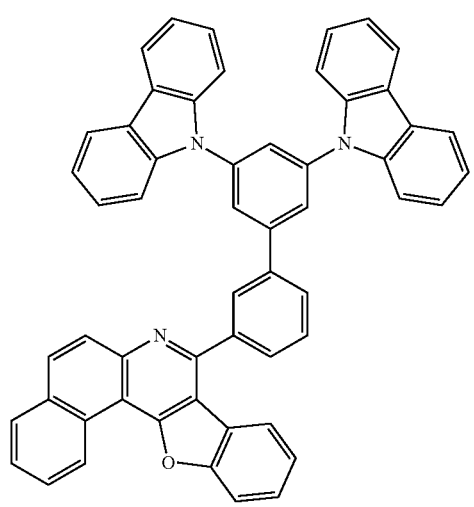
179
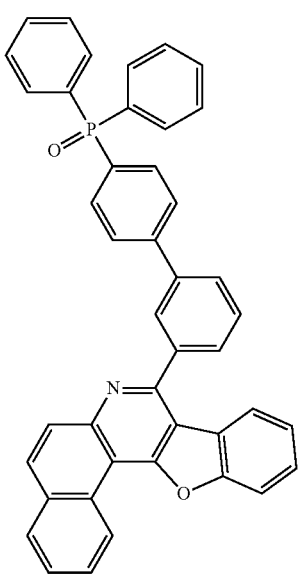 [SMILES: O=P(c1ccccc1)(c1ccccc1)c1ccc(-c2cccc(-c3nc4ccc5ccccc5c4c4oc5ccccc5c34)c2)cc1]

-continued
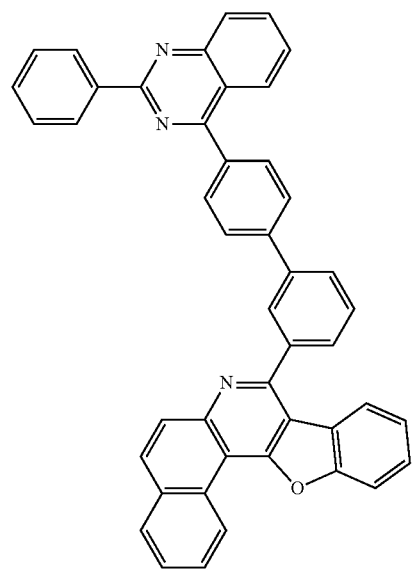
180
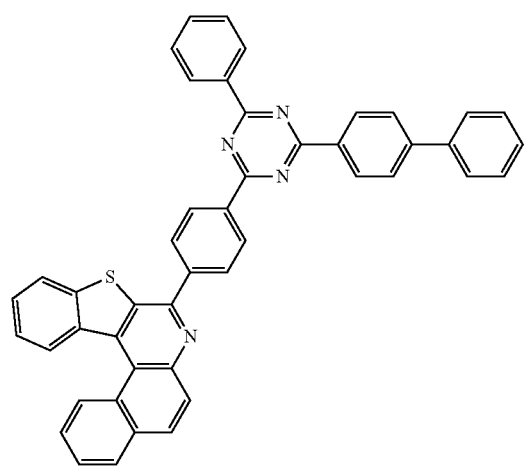 [SMILES: c1ccc(-c2ccc(-c3nc(-c4ccccc4)nc(-c4ccc(-c5nc6ccc7ccccc7c6c6c5oc5ccccc56)cc4)n3)cc2)cc1]
181
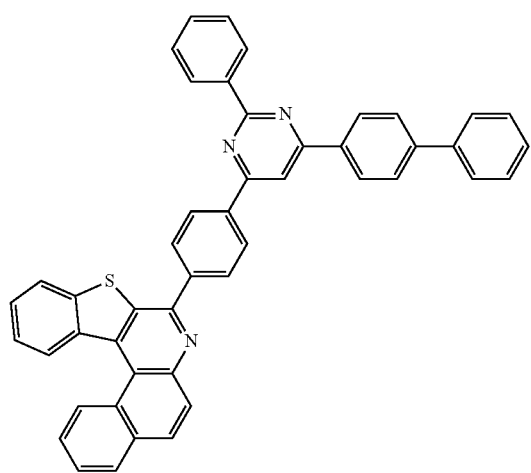
182

-continued
183
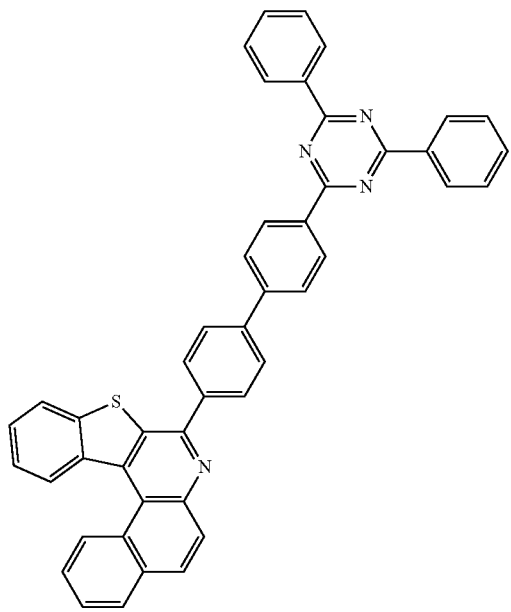
184
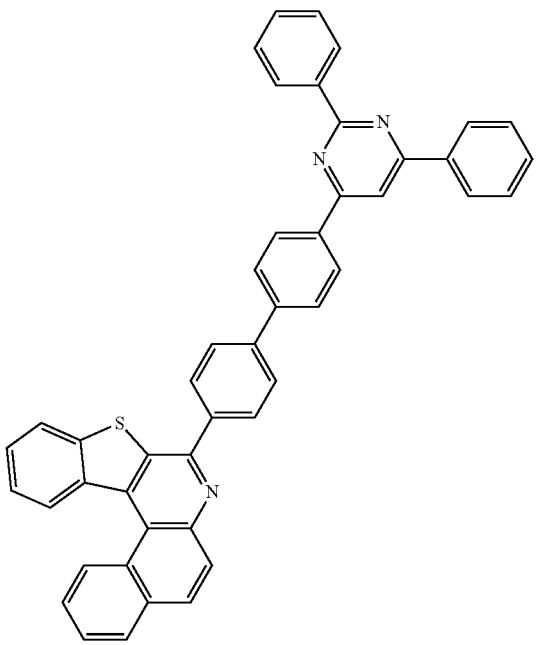
185
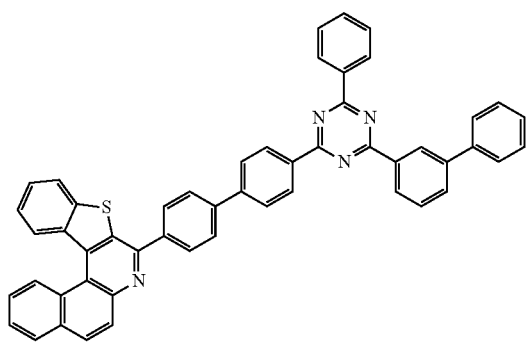
186
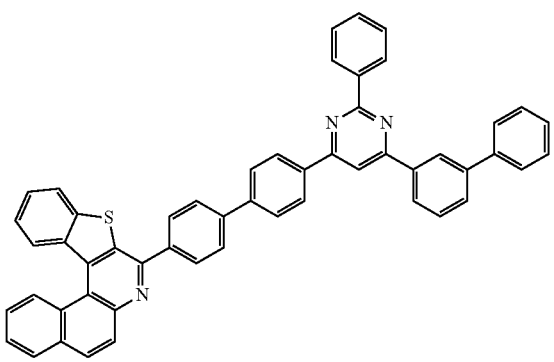
187
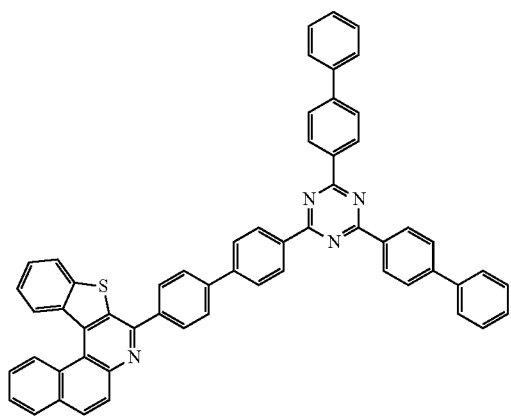
188
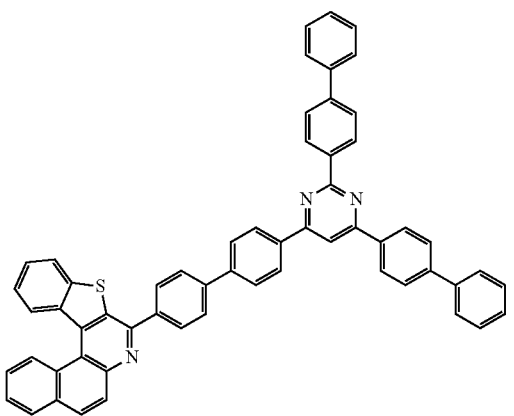

-continued
189
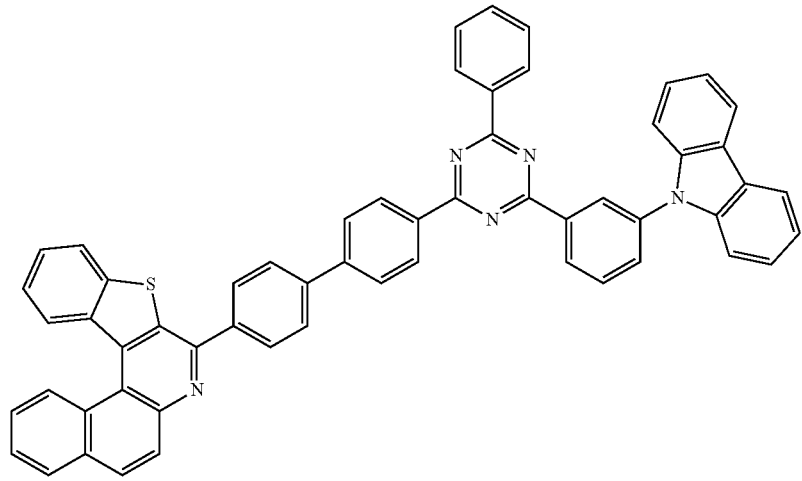
190
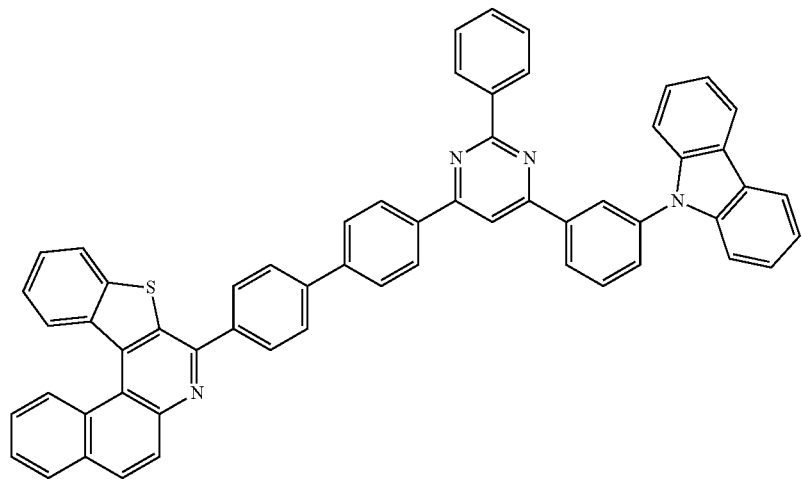
191
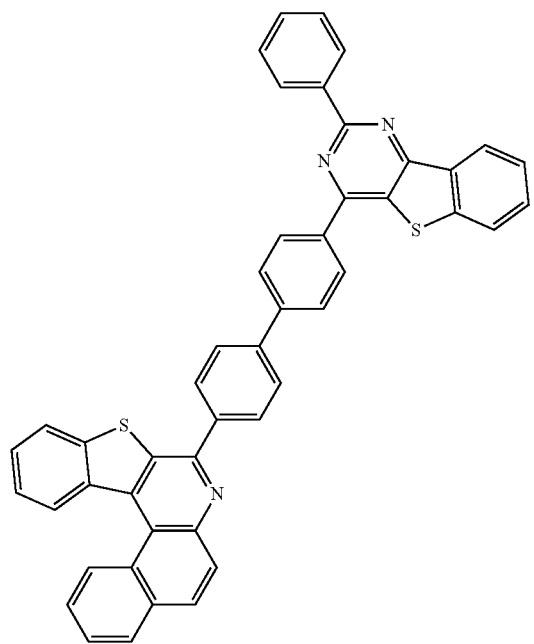
192
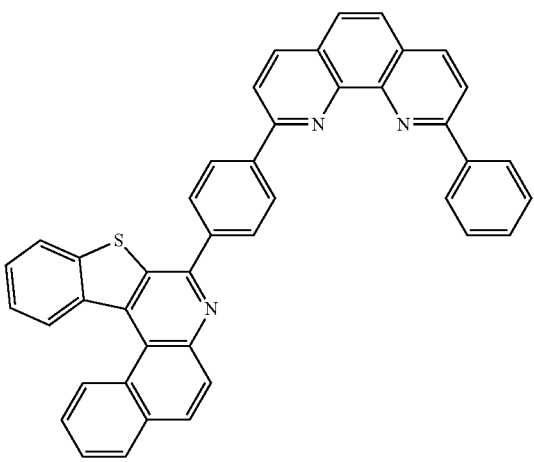

-continued
193 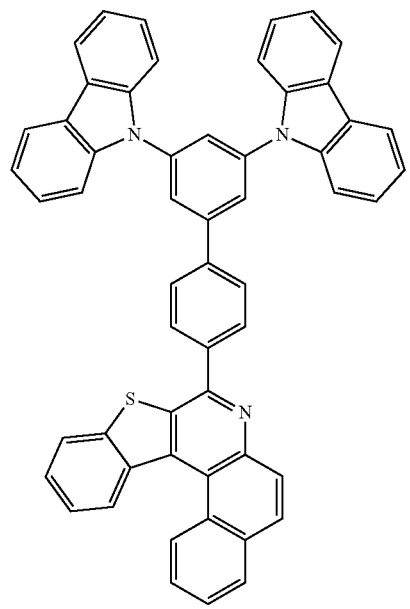
194 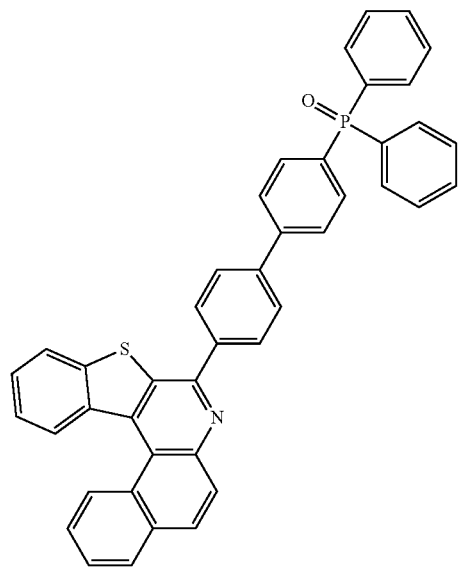
195 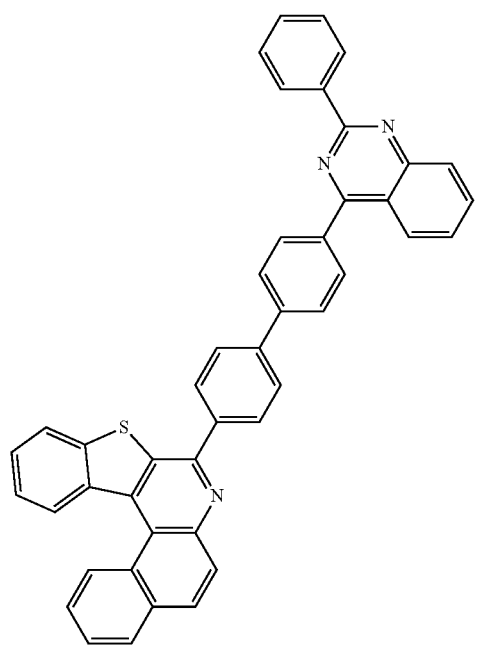
196 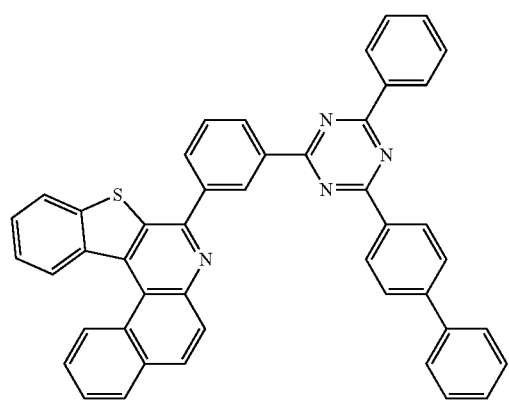
197 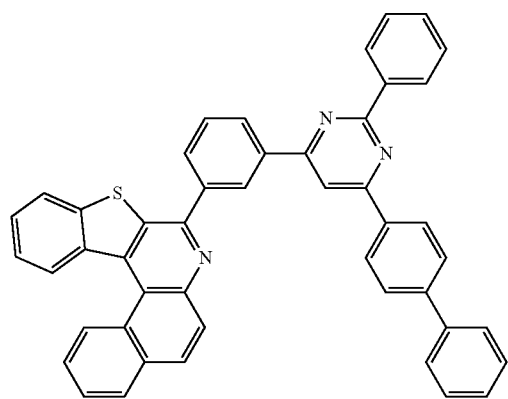
198 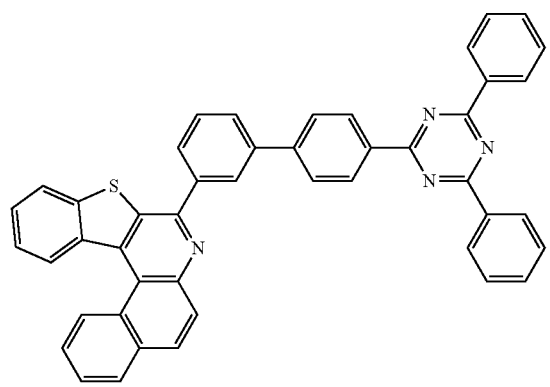

-continued
199
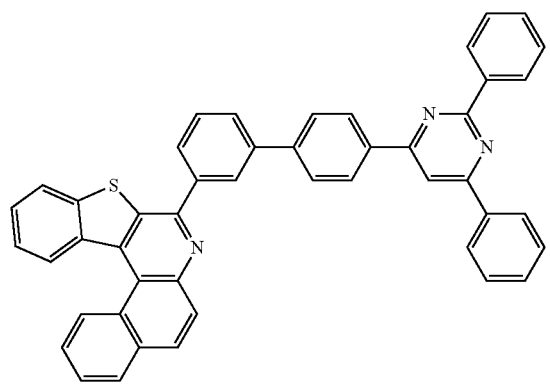 [SMILES: c1ccc(-c2cc(-c3ccc(-c4cccc(-c5nc6ccc7ccccc7c6c6c5sc5ccccc56)c4)cc3)nc(-c3ccccc3)n2)cc1]
200
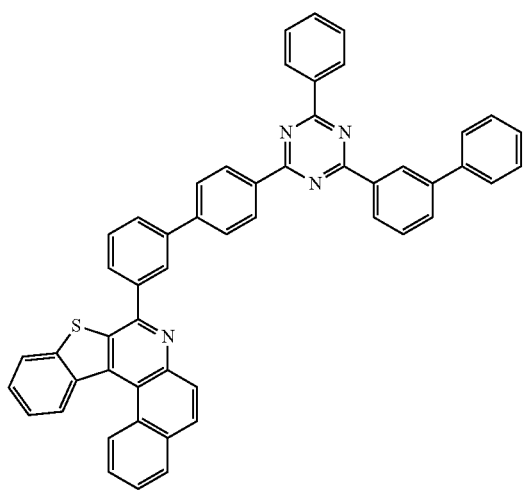
201
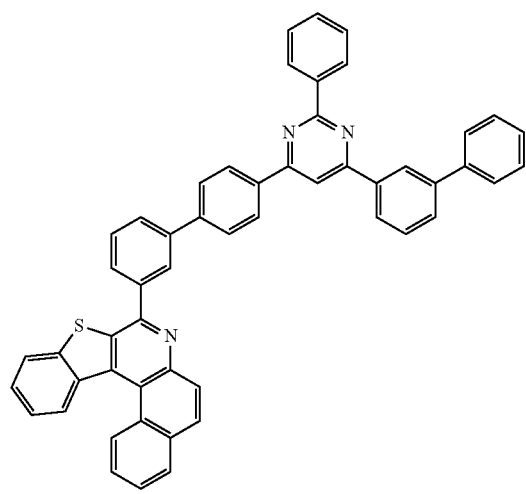
202
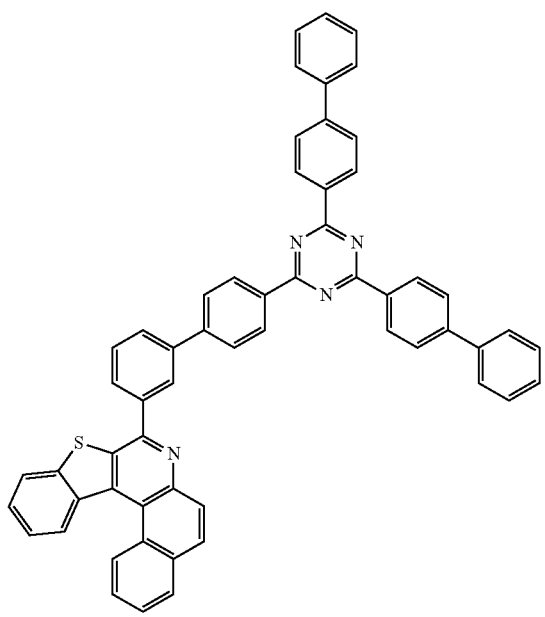 [SMILES: c1ccc(-c2ccc(-c3cc(-c4ccc(-c5cccc(-c6nc7ccc8ccccc8c7c7c6oc6ccccc67)c5)cc4)nc(-c4ccc(-c5ccccc5)cc4)n3)cc2)cc1]

-continued
321
203
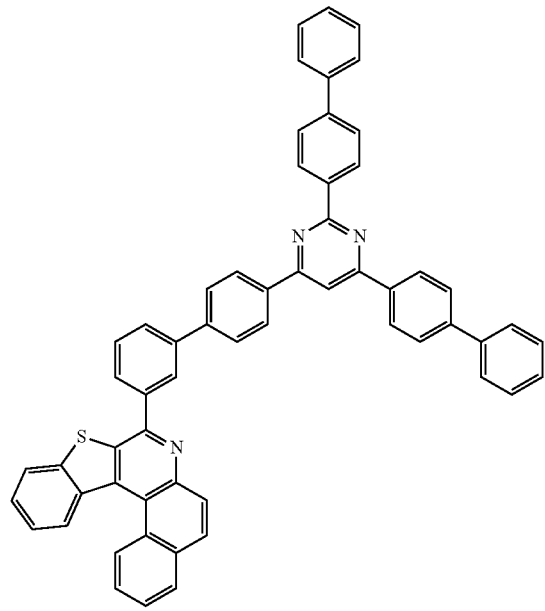
322
204
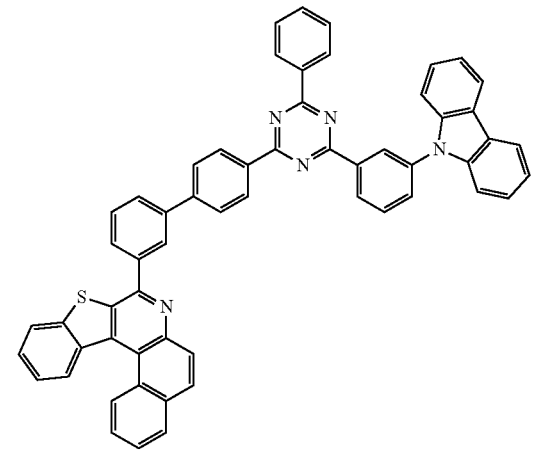
205
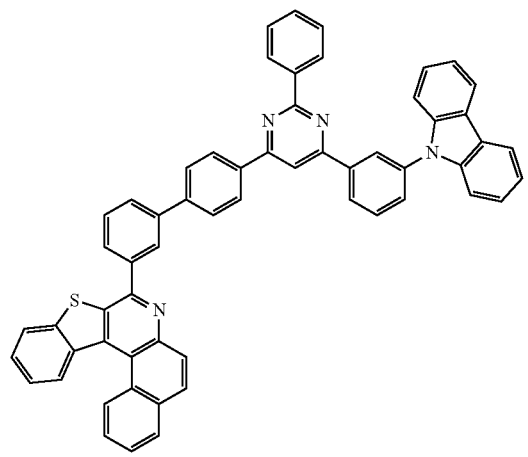
206
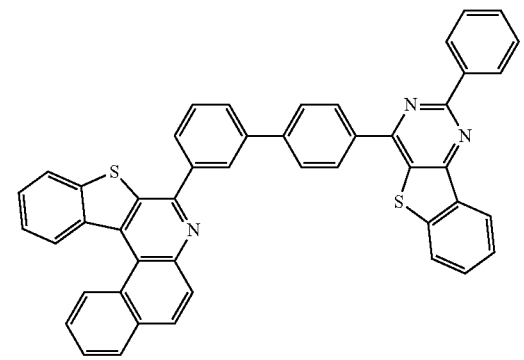
207
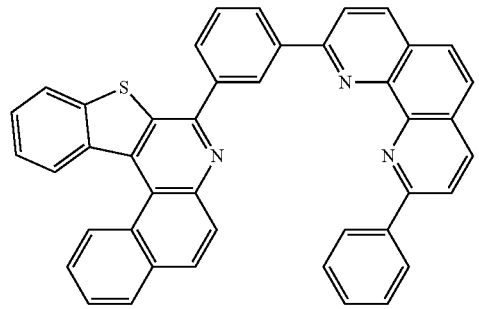
208
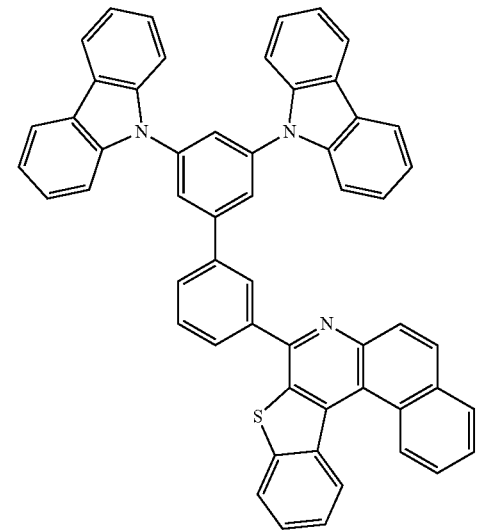

-continued
209
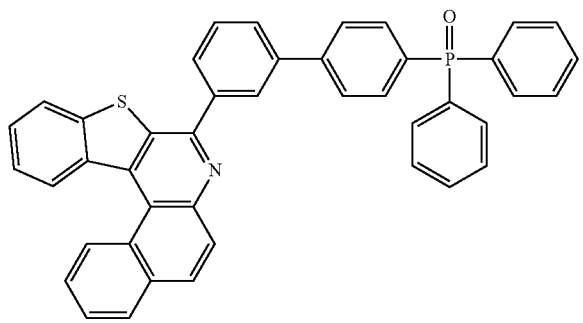
210
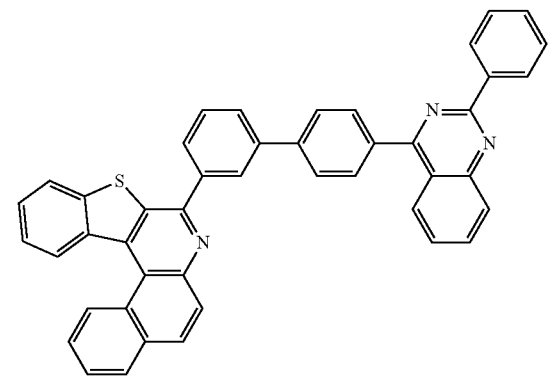
211
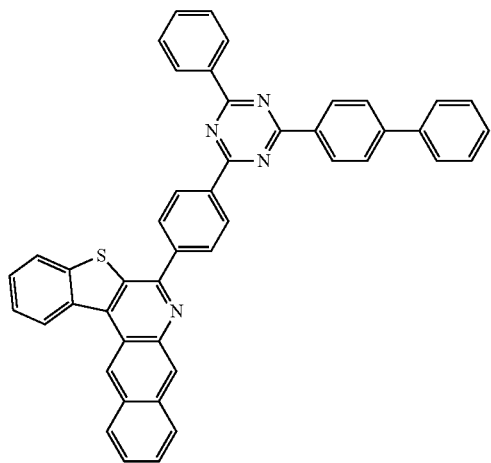
212
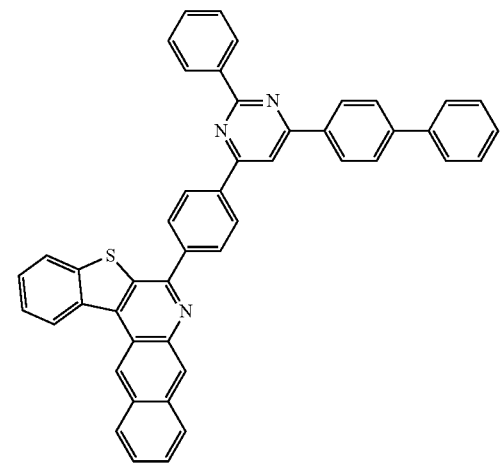
213
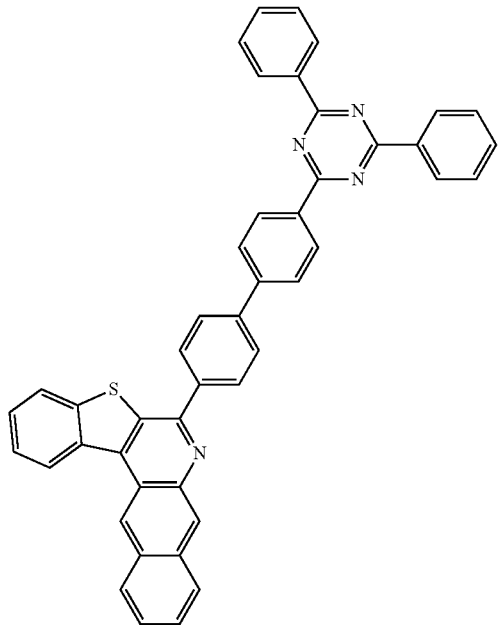
214
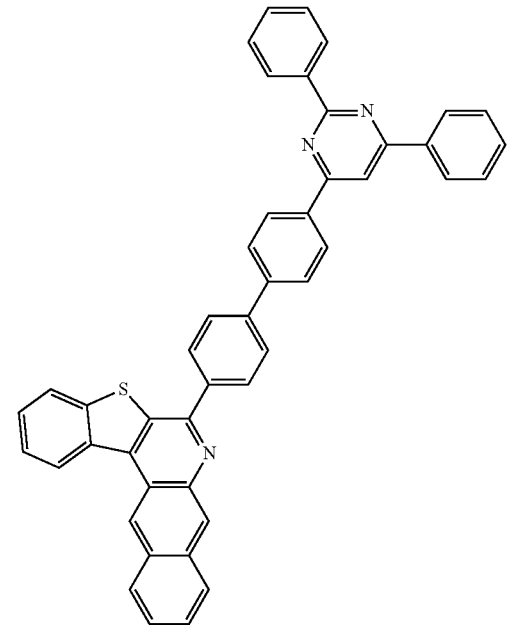

-continued
215
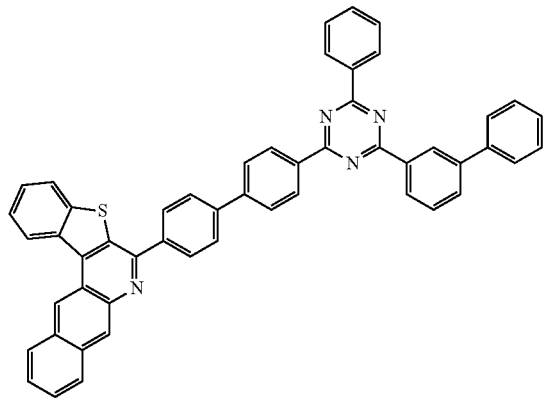
216
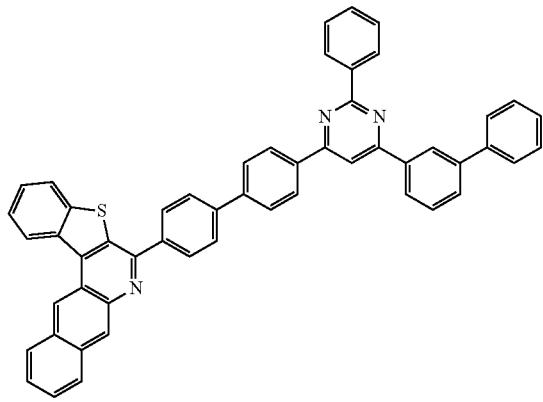
217
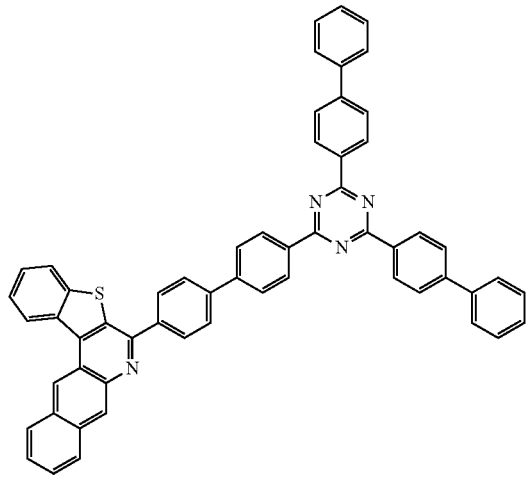
218
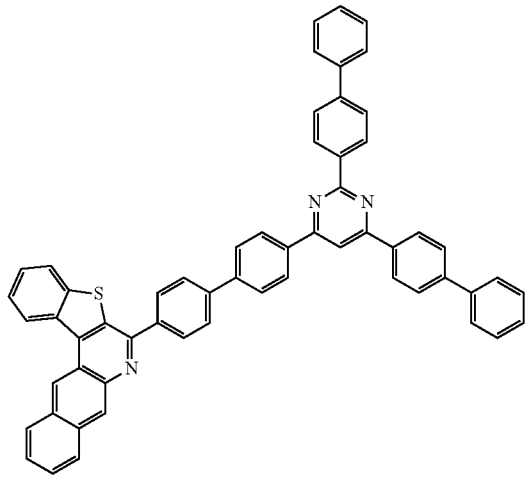
219
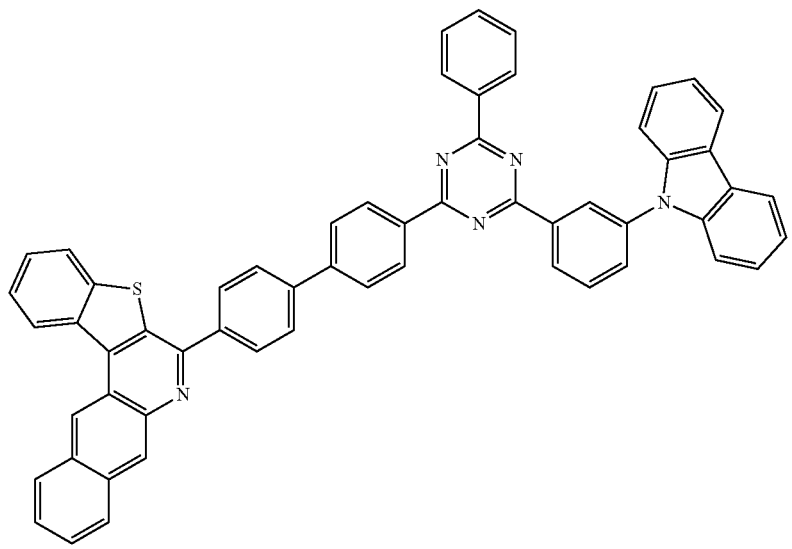

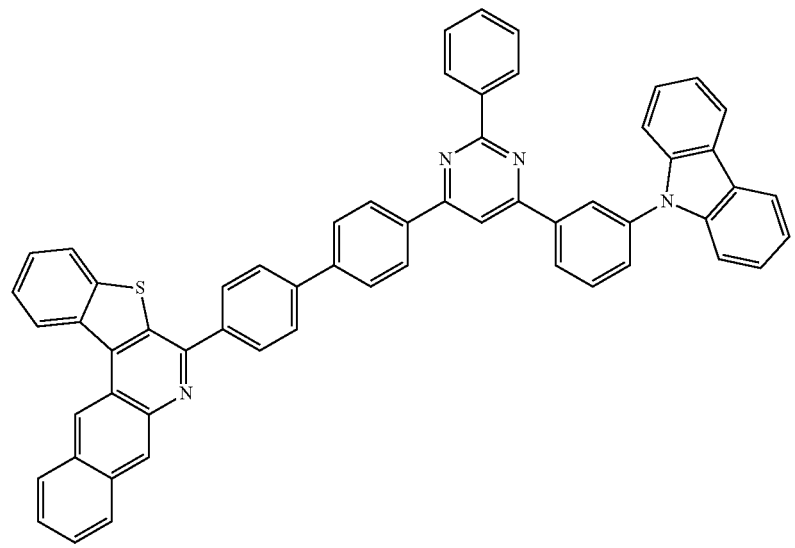
220
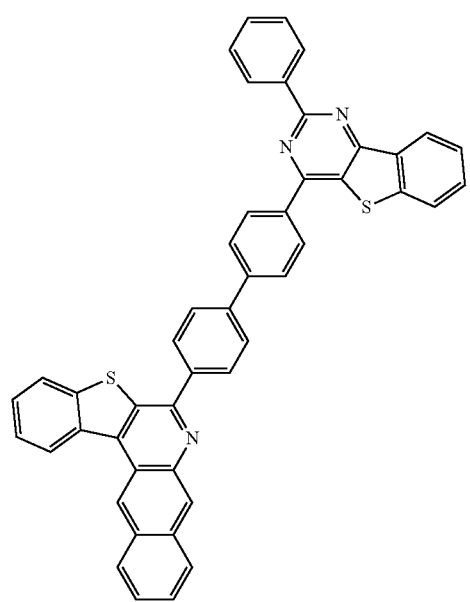
221
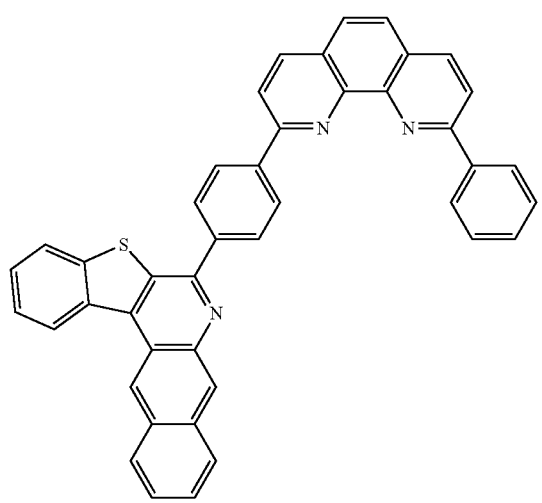
222

223
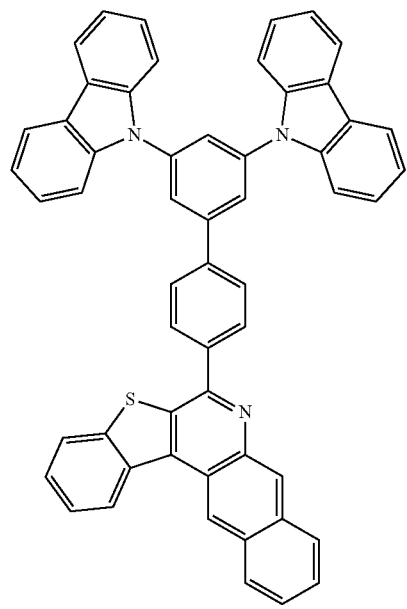
224
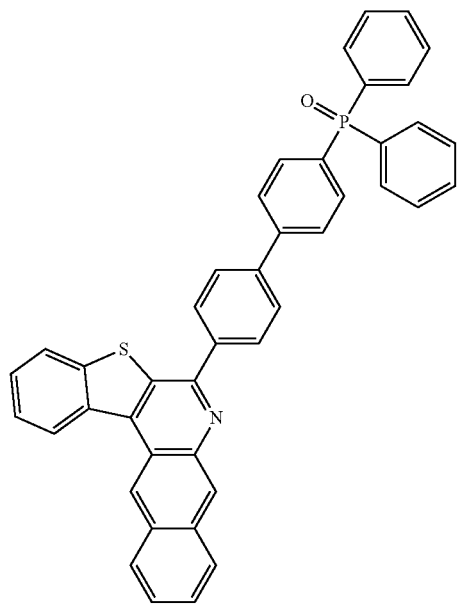
225
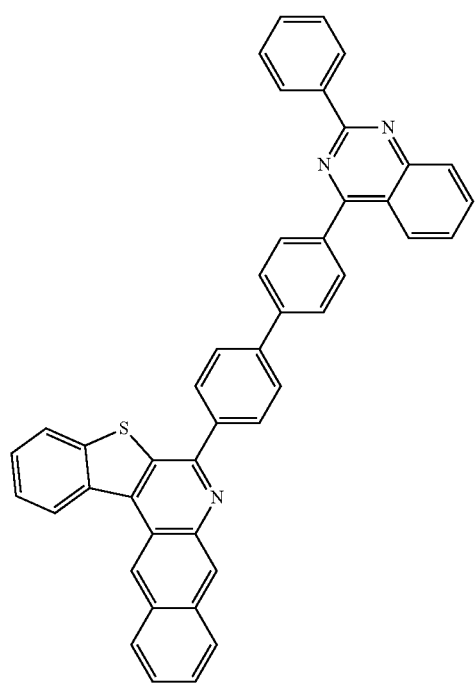
226
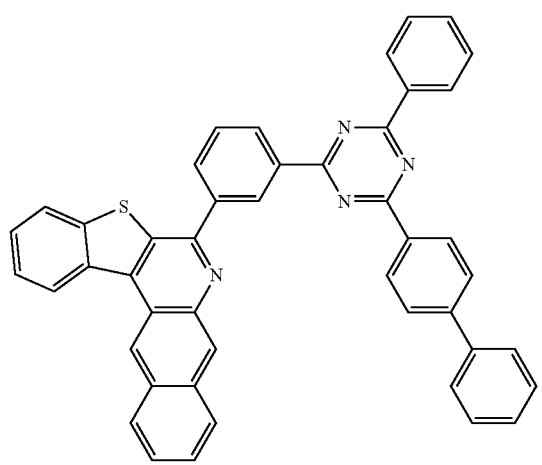

-continued
227
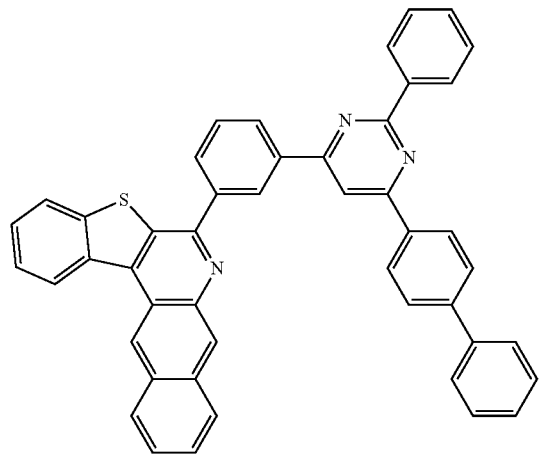
228
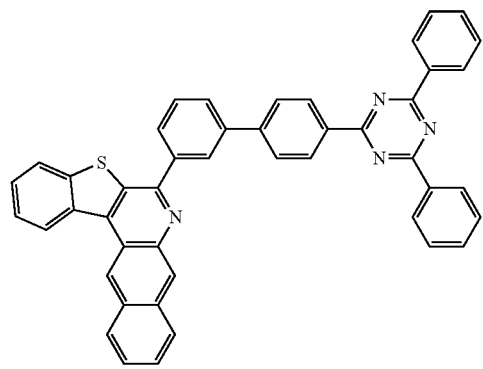
229
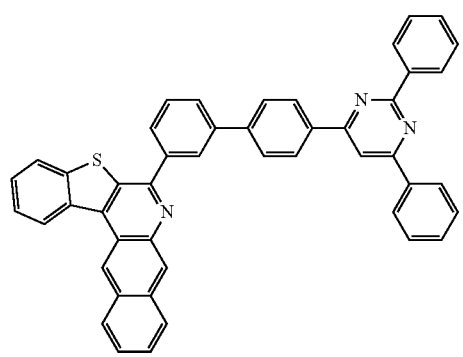
230
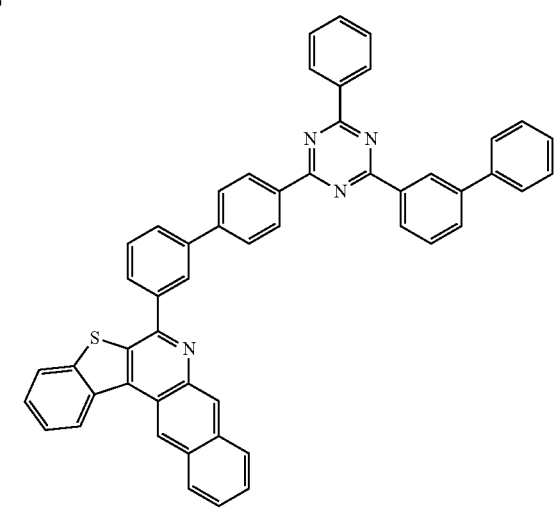
231
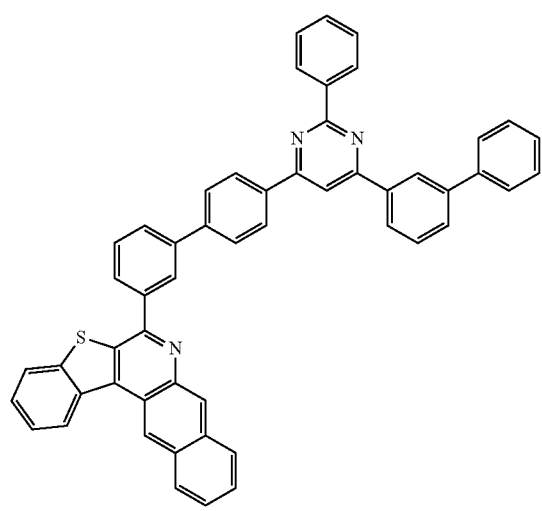
232
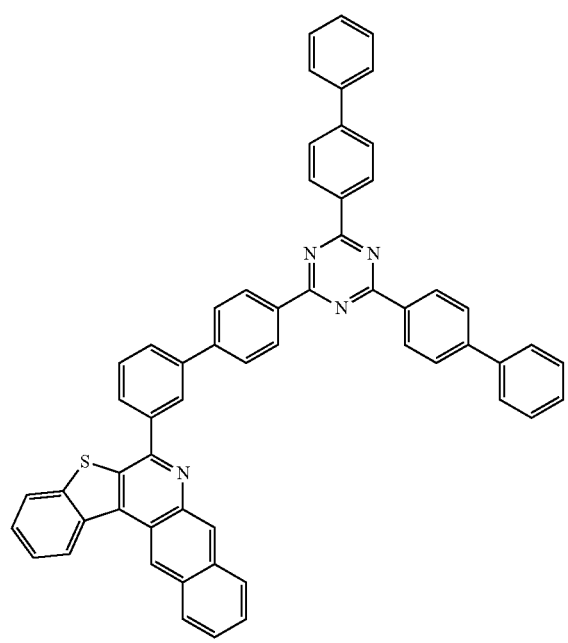

333
234
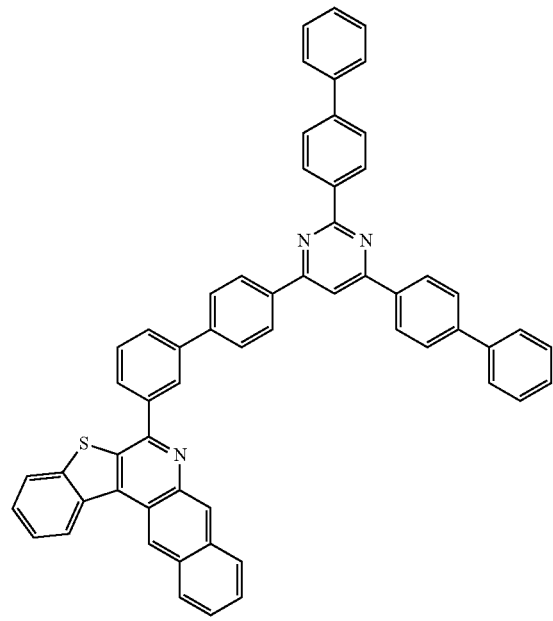
334
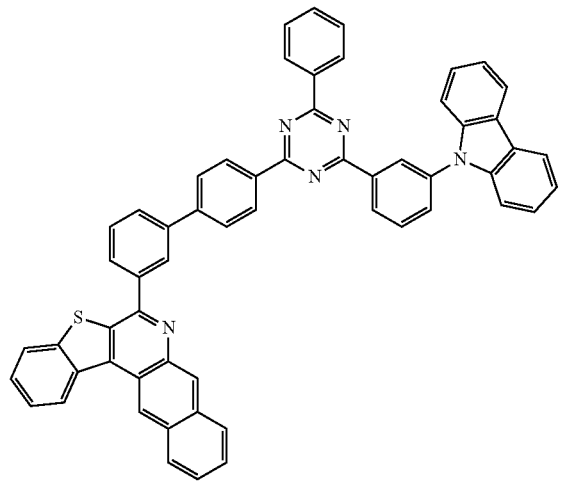
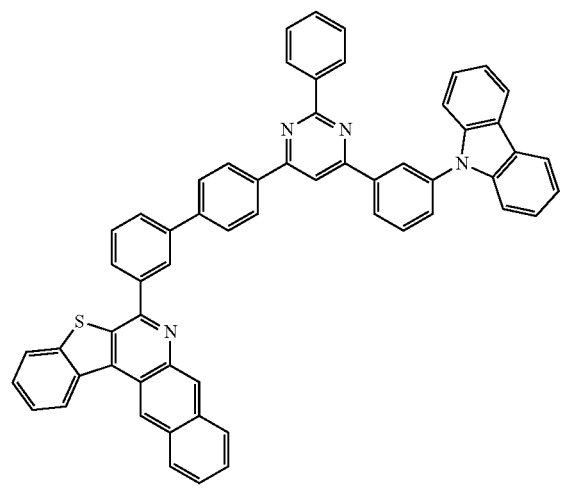
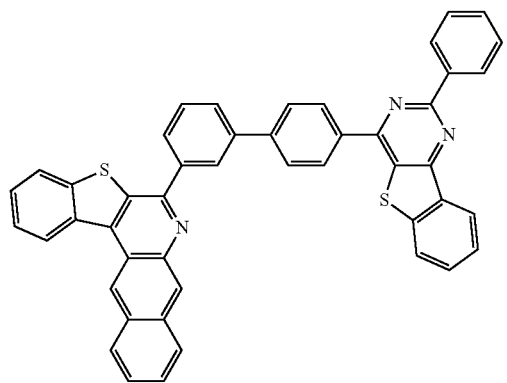

-continued
237
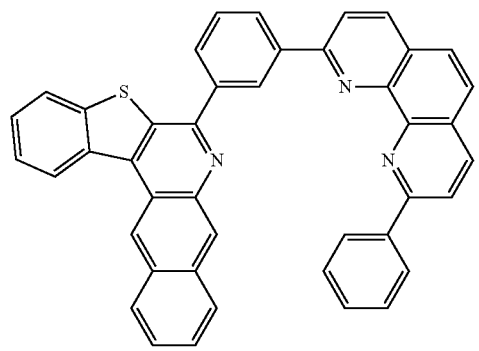
238
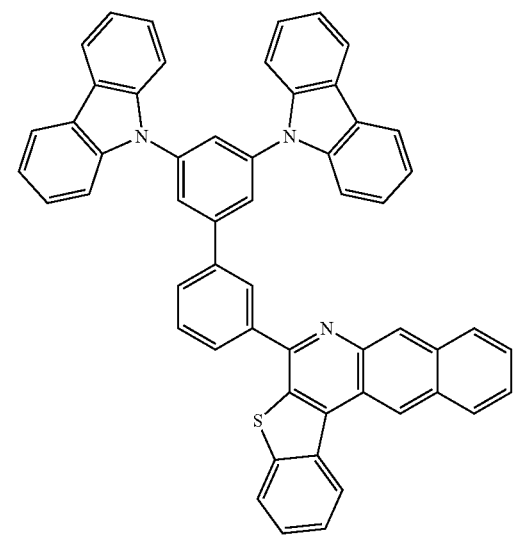
239
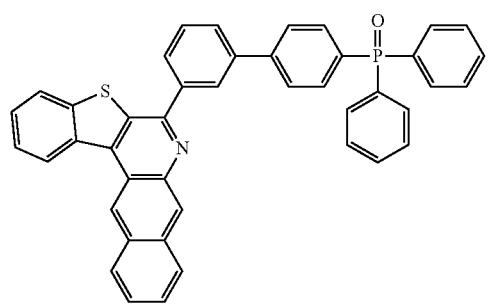
240
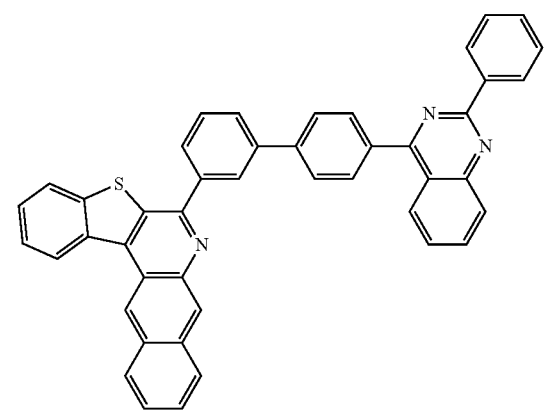
241
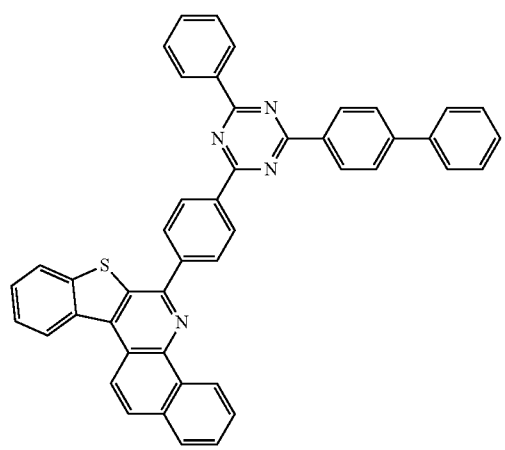
242
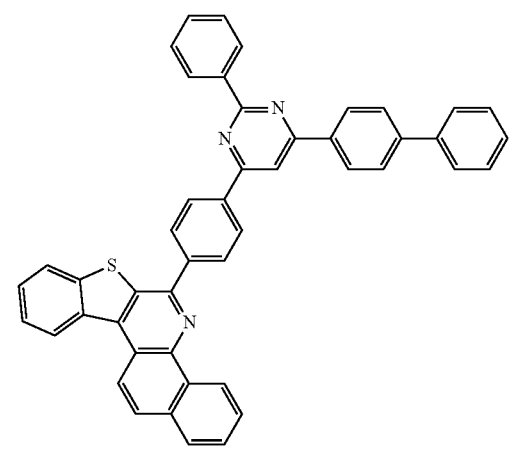

-continued
243
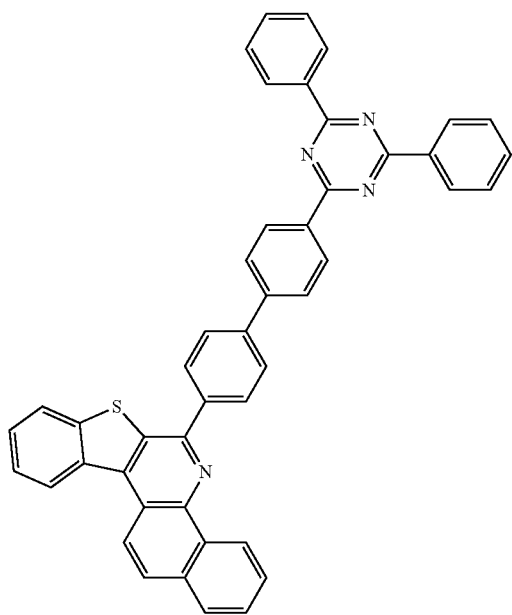
244
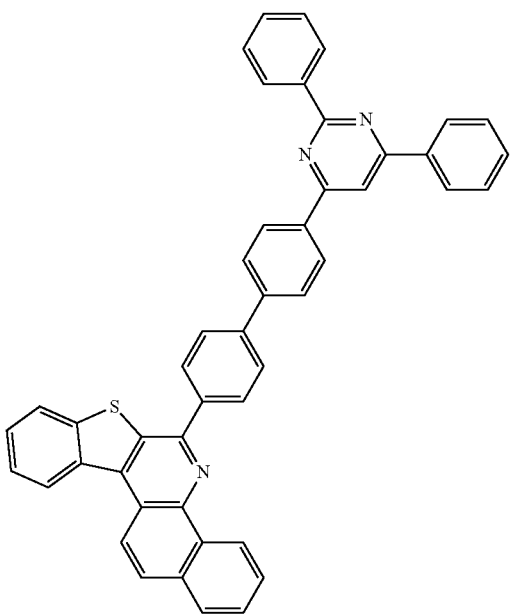 [SMILES: c1ccc(-c2cc(-c3ccc(-c4ccc(-c5nc6c7ccccc7ccc6c6c5sc5ccccc56)cc4)cc3)nc(-c3ccccc3)n2)cc1]
245
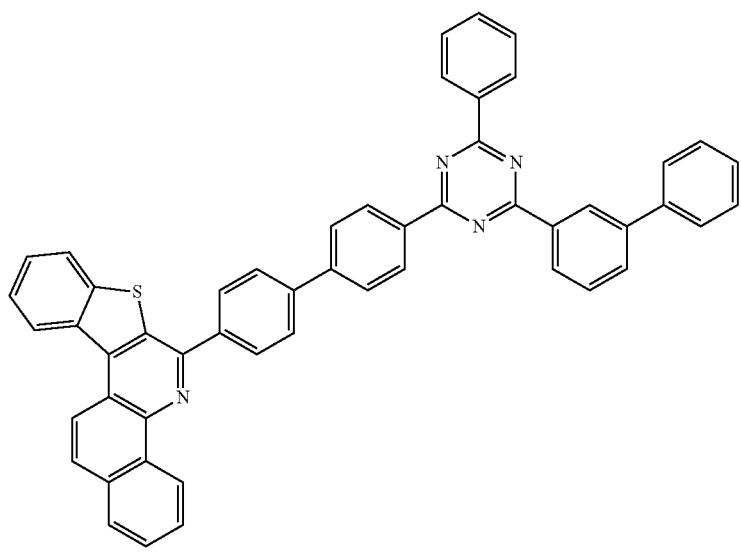

-continued
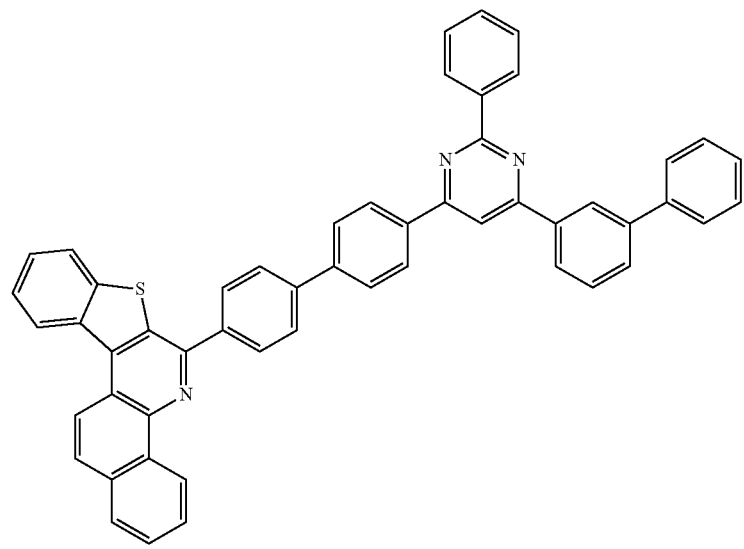
246
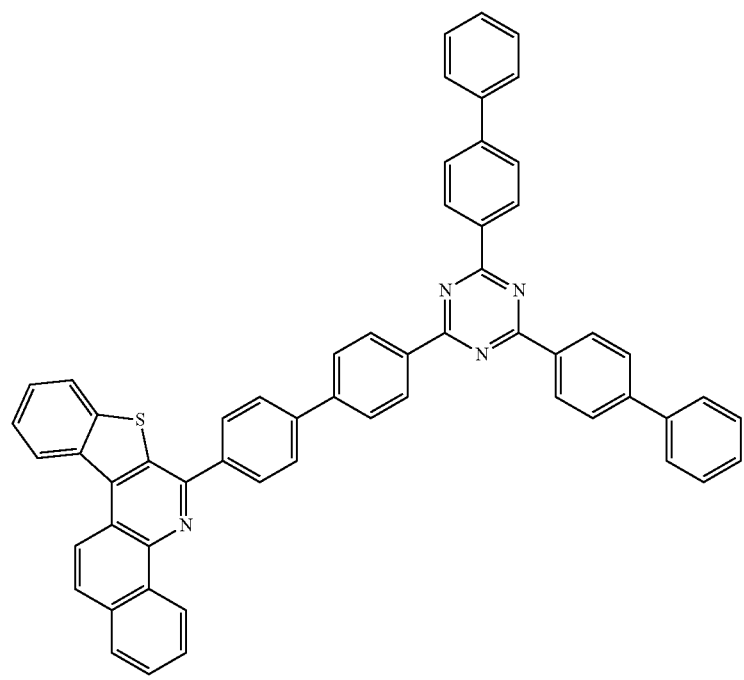
247

-continued
248
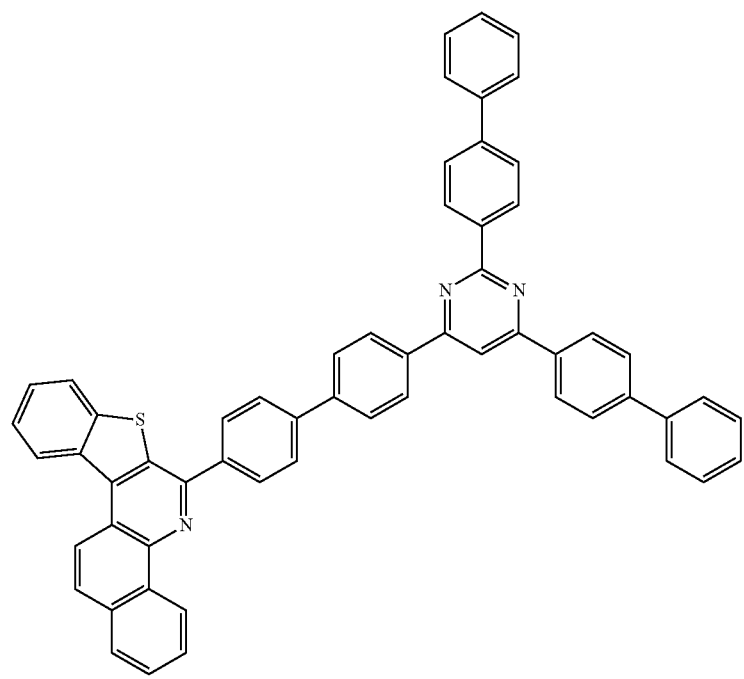
249
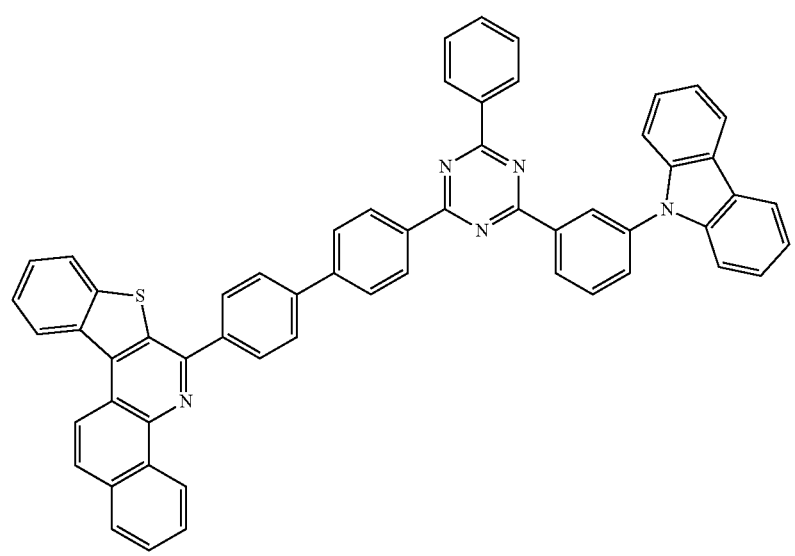

-continued
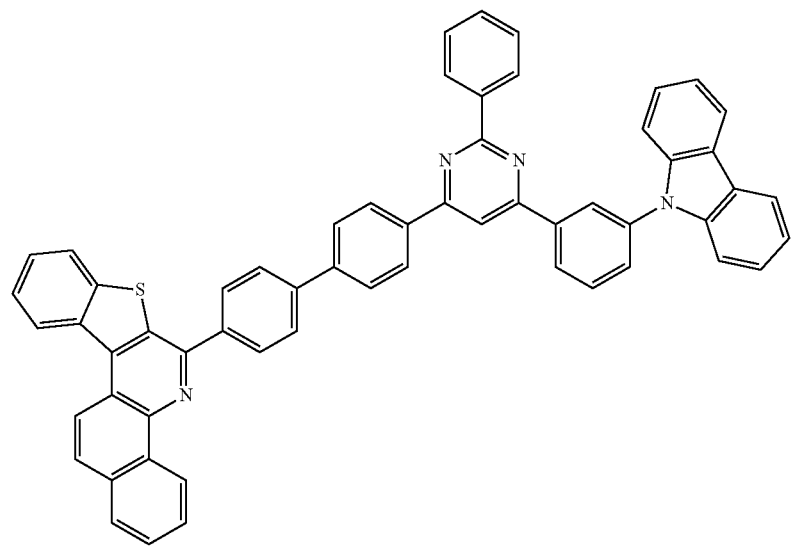
250
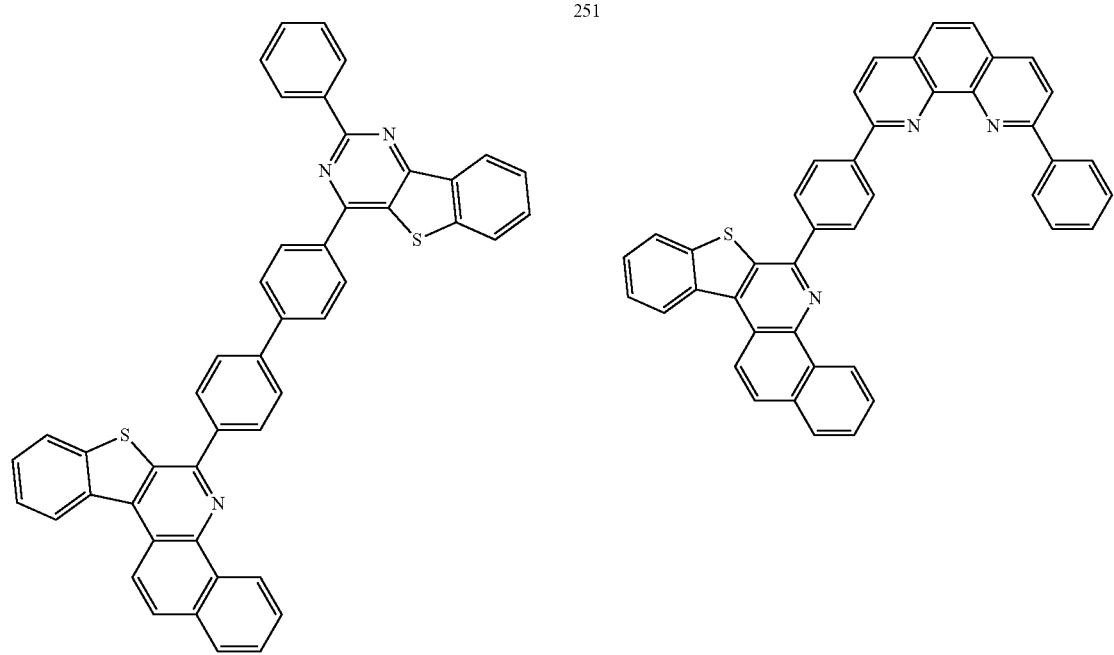
251
252

-continued
253
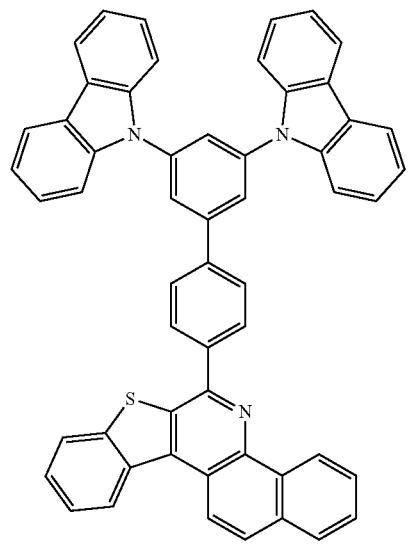
254
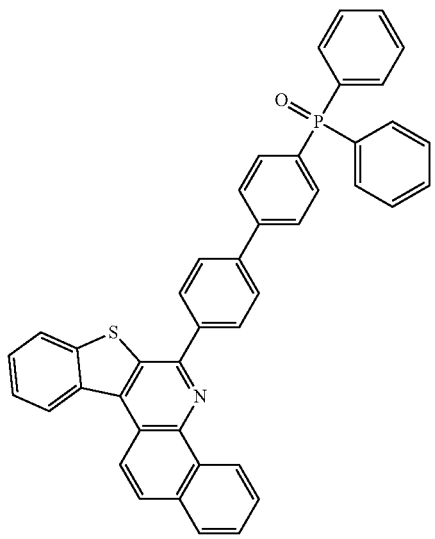
255
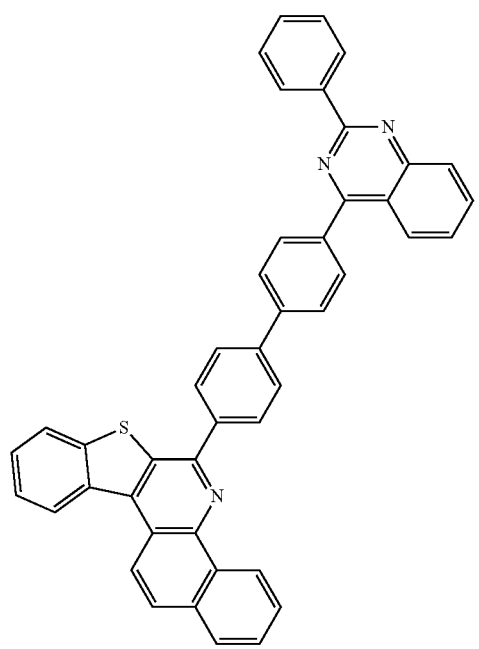
256
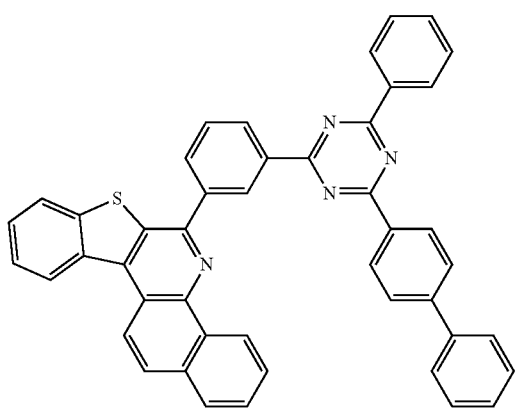
257
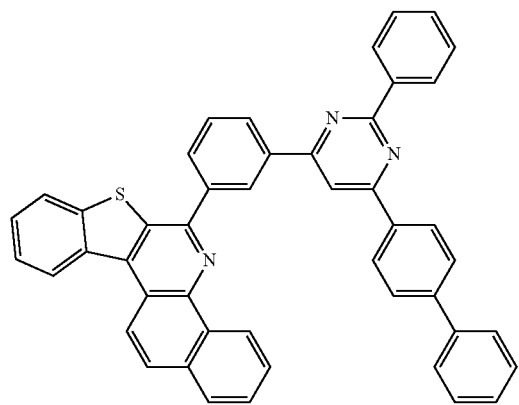 [SMILES: c1ccc(-c2ccc(-c3cc(-c4cccc(-c5nc6c7ccccc7ccc6c6c5sc5ccccc56)c4)nc(-c4ccccc4)n3)cc2)cc1]
258
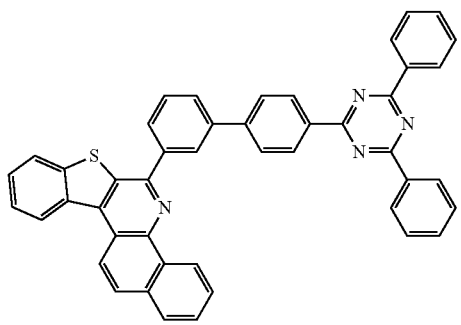

-continued
259
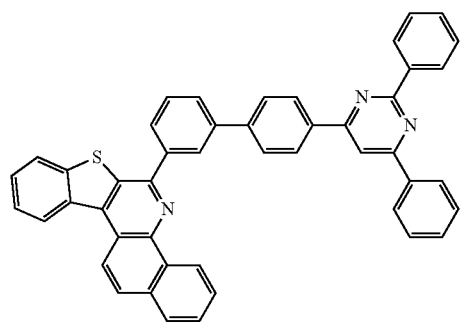
260
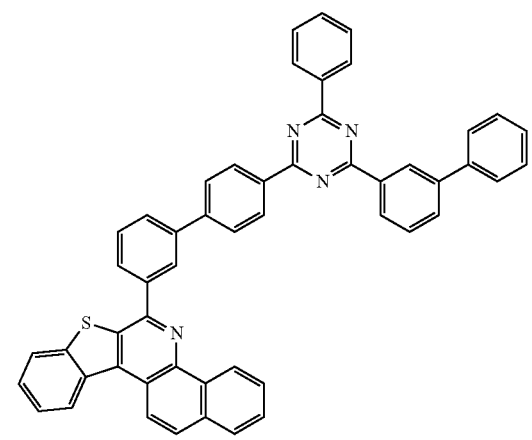
261
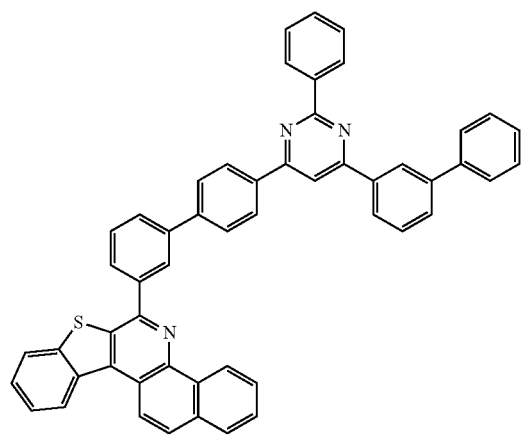
262
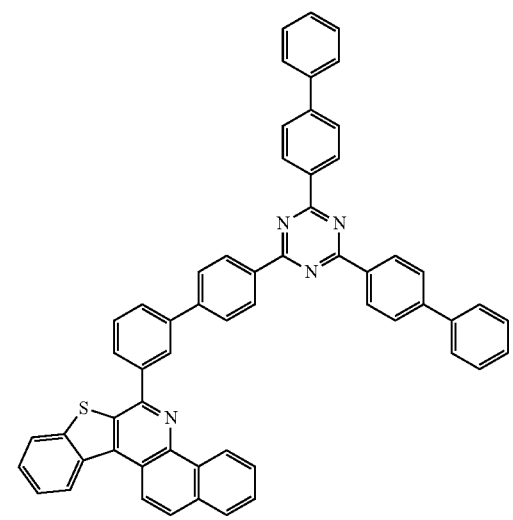 [SMILES: c1ccc(-c2ccc(-c3cc(-c4ccc(-c5cccc(-c6nc7c8ccccc8ccc7c7c6sc6ccccc67)c5)cc4)nc(-c4ccc(-c5ccccc5)cc4)n3)cc2)cc1]
263
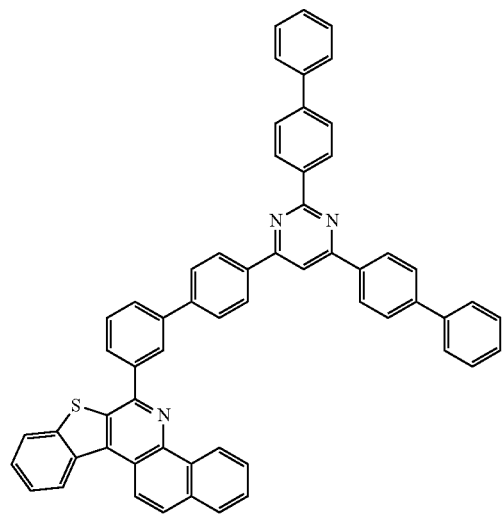
264
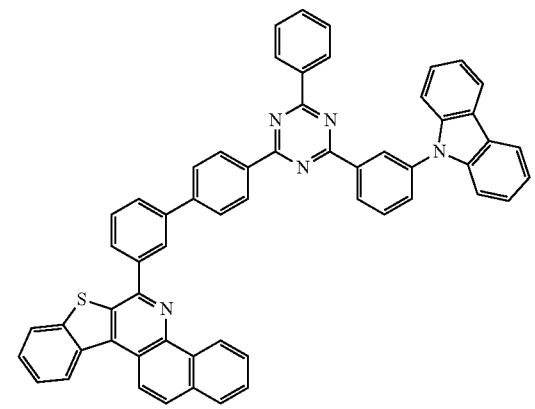

-continued
265
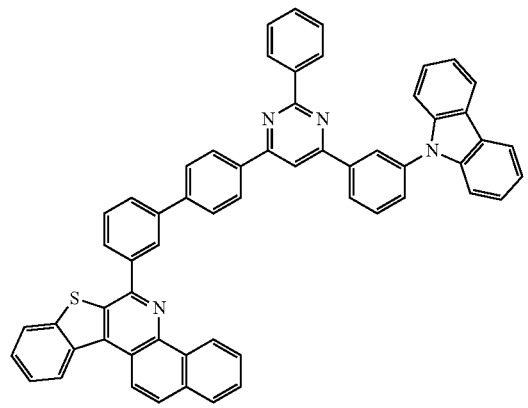
266
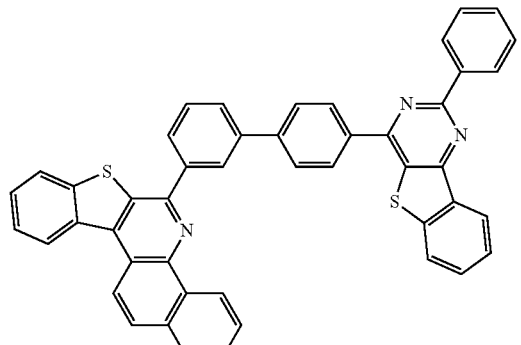
267
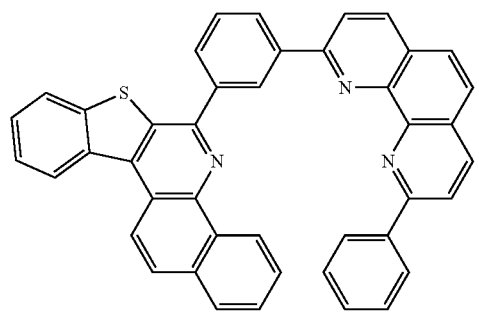
268
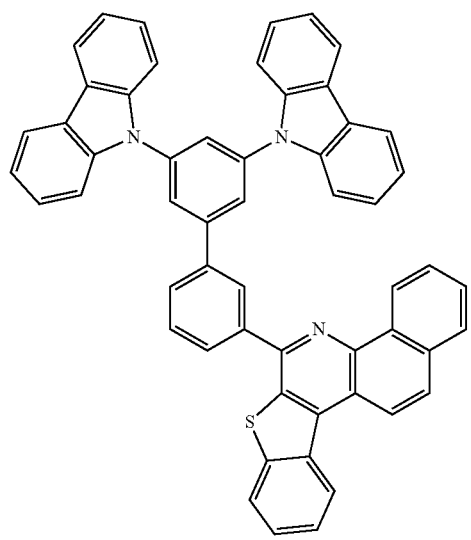
269
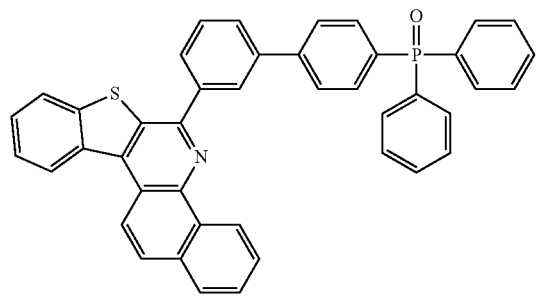 [SMILES: O=P(c1ccccc1)(c1ccccc1)c1ccc(-c2cccc(-c3nc4c5ccccc5ccc4c4c3sc3ccccc34)c2)cc1]
270
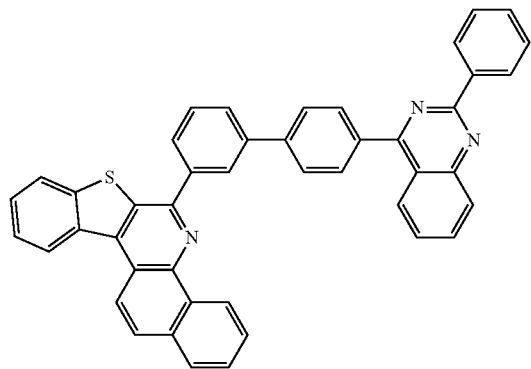

-continued
271
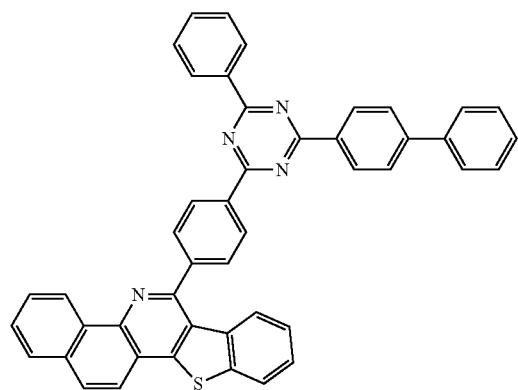
272
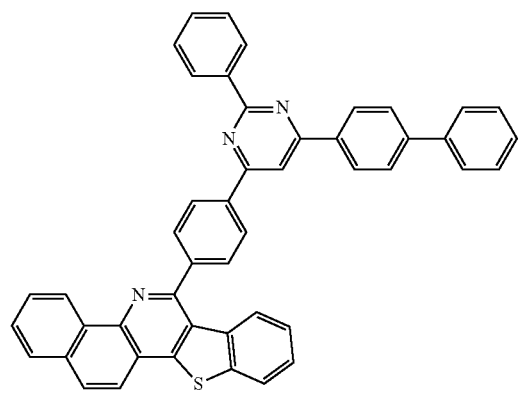
273
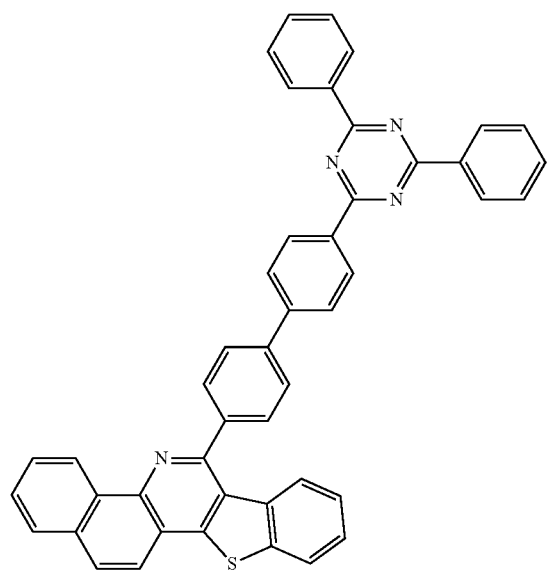
274
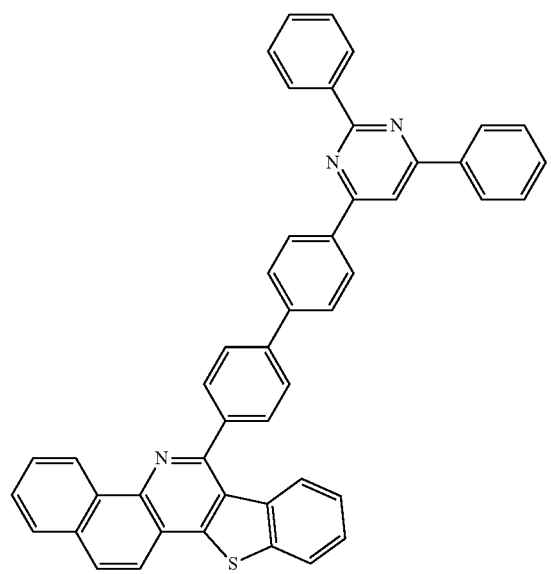
275
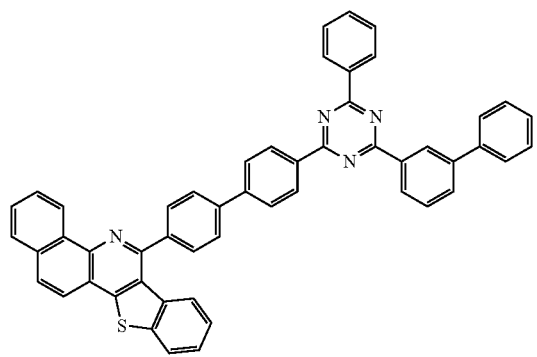
276
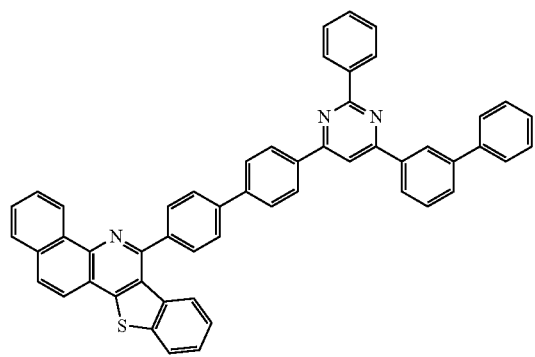

-continued
277
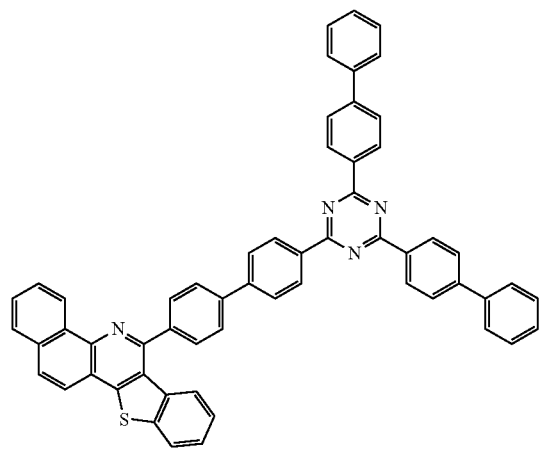
278
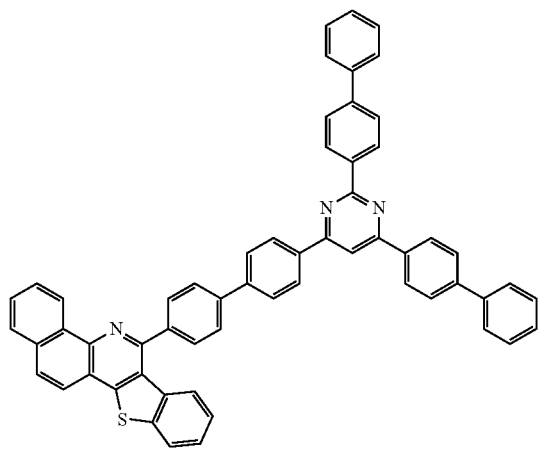
279
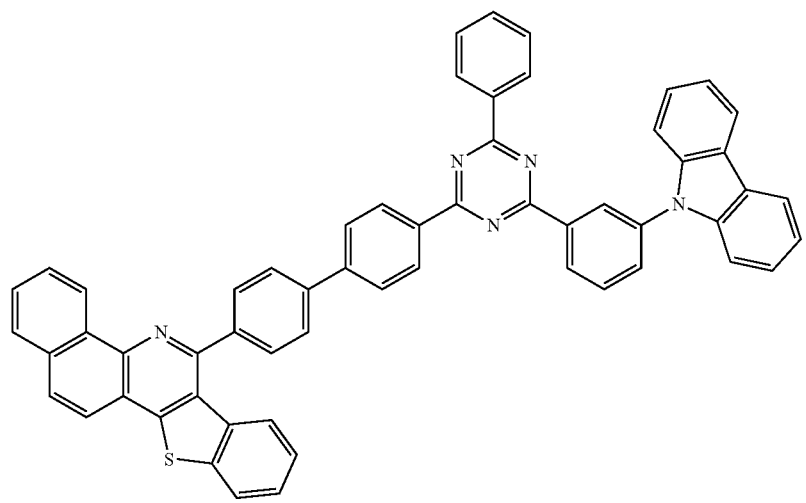
280
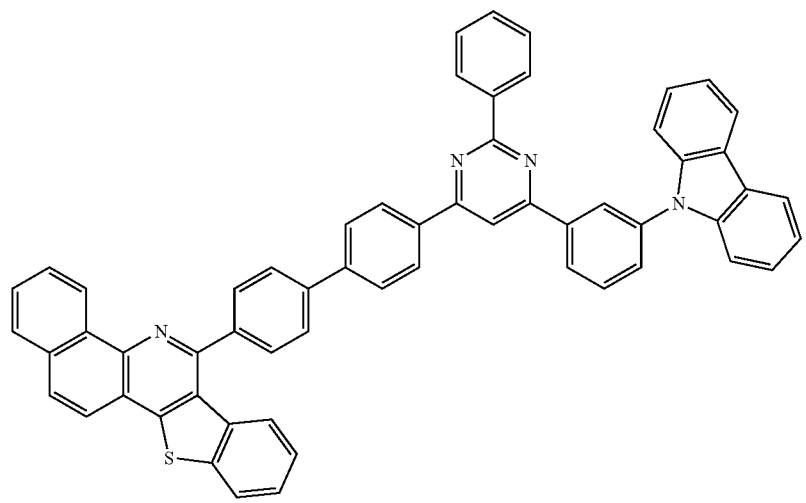

-continued
281
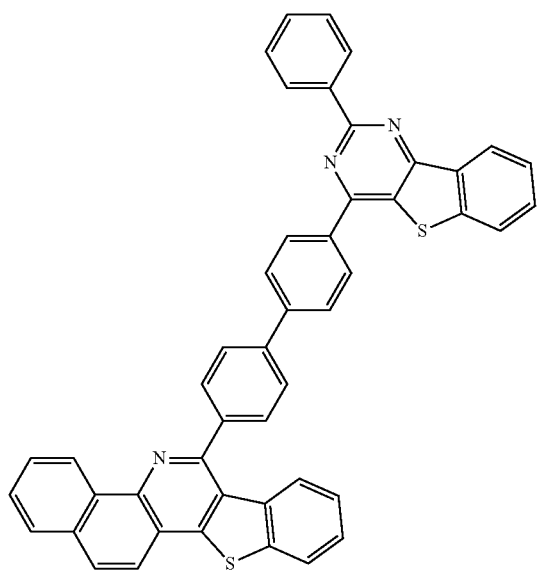 [SMILES: C1=CC2Sc3c(-c4ccc(-c5ccc(-c6nc7c8ccccc8ccc7c7oc8ccccc8c67)cc5)cc4)nc(-c4ccccc4)nc3C2C=C1]
282
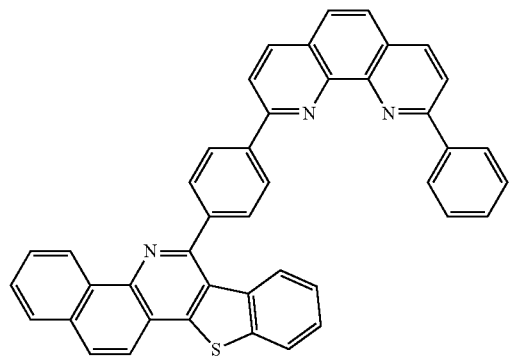
283
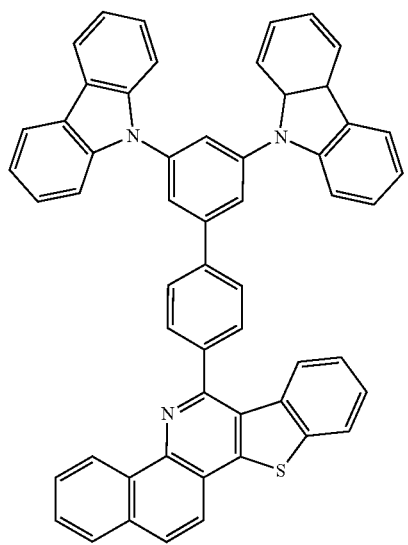
284
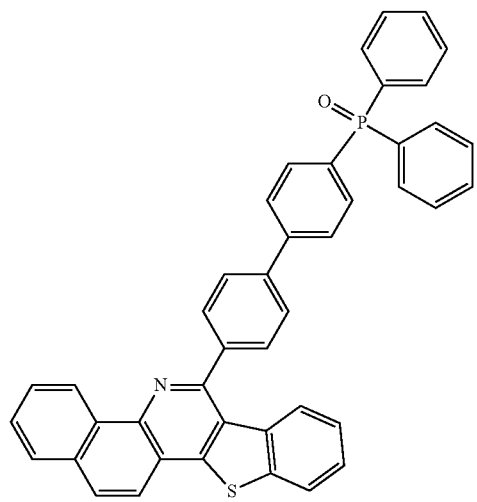

-continued
285
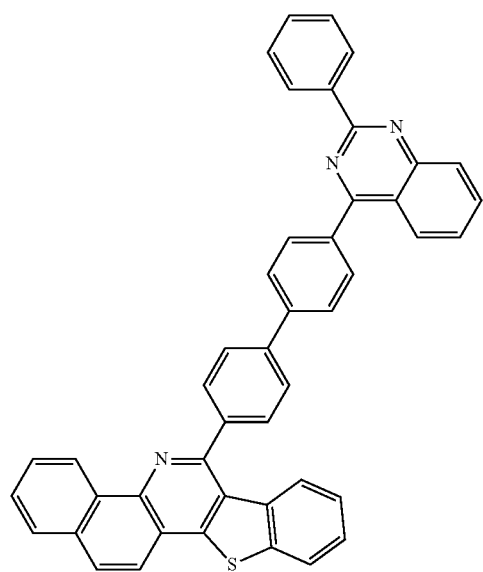
286
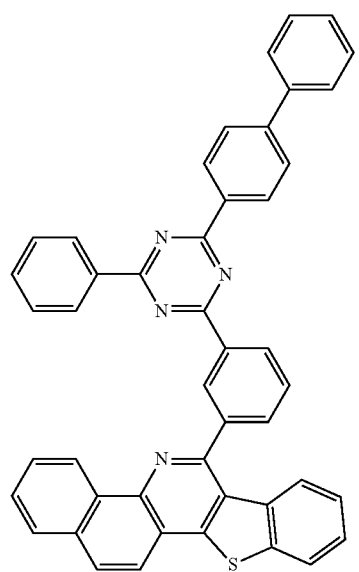
287
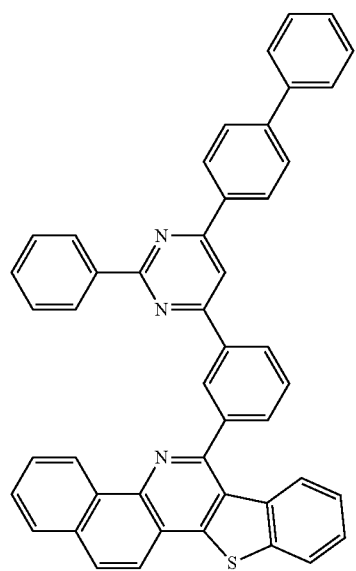
288
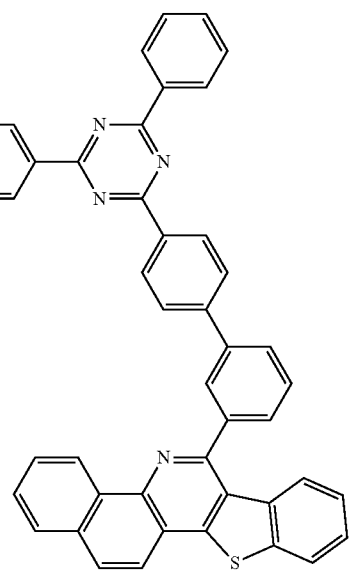

-continued
289
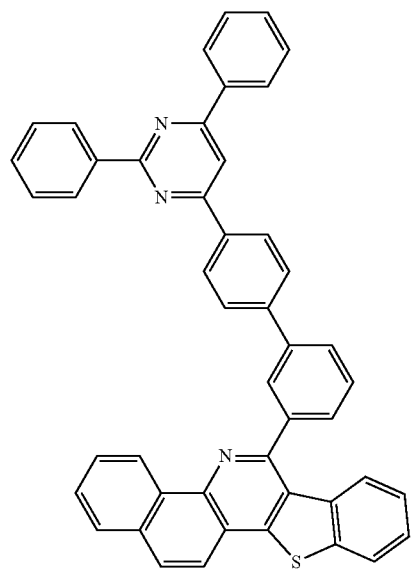
290
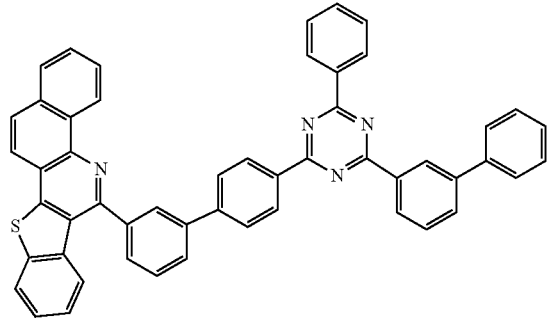
291
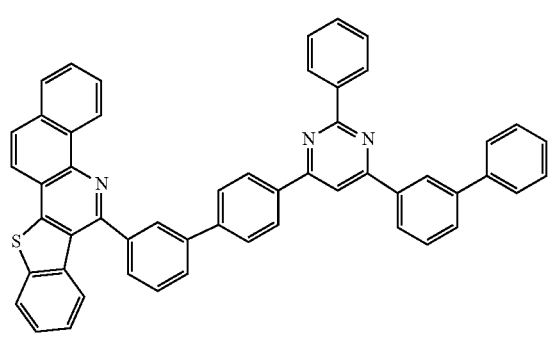
292
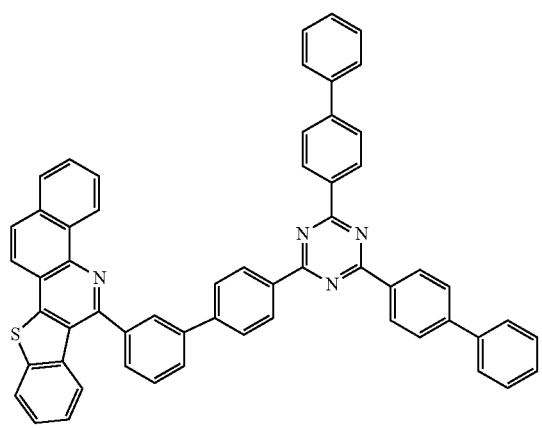
293
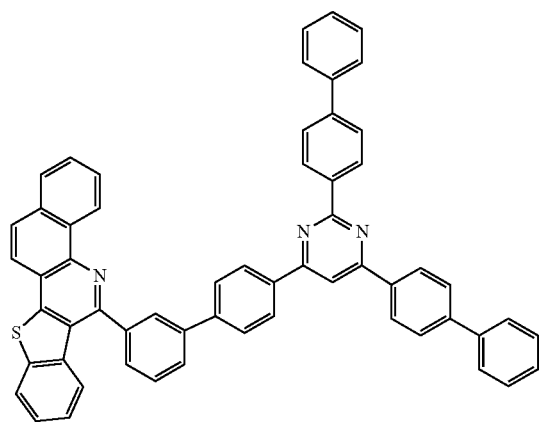
294
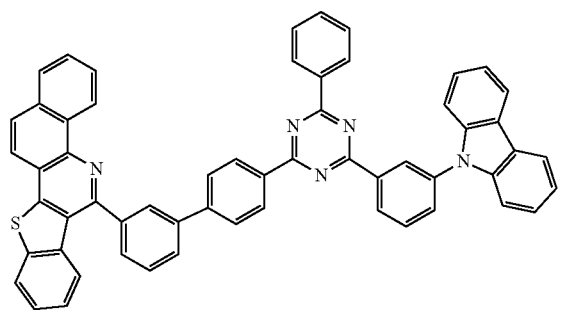

-continued
295
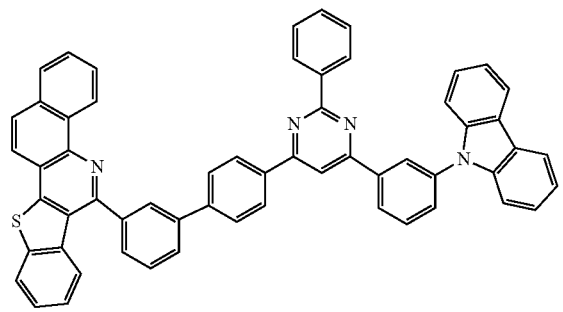
296
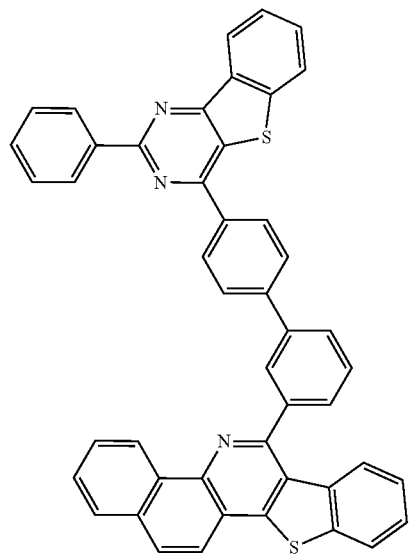
297
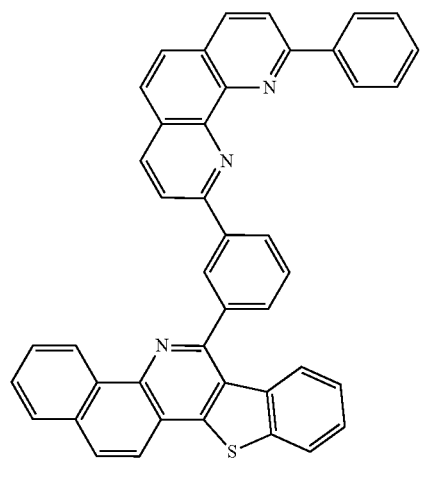 [SMILES: c1ccc(-c2ccc3ccc4ccc(-c5cccc(-c6nc7c8ccccc8ccc7c7sc8ccccc8c67)c5)nc4c3n2)cc1]
298
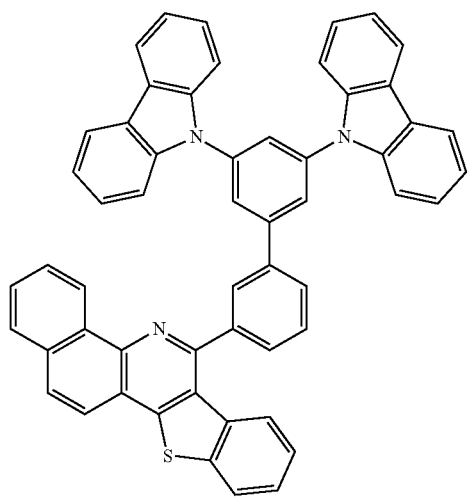
299
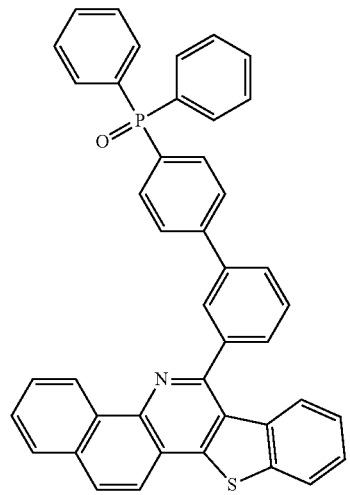
300
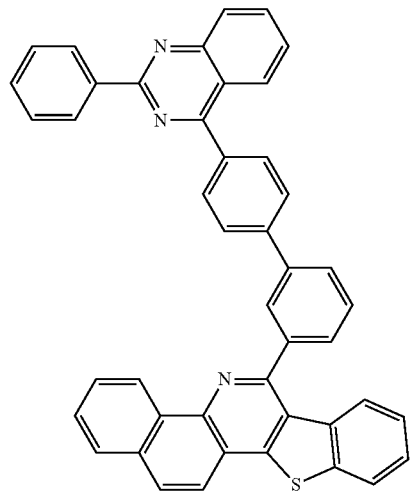

-continued
301
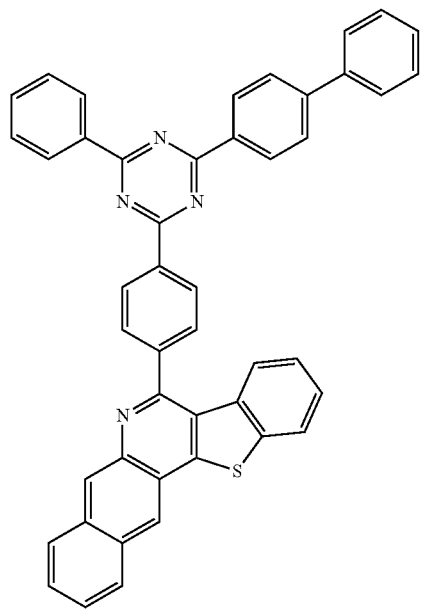
302
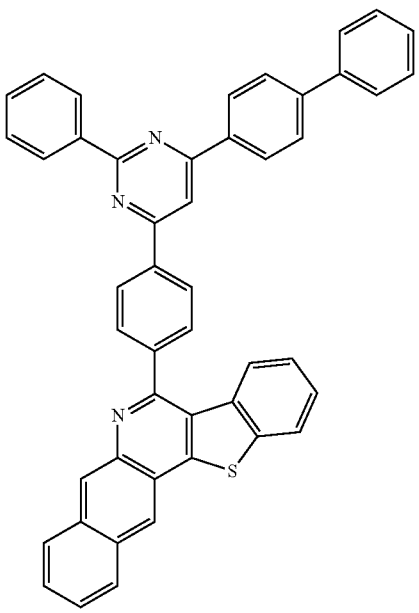
303
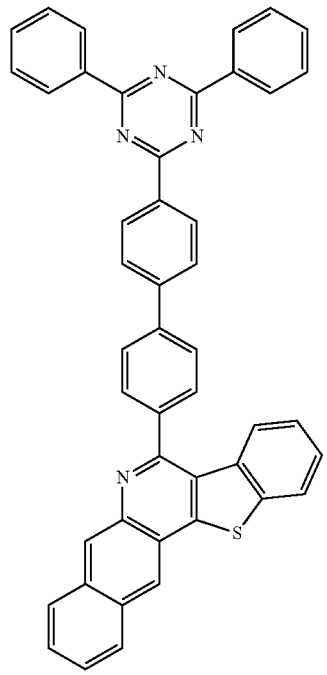
304
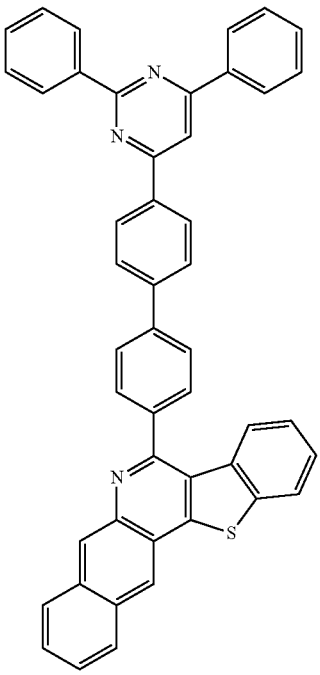

305
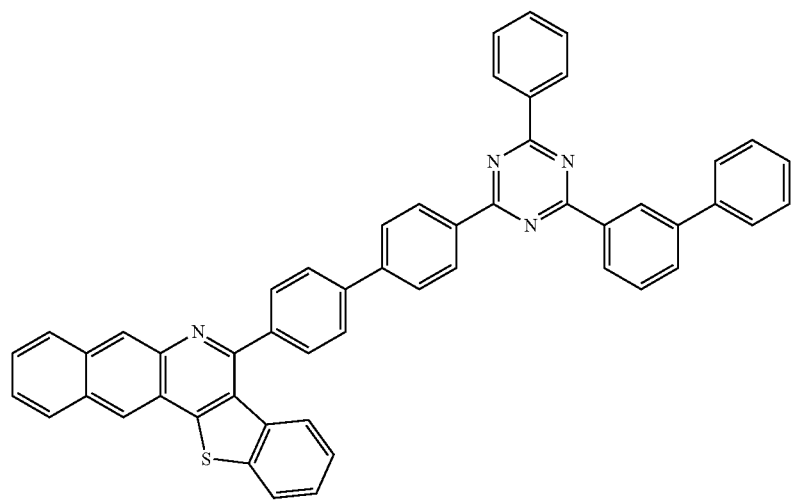
306
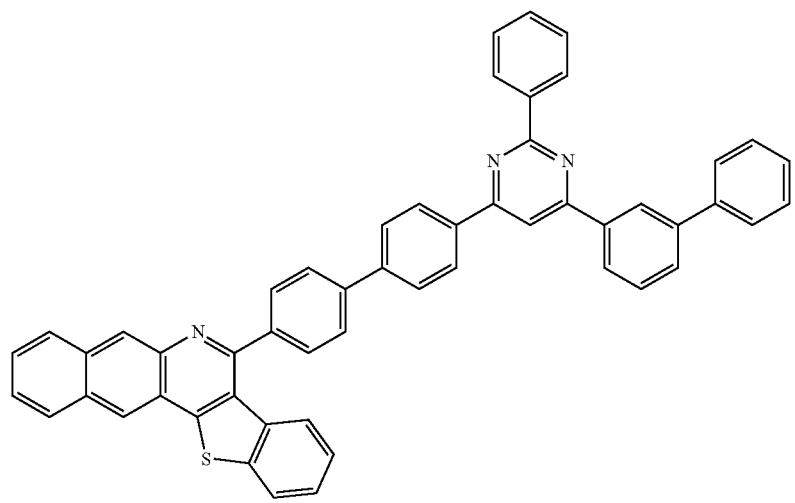
307
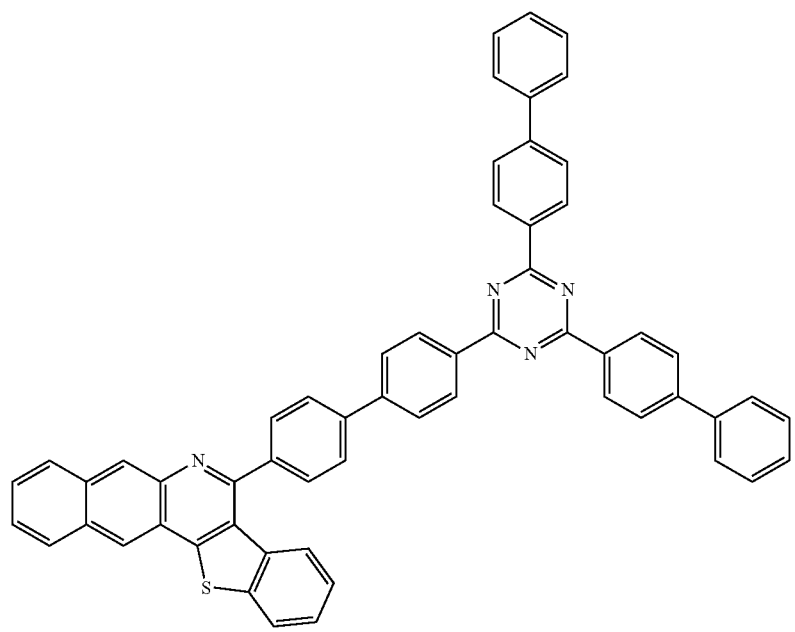

-continued
308
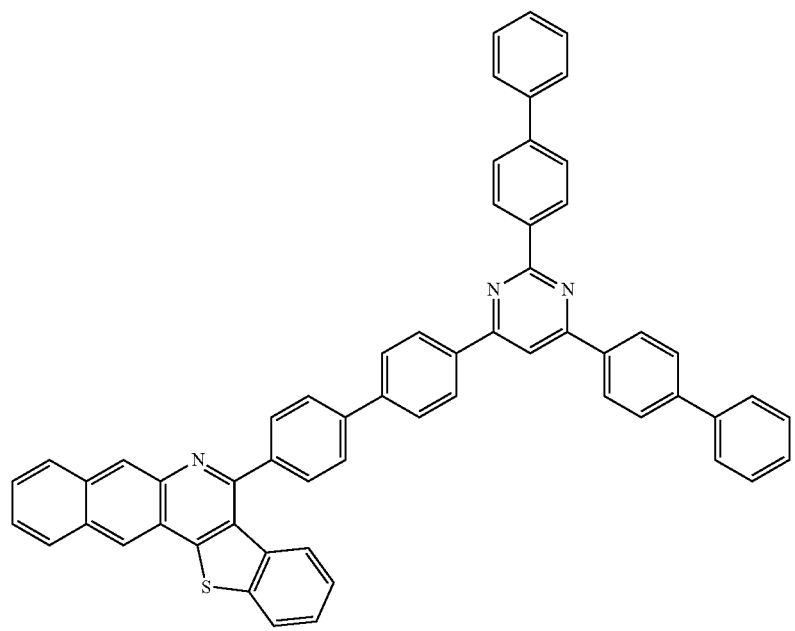
309
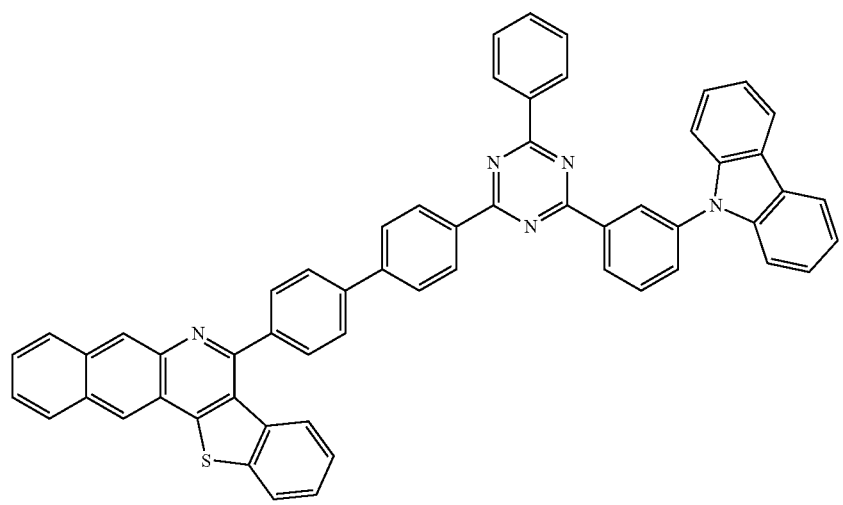
310
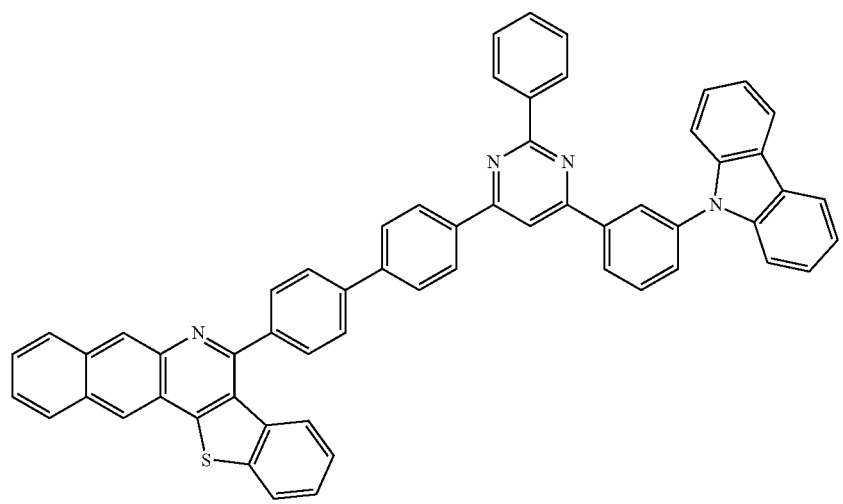

-continued
311
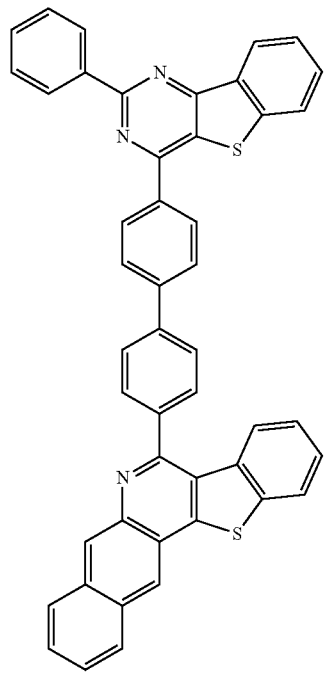
312
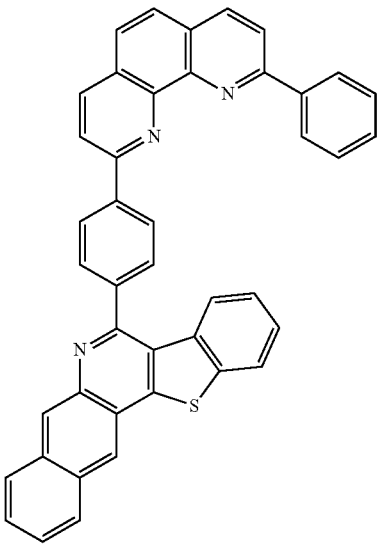
313
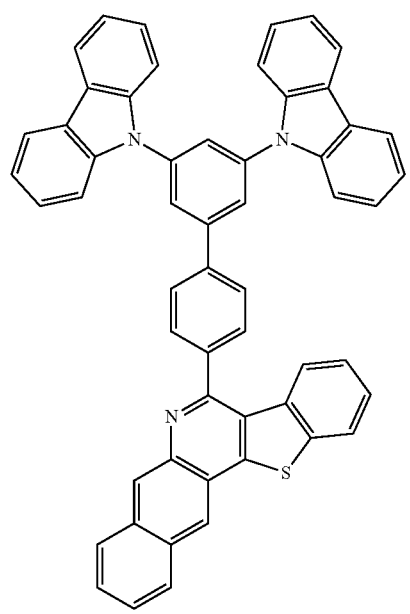
314
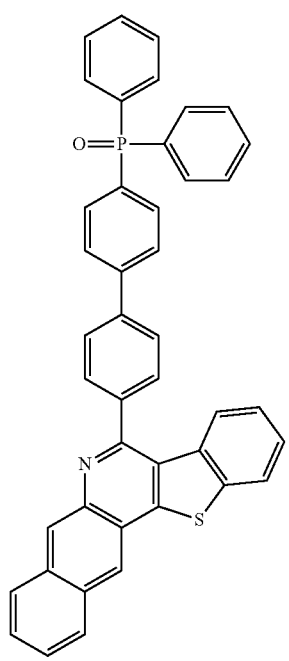

-continued
315 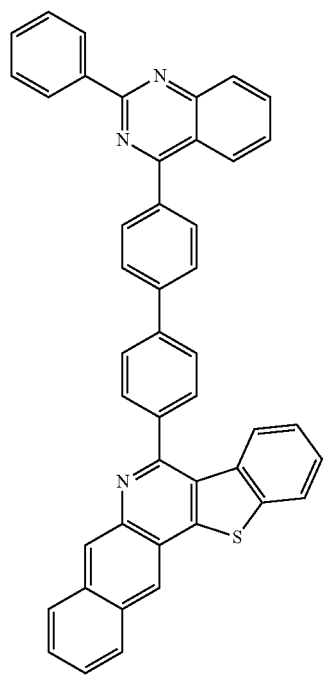
316 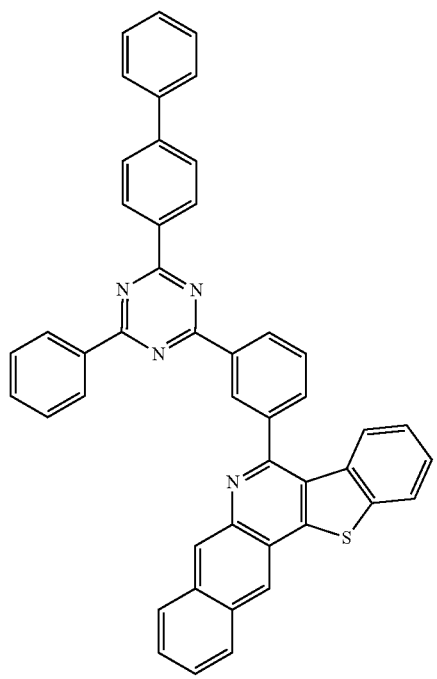
317 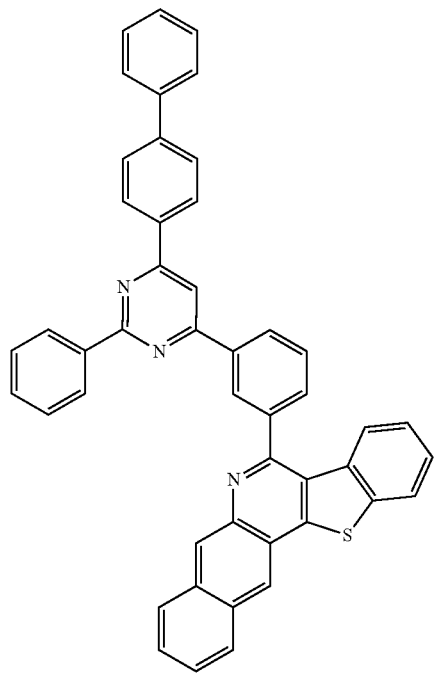
318 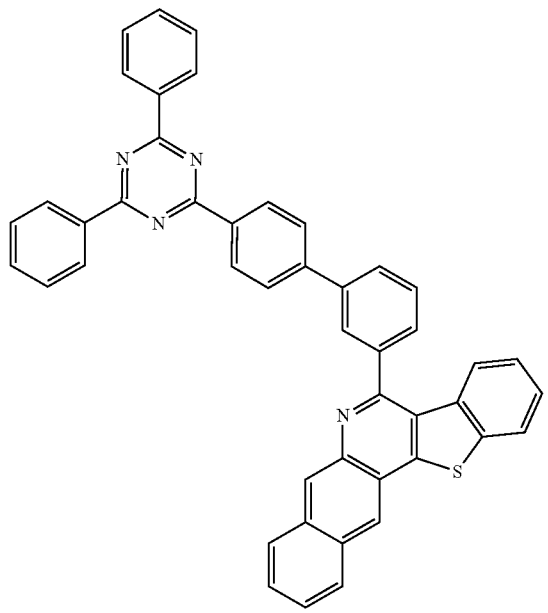

-continued
319
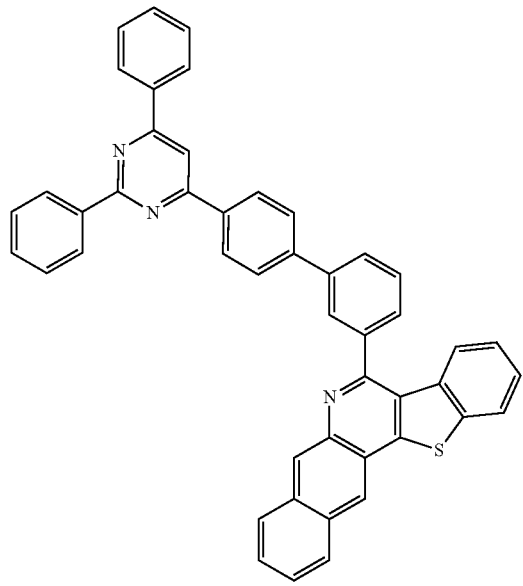
320
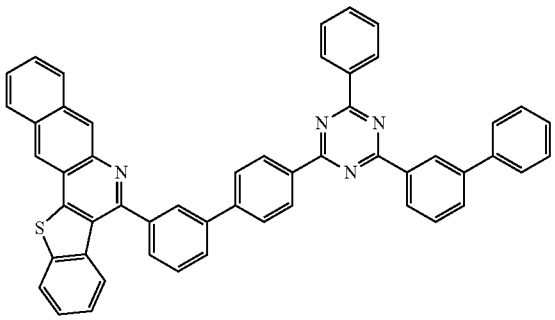
321
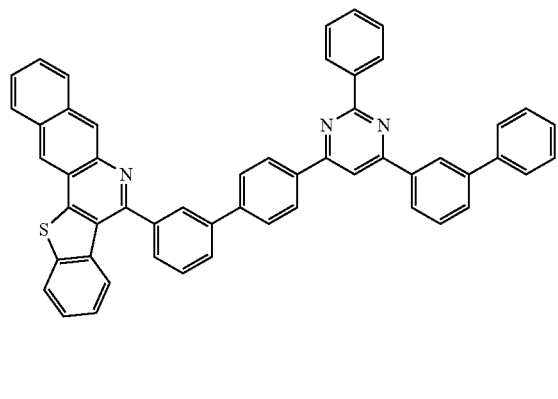
322
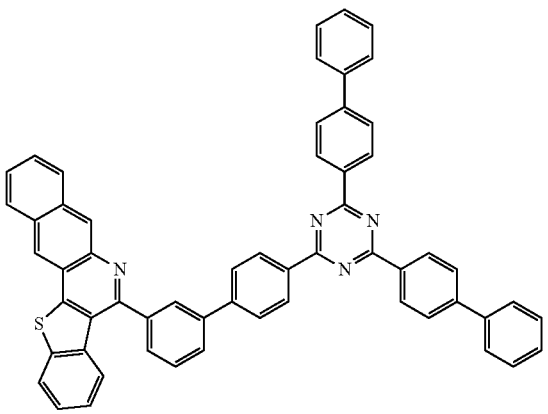
323
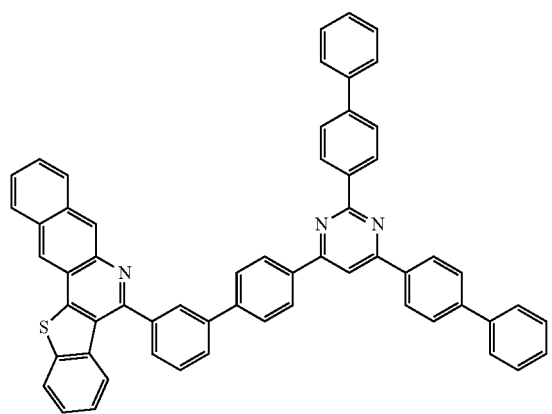
324
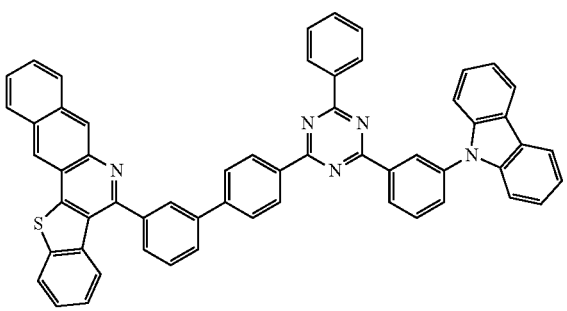

-continued
325 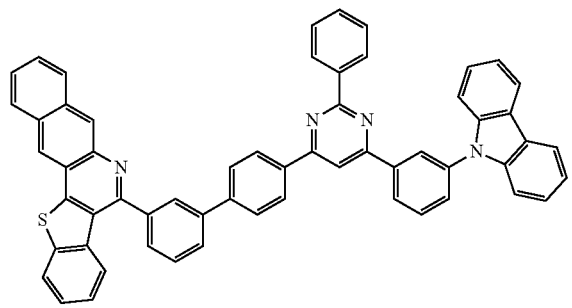
326 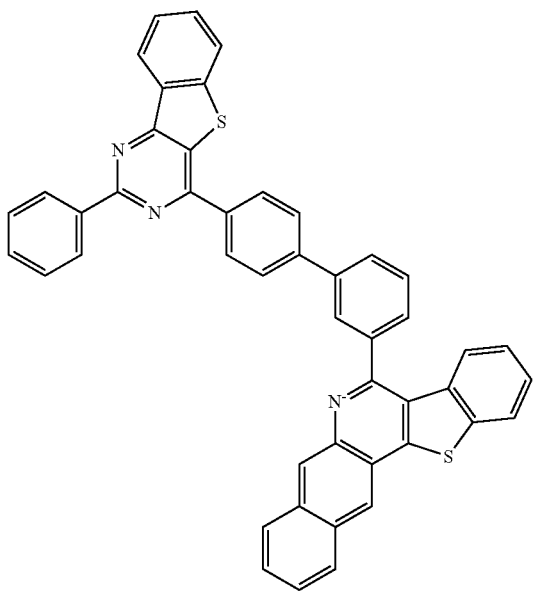
327 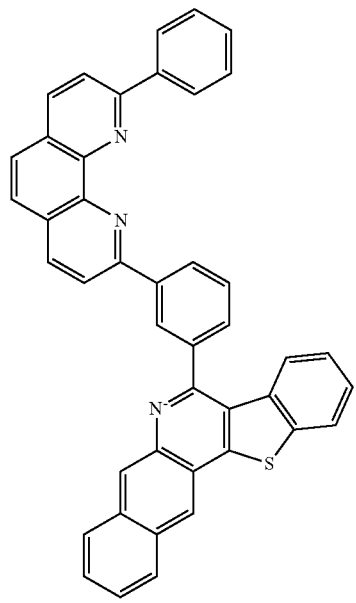
328 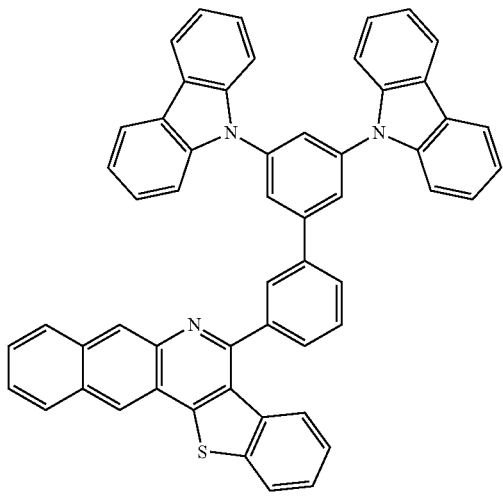

-continued
329
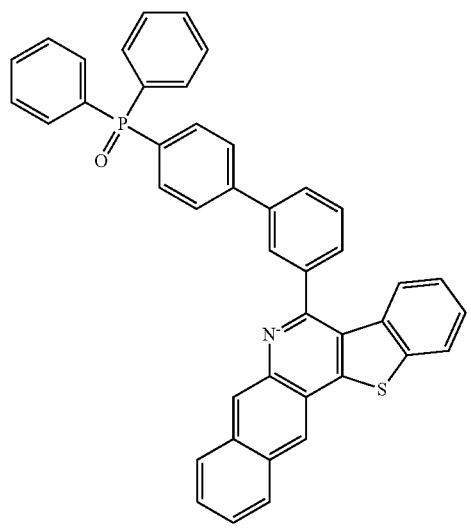
330
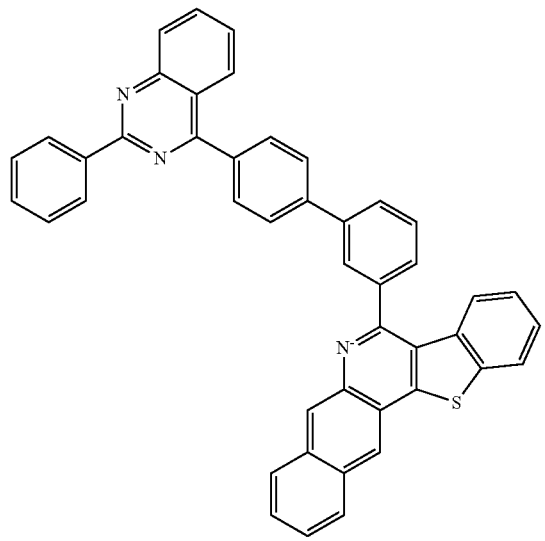
331
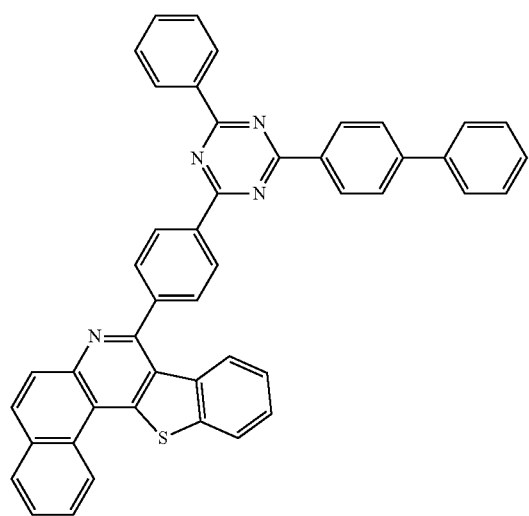
332
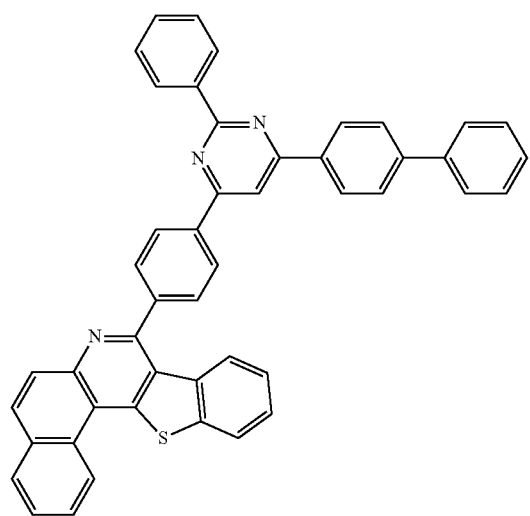 [SMILES: c1ccc(-c2ccc(-c3cc(-c4ccc(-c5nc6ccc7ccccc7c6c6oc7ccccc7c56)cc4)nc(-c4ccccc4)n3)cc2)cc1]

-continued
333
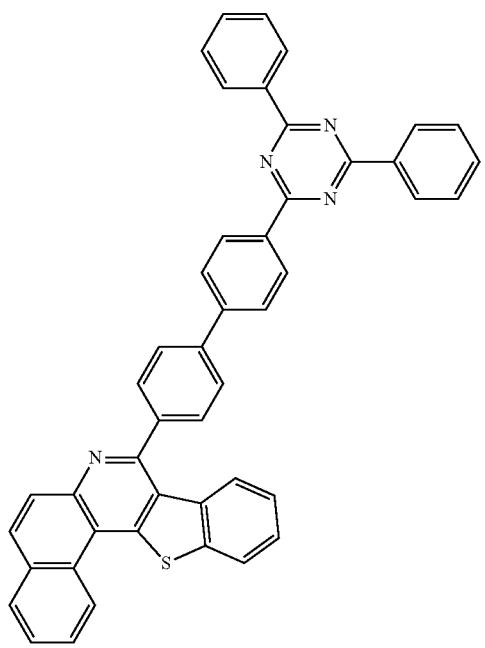
334
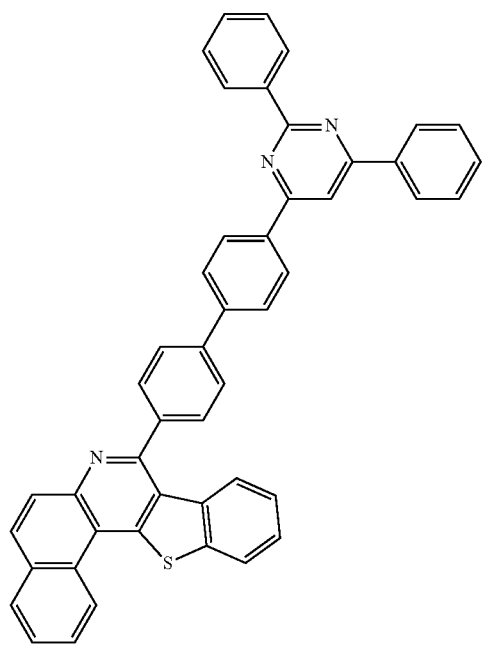
335
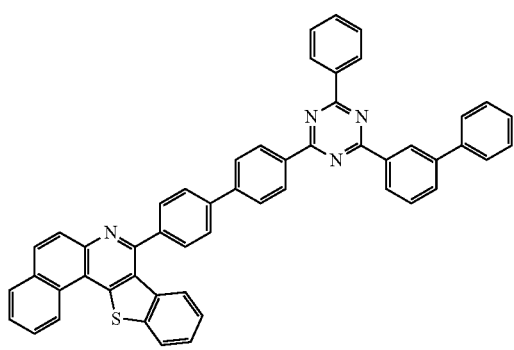
336
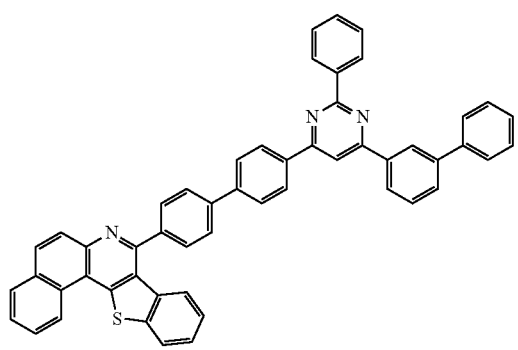
337
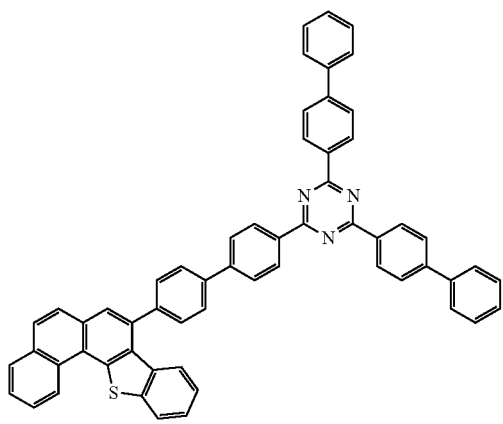
338
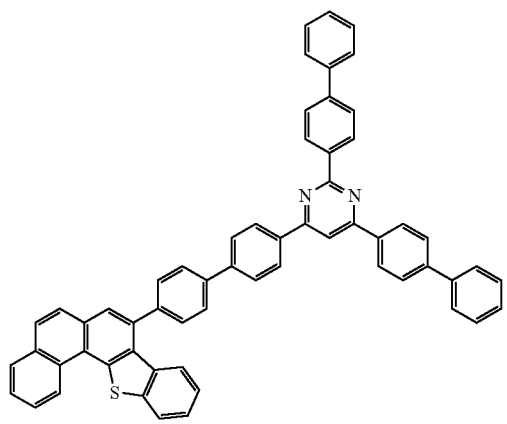

339
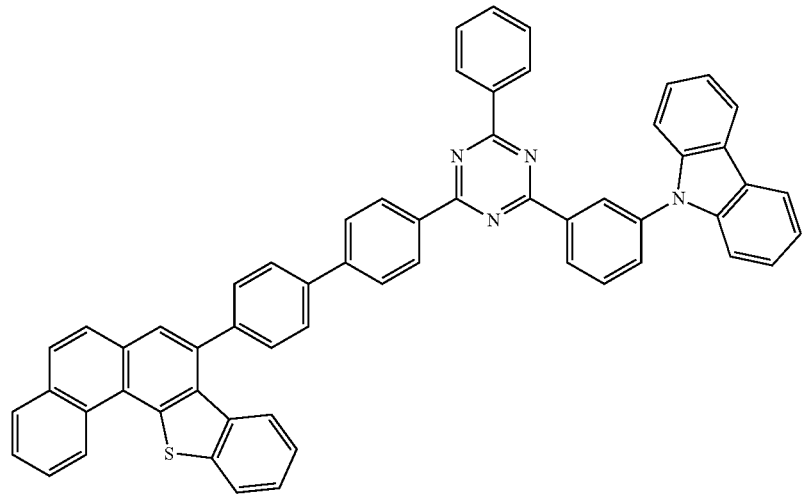
340
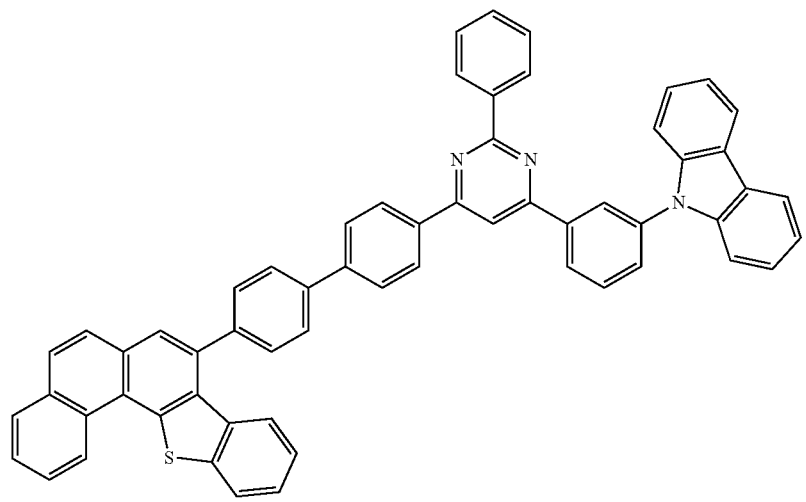
341 342
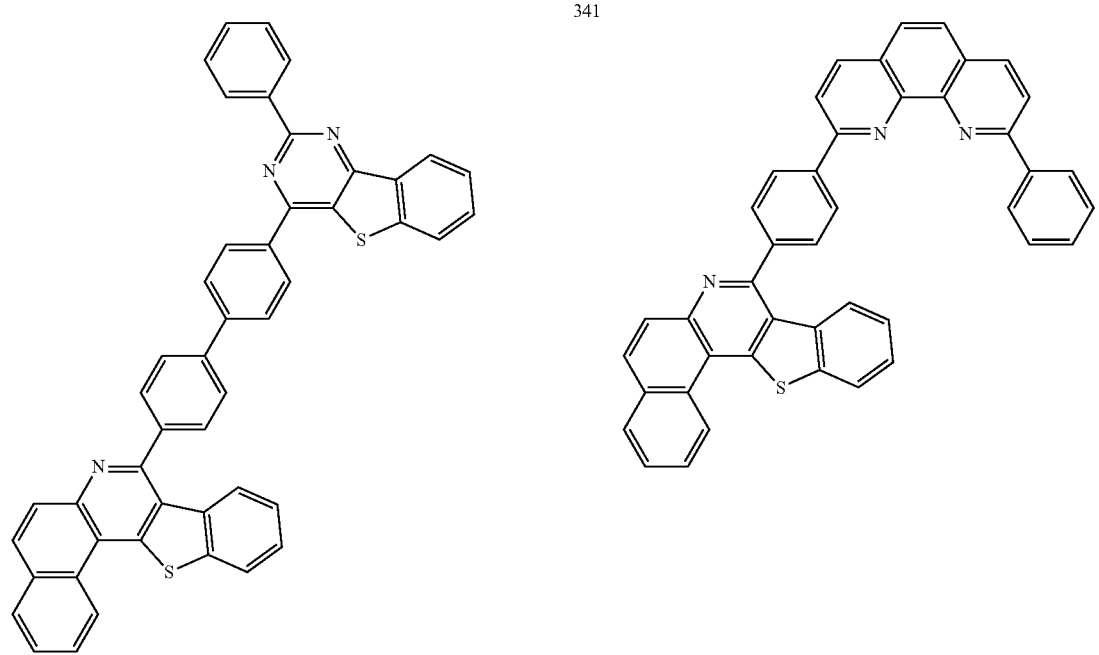

-continued
383
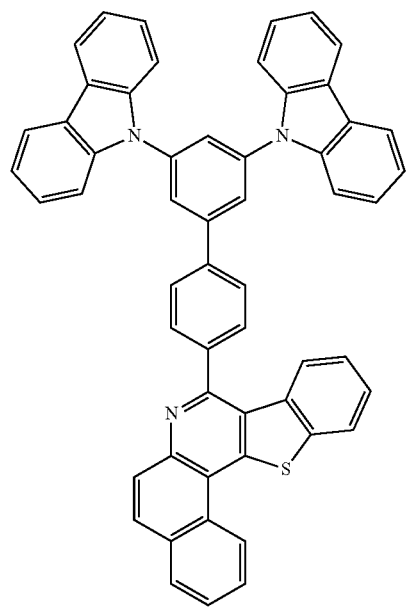
384
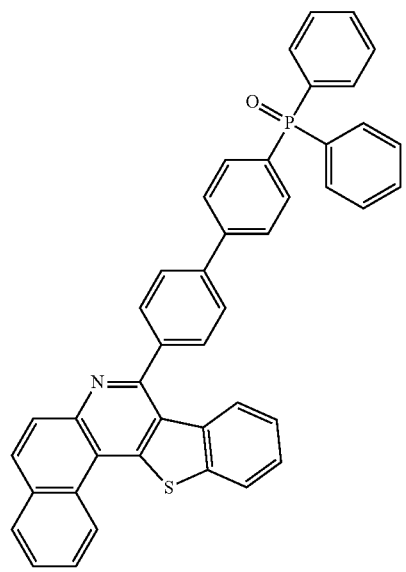
345
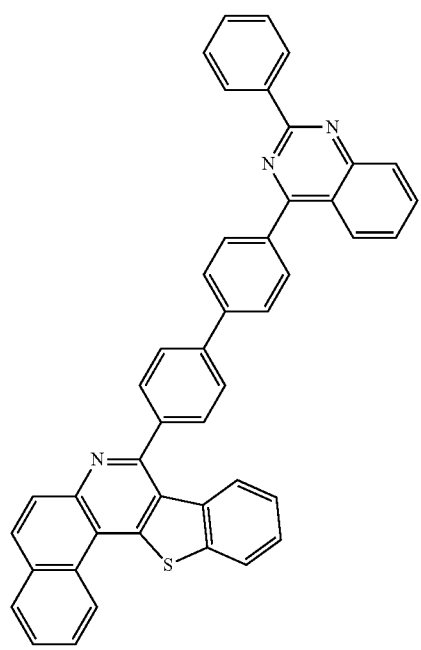
346
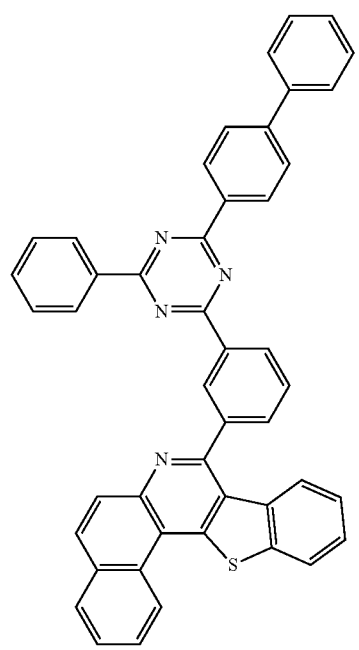

-continued
347
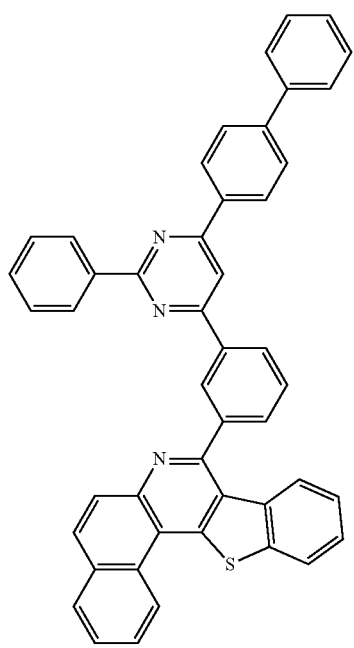
348
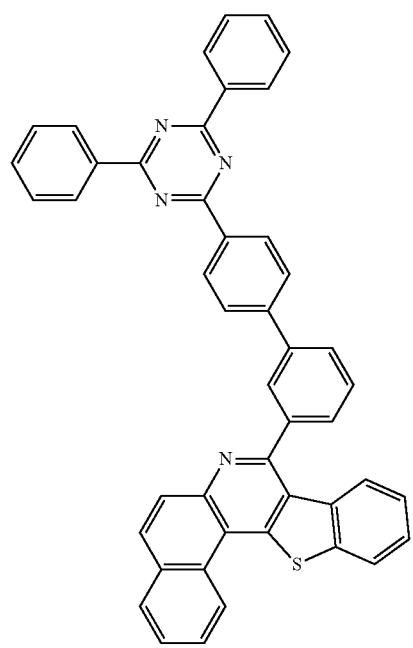
349
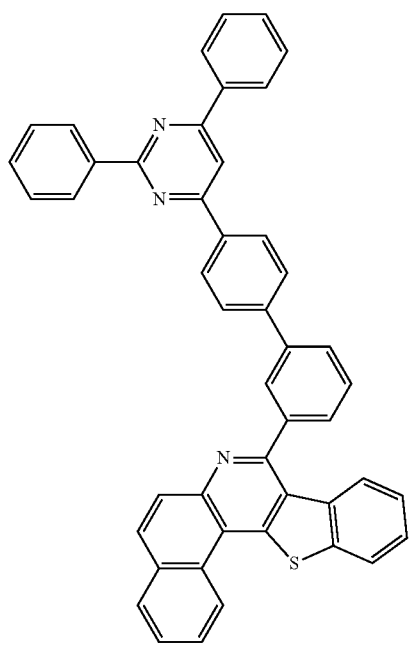
350
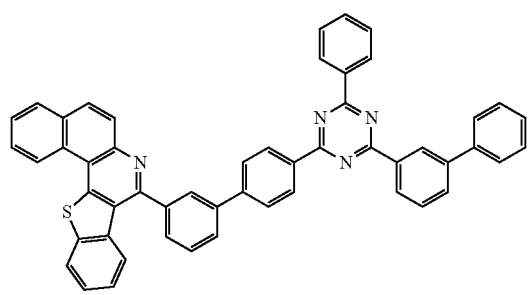
351
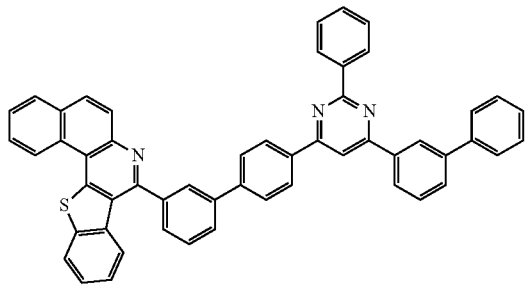
352
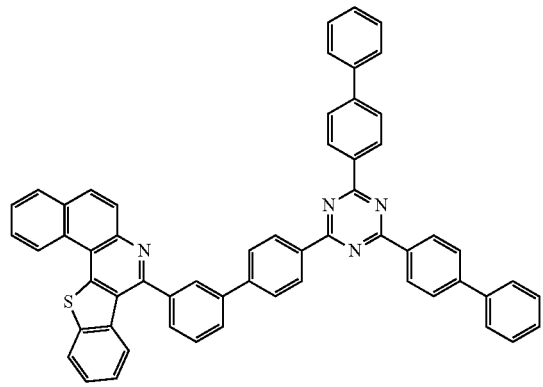

353
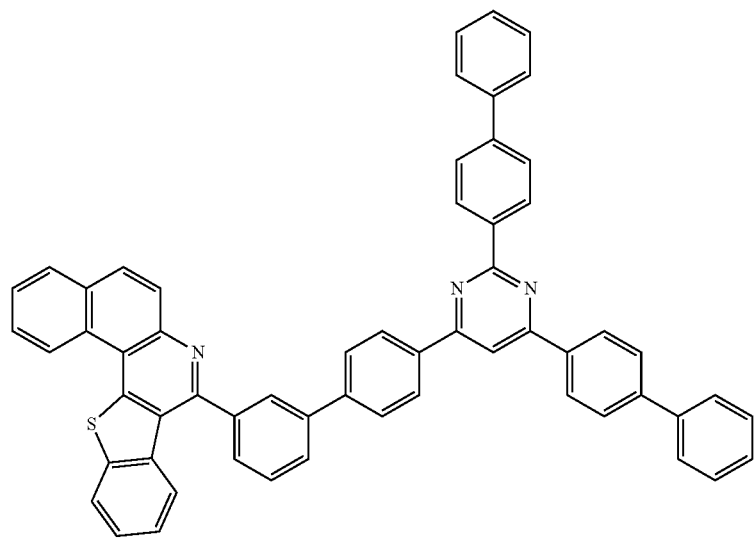 [SMILES: c1ccc(-c2ccc(-c3cc(-c4ccc(-c5cccc(-c6nc7ccc8ccccc8c7c7oc8ccccc8c67)c5)cc4)nc(-c4ccc(-c5ccccc5)cc4)n3)cc2)cc1]
354
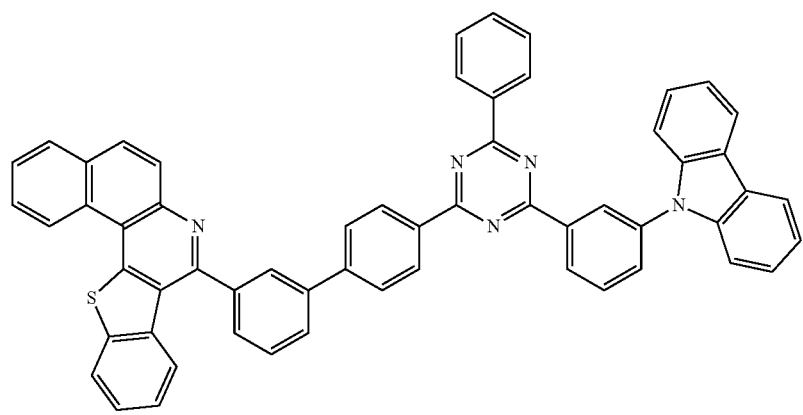
355
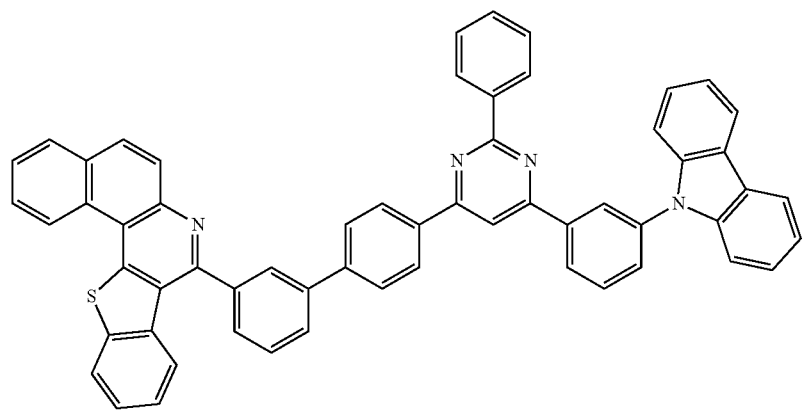

-continued
356
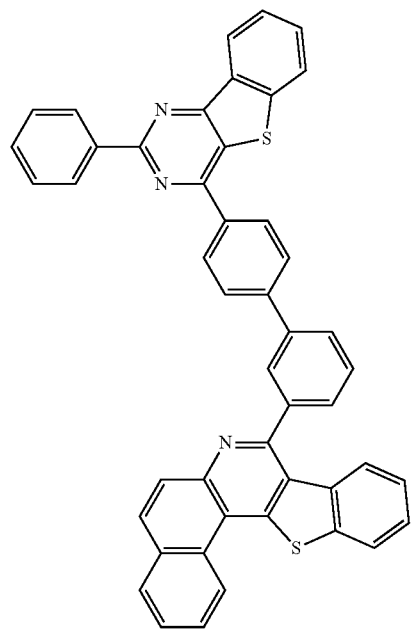 [SMILES: C1=CC2Sc3c(-c4ccc(-c5cccc(-c6nc7ccc8ccccc8c7c7sc8ccccc8c67)c5)cc4)nc(-c4ccccc4)nc3C2C=C1]
357
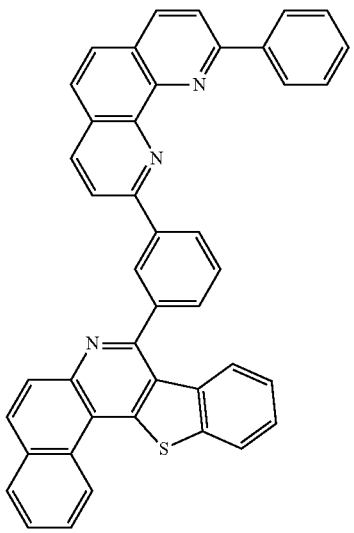
358
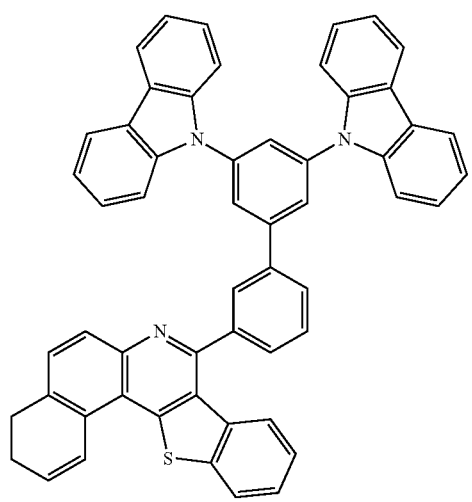
359
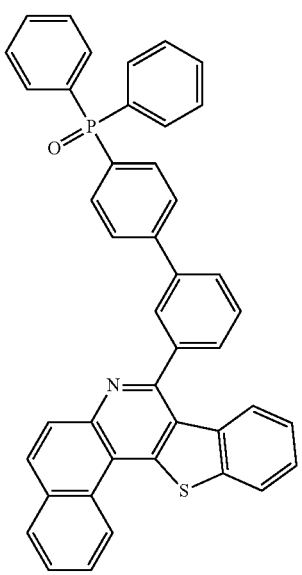

-continued

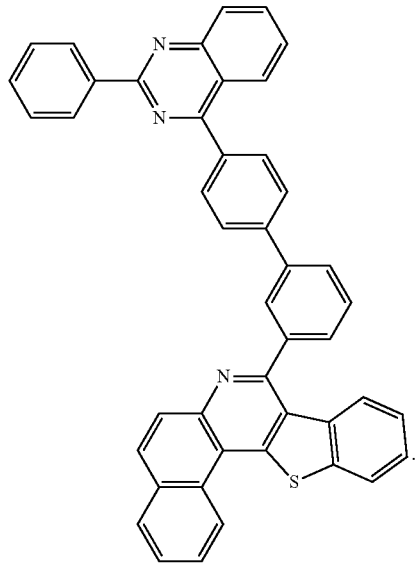
360

4. An organic light emitting device comprising:
first electrode;
a second electrode provided opposite to the first electrode; and
one or more organic material layers provided between the first electrode and the second electrode,
wherein one or more layers of the organic material layers include the heterocyclic compound of claim 1.

5. The organic light emitting device of claim 4, wherein the organic material layer includes a light emitting layer, and the light emitting layer includes the heterocyclic compound.

6. The organic light emitting device of claim 4, wherein the organic material layer includes an electron injection layer or an electron transfer layer, and the electron injection layer or the electron transfer layer includes the heterocyclic compound.

7. The organic light emitting device of claim 4, wherein the organic material layer includes an electron blocking layer or a hole blocking layer, and the electron blocking layer or the hole blocking layer includes the heterocyclic compound.

8. The organic light emitting device of claim 4, further comprising one, two or more layers selected from the group consisting of a light emitting layer, a hole injection layer, a hole transfer layer, an electron injection layer, an electron transfer layer, an electron blocking layer and a hole blocking layer.

9. The organic light emitting device of claim 4, comprising:
a first electrode;
a first stack provided on the first electrode and including a first light emitting layer;
a charge generation layer provided on the first stack;
a second stack provided on the charge generation layer and including a second light emitting layer; and
a second electrode provided on the second stack.

10. The organic light emitting device of claim 9, wherein the charge generation layer includes the heterocyclic compound.

11. The organic light emitting device of claim 10, wherein the charge generation layer is an N-type charge generation layer, and the charge generation layer includes the heterocyclic compound.

* * * * *